US012723266B2

(12) United States Patent
Čermák

(10) Patent No.: US 12,723,266 B2
(45) **Date of Patent: *Sep. 1, 2026**

(54) HOMOLOGY DEPENDENT REPAIR GENOME EDITING

(71) Applicant: Inari Agriculture Technology, Inc., Cambridge, MA (US)

(72) Inventor: Tomáš Čermák, Brookline, MA (US)

(73) Assignee: Inari Agriculture Technology, Inc., Cambridge, MA (US)

( * ) Notice: Subject to any disclaimer, the term of this patent is extended or adjusted under 35 U.S.C. 154(b) by 1414 days.

This patent is subject to a terminal disclaimer.

(21) Appl. No.: 17/326,891

(22) Filed: May 21, 2021

(65) Prior Publication Data

US 2021/0277422 A1 Sep. 9, 2021

Related U.S. Application Data

(63) Continuation of application No. 16/911,156, filed on Jun. 24, 2020, now Pat. No. 11,041,172.

(60) Provisional application No. 62/866,317, filed on Jun. 25, 2019.

(51) Int. Cl.
*C12N 15/90* (2006.01)
*C12N 9/22* (2006.01)

(52) U.S. Cl.
CPC ............. *C12N 15/902* (2013.01); *C12N 9/22* (2013.01); *C12N 15/907* (2013.01); *C12N 2310/20* (2017.05); *C12N 2800/80* (2013.01)

(58) Field of Classification Search
CPC .... C12N 15/902; C12N 9/22; C12N 2310/20; C12N 15/8213; C12N 15/907
See application file for complete search history.

(56) References Cited

U.S. PATENT DOCUMENTS

| | | | |
|---|---|---|---|
| 5,310,667 | A | 5/1994 | Eichholtz et al. |
| 5,322,938 | A | 6/1994 | McPherson et al. |
| 5,366,892 | A | 11/1994 | Foncerrada et al. |
| 5,593,881 | A | 1/1997 | Thompson et al. |
| 5,602,321 | A | 2/1997 | John |
| 5,641,876 | A | 6/1997 | McElroy et al. |
| 5,703,049 | A | 12/1997 | Rao |
| 5,723,756 | A | 3/1998 | Peferoen et al. |
| 5,736,514 | A | 4/1998 | Tizuka et al. |
| 5,747,450 | A | 5/1998 | Ohba et al. |
| 5,792,931 | A | 8/1998 | Duvick et al. |
| 5,850,016 | A | 12/1998 | Jung et al. |
| 5,858,742 | A | 1/1999 | Fraley et al. |
| 5,866,775 | A | 2/1999 | Eichholtz et al. |
| 5,885,801 | A | 3/1999 | Rao |
| 5,885,802 | A | 3/1999 | Rao |
| 5,990,389 | A | 11/1999 | Rao et al. |
| 6,090,627 | A | 7/2000 | Kemp et al. |
| 6,225,114 | B1 | 5/2001 | Eichholtz et al. |
| 6,248,876 | B1 | 6/2001 | Barry et al. |
| 6,453,242 | B1 | 9/2002 | Eisenberg et al. |
| 6,479,626 | B1 | 11/2002 | Kim et al. |
| 6,534,261 | B1 | 3/2003 | Cox et al. |
| 6,794,136 | B1 | 9/2004 | Eisenberg et al. |
| 6,867,293 | B2 | 3/2005 | Andrews et al. |
| 6,903,185 | B2 | 6/2005 | Kim et al. |
| RE39,247 | E | 8/2006 | Barry et al. |
| 7,151,204 | B2 | 12/2006 | Houmard et al. |
| 7,153,949 | B2 | 12/2006 | Kim et al. |
| 7,169,970 | B2 | 1/2007 | Warner et al. |
| 7,361,811 | B2 | 4/2008 | Meyer et al. |
| 7,626,077 | B2 | 12/2009 | Held et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,215,849 | B2 | 12/2015 | Chan et al. |
| 9,464,124 | B2 | 10/2016 | Bancel et al. |
| 9,677,082 | B2 | 6/2017 | Chintamanani et al. |
| 9,738,897 | B2 | 8/2017 | Schoenherr et al. |
| 9,944,925 | B2 | 4/2018 | Konieczka et al. |
| 11,041,172 | B2 * | 6/2021 | Cermak ............ C12N 15/8213 |
| 2002/0192813 | A1 | 12/2002 | Conner et al. |

(Continued)

FOREIGN PATENT DOCUMENTS

| | | | |
|---|---|---|---|
| CN | 108085328 | A | 5/2018 |
| WO | WO-2015026887 | A1 | 2/2015 |

(Continued)

OTHER PUBLICATIONS

Gratz et al., (Genetics, vol. 196, 961-971, 2014) (Year: 2014).*
Mao et al., (Cell. Mol. Life Sci. 74: 1075-1093, 2017) (Year: 2017).*
Ander et al., (2015). "A Single-Strand Annealing Protein Clamps DNA to Detect and Secure Homology," PLOS Biology, 13(8):e1002213.
Baim et al., (1991). "A chimeric mammalian transactivator based on the lac repressor that is regulated by temperature and isopropyl beta-D-thiogalactopyranoside," Proc. Natl. Acad. Sci. USA, 88(12):5072-6.
Bernad et al., (1989). "A conserved 3'-5' exonuclease active site in prokaryotic and eukaryotic DNA polymerases," Cell, 59(1):219-28.
Bhaskaran et al., (1990). "Regeneration in Cereal Tissue Culture: a Review," Crop Sci. 30(6):1328-37.

(Continued)

*Primary Examiner* — Tracy Vivlemore
(74) *Attorney, Agent, or Firm* — MORRISON & FOERSTER LLP

(57) ABSTRACT

Eukaryotic cells and related reagents, systems, methods, and compositions for increasing the frequency of homology directed repair (HDR) of target editing sites with genome editing molecules are provided.

37 Claims, 11 Drawing Sheets

Specification includes a Sequence Listing.

(56) References Cited

U.S. PATENT DOCUMENTS

2008/0050506 A1 2/2008 Manjunath et al.
2010/0311168 A1 12/2010 Samuel et al.
2011/0093982 A1 4/2011 Samuel et al.
2011/0247100 A1 10/2011 Samboju et al.
2012/0023619 A1 1/2012 Samboju et al.
2012/0244569 A1 9/2012 Samuel et al.
2013/0145488 A1 6/2013 Wang et al.
2013/0185823 A1 7/2013 Kuang et al.
2013/0210681 A1 8/2013 Zhang et al.
2014/0096284 A1 4/2014 Martin-Ortigosa et al.
2014/0287509 A1 9/2014 Sharei et al.
2014/0356414 A1 12/2014 Wang et al.
2015/0040268 A1 2/2015 Lapidot et al.
2015/0047074 A1 2/2015 Strano et al.
2015/0059010 A1 2/2015 Cigan et al.
2015/0082478 A1 3/2015 Cigan et al.
2015/0089681 A1 3/2015 Van Der Oost et al.
2015/0208663 A1 7/2015 Khodakovskaya et al.
2015/0344912 A1 12/2015 Kim et al.
2016/0138008 A1 5/2016 Doudna et al.
2016/0145631 A1 5/2016 Voytas et al.
2016/0208243 A1 7/2016 Zhang et al.
2016/0208271 A1 7/2016 Cigan et al.
2017/0121722 A1 5/2017 Anand et al.
2017/0175140 A1 6/2017 Hummel et al.
2017/0260513 A1 9/2017 Silva et al.
2017/0273284 A1 9/2017 Shen
2017/0275636 A1 9/2017 Gilbertson et al.
2018/0230494 A1 8/2018 Joung et al.
2018/0273932 A1 9/2018 Bothmer et al.
2018/0298392 A1 10/2018 Cotta-Ramusino
2018/0298421 A1 10/2018 Carpenter et al.
2019/0093104 A1 3/2019 Stark et al.

FOREIGN PATENT DOCUMENTS

WO WO-2015131101 A1 9/2015
WO WO-2016007347 A1 1/2016
WO WO-2016100272 A1 6/2016
WO WO-2017184227 A2 2/2018
WO WO-2018067846 A1 4/2018
WO WO-1998020133 A2 5/2018
WO WO-2018085693 A1 5/2018
WO WO-2019123014 A1 6/2019
WO WO-2020003311 A1 1/2020
WO WO-2020041172 A1 2/2020

OTHER PUBLICATIONS

Bressan et al., (2017). "Efficient CRISPR/Cas9-assisted gene targeting enables rapid and precise genetic manipulation of mammalian neural stem cells", Development, 144(4):635-648.

Brettschneider et al., (1997). "Efficient Transformation of Scutellar Tissue of Immature Maize Embryos," Theoretical and Applied Genetics, 94:737-48.

Broothaerts et al., (2005). "Gene transfer to plants by diverse species of bacteria," Nature, 433:629-33.

Brown et al., (1987). "Lac repressor can regulate expression from a hybrid SV40 early promoter containing a lac operator in animal," Cell 49:603-12.

Burstein et al., (2017). "New CRISPR-Cas systems from uncultivated microbes," Nature, 542(7640):237-41, 28 pages.

Cai et al., (2019). "In vivo genome editing rescues photoreceptor degeneration via a Cas9/RecA-mediated homology-directed repair pathway," Sci Adv., 5(4):eaav3335, 12 pages.

Castle et al., (2004). "Discovery and directed evolution of a glyphosate tolerance gene," Science 304:1151-4.

Čermák et al., (2017). "A Multipurpose Toolkit to Enable Advanced Genome Engineering in Plants," The Plant Cell, 29(6): 1196-1217.

Certo et al., (2013). "Coupling endonucleases with DNA endprocessing enzymes to drive gene disruption," Nat Methods, 9(10):973-5, 10 pages.

Chen et al., (2017). "EXO1 suppresses double-strand break induced homologous recombination between diverged sequences in mammalian cells," DNA Repair, 57:98-106, 21 pages.

Choi et al., (2016). "Efficient mRNA delivery with graphene oxide-polyethylenimine for generation of footprint-free human induced pluripotent stem cells," J. Controlled Release, 235:222-35.

Christopherson et al., (1992). "Ecdysteroid-dependent regulation of genes in mammalian cells by a *Drosophila* ecdysone receptor and chimeric transactivators," Proc. Natl. Acad. Sci. USA, 89:6314-8.

Chung et al., (2017). "Enhanced Integration of Large DNA Into *E. coli* Chromosome by CRISPR/Cas9," Biotechnology and Bioengineering, 114:172-183.

Clark et al., (2005). "Estimating a Nucleotide Substitution Rate for Maize from Polymorphism at a Major Domestication Locus," Molecular Biology and Evolution, 22(11):2304-12.

Cong et al., (2013). "Multiplex Genome Engineering Using CRISPR/Cas Systems," Science, 339:819-23.

Dasgupta et al., (1998). "Co-ordinated expression of multiple enzymes in different subcellular compartments in plants," Plant J., 16(1):107-16.

Degenkolb et al., (1991). "Structural requirements of tetracycline-Tet repressor interaction: determination of equilibrium binding constants for tetracycline analogs with the Tet repressor," Antimicrob Agents Chemother, 35:1591-5.

Deuschle et al., (1989). "Regulated expression of foreign genes in mammalian cells under the control of coliphage T3 RNA polymerase and lac repressor," Proc. Natl. Acad. Sci. USA, 86:5400-4.

Deuschle et al., (1990). "RNA polymerase II transcription blocked by *Escherichia coli* lac repressor," Science, 248:480-3.

Dotson et al., (1996). "A phosphonate monoester hydrolase from Burkholderia caryophilli PG2982 is useful as a conditional lethal gene in plants," Plant J., 10(2):383-92.

Ezzat et al., (2011). "PepFect 14, a novel cell-penetrating peptide for oligonucleotide delivery in solution and as solid formulation," Nucleic Acids Res., 39:5284-98.

Fanning et al., (2006). "A dynamic model for replication protein A (Rpa) function in DNA processing pathways," Nucleic Acid Research, 34(15):4126-37.

Ferré-D'Amaré et al., (2014). "Small Self-cleaving Ribozymes," Cold Spring Harbor Perspectives Biol., 2:a003574, 10 pages.

Figge et al., (1988). "Stringent regulation of stably integrated chloramphenicol acetyl transferase genes by *E. coli* lac repressor in monkey cells," Cell, 52:713-22.

Filsinger et al., (2020). "Characterizing the portability of RecT-mediated oligonucleotide recombination," bioRxiv, 25 pages.

Frame et al., (2011). "Genetic Transformation Using Maize Immature Zygotic Embryos," Methoads in Molecular Biology, 710: 327-41.

Fu et al., (2019). "Target-dependent nickase activities of the CRISPR-Cas nucleases Cpf1 and Cas9," Nat Microbiol., 4(5):888-97, 22 pages.

Fuerst et al., (1989). "Transfer of the inducible lac repressor/operator system from *Escherichia coli* to a vaccinia virus expression vector," Proc. Natl. Acad. Sci. USA, 86:2549-53.

Geiser et al., (1986). "The hypervariable region in the genes coding for entomopathogenic crystal proteins ofBacillus thuringiensis: nucleotide sequence of the kurhdl gene of subsp. *kurstaki* HD1," Gene, 48:109-18.

Gill et al., (1988). "Negative effect of the transcriptional activator GAL4," Nature, 334:721-4.

Giraldo et al., (2014). "Plant nanobionics approach to augment photosynthesis and biochemical sensing," Nature Materials, 13:400-9.

Gossen et al., (1992). "Tight control of gene expression in mammalian cells by tetracycline-responsive promoters," Proc. Natl. Acad. Sci. USA, 89:5547-51.

Guo et al., (2010). "Directed evolution of an enhanced and highly efficient FokI cleavage domain for zinc finger nucleases," J. Mol. Biol., 400:96-107.

Halpin et al., (1999). "Self-processing 2A-polyproteins—a system for co-ordinate expression of multiple proteins in transgenic plants," Plant J., 17(4):453-9.

(56) References Cited

OTHER PUBLICATIONS

Hamada et al., (2018). "Biolistic-Delivery-Based Transient CRISPR/Cas9 Expression Enables in Planta Genome Editing in Wheat." Scientific Reports, 8(1):14422.
Hartlerode et al., (2010). "Mechanisms of double-strand break repair in somatic mammalian cells," Biochem J ., 423:157-168.
Hendel et al., (2015). "Chemically modified guide RNAs enhance CRISPR-Cas genome editing in human primary cells," Nature Biotechnol., 33(9):985-91, 14 pages.
Hillen et al., (1989). "Tet repressor-tet operator interaction," Topics Mol Struc Biol., 10:143-162.
Honig et al., (2015). "Transient Expression of Virally Delivered Meganuclease In Planta Generates Inherited Genomic Deletions." Molecular Plant, 8(8):1292-94.
Hu et al., (1987). "The inducible lac operator-repressor system is functional in mammalian cells," Cell, 48:555-66.
Iftode et al., (1999). "Replication Protein A (Rpa): The Eukaryotic Ssb," Critical Reviews In Biochemistry And Molecular Biology, 34(3):141-180.
Ikeuchi et al., (2016). "Plant regeneration: cellular origins and molecular mechanisms," Development, 143:1442-51.
Ishida et al., (2007). "Agrobacterium-mediated Transformation of Maize," Nature Protocols, 2:1614-21.
Iyer et al., (2002). "Classification and evolutionary history of the single-strand annealing proteins, RecT, Redbeta, ERF and RAD52," Bmc Genomics, 3:8, 11 pages.
Jiang et al., (2013). "RNA-guided editing of bacterial genomes using CRISPR-Cas systems," Nat Biotechnol., 31(3):233-9.
Jinek et al., (2012). "A programmable dual RNA-guided DNA endonuclease in adaptive bacterial immunity," Science, 337(6096):816-21.
Jones et al., (1994). "Isolation of the tomato cf-9 gene for resistance to cladosporium fulvum by transposon tagging," Science, 266:789-93.
Kawasaki et al., (1991). "DNA Sequence Recognition by a Eukaryotic Sequence-Specific Endonuclease, Endo.Scel, from *Saccharomyces cerevisie*," The Journal of Biological Chemistry, 166(8):5342-5347.
Kim et al., (2011). "Graphene Oxide-Polyethylenimine Nanoconstruct as a Gene Delivery Vector and Bioimaging Tool," Bioconjugate Chem., 22:2558-67.
Kim et al., (2012). "Precision genome engineering with programmable DNA-nicking enzymes," Genome Res., 22(7):1327-33.
Kirienko et al., (2012). "Reliable transient transformation of intact maize leaf cells for functional genomics and experimental study," Plant Physiol., 159(4):1309-18.
Kirihara et al., (1988). "Isolation and sequence of a gene encoding a methionine-rich 10-kDa zein protein from maize," Gene, 71:359-70.
Kleinschmidt et al., (1988). "Dynamics of repressor-operator recognition: Tn10-encoded tetracycline resistance control," Biochemistry, 27:1094-1104.
Kosugi et al., (2009). "Six classes of nuclear localization signals specific to different binding grooves of importin alpha," J Biol Chem., 284(1):478-85.
Labow et al., (1990). "Conversion of the lac repressor into an allosterically regulated transcriptional activator for mammalian cells," Mol Cell Biol, 10:3343-56.
Leduc et al., (1996). "Isolated Maize Zygotes Mimicin VivoEmbryonic Development and Express Microinjected Genes When Cultured in Vitro," Developmental Biology, 177(1):190-203.
Lee et al., (1988). "The molecular basis of sulfonylurea herbicide resistance in tobacco," EMBO J, 7:1241-8.
Leonelli et al., (2016). "Transient expression in Nicotiana benthamiana for rapid functional analysis of genes involved in non-photochemical quenching and carotenoid biosynthesis," The Plant Journal, 88:375-86.
Li et al., (2009). "The FAST technique: a simplified Agrobacterium-based transformation method for transient gene expression analysis in seedlings of *Arabidopsis* and other plant species," Plant methods, 5:6, 15 pages.
Li et al., (2015). "Cas9-Guide RNA Directed Genome Editing in Soybean", Plant Physiology, 169(2):960-970.
Li et al., (2016). "TALEN-Mediated Homologous Recombination Produces SiteDirected DNA Base Change and Herbicide-Resistant Rice", Journal Of Genetics And Genomics, 43(5):297-305. (Manuscript version).
Lilley et al. (1989). "Isolation and Primary Structure for a Novel, Methionine-rich Protein from Sunflower seeds (*Helianthus annus*. L.)," Proceedings of the World Congress on Vegetable Protein Utilization in Human Foods and Animal Feedstuffs, pp. 497-502.
Lindsay et al., (2016). "CrispRVariants Charts the Mutation Spectrum of Genome Engineering Experiments," Nature Biotechnology, 34:701-2.
Liu et al., (2013). "Advanced Genetic Tools for Plant Biotechnology." Nature Reviews, Genetics, 14(11):781-93.
Long et al., (2018). "Optimization of CRISPR/Cas9 genome editing in cotton by improved sgRNA expression," Plant Methods, 14:85, 9 pages.
Lu et al., (2010). "Arginine-Rich Intracellular Delivery Peptides Synchronously Deliver Covalently and Noncovalently Linked Proteins into Plant Cells," J. Agric. Food Chem., 58:2288-94.
Lynch, (2010). "Evolution of the mutation rate," Trends Genet., 26(8):345-52, 16 pages.
Mahfouz et al., (2011). "De novo-engineered transcription activator-like effector (TALE) hybrid nuclease with novel DNA binding specificity creates double-strand breaks," Proc. Natl. Acad. Sci. USA, 108:2623-8.
Mahfouz et al., (2011). "TALE nucleases and next generation GM crops," GM Crops, 2:99-103.
Martin et al., (1993). "Map-based cloning of a protein kinase gene conferring disease resistance in tomato," Science, 262:1432-6.
Martin-Ortigosa et al., (2014). "Proteolistics: A Biolistic Method for Intracellular Delivery of Proteins," Transgenic Research, 23(5):743-56.
Martin-Ortigosa et al., (2015). "Mesoporous Silica Nanoparticle-Mediated Intracellular Cre Protein Delivery for Maize Genome Editing via loxP Site Excision," Plant Physiol., 164:537-47.
Masumura et al., (1989). "cDNA cloning of an mRNA encoding a sulfur-rich 10 kDa prolamin polypeptide in rice seeds," Plant Mol. Biol., 12:123-30.
Miki et al., (2018). "CRISPR/Cas9-mediated gene targeting in *Arabidopsis* using sequential transformation", Nature Communications, 9:1967, 9 pages.
Mindrinos et al., (1994). "The *A. thaliana* disease resistance gene RPS2 encodes a protein containing a nucleotide-binding site and leucine-rich repeats," Cell, 78:1089-9.
Murphy, (2016). "λ Recombination and Recombineering," EcoSal Plus, 7(1), 70 pages.
Nagle et al., (2018). "Opportunities for Innovation in Genetic Transformation of Forest Trees," Front Plant Sci., 9:1443, 8 pages.
Negrotto et al. (2000). "The use of phosphomannose-isomerase as a selectable marker to recover transgenic maize plants (*Zea mays* L.) via Agrobacterium transformation," Plant Cell Reports 19:798-803.
Noguchi et al., (2003). "PDX-1 Protein Containing Its Own Antennapedia-Like Protein Transduction Domain Can Transduce Pancreatic Duct and Islet Cells," Diabetes, 52(7):1732-7.
Nuccio et al., (2015). "Chapter 2: Plant Trait Gene Expression Cassette Design," Recent Advancements in Gene Expression and Enabling Technologies in Crop Plants, pp. 41-77.
Nussaume et al., (1991). "Constitutive Nitrate Reductase: a dominant conditional marker for plant genetics," The Plant J., 1(2):267-74.
O'Brian et al., (2011). "Nano-biolistics: a method of biolistic transfection of cells and tissues using a gene gun with novel nanometer-sized projectiles," BMC Biotechnol., 11:66, 6 pages.
Oliva et al., (1992). "Evidence that tetracycline analogs whose primary target is not the bacterial ribosome cause lysis of *Escherichia coli*," Antimicrob Agents Chemother, 36:913-9.
O'Reilly (2019). "Extensive CRISPR RNA modification reveals chemical compatibility and structure-activity relationships for Cas9 biochemical activity," Nucleic Acids Res., 47(2):546-58.

(56) References Cited

OTHER PUBLICATIONS

Paulsen et al., (2017). "Ectopic expression of RAD52 and dn53BP1 improves homology-directed repair during CRISPR-Cas9 genome editing," Nat Biomed Eng., 1(11):878-88, 27 pages.
Pedersen et al., (1986). "Sequence analysis and characterization of a maize gene encoding a high-sulfur zein protein of $M_r$ 15,000," J. Biol. Chem., 261:6279-84.
Peng et al., (1999). "'Green revolution' genes encode mutant gibberellin response modulators," Nature, 400:256-61.
Pyne et al., (2015). "Coupling the CRISPR/Cas9 System with Lambda Red Recombineering Enables Simplified Chromosomal Gene Replacement in *Escherichia coli*," Applied And Environmental Microbiology, 81(15):5103-5114.
Ran et al., (2013). "Genome engineering using the CRISPR-Cas9 system," Nature Protocols, 8:2281-2308.
Rasco-Gaunt et al., (2003). "Characterisation of the expression of a novel constitutive maize promoter in transgenic wheat and maize," Plant Cell Rep., 21:569-76.
Ravi et al., (2014). "A haploid genetics toolbox for *Arabidopsis thaliana*," Nature Communications, 5:5334, 8 pages.
Reines et al., (1993). "Elongation factor SII-dependent transcription by RNA polymerase II through a sequence-specific DNA-binding protein," Proc. Natl. Acad. Sci. USA, 90:1917-21.
Reznikoff, (1992). "The lactose operon-controlling elements: a complex paradigm," Mol Microbiol., 6:2419-22.
Roest et al., (1989). "Plant regeneration from protoplasts: a literature review," Acta Bot. Neerl., 38(1):1-23.
Sawatsubashi et al., (2018). "Development of versatile non-homologous end joining-based knock-in module for genome editing," Scientific Reports, 8:1-10.
Schindele et al., (2018). "Transforming plant biology and breeding with CRISPR/Cas9, Cas12 and Cas13," FEBS Lett., 592(12):1954-67.
Schlaman et al., (1997). "Effectiveness of the bacterial gene codA encoding cytosine deaminase as a negative selectable marker in Agrobacterium mediated plant transformation," Plant Journal, 11(6):1377-85.
Schubert et al., (1988). "Cloning of the Alcaligenes eutrophus genes for synthesis of poly-beta-hydroxybutyric acid (PHB) and synthesis of PHB in *Escherichia coli*," J. Bacteriol., 170:5837-47.
Sebo et al., (2013). "A simplified and efficient germline-specific CRISPR/Cas9 system for *Drosophila* genomic engineering", Fly, 8(1):52-57.
Shao et al., (2017). "Enhancing CRISPR/Cas9-mediated homology-directed repair in mammalian cells by expressing *Saccharomyces cerevisiae* Rad52," Int J Biochem Cell Biol., 92:43-52.
Shao et al., (2017). "Supplementary Information: Enhancing CRISPR/Cas9-mediated homology-directed repair in mammalian cells by expressing *Saccharomyces cerevisiae* Rad52", International Journal Of Biochemistry And Cell Biology, 11 pages.
Shen et al., (2012). "Biomedical Applications of Graphene," Theranostics, 2:283-94.
Shmakov et al., (2015). "Discovery and Functional Characterization of Diverse Class 2 CRISPR-Cas Systems," Mol. Cell, 60:385-97.
Sivamani et al., (2019). "A study on optimization of pat gene expression cassette for maize transformation," Mol Biol Rep, 36:3009-17.
Soda et al., (2019). "CRISPR-Cas9 Based Plant Genome Editing: Significance, Opportunities and Recent Advances." Plant Physiology and Biochemistry, 131:2-11.
Svab et al., (1990). "Aminoglycoside-3"-adenyltransferase confers resistance to spectinomycin and streptomycin in Nicotiana tabacum," Plant Mol Biol., 14:197-205.
Tran et al., (2019). "Enhancement of Precise Gene Editing by the Association of Cas9 With Homologous Recombination Factors," Front Genet., 10:365, 13 pages.
Trehin et al., (2004). "Cellular uptake but low permeation of human calcitonin-derived cell penetrating peptides and Tat (47-57) through well-differentiated epithelial models," Pharm. Research, 21: 1248-56.
Unnamalai et al., (2004). "Cationic oligopeptide-mediated delivery of dsRNA for post-transcriptional gene silencing in plant cells," FEBS Letters, 566:307-10.
Urnov et al., (2010). "Genome Editing with Engineered Zinc Finger Nucleases." Nature Reviews Genetics, 11(9): 636-46.
Urwin et al., (1998). "Enhanced transgenic plant resistance to nematodes by dual proteinase inhibitor constructs," Planta, 204(4):472-9.
Van Eck et al., (2019). "Agrobacterium tumefaciens-Mediated Transformation of Tomato," Methods in Molecular Biology, 1864:225-34.
Verma et al., (1998). "Modified oligonucleotides: synthesis and strategy for users," Annu. Rev. Biochem., 67:99-134.
Vidarsson et al., (2014). "IgG subclasses and allotypes: from structure to effector functions," Front Immunol., 5:520, 17 pages.
Wang et al., (2009). "Biolistic Gun-Mediated Maize Genetic Transformation." Methods in Molecular Biology, 526: 29-45.
Wang et al., (2010). "Aptamer/Graphene Oxide Nanocomplex for in Situ Molecular Probing in Living Cells," J. Am. Chem. Soc. Comm., 132:9274-6.
Wang et al., (2016). "Defining synonymous codon compression schemes by genome recoding," Nature, 539:59-64, 38 pages.
Wang et al., (2017). "Enhancing Targeted Genomic DNA Editing in Chicken Cells Using the CRISPR/Cas9 System," PLoS One, 12(1):e0169768, 17 pages.
Wang et al., (2018). "Transgenerational CRISPR-Cas9 Activity Facilitates Multiplex Gene Editing in Allopolyploid Wheat," The CRISPR Journal, 1(1):65-74.
Wender et al., (2000). "The design, synthesis, and evaluation of molecules that enable or enhance cellular uptake: Peptoid molecular transporters," Proc. Natl. Acad. Sci. USA, 97:13003-8.
White et al., (1990). "A cassette containing the bar gene of Streptomyces hygroscopicus: a selectable marker for plant transformation," Nucl. Acids Res., 18(4):1062.
Williamson et al., (1987). "Nucleotide sequence of barley chymotrypsin inhibitor-2 (CI-2) and its expression in normal and high-lysine barley," Eur. J. Biochem., 165:99-106.
Wong et al. (2016). "Lipid Exchange Envelope Penetration (LEEP) of Nanoparticles for Plant Engineering: A Universal Localization Mechanism," Nano Lett., 16:1161-72.
Wu et al., (2014). "TALE nickase mediates high efficient targeted transgene integration at the human multi-copy ribosomal DNA locus," Biochem Biophys Res Commun, 446(1):261-6.
Wyborski et al., (1991). "Analysis of inducers of the *E. coli* lac repressor system mammalian cells and whole animals," Nucleic Acids Res, 19:4647-53.
Xing et al., (2014). "A CRISPR/Cas9 toolkit for multiplex genome editing in plants," BMC Plant Biol., 14:327, 12 pages.
Yamano et al., (2016). "Crystal Structure of Cpf1 in Complex with Guide RNA and Target DNA," Cell, 165(4):949-62.
Yan et al., (2019). "Functionally diverse type V CRISPR-Cas systems," Science, 363(6422):88-91.
Yao et al., (1992). "*Drosophila* ultraspiracle modulates ecdysone receptor function via heterodimer formation," Cell, 71:63-72.
Yarranton, (1992). "Inducible vectors for expression in mammalian cells," Curr Opin Biotech, 3:506-11.
Yin et al., (2017). "Structure-guided chemical modification of guide RNA enables potent non-viral in vivo genome editing," Nat. Biotechnol., 35(12):1179-87, 22 pages.
Yin et al., (2019). "Single-Stranded DNA-Binding Protein and Exogenous RecBCD Inhibitors Enhance Phage-Derived Homologous Recombination in Pseudomonas," iScience, 14:1-14, 39 pages.
Zambretti et al., (1992). "A mutant p53 protein is required for maintenance of the transformed phenotype in cells transformed with p53 plus ras cDNAs," Proc. Natl. Acad. Sci. USA, 89:3952-6.
Zender et al., (2002). "VP22-mediated intercellular transport of p53 in hepatoma cells in vitro and in vivo," Cancer Gene Ther., 9(6):489-96.
Zetsche et al., (2015). "Cpf1 is a single RNA-guided endonuclease of a class 2 CRISPR-Cas system," Cell, 163:759-71.
Zhang et al., (2007). "Cationic lipids and polymers mediated vectors for delivery of siRNA" J. Controlled Release, 123:1-10.

(56) References Cited

OTHER PUBLICATIONS

Zhang et al., (2016). "Efficient and Transgene-Free Genome Editing in Wheat through Transient Expression of CRISPR/Cas9 DNA or RNA." Nature Communications, 7:12617, 8 pages.
Zhao et al., (2016). "In Vivo Bio-distribution and Efficient Tumor Targeting of Gelatin/Silica Nanoparticles for Gene Delivery," Nanoscale Res. Lett., 11:195, 9 pages.

* cited by examiner

FIG. 1
35S promoter
mgfp6
pea rbcS E9 terminator
AtU6 promoter
guide RNA
HSP terminator
Cas nuclease CDS
StUBI10 promoter
12,733 bp

HOMOLOGY DEPENDENT REPAIR GENOME EDITING

CROSS-REFERENCE TO RELATED APPLICATIONS

This application is continuation of U.S. application Ser. No. 16/911,156, filed Jun. 24, 2020, which claims priority to U.S. Provisional Application No. 62/866,317, filed on Jun. 25, 2019, the contents of which are hereby incorporated by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165362000601SEQLIST.TXT, date recorded: May 10, 2021, size: 284 KB).

FIELD OF THE INVENTION

The present application is related to methods, kits, and compositions for gene editing.

BACKGROUND

Homology-Directed Repair (HDR) is a genome editing method that can be used for precise replacement of a target genomic DNA site with the sequence from a provided DNA template containing the desired replacement sequence. While the results of HDR are quite desirable, it does not work well for a number of reasons. One of the biggest problems is its low overall occurrence frequency, especially when compared to the alternative non-homologous end-joining (NHEJ) repair mechanism often triggered by the genome editing molecules that cleave targeted editing sites in the genome. While most cells may have several pathways that could mediate HDR, some of them are most active during the cell cycle, diminishing the success rate of HDR in typical cell culture conditions.

In prokaryotic hosts such as *E. coli*, homologous gene replacements can be effected with bacteriophage λ Red homologous recombination systems which comprise a bacteriophage λ exonuclease, a bacteriophage λ Beta protein, a single-stranded DNA annealing protein (SSAP) which facilitates annealing of complementary DNA strands, and a DNA template (Murphy, 2016). Bacteriophage λ Red homologous recombination systems have been combined with CRISPR-Cas9 systems in prokaryotes to effect recombination at target sequences in bacterial genomes (Jiang et al., 2013; Wang et al., 2016).

SUMMARY

Disclosed herein are methods, systems, eukaryotic cells (e.g., plant cells or mammalian cells), and compositions (e.g., cell culture compositions, nucleic acids, vectors, kits, or cells) that can provide for increased frequencies of modification of a target editing site of the eukaryotic cell genome with a donor template polynucleotide by Homology-Directed Repair (HDR) in comparison to a control. Features of such methods, systems, eukaryotic cells (e.g., plant cells or mammalian cells), and compositions (e.g., cell culture compositions, nucleic acids, vectors, kits, or cells) that can provide for such increased frequencies of HDR include provision of HDR promoting agents comprising a single-stranded DNA annealing protein (SSAP), an exonuclease which can at least partially convert a double stranded DNA substrate to a single stranded DNA product, and a single stranded DNA binding protein (SSB) in combination with genome editing molecules comprising at least one sequence-specific endonuclease which cleaves a target editing site in a eukaryotic cell genome and a donor template DNA molecule having homology to the target editing site. In certain embodiments, the donor template DNA molecule is flanked by copies of an endonuclease recognition sequence.

Methods provided herein include methods for increasing Homology Directed Repair (HDR)-mediated genome modification of a target editing site of a eukaryotic cell genome, comprising: providing genome-editing molecules and HDR promoting agents to a eukaryotic cell, wherein the genome editing molecules comprise: (i) at least one sequence-specific endonuclease which cleaves a DNA sequence in the target editing site or at least one polynucleotide encoding the sequence-specific endonuclease; and (ii) a donor template DNA molecule having homology to the target editing site; and wherein the HDR promoting agents comprise a single-stranded DNA annealing protein (SSAP), an exonuclease which can at least partially convert a double stranded DNA substrate to a single stranded DNA product, and a single stranded DNA binding protein (SSB); whereby the genome editing molecules and HDR promoting agents provide for modification of the target editing site of the eukaryotic cell genome with the donor template polynucleotide by HDR at a frequency that is increased in comparison to a control.

Methods provided herein also include methods for making a eukaryotic cell having a genomic modification, comprising: providing genome editing molecules and Homology Directed Repair (HDR) promoting agents to a eukaryotic cell, wherein the genome editing molecules comprise: (i) at least one sequence-specific endonuclease which cleaves a DNA sequence in the target editing site or at least one polynucleotide encoding the sequence-specific endonuclease and a donor template DNA molecule having homology to the target editing site; and wherein the HDR promoting agents comprise a single-stranded DNA annealing protein (SSAP), an exonuclease which can at least partially convert a double stranded DNA substrate to a single stranded DNA product, and a single stranded DNA binding protein (SSB);whereby the genome editing molecules and HDR promoting agents provide for modification of the target editing site of the eukaryotic cell genome with the donor template polynucleotide by HDR at a frequency that is increased in comparison to a control; and isolating or propagating a eukaryotic cell comprising the genome modification.

Systems provided herein include systems for increasing Homology Directed Repair (HDR)-mediated genome modification of a target editing site of a eukaryotic cell genome, comprising:

(a) a eukaryotic cell;

(b) HDR promoting agents comprising a single-stranded DNA annealing protein (SSAP), an exonuclease which can at least partially convert a double stranded DNA substrate to a single stranded DNA product, and a single stranded DNA binding protein (SSB); and (c) genome editing molecule(s) comprising at least one sequence-specific endonuclease which cleaves a DNA sequence in the target editing site or at least one polynucleotide encoding the sequence-specific endonuclease and a donor template DNA molecule having homology to the target editing site; wherein the eukaryotic cell is associated with, contacts, and/or contains and effective amount of the HDR promoting agents and the genome editing molecule(s).

Methods provided herein also include a method of genetic engineering of a eukaryotic cell comprising providing to the eukaryotic cell: i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB), wherein the target editing site of the cell is modified by the donor template DNA molecule.

Methods provided herein also include a method for producing a eukaryotic cell with a genetically modified target editing site comprising: (a) providing at least one sequence-specific endonuclease which cleaves a DNA sequence at least one endonuclease recognition sequence in said target editing site or at least one polynucleotide encoding said at least one sequence-specific endonuclease, and (b) providing at least one donor molecule comprising at least one double-stranded DNA sequence, wherein (i) said DNA sequence has a homology of at least 90% over a length of at least 50 nucleotides to sequences flanking the target editing site and (ii) wherein said donor sequence comprises at least one modification in comparison to said target editing site; and (c) providing at least one Homology Directed Repair (HDR) promoting agent comprising (i) at least one single-stranded DNA annealing protein (SSAP), and (ii) at least one exonuclease which can at least partially convert a double stranded DNA substrate to a single stranded DNA product, and (iii) at least one single stranded DNA binding protein (SSB); and whereby the at least one sequence-specific endonucleases, the at least one donor molecule, and the at least one HDR promoting agent introduce said modification into said target editing site of said eukaryotic cell; and (d) isolating a eukaryotic cell comprising a modification in said target editing site.

Compositions provided herein include a composition comprising nucleic acids encoding one or more of i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

Vectors provided herein include a vector comprising nucleic acids encoding one or more of i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

Kits provided herein include a kit comprising nucleic acids encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB) and instructions for use for genetically engineering a eukaryotic cell.

Cells provided herein include a cell comprising i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

Cells provided herein also include a progenitor eukaryotic cell or organism for genetic engineering at a target editing site, comprising a subset of i) at least one sequence-specific endonuclease, ii) a donor template molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB), wherein the cell does not comprises at least one of i)-v), wherein providing the cell or organism with the at least one of i)-v) that is not comprised in the progenitor cell or organism results in modification of the target editing site by the donor template molecule.

BRIEF DESCRIPTION OF THE DRAWINGS

FIG. 9A shows a schematic diagram of the vector pIN1705. Length in base pairs is indicated by the labels outside of the vector. Beginning at base pair 1, the vector includes a kanamycin resistance marker (KanR), left T-DNA border, a 5-enolpyruvylshikimate-3-phosphate (EPSPS) synthase expression cassette (i.e., the EPSPS coding sequence (CDS) under control of the *A. thaliana* ubiquitin promoter (AtUbil0) and pea rbcS E9 terminator), a Cas expression cassette (tomato S1UBI10 promoter, Cas nuclease coding sequence (Cas nuclease CDS), and HSP terminator), a guide RNA and ribozyme expression cassette (35S promoter, sequence encoding a hammerhead (HH) ribozyme, sequence encoding a guide RNA, sequence encoding a hepatitis delta virus (HDV) ribozyme, 35S terminator), a HDR promoting agents expression cassette (PcUbi promoter, c2 NLS fused to an *E. coli* SSB coding sequence (*E. coli* SSB CDS), pea 3A terminator, tomato S1UBI10 promoter, c2 NLS fused to a SSAP coding sequence (Red Beta CDS), HSP terminator, 2x 35S promoter, c2 NLS fused to an exonuclease coding sequence (Red Exo CDS), and 35S terminator), ANT1 donor template, right T-DNA border, STA region from pVS1, pVS1 origin of replication (ori), and an origin of replication (ori). FIG. 9B shows schematic diagrams of the regions between the left and right borders of *Agrobacterium* T-DNA vectors for chromosomal integration into the genome of tomato cotyledons. Shown, from top to bottom, are regions of the pIN1703, pIN1704, and pIN1705 vectors. CS indicates cut sites, EPSPS indicates the EPSPS expression cassette, CasS indicates the Cas expression cassette, ANTi donor indicates the donor template, HDR agents indicates the HDR promoting agents expression cassette encoding the SSAP, SSB, and exonuclease, and GFP indicates the green fluorescent protein coding sequence.

DETAILED DESCRIPTION

I. Definitions

Figure 1:
FIG. 1 shows a schematic diagram of the vector pRSO8t Length in base pairs is indicated by the labels outside of the vector. Beginning at base pair 1, the vector includes a high copy number origin of replication (High Copy Ori), Cas expression cassette (tomato S1UBI10 promoter, Cas nuclease coding sequence (Cas nuclease CDS), and HSP terminator), guide RNA expression cassette (*A. thaliana* U6 promoter (AtU6), sequence encoding a guide RNA, and 35S promoter), mGFP6 sequence, pea rbcS E9 terminator, ANTi donor template, and spectinomycin resistance marker (SpnR).

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate embodiments described by the plural of that term.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "Cpf1" and "Cas12a" are used interchangeably herein to refer to the same RNA directed nuclease.

As used herein, the phrase "genome-editing molecules" refers to one or more sequence-specific endonuclease(s) or polynucleotide(s) encoding the sequence-specific endonuclease(s) that cleave at least one DNA sequence at an endonuclease recognition site.

As used herein, an "exogenous" agent or molecule refers to any agent or molecule from an external source that is provided to or introduced into a system, composition, a eukaryotic or plant cell culture, reaction system, or a eukaryotic or plant cell. In certain embodiments, the exogenous agent (e.g., polynucleotide, protein, or compound) from the external source can be an agent that is also found in a eukaryotic or plant cell. In certain embodiments, the exogenous agent (e.g., polynucleotide, protein, or compound) from the external source can be an agent that is heterologous to the eukaryotic or plant cell.

As used herein, a "heterologous" agent or molecule refers: (i) to any agent or molecule that is not found in a wild-type, untreated, or naturally occurring composition, eukaryotic cell, or plant cell; and/or (ii) to a polynucleotide or peptide sequence located in, e.g., a genome or a vector, in a context other than that in which the sequence occurs in nature. For example, a promoter that is operably linked to a gene other than the gene that the promoter is operably linked to in nature is a heterologous promoter.

As used herein, the terms "include," "includes," and "including" are to be construed as at least having the features to which they refer while not excluding any additional unspecified features.

The term "homologous recombination" as used herein refers to the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology.

As used herein Homology-directed repair (HDR) means a method of DNA repair that results in precise editing of a target editing site by incorporating a provided donor sequence.

As used herein, phrases such as "frequency of HDR," "HDR frequency," and the like refer to the number of HDR-mediated events at a target editing site in comparison to the total number target-editing sites analyzed. The total number of target editing sites is the sum of: (a) target editing sites having NHEJ-mediated events; (b) target editing sites having no changes; and (c) target editing sites having HDR-mediated events. HDR-mediated events include precise insertions of heterologous sequences into a target editing site that do not contain any unintended nucleotide insertions, deletions, or substitutions in either the inserted heterologous sequence, the homologous sequences that flank the heterologous insert, or in the sequences located at the junction of the heterologous sequence and the homologous sequences.

As used herein, the phrase "eukaryotic cell" refers to any cell containing a nucleus and thus includes mammalian (e.g., human, livestock, and companion animal cells), insect cells, reptile cells, plant cells (e.g., monocot and dicot plant cells), yeast cells, and fungal cells (e.g., filamentous and non-filamentous fungi).

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

As used herein, the phrase "plant cell" can refer either a plant cell having a plant cell wall or to a plant cell protoplast lacking a plant cell wall.

The term "polynucleotide" where used herein is a nucleic acid molecule containing two (2) or more nucleotide residues. Polynucleotides are generally described as single- or double-stranded. Where a polynucleotide contains double-stranded regions formed by intra- or intermolecular hybridization, the length of each double-stranded region is conveniently described in terms of the number of base pairs. Embodiments of the systems, methods, and compositions provided herein can employ or include: (i) one or more polynucleotides of 2 to 25 residues in length, one or more polynucleotides of more than 26 residues in length, or a mixture of both. Polynucleotides can comprise single- or double-stranded RNA, single- or double-stranded DNA, double-stranded DNA/RNA hybrids, chemically modified analogues thereof, or a mixture thereof. In certain embodiments, a polynucleotide can include a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or can include non-canonical nucleotides such as inosine, thiouridine, or pseudouridine. In certain embodiments, the polynucleotide includes chemically modified nucleotides (see, e.g., Verma and Eckstein (1998) Annu. Rev. Biochem., 67:99-134). Chemically modified nucleotides that can be used in the polynucleotides provided herein include: (i) phosphorothioate, phosphorodithioate, or methylphosphonate internucleotide linkage modifications of the phosphodiester backbone; (ii) nucleosides comprising modified bases and/or modified sugars; and/or (iii) detectable labels including a fluorescent moiety (e.g., fluorescein or rhodamine or a fluorescence resonance energy transfer or FRET pair of chromophore labels) or other label (e.g., biotin or an isotope). Polynucleotides provided or used herein also include modified nucleic acids, particularly modified RNAs, which are disclosed in U.S. Pat. No. 9,464,124, which is incorporated herein by reference in its entirety.

A "recombinant AAV vector (rAAV vector)" refers to a polynucleotide vector comprising one or more heterologous sequences (i.e., nucleic acid sequence not of AAV origin) that are flanked by at least one, and in some embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), men the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

A "recombinant adenoviral vector" refers to a polynucleotide vector comprising one or more heterologous sequences (i.e., nucleic acid sequence not of adenovirus origin) that are flanked by at least one adenovirus inverted terminal repeat sequence (ITRs). In some embodiments, the recombinant nucleic acid is flanked by two inverted terminal repeat sequences (ITRs). Such recombinant viral vectors can be replicated and packaged into infectious viral particles when present in a host cell that is expressing essential adenovirus genes deleted from the recombinant viral genome (e.g., El genes, E2 genes, E4 genes, etc.). When a recombinant viral vector is incorporated into a larger polynucleotide (e.g., in a chromosome or in another vector such as a plasmid used for cloning or transfection), men the recombinant viral vector may be referred to as a "pro-vector" which can be "rescued" by replication and encapsidation in the presence of adenovirus packaging functions. A recombinant viral vector can be in any of a number of forms, including, but not limited to, plasmids, linear artificial chromosomes, complexed with lipids, encapsulated within liposomes, and encapsidated in a viral particle, for example, an adenovirus particle. A recombinant viral vector can be packaged into an adenovirus virus capsid to generate a "recombinant adenoviral particle."

A "recombinant lentivirus vector" refers to a polynucleotide vector comprising one or more heterologous sequences (i.e., nucleic acid sequence not of lentivirus origin) that are flanked by at least one lentivirus terminal repeat sequences (LTRs). In some embodiments, the recombinant nucleic acid is flanked by two lentiviral terminal repeat sequences (LTRs). Such recombinant viral vectors can be replicated and packaged into infectious viral particles when present in a host cell that has been infected with a suitable helper functions. A recombinant lentiviral vector can be packaged into a lentivirus capsid to generate a "recombinant lentiviral particle."

A "recombinant herpes simplex vector (recombinant HSV vector)" refers to a polynucleotide vector comprising one or more heterologous sequences (i.e., nucleic acid sequence not of HSV origin) that are flanked by HSV terminal repeat sequences. Such recombinant viral vectors can be replicated and packaged into infectious viral particles when present in a host cell that has been infected with a suitable helper functions. When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of HSV packaging functions. A recombinant viral vector can be in any of a number of forms, including, but not limited to, plasmids, linear artificial chromosomes, complexed with lipids, encapsulated within liposomes, and encapsidated in a viral particle, for example, an HSV particle. A recombinant viral vector can be packaged into an HSV capsid to generate a "recombinant herpes simplex viral particle."

As used herein, the phrase "target editing site" refers to a DNA sequence that is modified by a donor nucleic acid.

As used herein, the phrase "target gene" can refer to a gene located in the genome that is to be modified by gene editing molecules provided in a system, method, composition and/or eukaryotic cell provided herein. Embodiments of target genes include (protein-) coding sequence, non-coding sequence, and combinations of coding and non-coding sequences. Modifications of a target gene include nucleotide substitutions, insertions, and/or deletions in one or more elements of a gene that include a transcriptional enhancer or promoter, a 5' or 3' untranslated region, a mature or precursor RNA coding sequence, an intron, a splice donor and/or acceptor, a protein coding sequence, a polyadenylation site, and/or a transcriptional terminator. In certain embodiments, all copies or all alleles of a given target gene in a diploid or polyploid plant cell are modified to provide homozygosity of the modified target gene in the plant cell. In embodiments, where a desired trait is conferred by a loss-of-function mutation that is introduced into the target gene by gene editing, a plant cell, population of plant cells, plant, or seed is homozygous for a modified target gene with the loss-of-function mutation. In other embodiments, only a subset of the copies or alleles of a given target gene are modified to provide heterozygosity of the modified target gene in the plant cell. In certain embodiments where a desired trait is conferred by a dominant mutation that is introduced into the target gene by gene editing, a plant cell, population of plant cells, plant, or seed is heterozygous for a modified target gene with the dominant mutation. Traits imparted by such modifications to certain plant target genes include improved yield, resistance to insects, fungi, bacterial pathogens, and/or nematodes, herbicide tolerance, abiotic stress tolerance (e.g., drought, cold, salt, and/or heat tolerance), protein quantity and/or quality, starch quantity and/or quality, lipid quantity and/or quality, secondary metabolite quantity and/or quality, and the like, all in comparison to a control plant that lacks the modification. The plant having a genome modified by gene editing molecules provided in a system, method, composition and/or plant cell provided herein differs from a plant having a genome modified by traditional breeding (i.e., crossing of a male parent plant and a female parent plant), where unwanted and random exchange of genomic regions as well as random mitotically or meiotically generated genetic and epigenetic changes in the genome typically occurs during the cross and are then found in the progeny plants. Thus, in embodiments of the plant (or plant cell) with a modified genome, the modified genome is more than 99.9% identical to the original (unmodified) genome. In embodiments, the modified genome is devoid of random mitotically or meiotically generated genetic or epigenetic changes relative to the original (unmodified) genome. In embodiments, the modified genome includes a difference of epigenetic changes in less than 0.01% of the genome relative to the original (unmodified) genome. In embodiments, the modified genome includes: (a) a difference of DNA methylation in less than 0.01% of the genome, relative to the original (unmodified) genome; or (b) a difference of DNA methylation in less than 0.005% of the genome, relative to the original (unmodified) genome; or (c) a difference of DNA methylation in less than 0.001% of the genome, relative to the original (unmodified) genome. In embodiments, the gene of interest is located on a chromosome in the plant cell, and the modified genome includes: (a) a difference of DNA methylation in less than 0.01% of the portion of the genome that is contained within the chromosome containing the gene of interest, relative to the original (unmodified) genome; or (b) a difference of DNA methylation in less than 0.005% of the portion of the genome that is contained within the chromosome containing the gene of interest, relative to the original (unmodified) genome; or (c) a difference of DNA methylation in less than 0.001% of the portion of the genome that is contained within the chromosome containing the gene of interest, relative to the original (unmodified) genome. In embodiments, the modified genome has not more unintended changes in comparison to the original (unmodified) genome than 1×10^−8 mutations per base pair per replication. In certain embodiments, the modified genome has not more unintended changes than would occur at the natural mutation rate. Natural mutation rates can be determined empirically or are as described in the literature (Lynch, M., 2010; Clark et al., 2005).

A "vector," as used herein, refers to a recombinant plasmid that comprises a nucleic acid to be delivered into a host cell, either in vitro or in vivo.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

II. Methods and Compositions

A. Methods for Increasing Homology Directed Repair-Mediated Genome Modification Various reagents, systems, methods, and compositions that comprise HDR promoting agents (an SSAP, exonuclease, and SSB) and genome-editing molecules and that provide for increased frequencies of homology dependent repair (HDR) in eukaryotic cell gene editing experiments in comparison to control experiments are provided herein. In certain embodiments, the frequency of HDR is increased by at least 2-fold, 3-fold, 5-fold, or 10-fold in comparison to a control method wherein a control eukaryotic cell is provided with the genome editing molecules but is not exposed to at least one of the HDR promoting agents (SSAPs, exonucleases, and SSBs). In certain embodiments, the frequency of HDR is increased by at least 2-fold, 3-fold, or 5-fold to about 12-fold, 15-fold, 20-fold, 25-fold, or 30-fold in comparison to a control method wherein a control eukaryotic cell is provided with the genome editing molecules but is not exposed to at least one of the HDR promoting agents (SSAPs, exonucleases, and SSBs). In some embodiments, the present methods can be employed on cells not undergoing mitosis or meiosis. In some embodiments, the present methods do not require DNA replication.

i. Nuclear Localization Signals (NLS)

Nuclear localization signals (NLS) that can direct SSAP, exonucleases, SSB, and/or gene editing molecules provided herein include monopartite and bipartite nuclear localization signals (Kosugi et al., 2009). Examples of monopartite NLS that can be used include NLS that comprise at least 4 consecutive basic amino acids such as the SV40 large T antigen NLS (PKKKRKV; SEQ ID NO:11) and another class having only three basic amino acids with a K(K/R)X(K/R) consensus sequence (SEQ ID NO:12). Examples of bipartite NLS that can be used in the provided herein include (K/R)(K/R)$X_{10-12}$(K/R)3/5 (SEQ ID NO:13) where $(K/R)_{3/5}$ represents at least three of either lysine or arginine of five consecutive amino acids. An NLS can also comprise a plant-specific class 5 NLS having a consensus sequence of LGKR(K/R)(W/F/Y) (SEQ ID NO:14). Examples of specific NLS that can be used further include the maize opaque-2 nuclear localization signal (SEQ ID NO:10, a bhendi yellow vein mosaic virus (BYVMV) c2 NLS (SEQ ID NO:15, and an extended SV40 large T antigen NLS (SEQ ID NO:16).

In some embodiments, the NLS is a mammalian (such as a human NLS) In some embodiments, the NLS is an SV40 NLS. In some embodiments, the NLS is an SV40 NLS with an amino acid linker. In some embodiments, the NLS has the amino acid sequence MAPKKKRKVGGSGS (SEQ ID NO:148).

In certain embodiments, the NLS elements or other desired elements (e.g., epitope tags) can be operably linked to the SSAP, exonucleases, SSB, and/or gene editing molecules provided herein via either a direct covalent linkage of the elements and domain or by a use of a linker peptide or flexible hinge polypeptide. Flexible hinge polypeptides include glycine-rich or glycine/serine containing peptide sequence. Such sequences can include, but are not limited to, a (Gly4)n sequence, a (Gly4Ser)n sequence, a Ser($Gly_4$Ser)n sequence, combinations thereof, and variants thereof, wherein n is a positive integer equal to 1, 2, 3, 4, 5, 6, 7, 8, 9 or 10. In certain embodiments, such glycine-rich or glycine/serine containing hinge peptides can also contain threonyl and/or alanyl residues for flexibility as well as polar lysyl and/or glutamyl residues. Other examples of hinge peptides that can be used include immunoglobulin hinge peptides (Vidarsson et al., 2014).

A variety of cell-penetrating peptides (CPP) can also be used in the SSAP, exonucleases, SSB, and/or gene editing molecules provided herein. CPPs that can be used include a minimal undecapeptide protein transduction domain (corresponding to residues 47-57 of HIV-1 TAT comprising YGRKKRRQRRR; SEQ ID NO:17); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); RRQRRTSKLMKR (SEQ ID NO:18); Transportan (e.g., GWTLNSAGYLLGKINLKALAALAK-KIL (SEQ ID NO:19); KALAWEAKLAKALAKA-LAKHLAKALAKALKCEA (SEQ ID NO:20); and RQIKIWFQNRRMKWKK (SEQ ID NO:21). Exemplary CPP amino acid sequences also include YGRKKRRQRRR (SEQ ID NO:22; RKKRRQRR (SEQ ID NO:23); YARAAARQARA (SEQ ID NO:24); THRLPRRRRRR (SEQ ID NO:25); and GGRRARRRRRR (SEQ ID NO:26).

ii. Single-Stranded DNA Annealing Proteins (SSAPs)

In certain embodiments, the single-stranded DNA annealing protein (SSAP) used in the methods, systems, cells, and cell culture compositions provided herein include proteins which promote or catalyze DNA strand exchange and base pairing of complementary DNA strands of homologous DNA molecules. Characteristics of the SSAPs used herein include stimulation of RecA dependent and independent pathways, oligomeric rings and/or filaments formation in vitro, ssDNA binding activity, and ATPase-independent stimulation of complementary ssDNA strand annealing. Characteristics of SSAP proteins in the RecT/Redβ-, ERF-, or RAD52-families of proteins have been disclosed in Murphy, 2016 and Iyer et al., 2002. In certain embodiments, the SSAP is a member of the RecT/Redβ-family of proteins that include a Rac bacterial prophage RecT protein, a bacteriophage λ beta protein, a bacteriophage SPP1 35 protein, or related protein with equivalent SSAP activity. Characteristics of certain RecT/Redβ-family of proteins include an α+β domain with a core of five β-strands and five α-helices, $Mg^{+2}$ dependent single strand annealing activity and conservation of two c-terminal acidic residues in most but not all members (Iyer et al., 2002). In certain embodiments, the RecT/Redβ-family protein comprises a protein having at least 70%, 75%, 80%, 85%, 90%, 95%, or 99% sequence identity to SEQ ID NO: 1, 2, or 3 and optionally a conserved a +R domain with a core of five 0-strands and five α-helices, $Mg^{+2}$ dependent single strand annealing activity, and/or conservation of two c-terminal acidic residues. In certain embodiments, the SSAP is an ERF-family protein. Characteristics of EFR-family of proteins include a conserved region of about 150 amino acid residues comprising a GuXXoYhp+YXhXXhh (SEQ ID NO:32) motif, where G is glycine, Y-tyrosine, u is a "tiny" residue (glycine, serine, alanine), h-hydrophobic (alanine, valine, leucine, isoleucine, phenylalanine, methionine), p is a polar residue (lysine, arginine, glutamate, aspartate, asparagine, threonine, serine), o is an alcohol-containing amino acid residue (serine or threonine), +is a basic residue, and X is any residue (Iyer et al., 2002). ERF family proteins include a bacteriophage P22 ERF protein or a protein having at least 70%, 75%, 80%, 85%, 90%, 95%, or 99% sequence identity to SEQ ID NO: 4, and can optionally further comprise the GuXXoYhp+YXhXXhh (SEQ ID NO:32) motif. SSAP in the ERF-family also include proteins set forth in the NCBI database on the world wide web site ncbi.nlm.nih.gov/protein under accession (gi or gene identifier) numbers 9634188, 9635694, 16804357, 12719409, 458219, 11497308, 11497280, 1497168, 11527300, 9634634, 9635643, 13491642, 6015511, 11138335, 9627938, 9628668, and 15088753. In certain embodiments, the SSAP used herein include RAD52-family proteins from *Saccharomyces cerevisiae, Schizosaccharomycespombe*, and *Kluyveromyces lactis* as well as variants thereof having at least 85%, 90%, 95%, 97%, 98%, or 99% sequence identity across the entire length of SEQ ID NO:5, 6, and 7, respectively; or variants having at one or more conservative and/or semi-conservative amino acid substitutions in SEQ ID NO: 5, 6, or 7. Characteristics of RAD52-family of proteins include conserved helix-hairpin-helix (HhH) motifs with DNA binding activity (Iyer et al., 2002). SSAP used herein can further include proteins identified as "recombinases" that are set forth in at least Tables 1, 2, 3, 4, 5, and 6 of U.S. patent application Ser. No. 16/075,281, a US National Stage of PCT/US2017/016184, published as WO 2017/184227, the continents of which are incorporated herein by reference in their entireties. In certain embodiments, the SSAP can comprise an allelic variant of any of the aforementioned SSAP. In certain embodiments, any of the aforementioned SSAP can be provided to a cell by way of a nucleic acid that encodes the SSAP (e.g., an expression vector, mRNA, or viral expression vector). In certain embodiments, any of the aforementioned SSAP can be provided to a cell as proteins, fusion proteins (e.g., with a cell penetrating peptide and/or a nuclear localization sequence), or as polyproteins comprising protease recognition sites or self-processing protein sequences inserted between the SSAP and other proteins (e.g., in combination with an SSB and/or an exonuclease).

iii. Exonucleases

In certain embodiments, the exonucleases used in the methods, systems, cells, and cell culture compositions provided herein include exonucleases with a 5' to 3' or a 3' to 5' exonuclease activity on a double-stranded DNA (dsDNA) substrate that can result in product comprising an at least partially single stranded DNA (ssDNA) having an exposed 3' terminus or an exposed 5' terminus, respectively. In certain embodiments, the exonuclease will recognize a dsDNA substrate with a blunt end, including a blunt end with a 5' phosphate group. In certain embodiments, the exonuclease will recognize a dsDNA substrate with an overhang of ssDNA (e.g., a 5' or 3' ssDNA region at a terminus of a dsDNA molecule, including ends produced by endonucleases which provide staggered cuts in dsDNA substrates). In certain embodiments, the exonuclease will recognize a dsDNA substrate having an internal break in one strand (e.g., a nicked dsDNA). Exonucleases with 5' to 3' exonuclease activity that can be used herein include a bacteriophage lambda exo protein (e.g., SEQ ID NO:8), an Rac prophage RecE exonuclease protein (e.g., SEQ ID NO:9), an Artemis protein (e.g., SEQ ID NO: 136), an Apollo protein (e.g., SEQ ID NO: 137), a DNA2 exonuclease protein (e.g., SEQ ID NO: 138), an Exo1 exonuclease protein (e.g., SEQ ID NO: 139), a herpesvirus SOX protein (e.g., SEQ ID NO: 140), UL12 exonuclease protein (e.g., SEQ ID NO: 141), an enterobacterial exonuclease VIII protein (e.g., SEQ ID NO: 142), a T7 phage exonuclease protein (e.g., SEQ ID NO:143) or a related protein with equivalent 5' to 3' exonuclease activity, or a protein having at least 70%, 75%, 80%, 85%, 90%, 95%, or 99% sequence identity to SEQ ID NO: 8, 9, 136, 137, 138, 139, 140, 141, 142, or 143. In certain embodiments, the exonucleases with 5' to 3' exonuclease activity provided herein include the proteins set forth in SEQ ID NO: 8, 9, 136, 137, 138, 139, 140, 141, 142, or 143 that have at least one or more conservative and/or semi-conservative amino acid substitutions in SEQ ID NO:8, 9, 136, 137, 138, 139, 140, 141, 142, or 143. Exonucleases with 3' to 5' exonuclease activity that can be used herein include an *E. coli* Exonuclease III protein (e.g., SEQ ID NO: 144), a mammalian Trex2 exonuclease protein (e.g., SEQ ID NO: 145), a related protein with equivalent 3' to 5' exonuclease activity, or a protein having at least 70%, 75%, 80%, 85%, 90%, 95%, or 99% sequence identity to SEQ ID NO: 144 or 145. In certain embodiments, the exonucleases with a 3' to 5' exonuclease activity provided herein include the proteins set forth in set forth SEQ ID NO: 144 or 145 that have at least one or more conservative and/or semi-conservative amino acid substitutions in SEQ ID NO: 144 or 145. In certain embodiments, the aforementioned exonucleases will comprise conserved DEDD catalytic residues characteristic of the DEDD/DnaQ superfamily of exonucleases (Bernad et al., 1989). In certain embodiments, any of the aforementioned exonucleases can be provided to a cell as proteins, fusion proteins (e.g., with a cell penetrating peptide and/or a nuclear localization sequence), or as polyproteins comprising protease recognition sites or self-processing protein sequences inserted between the exonuclease and other proteins (e.g., in combination with an SSB and/or an SSAP). In certain embodiments, the exonuclease can comprise an allelic variant of any of the aforementioned exonucleases. In certain embodiments, any of the aforementioned exonucleases can be provided to a cell by way of a nucleic acid that encodes the exonuclease (e.g., an expression vector, mRNA, or viral expression vector). In some embodiments, the sequence-specific endonuclease is a nickase.

iv. Single Stranded DNA Binding Proteins (SSBs)

Various single stranded DNA binding proteins (SSB) can be used in the methods, systems, cells, and cell culture compositions provided herein. In certain embodiments, the SSBs include a bacterial SSB or optionally an Enterobacteriaceae sp. SSB. In certain embodiments, the SSB is an *Escherichia* sp., a *Shigella* sp., an *Enterobacter* sp., a *Klebsiella* sp., a *Serratia* sp., a *Pantoea* sp., or a *Yersinia* sp. SSB provided herein include the set forth in SEQ ID NO: 31, and SEQ ID NO: 34-131, and 132, as well as variants thereof having at least 85%, 90%, 95%, 97%, 98%, or 99% sequence identity across the entire length of SEQ ID NO: 31, SEQ ID NO: 34-131, or 132; or having at one or more conservative and/or semi-conservative amino acid substitutions in SEQ ID NO: 31, or SEQ ID NO: 34-131, or 132. SSB used herein can include SSB proteins that are set forth in the disclosure and at least Tables 7 and 8 of U.S. patent application Ser. No. 16/075,281, a US National Stage of PCT/US2017/016184, published as WO 2017/184227, the continents of which are incorporated herein by reference in their entireties. In certain embodiments, the SSB can comprise an allelic variant of any of the aforementioned SSBs. In certain embodiments, any of the aforementioned SSB can be provided to a cell by way of a nucleic acid that encodes the SSB (e.g., an expression vector, mRNA, or viral expression vector). In certain embodiments, any of the aforementioned SSB can be provided to a cell as proteins, fusion proteins (e.g., with a cell penetrating peptide and/or a nuclear localization sequence), or as polyproteins comprising protease recognition sites or self-processing protein sequences inserted between the SSB and other proteins (e.g., in combination with an SSAP and/or an exonuclease).

In some embodiments, the SSB and SSAP used in the present methods are are from the same organism or from a phage and a bacterial host of the phage.

In some embodiments, an SSB is not required. In some embodmients, SSAP is fused with an replication protein A (RPA)-binding partner (Fanning et al. Nucleic acids research, 34(1 5), 4126-4137). In some embodiments, the SSB is an endogenous SSB. In some embodiments, an SSAP that is modified to bind to an endogenous SSB is provided.

In some embodments, the components used in the methods provided herein are provided as a fusion proteins. In some embodiments SSAP is fused with SSB. In some embodments, SSAP is fused to a replication protein A (RPA).

v. Plants, Plant Tissues, and Plant Cells

In certain embodiments, HDR is increased in isolated plant cells or plant protoplasts (i.e., are not located in undissociated or intact plant tissues, plant parts, or whole plants). In certain embodiments, the plant cells are obtained from any plant part or tissue or callus. In certain embodiments, the culture includes plant cells obtained from a plant tissue, a cultured plant tissue explant, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, callus, or plant cell suspension. In certain embodiments, the plant cell is derived from the L1 or L2 layer of an immature or mature embryo of a monocot plant (e.g., maize, wheat, sorghum, or rice).

In certain embodiments, HDR is increased in plant cells that are located in undissociated or intact plant tissues, plant parts, plant explants, or whole plants. In certain embodiments, the plant cell can be located in an intact nodal bud, a cultured plant tissue explant, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, or callus. In certain embodiments, the explants used include immature embryos. Immature embryos (e.g., immature maize embryos) include 1.8-2.2 mm embryos, 1-7 mm embryos, and 3-7 mm embryos. In certain embodiments, the aforementioned embryos are obtained from mature ear-derived seed, leaf bases, leaves from mature plants, leaf tips, immature inflorescences, tassels, immature ears, and silks. In various aspects, the plant-derived explant used for transformation includes immature embryos, 1.8-2.2 mm embryos, 1-7 mm embryos, and 3.5-7 mm embryos. In an aspect, the embryos used in the disclosed methods can be derived from mature ear-derived seed, leaf bases, leaves from mature plants, leaf tips, immature inflorescences, tassel, immature ear, or silks. In certain embodiments, the plant cell is a pluripotent plant cell (e.g., a stem cell or meristem cell). In certain embodiments, the plant cell is located within the L1 or L2 layer of an immature or mature embryo of a monocot plant (e.g., maize, wheat, sorghum, or rice). In certain embodiments, methods of editing genomes of whole plants, seeds, embryos, explants, or meristematic tissue published in WO2018085693, which is incorporated herein by reference in its entirety, can be adapted for use in the plant cells and related systems, methods, compositions, or cultures provided herein.

In certain embodiments, the plant cells can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) Nature Communications, 5:5334, doi: 10.1038/ncomms6334). Haploids can also be obtained in a wide variety of monocot plants (e.g., maize, wheat, rice, sorghum, barley) or dicot plants (e.g., soybean, *Brassica* sp. including canola, cotton, tomato) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e. homozygosity) in the least possible time. Doubled haploid production can be particularly advantageous in slow-growing plants, such as fruit and other trees, or for producing hybrid plants that are offspring of at least one doubled-haploid plant.

In certain embodiments where HDR is increased in plant cells, as well as the related methods, systems, compositions, or reaction mixtures provided herein can include plant cells obtained from or located in any monocot or dicot plant species of interest, for example, row crop plants, fruit-producing plants and trees, vegetables, trees, and ornamental plants including ornamental flowers, shrubs, trees, groundcovers, and turf grasses. In certain non-limiting embodiments, the plant cells are obtained from or located in alfalfa (*Medicago sativa*), almonds (*Prunus dulcis*), apples (Malus x *domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C.frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), *eucalyptus* (*Eucalyptus* spp.), flax (*Linum usitatissumum L.*), geraniums (*Pelargonium* spp.), grapefruit (*Citrus* x *paradisi*), grapes (*Vitus* spp.) including wine grapes (Vitus *vinifera*), guava (*Psidium guajava*), hemp and *cannabis* (e.g., *Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius L*), sesame seed (*Sesame indium*), sorghum (*Sorghum bicolor*), soybean (*Glycine max* L.), squash (*Cucurbita pepo*), strawberries (Fragaria spp., *Fragaria x ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (Tulipa spp.), turnip (*Brassica rapa rapa*), walnuts (*Juglans* spp. *L.*), watermelon (*Citrulus lanatus*), wheat (*Tritium aestivum*), or yams (*Discorea* spp.).

vi. Eukaryotic Cells

In certain embodiments, the eukaryotic cells (e.g., plant cells) where HDR is increased can be cells that are (a) encapsulated or enclosed in or attached to a polymer (e.g., pectin, agarose, or other polysaccharide) or other support (solid or semi-solid surfaces or matrices, or particles or nanoparticles); (b) encapsulated or enclosed in or attached to a vesicle or liposome or other fluid compartment; or (c) not encapsulated or enclosed or attached. In certain embodiments, the cells can be in liquid or suspension culture, or cultured in or on semi-solid or solid media, or in a combination of liquid and solid or semi-solid media (e.g., plant cells or protoplasts cultured on solid medium with a liquid medium overlay, or plant cells or protoplasts attached to solid beads or a matrix and grown with a liquid medium). In certain embodiments, the cells encapsulated in a polymer (e.g., pectin, agarose, or other polysaccharide) or other encapsulating material, enclosed in a vesicle or liposome, suspended in a mixed-phase medium (such as an emulsion or reverse emulsion), or embedded in or attached to a matrix or other solid support (e.g., beads or microbeads, membranes, or solid surfaces).

In a related aspect, the disclosure provides arrangements of eukaryotic cells (e.g., plant cells) having improved HDR frequencies in the systems, methods, and compositions described herein, such as arrangements of cells convenient for screening purposes or for high-throughput and/or multiplex transformation or gene editing experiments. In an embodiment, the disclosure provides an arrangement of multiple cells comprising: (a) the HDR promoting agents; and optionally (b) genome editing molecules. In certain embodiments, the arrangements of cells can further comprise at least one chemical, enzymatic, or physical delivery agent. In another embodiment, the disclosure provides an array including a plurality of containers, each including at least one cell having increased HDR-mediated genome modification frequencies. In an embodiment, the disclosure provides arrangements of cells having the HDR promoting agents and optionally the genome editing molecules, wherein the cells are in an arrayed format, for example, in multi-well plates, encapsulated or enclosed in vesicles, liposomes, or droplets (useful, (e.g., in a microfluidics device), or attached discretely to a matrix or to discrete particles or beads; a specific embodiment is such an arrangement of multiple cells having increased HDR-mediated genome modification frequencies provided in an arrayed format, further including at least one genome editing molecules (e.g., an RNA-guided DNA nuclease, at least one guide RNA, or a ribonucleoprotein including both an RNA-guided DNA nuclease and at least one guide RNA), which may be different for at least some locations on the array or even for each location on the array, and optionally at least one chemical, enzymatic, or physical delivery agent.

In the systems and methods provided herein, eukaryotic cells (e.g., plant cells) can be exposed to one or more HDR promoting agents and/or one or more gene editing molecules in any temporal order. In certain embodiments, the HDR promoting agents and gene editing molecules are provided simultaneously. In other embodiments, the genome editing molecules are provided after the HDR promoting agents are provided. In other embodiments, the gene editing molecules are provided before the HDR promoting agents are provided. In summary, the HDR promoting agents can be provided to a eukaryotic cell (e.g., a plant cell) either previous to, concurrently with, or subsequent to exposing the cell to the gene editing molecules.

Eukaryotic cells (e.g., plant cells) having increased Homology Directed Repair (HDR)-mediated genome modification frequencies conferred by HDR promoting agents (e.g., SSAP, exonucleases, and SSB) and/or modified DNA donor templates are provided herein. Also provided by the disclosure are compositions derived from or grown from the plant cell or plant protoplast having increased HDR-mediated genome modification frequencies, provided by the systems and methods disclosed herein; such compositions include multiple protoplasts or cells, callus, a somatic embryo, a somatic meristem, embryogenic callus, or a regenerated plant grown from the plant cell or plant protoplast having increased HDR-mediated genome modification frequencies. Increased HDR-mediated genome modification frequencies in cells that have been subjected to HDR promoting agents and/or modified DNA donor templates can be assessed by a variety of techniques. In certain embodiments, such techniques can compare the frequency of HDR observed in cells subjected to the HDR promoting agents versus the frequency of HDR in control cells that were not subjected to HDR promoting agents (e.g., SSAP, exonucleases, and SSB) and/or modified DNA donor templates.

In certain embodiments, the eukaryotic cells (e.g., plant cells) used in the systems, methods, and compositions provided herein can include non-dividing cells. Such non-dividing cells can include plant cell protoplasts, eukaryotic cells subjected to one or more of a genetic and/or pharmaceutically-induced cell-cycle blockage, and the like. In certain embodiments, the non-dividing cells can be induced to divide (e.g., by reversing or removing a genetic or pharmaceutical cell-cycle blockages) following treatment with the HDR-promoting agents (e.g., SSAP, exonucleases, and SSB) and/or gene-editing molecules that can optionally include modified DNA donor templates provided herein.

In certain embodiments, the eukaryotic cells (e.g., plant cells) in used in the systems, methods, and compositions provided herein can include dividing cells. Dividing cells can include those cells found in various plant tissues including leaves, meristems, and embryos. These tissues include, but are not limited to dividing cells from young maize leaf, meristems and scutellar tissue from about 8 or 10 to about 12 or 14 days after pollination (DAP) embryos. The isolation of maize embryos has been described in several publications (Brettschneider, Becker, and Lorz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the HDR-mediated gene editing.

vii. Plant Regeneration

In some embodiments, methods provided herein can include the additional step of growing or regenerating a plant from a plant cell that had been subjected to the improved HDR-mediated gene editing or from a regenerable plant structure obtained from that plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RNA-guided DNA nuclease), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a target gene edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous populations, arrays, or libraries of such plants, succeeding generations or seeds of such plants grown or regenerated from the plant cells or plant protoplasts, having a target gene edit or genome edit, parts of the plants (including plant parts used in grafting as scions or rootstocks), or products (e.g., fruits or other edible plant parts, cleaned grains or seeds, edible oils, flours or starches, proteins, and other processed products) made from the plants or their seeds. Embodiments include plants grown or regenerated from the plant cells having a target gene edit or genome edit, wherein the plants contain cells or tissues that do not have a genetic or epigenetic modification, e.g., grafted plants in which the scion or rootstock contains a genetic or epigenetic modification, or chimeric plants in which some but not all cells or tissues contain a genetic or epigenetic modification. Plants in which grafting is commonly useful include many fruit trees and plants such as many citrus trees, apples, stone fruit (e.g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. The intact plant itself may be desirable, e.g., plants grown as cover crops or as ornamentals. In other embodiments, processed products are made from the plant or its seeds, such as extracted proteins, oils, sugars, and starches, fermentation products, animal feed or human food, wood and wood products, pharmaceuticals, and various industrial products.

viii. Provision of HDR Promoting Agents to a Eukaryotic Cell

An SSAP, exonuclease, and/or SSB that increase HDR frequency can be provided to a eukaryotic cell (e.g., a plant cell or plant protoplast) by any suitable technique. In certain embodiments, the SSAP, exonuclease, and/or SSB is provided by directly contacting a cell with the SSAP, exonuclease, and/or SSB or the polynucleotide that encodes the SSAP, exonuclease, and/or SSB. In certain embodiments, the SSAP, exonuclease, and/or SSB is provided by transporting the SSAP, exonuclease, and/or SSB or a polynucleotide that encodes SSAP, exonuclease, and/or SSB into a cell using a chemical, enzymatic, or physical agent. In certain embodiments, the SSAP, exonuclease, and/or SSB is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the SSAP, exonuclease, and/or SSB; see, e.g., Broothaerts et al. (2005) Nature, 433:629-633. In an embodiment, the SSAP, exonuclease, and/or SSB is provided by transcription in a plant cell or plant protoplast of a DNA that encodes the SSAP, exonuclease, and/or SSB and is stably integrated in the genome of the plant cell or is provided to the plant cell or plant protoplast in the form of a plasmid or expression vector (e.g., a viral vector) that encodes the SSAP, exonuclease, and/or SSB. In certain embodiments, the SSAP, exonuclease, and/or SSB is provided to the plant cell or plant protoplast as a polynucleotide that encodes SSAP, exonuclease, and/or SSB, e.g., in the form of an RNA (e.g., mRNA or RNA containing an internal ribosome entry site (IRES)) encoding the SSAP, exonuclease, and/or SSB. In certain embodiments, the SSAP, exonuclease, and/or SSB is provided to the plant cell or plant protoplast as a polynucleotide that encodes a polyprotein comprising in any order the SSAP, exonuclease, and/or SSB with amino acid sequences comprising protease recognition sites or self-processing protein sequences inserted between the encoded SSAP, exonuclease, and/or SSB. Examples of such protease recognition sequences include a spacer region of a plant metallothionein-like protein (PsMTa) which can be cleaved by endogenous plant proteases (Unwin et al., 1998) or a recognition sequence of a specific protease (e.g., the TVMV Nia proteinase; Dasgupta, et al., 1998) which is also provided in the cell. Examples of such self-processing protein sequences include a foot-and-mouth disease virus (FMDV) 2A sequence (SEQ ID NO:33; Halpin, C., et al, 1999). Genome editing molecules can also be introduced into the plant cells by similar techniques.

ix. Transient Expression of HDR Promoting Agents

In certain embodiments of the methods, systems, cells, and compositions provided herein, transient expression of the HDR promoting agents and/or genome editing molecules is used. Transient expression of an SSAP, exonuclease, and/or SSB that increase HDR frequency or genome editing molecules can be achieved by a variety of techniques. In some embodments, expression of a HDR promoting agent is inducible. In certain embodiments, the SSAP, exonuclease, SSB, and/or genome editing molecules are provided directly to the cells, systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, SSAP, exonuclease, SSB, and/or genome editing molecules) are targeted to the cell or cell nucleus in a manner that insures transient expression (e.g., by methods adapted from Gao et al. 2016; or Li et al. 2009). In certain embodiments, the SSAP, exonuclease, SSB, and/or genome editing molecules are delivered into the cell by delivery of the SSAP, exonuclease, SSB, and/or genome editing molecule in the absence of any polynucleotide that encodes the SSAP, exonuclease, SSB, and/or genome editing molecule. Examples of exogenous agents that can be delivered in the absence of any encoding polynucleotides include SSAP, exonuclease, SSB, sequence-specific endonucleases, and RNA guides. RNA-guided DNA binding polypeptide/RNA guides can be delivered separately and/or as RNP complexes. In certain embodiments, SSAP, exonuclease, and/or SSB proteins can be produced in a heterologous system, purified and delivered to plant cells by particle bombardment (e.g., by methods adapted from Martin-Ortigosa and Wang 2014). In embodiments where the SSAP, exonuclease, and/or SSBs are delivered in the absence of any encoding polynucleotides, the delivered agent is expected to degrade over time in the absence of ongoing expression from any introduced encoding polynucleotides to result in transient expression. In certain embodiments, the SSAP, exonuclease, and/or SSB is delivered into the cell by delivery of a polynucleotide that encodes the SSAP, exonuclease, and/or SSB. In certain embodiments, SSAP, exonuclease, and/or SSB can be encoded on a bacterial plasmid and delivered to plant tissue by particle bombardment (e.g., by methods adapted from Hamada et al. 2018; or Kirienko, Luo, and Sylvester 2012). In certain embodiments, SSAP, exonuclease, and/or SSB can be encoded on a T-DNA and transiently transferred to plant cells using *agrobacterium* (e.g., by methods adapted from Leonelli et al. 2016; or Wu et al. 2014). In certain embodiments, SSAP, exonuclease, and/or SSB can be encoded in a viral genome and delivered to plants (e.g., by methods adapted from Honig et al. 2015). In certain embodiments, SSAP, exonuclease, and/or SSB can be encoded in mRNA or an RNA comprising an IRES and delivered to target cells. In certain embodiments where the SSAP, exonuclease, and/or SSB comprises an RNA-guided DNA binding polypeptide and an RNA guide, the polypeptide or guide can be delivered by a combination of: (i) an encoding polynucleotide for either polypeptide or the guide; and (ii) either polypeptide or the guide itself in the absence of an encoding polynucleotide. In certain embodiments, the SSAP, exonuclease, and/or SSB is delivered into the plant cell by delivery of a polynucleotide that encodes the HDR promoting agent. In certain embodiments, the polynucleotide that encodes the SSAP, exonuclease, and/or SSB is not integrated into a plant cell genome (e.g., as a polynucleotide lacking sequences that provide for integration, by agroinfiltration on an integration deficient T-DNA vector or system, or in a viral vector), is not operably linked to polynucleotides which provide for autonomous replication, and/or only provided with factors (e.g., viral replication proteins) that provide for autonomous replication. Suitable techniques for transient expression including biolistic and other delivery of polynucleotides, agroinfiltration, and use of viral vectors disclosed by Canto, 2016 and others can be adapted for transient expression of the SSAP, exonuclease, and/or SSB provided herein. Transient expression of the agent encoded by a non-integrated polynucleotide effectuated by excision of the polynucleotide and/or regulated expression of the agent. In certain embodiments, the polynucleotide that encodes the SSAP, exonuclease, and/or SSB is integrated into a eukaryotic cell genome (e.g., a plant nuclear or plastid genome) and transient expression of the agent is effectuated by excision of the polynucleotide and/or regulated expression of the SSAP, exonuclease, and/or SSB. Excision of a polynucleotide encoding the agent can be provided by use of site-specific recombination systems (e.g., Cre-Lox, FLP-FRT). Regulated expression of the agent can be effectuated by methods including: (i) operable linkage of the polynucleotide encoding the agent to a developmentally-regulated, de-repressible, and/or inducible promoter; and/or (ii) introduction of a polynucleotide (e.g., dsRNA or a miRNA) that can induce siRNA-mediated inhibition of the agent. Suitable site-specific recombination systems as well as developmentally-regulated, de-repressible, and/or inducible promoters include those disclosed in US Patent Application Publication No. 20170121722, which is incorporated herein by reference in its entirety and specifically with respect to such disclosure.

Polynucleotides that can be used to effectuate transient expression of an SSAP, exonuclease, SSB, and/or genome editing molecules (e.g., a polynucleotide encoding an SSAP, exonuclease, SSB, sequence-specific endonuclease, RNA-guided endonuclease, and/or a guide RNA) include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e.g., a sequence-specific recombinase or endonuclease site), T-DNA (e.g., DNA sequence encoding an SSAP, exonuclease, and/or SSB is enclosed between left and right T-DNA borders from *Agrobacterium* spp. or from other bacteria that infect or induce tumors in plants), a DNA nuclear-targeting sequence, a regulatory sequence such as a promoter sequence, and a transcript-stabilizing or -destabilizing sequence. Certain embodiments of the polynucleotide include those wherein the polynucleotide is complexed with, or covalently or non-covalently bound to, a non-nucleic acid element, e.g., a carrier molecule, an antibody, an antigen, a viral movement protein, a cell-penetrating or pore-forming peptide, a polymer, a detectable label, a quantum dot, or a particulate or nanoparticulate. In some embodiments, one or more of the components provided herein is transiently expressed by induction of an inducible promoter.

x. Delivery of HDR Promoting Agents

Various treatments are useful in delivery of gene editing molecules and/or an SSAP, exonuclease, and/or SSB that increase HDR frequency to a eukaryotic cell (e.g., a plant cell). In certain embodiments, one or more treatments is employed to deliver the HDR promoting agent (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the agent(s) are delivered directly, for example by direct contact of the composition with a eukaryotic cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a eukaryotic cell, eukaryotic tissue, eukaryotic organ, eukaryotic organism, plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid SSAP, exonuclease, and/or SSB-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the agent (e.g., SSAP, exonucleases, SSB, sequence-specific endonuclease, and/or guide RNA); see, e.g., Broothaerts et al. (2005) *Nature,* 433:629-633. Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated. In certain embodiments, the aforementioned methods can also be used to introduce a genome editing molecule into the eukaryotic cell (e.g., plant cell).

In embodiments, a treatment employed in delivery of a SSAP, exonuclease, and/or SSB that increase HDR frequency to a eukaryotic cell (e.g., plant cell) is carried out under a specific thermal regime, which can involve one or more appropriate temperatures, e.g., chilling or cold stress (exposure to temperatures below that at which normal plant growth occurs), or heating or heat stress (exposure to temperatures above that at which normal plant growth occurs), or treating at a combination of different temperatures. In certain embodiments, a specific thermal regime is carried out on the plant cell, or on a plant, plant explant, or plant part from which a plant cell or plant protoplast is subsequently obtained or isolated, in one or more steps separate from the agent delivery. In certain embodiments, the aforementioned methods can also be used to introduce a genome editing molecule into the eukaryotic cell.

In certain embodiments of the plant parts, systems, methods, and compositions provided herein, a whole plant or plant part or seed, or an isolated plant cell, a plant explant, or the plant or plant part from which a plant cell or plant protoplast is obtained or isolated, is treated with one or more delivery agents which can include at least one chemical, enzymatic, or physical agent, or a combination thereof. In certain embodiments, an SSAP, exonuclease, and/or SSB that increase HDR frequency further includes one or more than one chemical, enzymatic, or physical agents for delivery. Treatment with the chemical, enzymatic or physical agent can be carried out simultaneously with the agent delivery or in one or more separate steps that precede or follow the agent delivery. In certain embodiments, a chemical, enzymatic, or physical agent, or a combination of these, is associated or complexed with the polynucleotide composition, with the donor template polynucleotide, with the SSAP, exonuclease, and/or SSB; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, the SSAP, exonuclease, and/or SSB is provided as a liposomal complex with a cationic lipid; the SSAP, exonuclease, and/or SSB is provided as a complex with a carbon nanotube; and/or SSAP, exonuclease, and/or SSB is provided as a fusion protein between the agent and a cell-penetrating peptide. Examples of agents useful for delivering the SSAP, exonuclease, and/or SSB include the various cationic liposomes and polymer nanoparticles reviewed by Zhang et al. (2007) *J. Controlled Release,* 123:1-10, and the cross-linked multilamellar liposomes described in US Patent Application Publication 2014/0356414 A1, incorporated by reference in its entirety herein. In any of the aforementioned embodiments, it is further contemplated that the aforementioned methods can also be used to introduce a genome-editing molecule into the eukaryotic cell (e.g., plant cell).

In certain embodiments, the chemical agent used to deliver an SSAP, exonuclease, and/or SSB protein or polynucleotide encoding the same that can increase HDR frequency can comprise:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot]html and Jarver (2012) *Mol. Therapy-Nucleic Acids,* 1:e27,1-17); octa-arginine or nona-arginine; poly-homoarginine (see Unnamalai et al. (2004) *FEBS Letters,* 566:307-310); see also the database of cell-penetrating peptides CPPsite 2.0 publicly available at crdd[dot]osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, MA), PepFect (see Ezzat et al. (2011) *Nucleic Acids Res.,* 39:5284-5298), TransIt® transfection reagents (Mirus Bio, LLC, Madison, WI), and poly-lysine, poly-homoarginine, and poly-arginine molecules including octo-arginine and nono-arginine as described in Lu et al. (2010) *J. Agric. Food Chem.,* 58:2288-2294);

(n) antibiotics, including non-specific DNA double-strand-break-inducing agents (e.g., phleomycin, bleomycin, talisomycin); and/or (o) antioxidants (e.g., glutathione, dithiothreitol, ascorbate).

In any of the aforementioned embodiments, it is further contemplated that the aforementioned chemical agents can also be used to introduce a genome-editing molecule into the eukaryotic cell (e.g., plant cell).

In certain embodiments, the chemical agent is provided simultaneously with the SSAP, exonuclease, and/or SSB that increase HDR frequency. In certain embodiments, SSAP, exonuclease, and/or SSB is covalently or non-covalently linked or complexed with one or more chemical agents; for example, an SSAP, exonuclease, SSB and/or sequence-specific endonuclease can be covalently linked to a peptide or protein (e.g., a cell-penetrating peptide or a pore-forming peptide) or non-covalently complexed with cationic lipids, polycations (e.g., polyamines), or cationic polymers (e.g., PEI). In certain embodiments, the SSAP, exonuclease, and/or SSB is complexed with one or more chemical agents to form, e.g., a solution, liposome, micelle, emulsion, reverse emulsion, suspension, colloid, or gel. In any of the aforementioned embodiments, it is further contemplated that genome editing molecules comprising polynucleotides and/or polypeptides can be also be delivered as described above.

In certain embodiments, the physical agent for delivery of an SSAP, exonuclease, and/or SSB that increase HDR frequency is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, CA), abrasive or scarifying agents, needles or microneedles, matrices, and grids. In certain embodiments, particulates and nanoparticulates are useful in delivery of the SSAP, exonuclease, and/or SSB. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites). In certain embodiments, such particulates and nanoparticulates are further covalently or non-covalently functionalized, or further include modifiers or cross-linked materials such as polymers (e.g., linear or branched polyethylenimine, poly-lysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, CA; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.,* 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, MO) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. In certain embodiments, physical agents for delivery of an SSAP, exonuclease, and/or SSBs can include materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moieties), and graphene or graphene oxide or graphene complexes. Such physical agents that can be adapted for delivery of SSAP, exonuclease, and/or SSBs include those disclosed in Wong et al. (2016) *Nano Lett.,* 16:1161-1172; Giraldo et al. (2014) *Nature Materials,* 13:400-409; Shen et al. (2012) *Theranostics,* 2:283-294; Kim et al. (2011) *Bioconjugate Chem.,* 22:2558-2567; Wang et al. (2010) *J. Am. Chem. Soc. Comm.,* 132:9274-9276; Zhao et al. (2016) *Nanoscale Res. Lett.,* 11:195-203; and Choi et al. (2016) *J. Controlled Release,* 235:222-235. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety. In any of the aforementioned embodiments, it is further contemplated that genome editing molecules comprising polynucleotides and/or polypeptides can be also be delivered as described above.

In some embodiments "provided" as used herein includes bringing together the components in a nucleus of a cell. In some embodiments, providing of one or more components is in the form of delivery of a polypeptide. In some embodiments, delivery of one or more components is in the form of a polypeptide complexed with a polynucleotide. In some embodiments, delivery of one or more components is in the form of a ribonucleoprotein (RNP). In some embodiments, Cas and guide RNA are delivered as ribonucleoproteins. In some embodiments the RNP is delivered to a cell using lipofection or electroporation. In some embodiments, the polypeptide or RNP is delivered to a cell through biolistics. In some embodiments, the polypeptide or RNP is delivered to a cell through PEG-mediated transfection. In some embodiments, components are delivered by sexual crossing.

In some embodiments, the components are provided as RNA or as DNA. For example in some embodiments, one or more components are provided as mRNA. In some embodiments, the mRNA encodes a protein that is one of the components. In some embodiments, the mRNA is translated in the cell to produce one or more components.

In some embodiments, one or more components are provided as a nucleic acid integrated into a chromosome.

In some embodiments, one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB) are provided by a progenitor cell comprising one or more of i)-v). In some embodiments, the progenitor cell is any one of the cells described herein, e.g., a plant, animal, fungal, or other eukaryotic cell. In some embodiments, the progenitor cell does not comprise at least one of the sequence-specific endonuclease, the donor template DNA molecule, the SSAP, the exonuclease, and the SSB protein. In some embodiments, the at least one of the sequence-specific endonuclease, the donor template DNA molecule, the SSAP, the exonuclease, and the SSB protein that is not comprised by the progenitor cell is subsequently provided by delivering a polypeptide, a DNA, or an mRNA to the progenitor cell and/or sexual crossing of the progenitor cell. In some embodiments, components are provided as shown in Table 1, below.

TABLE 1

Combinations of components provided by progenitor cell or by delivery and/or sexual crossing of the progenitor cell

| Combination Number | Component(s) Provided by progenitor Cell | Component(s) Provided by Delivery and/or sexual crossing of the progenitor cell |
|---|---|---|
| 1 | Donor template DNA molecule<br>SSAP<br>Exonuclease<br>SSB | Sequence-specific endonuclease |
| 2 | Sequence-specific endonuclease<br>SSAP<br>Exonuclease<br>SSB | Donor template DNA molecule |
| 3 | Sequence-specific endonuclease<br>Donor template DNA molecule<br>Exonuclease<br>SSB | SSAP |
| 4 | Sequence-specific endonuclease<br>Donor template DNA molecule<br>SSAP<br>SSB | Exonuclease |
| 5 | Sequence-specific endonuclease<br>Donor template DNA molecule<br>SSAP<br>Exonuclease | SSB |
| 6 | SSAP<br>Exonuclease<br>9SSB | Sequence-specific endonuclease<br>Donor template DNA molecule |
| 7 | Donor template DNA molecule<br>Exonuclease<br>SSB | Sequence-specific endonuclease<br>SSAP |
| 8 | Donor template DNA molecule<br>SSAP<br>SSB | Sequence-specific endonuclease<br>Exonuclease |
| 9 | Donor template DNA molecule<br>SSAP<br>Exonuclease | Sequence-specific endonuclease<br>SSB |
| 10 | SSAP<br>Exonuclease<br>SSB | Donor template DNA molecule<br>Sequence-specific endonuclease |
| 11 | Sequence-specific endonuclease<br>Exonuclease<br>SSB | Donor template DNA molecule<br>SSAP |
| 12 | Sequence-specific endonuclease<br>SSAP<br>SSB | Donor template DNA molecule<br>Exonuclease |
| 13 | Sequence-specific endonuclease<br>SSAP<br>Exonuclease | Donor template DNA molecule<br>SSB |
| 14 | Donor template DNA molecule<br>Exonuclease<br>SSB | SSAP<br>Sequence-specific endonuclease |
| 15 | Sequence-specific endonuclease<br>Exonuclease<br>SSB | SSAP<br>Donor template DNA molecule |

TABLE 1-continued

Combinations of components provided by progenitor cell or by delivery and/or sexual crossing of the progenitor cell

| Combination Number | Component(s) Provided by progenitor Cell | Component(s) Provided by Delivery and/or sexual crossing of the progenitor cell |
|---|---|---|
| 16 | Sequence-specific endonuclease<br>Donor template DNA molecule<br>SSB | SSAP<br>Exonuclease |
| 17 | Sequence-specific endonuclease<br>Donor template DNA molecule<br>Exonuclease | SSAP<br>SSB |
| 18 | Donor template DNA molecule<br>SSAP<br>SSB | Exonuclease<br>Sequence-specific endonuclease |
| 19 | Sequence-specific endonuclease<br>SSAP<br>SSB | Exonuclease<br>Donor template DNA molecule |
| 20 | Sequence-specific endonuclease<br>Donor template DNA molecule<br>SSB | Exonuclease<br>SSAP |
| 21 | Sequence-specific endonuclease<br>Donor template DNA molecule<br>SSAP | Exonuclease<br>SSE |
| 22 | Donor template DNA molecule<br>SSAP<br>Exonuclease | SSB<br>Sequence-specific endonuclease |
| 23 | Sequence-specific endonuclease<br>SSAP<br>Exonuclease | SSB<br>Donor template DNA molecule |
| 24 | Sequence-specific endonuclease<br>Donor template DNA molecule<br>Exonuclease | SSB<br>SSAP |
| 25 | Sequence-specific endonuclease<br>Donor template DNA molecule<br>SSAP | SSB<br>Exonuclease |
| 26 | Sequence-specific endonuclease<br>Donor template DNA molecule | SSAP<br>Exonuclease<br>SSB |
| 27 | Sequence-specific endonuclease<br>SSAP | Donor template DNA molecule<br>Exonuclease<br>SSB |
| 28 | Sequence-specific endonuclease<br>Exonuclease | Donor template DNA molecule<br>SSAP<br>SSB |
| 29 | Sequence-specific endonuclease<br>SSB | Donor template DNA molecule<br>SSAP<br>Exonuclease |
| 30 | Donor template DNA molecule<br>Sequence-specific endonuclease | SSAP<br>Exonuclease<br>SSB |
| 31 | Donor template DNA molecule<br>SSAP | Sequence-specific endonuclease<br>Exonuclease<br>SSB |
| 32 | Donor template DNA molecule<br>Exonuclease | Sequence-specific endonuclease<br>SSAP<br>SSB |
| 33 | Donor template DNA molecule<br>SSB | Sequence-specific endonuclease<br>SSAP<br>Exonuclease |
| 34 | SSAP<br>Sequence-specific endonuclease | Donor template DNA molecule<br>Exonuclease<br>SSB |
| 35 | SSAP<br>Donor template DNA molecule | Sequence-specific endonuclease<br>Exonuclease<br>SSB |
| 36 | SSAP<br>Exonuclease | Sequence-specific endonuclease<br>Donor template DNA molecule<br>SSB |
| 37 | SSAP<br>SSB | Sequence-specific endonuclease<br>Donor template DNA molecule<br>Exonuclease |
| 38 | Exonuclease<br>Sequence-specific endonuclease | Donor template DNA molecule<br>SSAP<br>SSB |
| 39 | Exonuclease<br>Donor template DNA molecule | Sequence-specific endonuclease<br>SSAP<br>SSB |
| 40 | Exonuclease<br>SSAP | Sequence-specific endonuclease<br>Donor template DNA molecule<br>SSB |
| 41 | Exonuclease<br>SSB | Sequence-specific endonuclease<br>Donor template DNA molecule<br>SSAP |
| 42 | SSB<br>Sequence-specific endonuclease | Donor template DNA molecule<br>SSAP<br>Exonuclease |
| 43 | SSB<br>Donor template DNA molecule | Sequence-specific endonuclease<br>SSAP<br>Exonuclease |
| 44 | SSB<br>SSAP | Sequence-specific endonuclease<br>Donor template DNA molecule<br>Exonuclease |
| 45 | SSB<br>Exonuclease | Sequence-specific endonuclease<br>Donor template DNA molecule<br>SSAP |
| 46 | Sequence-specific endonuclease | Donor template DNA molecule<br>SSAP<br>Exonuclease<br>SSB |
| 47 | Donor template DNA molecule | Sequence-specific endonuclease<br>SSAP<br>Exonuclease<br>SSB |
| 48 | SSAP | Sequence-specific endonuclease<br>Donor template DNA molecule<br>Exonuclease<br>SSB |
| 49 | Exonuclease | Sequence-specific endonuclease<br>Donor template DNA molecule<br>SSAP<br>SSB |
| 50 | SSB | Sequence-specific endonuclease<br>Donor template DNA molecule<br>SSAP<br>Exonuclease |

xi. Gene Editing Molecules

In certain embodiments wherein the gene editing molecules comprise a gRNA (or polynucleotide encoding the gRNA) is provided in a composition that further includes an RNA guided DNA binding polypeptide that is nuclease activity deficient (or a polynucleotide that encodes the same), one or more one chemical, enzymatic, or physical agent can similarly be employed. In certain embodiments, the RNA guide and the nuclease activity deficient RNA-guided DNA binding polypeptide (ndRGDBP) or polynucleotide encoding the same) are provided separately, e.g., in a separate composition. Such compositions can include other chemical or physical agents (e.g., solvents, surfactants, proteins or enzymes, transfection agents, particulates or nanoparticulates), such as those described above as useful in the polynucleotide compositions. For example, porous silica nanoparticles are useful for delivering a DNA recombinase into maize cells; see, e.g., Martin-Ortigosa et al. (2015) *Plant Physiol.,* 164:537-547, and can be adapted to providing a ndRGDBP or polynucleotide encoding the same into a maize or other plant cell. In one embodiment, the polynucleotide composition includes a gRNA and the ndRGDBP, and further includes a surfactant and a cell-penetrating peptide (CPP) which can be operably linked to the ndRGDBP. In an embodiment, the polynucleotide composition includes a plasmid or viral vector that encodes both the gRNA and the ndRGDBP, and further includes a surfactant and carbon nanotubes. In an embodiment, the polynucleotide composition includes multiple gRNAs and an mRNA encoding the ndRGDBP, and further includes particles (e.g., gold or tungsten particles), and the polynucleotide composition is delivered to a plant cell or plant protoplast by Biolistics. In any of the aforementioned embodiments, it is further contemplated that other polynucleotides of interest including genome editing molecules can also be delivered before, during, or after delivery of the gRNA and the ndRGDBP.

In certain embodiments, the plant, plant explant, or plant part from which a plant cell is obtained or isolated is treated with one or more chemical, enzymatic, or physical agent(s) in the process of obtaining, isolating, or treating the plant cell. In certain embodiments, the plant cell, plant, plant explant, or plant part is treated with an abrasive, a caustic agent, a surfactant such as Silwet L-77 or a cationic lipid, or an enzyme such as cellulase. In any of the aforementioned embodiments, it is further contemplated that other polynucleotides of interest including genome editing molecules can also be delivered before, during, or after delivery of the HDR promoting agents.

In certain embodiments, one or more than one chemical, enzymatic, or physical agent, separately or in combination with the polynucleotide composition encoding the SSAP, exonuclease, and/or SSB that increase HDR frequency, is provided/applied at a location in the plant or plant part other than the plant location, part, or tissue from which the plant cell is treated, obtained, or isolated. In certain embodiments, the polynucleotide composition is applied to adjacent or distal cells or tissues and is transported (e.g., through the vascular system or by cell-to-cell movement) to the meristem from which plant cells are subsequently isolated. In certain embodiments, the polynucleotide-containing composition is applied by soaking a seed or seed fragment or zygotic or somatic embryo in the polynucleotide-containing composition, whereby the polynucleotide is delivered to the plant cell. In certain embodiments, a flower bud or shoot tip is contacted with a polynucleotide-containing composition, whereby the polynucleotide is delivered to cells in the flower bud or shoot tip from which desired plant cells are obtained. In certain embodiments, a polynucleotide-containing composition is applied to the surface of a plant or of a part of a plant (e.g., a leaf surface), whereby the polynucleotide(s) are delivered to tissues of the plant from which desired plant cells are obtained. In certain embodiments a whole plant or plant tissue is subjected to particle- or nanoparticle-mediated delivery (e.g., Biolistics or carbon nanotube or nanoparticle delivery) of a polynucleotide-containing composition, whereby the polynucleotide(s) are delivered to cells or tissues from which plant cells are subsequently obtained. In any of the aforementioned embodiments, it is further contemplated that other polynucleotides of interest including genome editing molecules can also be delivered before, during, or after delivery of the HDR promoting agents.

Genome editing molecules include gene editing molecules for inducing a genetic modification in the plant cells having increased HDR-mediated genome modification frequencies provided herein. In certain embodiments, such genome editing molecules can include: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a nCas9, a type V Cas nuclease, a Cas12a, a nCas12a, a CasY, a CasX, a Cas12b, a Cas12c, Cas12i, Cas14, an engineered nuclease, a codon-optimized nuclease, a zinc-finger nuclease (ZFN), a transcription activator-like effector nuclease (TAL-effector nuclease), Argonaute, a meganuclease or engineered meganuclease; (iii) a polynucleotide encoding one or more nucleases capable of effectuating site-specific cleavage of a target nucleotide sequence; and/or (iv) a donor template DNA molecule. In certain embodiments, at least one delivery agent is selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; chelating agents such as ammonium oxalate, EDTA, EGTA, or cyclohexane diamine tetraacetate, non-specific DNA double-strand-break-inducing agents; and antioxidants; particles or nanoparticles, magnetic particles or nanoparticles, abrasive or scarifying agents, needles or microneedles, matrices, and grids. In certain embodiments, the eukaryotic cell (e.g., plant cell), system, method, or composition comprising the cells provided herein further includes (a) at least one cell having at least one Cas9, nCas9, Cas12a, nCas12a, a CasY, a CasX, a Cas12b, Cas12c, or a Cas12i nuclease or nickase; (b) at least one guide RNA; and (c) optionally, at least one chemical, enzymatic, or physical delivery agent.

Gene editing molecules of use in the cells, systems, methods, compositions, and reaction mixtures provided herein include molecules capable of introducing a double-strand break ("DSB") in double-stranded DNA, such as in genomic DNA or in a target gene located within the genomic DNA as well as accompanying guide RNA or donor template polynucleotides. Examples of such gene editing molecules include: (a) a nuclease selected from the group consisting of an RNA-guided nuclease, an RNA-guided DNA endonuclease, a type II Cas nuclease, a Cas9, a nCas9 nickase, a type V Cas nuclease, a Cas12a nuclease, a nCas12a nickase, a CasY, a CasX, a Cas12b, a Cas12c, Cas12i, Cas14 an engineered nuclease, a codon-optimized nuclease, a zinc-finger nuclease (ZFN) or nickase, a transcription activator-like effector nuclease (TAL-effector nuclease) or nickase, an Argonaute, and a meganuclease or engineered meganuclease; (b) a polynucleotide encoding one or more nucleases capable of effectuating site-specific alteration (such as introduction of a DSB) of a target editing site; (c) a guide RNA (gRNA) for an RNA-guided nuclease, or a DNA encoding a gRNA for an RNA-guided nuclease; and (d) donor template polynucleotides.

CRISPR-type genome editing can be adapted for use in the eukaryotic cells (e.g., plant cells), systems, methods, and compositions provided herein in several ways. CRISPR elements, i.e., gene editing molecules comprising CRISPR endonucleases and CRISPR single-guide RNAs or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the systems, methods, and compositions provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target editing site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. T-rich PAM sites (e.g., 5'-TTTV [1], where "V" is A, C, or G) are typically targeted for design of crRNAs or sgRNAs used with Cas12a proteins (e.g., SEQ ID NO:27, 28, 29, and 30). Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) *Mol. Cell,* 60:385-397) and CasX and CasY (see Burstein et al. (2016) Nature, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target editing site at the endonuclease recognition sequence is used. Blunt-end cutting RNA-guided endonucleases include Cas9, Cas12c, and Cas12h (Yan et al., 2019). In certain embodiments, an RNA-guided endonuclease that leaves a staggered single stranded DNA overhanging end following cleavage of the endonuclease recognition sequence is used. Staggered-end cutting RNA-guided endonucleases include Cas12a, Cas12b, and Cas12e.

The methods, systems, compositions, eukaryotic cells (e.g., plant cells) can also use sequence-specific endonucleases or sequence-specific endonucleases and guide RNAs that cleave a single DNA strand in a dsDNA at an endonuclease recognition sequence within the target editing site. Such cleavage of a single DNA strand in a dsDNA target editing site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). In any of the aforementioned embodiments where a nickase or nickase system is used, an exonuclease with 5' to 3' or 3' to 5' exonuclease activity that can recognize dsDNA substrate having an internal break in one strand can be used. In certain embodiments, a T7 phage exonuclease, *E. coli* Exonuclease III, a related protein with equivalent exonuclease activity, or a protein having at least 70%, 75%, 80%, 85%, 90%, 95%, or 99% sequence identity to SEQ ID NO: 143 or 144 can be used in conjunction with the nickase or nickase system, an SSAP, and an SSB.

For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Other sequence-specific endonucleases capable of effecting site-specific modification of a target nucleotide sequence in the systems, methods, and compositions provided herein include zinc-finger nucleases (ZFNs), transcription activator-like effector nucleases (TAL-effector nucleases or TALENs), Argonaute proteins, and a meganuclease or engineered meganuclease. Zinc finger nucleases (ZFNs) are engineered proteins comprising a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see, e.g., Urnov et al. (2010) *Nature Rev. Genet.,* 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare sequence-specific endonucleases referred to as TAL-effector nucleases or TALENs. As in the case of ZFNs, a restriction endonuclease, such as FokI, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonautes are proteins that can function as sequence-specific endonucleases by binding a polynucleotide (e.g., a single-stranded DNA or single-stranded RNA) that includes sequence complementary to a target nucleotide sequence) that guides the Argonaut to the target nucleotide sequence and effects site-specific alteration of the target nucleotide sequence; see, e.g., US Patent Application Publication 2015/0089681, incorporated herein by reference in its entirety.

In some embodiments, the endonuclease binds to an endonuclease recognition sequence. In some embodiments, the endonuclease cleaves the endonuclease recognition sequence. In some embodiments, the term "endonuclease recognition sequence" is used interchangeably with an endonuclease cleavage site sequence.

In some embodiments, an endonuclease is not required. In some embodiments, the method is carried out by providing a compound that non-specificially introduces a double strand break. Exemplary double strand break inducing compounds include hydroquinone (HQ), benzoquinone (BQ), benzenetriol (BT), hydrogen peroxide (H2O2), bleomycin (BLM) or sodium ascorbate (Vit C) are used to introduce a double strand break.

Donor template DNA molecules used in the methods, systems, eukaryotic cells (e.g., plant cells), and compositions provided herein include DNA molecules comprising, from 5' to 3', a first homology arm, a replacement DNA, and a second homology arm, wherein the homology arms containing sequences that are partially or completely homologous to genomic DNA (gDNA) sequences flanking an endonuclease recognition sequence in the gDNA and wherein the replacement DNA can comprise an insertion, deletion, or substitution of 1 or more DNA base pairs relative to the target gDNA. In certain embodiments, a donor DNA template homology arm can be about 20, 50, 100, 200, 400, or 600 to about 800, or 1000 base pairs in length. In certain embodiments, a donor template DNA molecule can be delivered to a eukaryotic cell (e.g., a plant cell) in a circular (e.g., a plasmid or a viral vector including a geminivirus vector) or a linear DNA molecule. In certain embodiments, a circular or linear DNA molecule that is used can comprise a modified donor template DNA molecule comprising, from 5' to 3', a first copy of an endonuclease recognition sequence, the first homology arm, the replacement DNA, the second homology arm, and a second copy of the endonuclease recognition sequence. Without seeking to be limited by theory, such modified DNA donor template molecules can be cleaved by the same sequence-specific endonuclease that is used to cleave an endonuclease recognition sequences within the target eiditng site genomic DNA of the eukaryotic cell to release a donor template DNA molecule that can participate in HDR-mediated genome modification of the target editing site in the eukaryotic cell genome. In certain embodiments, the donor DNA template can comprise a linear DNA molecule comprising, from 5' to 3', a cleaved endonuclease recognition sequence, the first homology arm, the replacement DNA, the second homology arm, and a cleaved endonuclease recognition sequence. In certain embodiments, the cleaved endonuclease sequence can comprise a blunt DNA end or a blunt DNA end that can optionally comprise a 5' phosphate group. In certain embodiments, the cleaved endonuclease sequence comprises a DNA end having a single-stranded 5' or 3' DNA overhang. Such cleaved endonuclease recognition sequences can be produced by either cleaving an intact target sequence or by synthesizing a copy of the cleaved target sequence-specific endonuclease recognition sequence. Donor DNA templates can be synthesized either chemically or enzymatically (e.g., in a polymerase chain reaction (PCR)).

Use of donor templates other than double-stranded DNA are also contemplated. For example in some embodiments, a precursor of a double stranded DNA is provided. In some embodiments, an RNA template of a reverse transcriptase is provided. In some embodiments, a revise transcriptase is provided in addition to an RNA. In some embodiments, the method comprises use of a single stranded DNA donor template. In some a single or double stranded RNA template is used. In some embodiments, the method comprises use of a DNA/RNA hybrid. In some embodiments, a PNA is used to generate the donor template.

In some embodiments, more than one donor template is provided. In some embodiments, 2, 3, 4, 5, 6, 7, 8, 9, 10 or more donor templates are provided. In some embodments, the donor templates target the same gene. In some embodiments, the donor templates target different genes in the same pathway. In some embodiments, the donor templates target multiple genes that perform the same function.

Other genome editing molecules used in plant cells and methods provided herein can be used on plants or cells having transgenes or vectors comprising the same. Such transgenes can confer useful traits that include herbicide tolerance, pest tolerance (e.g., tolerance to insects, nematodes, or plant pathogenic fungi and bacteria), improved yield, increased and/or qualitatively improved oil, starch, and protein content, improved abiotic stress tolerance (e.g., improved or enhanced water use efficiency or drought tolerance, osmotic stress tolerance, high salinity stress tolerance, heat stress tolerance, enhanced cold tolerance, including cold germination tolerance), and the like. Such transgenes include both transgenes that confer the trait by expression of an exogenous protein as well as transgenes that confer the trait by inhibiting expression of endogenous plant genes (e.g., by inducing an siRNA response which inhibits expression of the endogenous plant genes). Transgenes that can provide such traits are disclosed in US Patent Application Publication Nos. 20170121722 and 20170275636, which are each incorporated herein by reference in their entireties and specifically with respect to such disclosures.

In some embodiments, one or more polynucleotides or vectors driving expression of one or more polynucleotides encoding any of the aforementioned SSAP, exonuclease, and/or SSBs and/or genome editing molecules are introduced into a eukaryotic cell (e.g., plant cell). In certain embodiments, a polynucleotide vector comprises a regulatory element such as a promoter operably linked to one or more polynucleotides encoding SSAP, exonuclease, and/or SSBs or genome editing molecules. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD(P)-binding Rossmann-Fold protein, adipocyte plasma membrane-associated protein-like protein, Rieske [2Fe-2S]iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., FerréD'Amaré and Scott (2014) *Cold Spring Harbor Perspectives Biol.,* 2:a003574). In certain embodiments, the promoter is an RNA polymerase III promoter operably linked to a nucleotide sequence encoding one or more guide RNAs. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1, incorporated herein by reference.

In certain embodiments, a vector or polynucleotide comprising an expression cassette includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector or polynucleotide. Selectable markers include genes that confer resistance to herbicidal compounds, such as glyphosate, sulfonylureas, glufosinate ammonium, bromoxynil, imidazolinones, and 2,4-dichlorophenoxyacetate (2,4-D). Such selectable marker genes and selective agents include the maize HRA gene (Lee et al., 1988, EMBO J 7:1241-1248) which confers resistance to sulfonylureas and imidazolinones, the CP4 gene that confers resistance to glyphosate (US Reissue Patent RE039247, specifically incorporated herein by reference in its entirety and with respect to such genes and related selection methods), the GAT gene which confers resistance to glyphosate (Castle et al., 2004, Science 304:1151-1154), genes that confer resistance to spectinomycin such as the aadA gene (Svab et al., 1990, Plant Mol Biol. 14:197-205) and the bar gene that confers resistance to glufosinate ammonium (White et al., 1990, Nucl. Acids Res. 25:1062), and PAT (or moPAT for corn, see Rasco-Gaunt et al., 2003, Plant Cell Rep. 21:569-76; also see Sivamani et al., 2019) and the PMI gene that permits growth on mannose-containing medium (Negrotto et al., 2000, Plant Cell Rep. 22:684-690).

In certain embodiments, a counter-selectable marker can be used in the eukaryotic cells (e.g., plant), methods, systems, and compositions provided herein. Such counter-selectable markers can in certain embodiments be incorporated into any DNA that is not intended for insertion into a host cell genome at target editing sites. In such embodiments, non-limiting examples of DNAs with counter-selectable markers include any DNA molecules that are linked to DNAs encoding HDR-promoting agents (e.g., SSB, SSAP, and/or exonucleases), gene-editing molecules, and/or donor template DNA molecules. Vectors or DNA molecules comprising donor template DNA molecules wherein the counter-selectable marker is linked to the donor template DNA and optionally separated from the donor template DNA by a target editing site sequence. Examples of counter-selectable markers that can be used in Plants include cytosine deaminase genes (e.g., used in conjunction with 5-fluorocytosine; Schlaman and Hooykaas, 1997), phosphonate ester hydrolases (e.g., used in conjunction with phosphonate esters of glyphosate including glycerol glyphosate; Dotson, et al. 1996), a nitrate reductase (e.g., used in conjunction with chlorate on media containing ammonia as a sole nitrogen source; Nussaume, et al. 1991).

In certain embodiments, the use of a selectable marker is obviated by the increased frequency of HDR provided by the HDR promoting agents (i.e., SSAP, exonuclease, and/or SSBs) and/or modified template DNA molecules. In such embodiments, a selectable marker and/or a counter-selectable marker can be omitted from any of a donor template DNA molecule, a plasmid used to deliver a donor-template or other DNA molecule, or any other vector (e.g., viral vector) or polynucleotide used in the cells, system, method, or composition provided herein.

B. Methods of Genetic Engineering

In one aspect, the present disclosure provides a method of genetic engineering of a eukaryotic cell. In some embodiments, the method comprises providing i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB). In some embodiments, the method comprises delivering a nucleic acid encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

In another aspect, the present disclosure provides a method of genetic engineering of a eukaryotic cell. In some embodiments, the method comprises i) at least one sequence-specific endonuclease, ii) a donor template DNA molecule having homology to a target editing site in the eukaryotic cell, iii) a single-stranded DNA annealing protein (SSAP), and iv) an exonuclease which can at least partially convert a double stranded DNA substrate to a single stranded DNA product.

In another aspect, the method comprises i) a double strand break inducing compound, ii) a donor template DNA molecule having homology to a target editing site in the eukaryotic cell, iii) a single-stranded DNA annealing protein (SSAP), and iv) an exonuclease which can at least partially convert a double stranded DNA substrate to a single stranded DNA product.

i. Genetic Modifications

The genetic engineering may be a reduction in gene function (i.e. activity in the encoded gene product). This may require a corresponding repair template, as discussed herein, to provide the defective sequence or it may be through induction of a DSB. In particular, the gene perturbation is a gene knockdown. In some embodiments, the cell is a plant or an animal cell. In some embodiments, the genetic engineering is introduction of a stop codon within the gene. In some embodiments the genetic engineering is a mutation in the promoter or start codon.

Alternatively, the genetic engineering may be an increase in gene function (i.e. activity in the encoded gene product). This may require a corresponding repair template, as discussed herein, to provide the corrected sequence. In some embodiments, the genetic engineering is a substitution of one or more nucleotides in a protein coding gene.

In some embodiments the target editing site is located in a promoter region. In one embodiment the nucleotide sequence can be a promoter wherein the editing of the promoter results in any one of the following or any one combination of the following: an increased promoter activity, an increased promoter tissue specificity, a decreased promoter activity, a decreased promoter tissue specificity, a mutation of DNA binding elements and/or a deletion or addition of DNA binding elements.

In one embodiment the nucleotide sequence can be a regulatory sequence in the genome of a cell. A regulatory sequence is a segment of a nucleic acid molecule which is capable of increasing or decreasing the expression of specific genes within an organism. Examples of regulatory sequences include, but are not limited to, transcription activators, transcriptions repressors, and translational repressors, splicing factors, miRNAs, siRNA, artificial miRNAs, a CAAT box, a CCAAT box, a Pribnow box, a TATA box, SECIS elements and polyadenylation signals. In some embodiments the editing of a regulatory element results in altered protein translation, RNA cleavage, RNA splicing, or transcriptional termination.

In one embodiment, the guide polynucleotide/Cas endonuclease system can be used to insert a component of the TET operator repressor/operator/inducer system, or a component of the sulphonylurea (Su) repressor/operator/inducer system into plant genomes to generate or control inducible expression systems.

In another embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements and/or an addition of DNA binding elements. Promoter elements to be deleted can be, but are not limited to, promoter core elements, promoter enhancer elements or 35 S enhancer elements. The promoter or promoter fragment to be deleted can be endogenous, artificial, pre-existing, or transgenic to the cell that is being edited.

In one embodiment the nucleotide sequence to be modified can be a terminator wherein the editing of the terminator comprises replacing the terminator (also referred to as a "terminator swap" or "terminator replacement") or terminator fragment with a different terminator (also referred to as replacement terminator) or terminator fragment (also referred to as replacement terminator fragment), wherein the terminator replacement results in any one of the following or any one combination of the following: an increased terminator activity, an increased terminator tissue specificity, a decreased terminator activity, a decreased terminator tissue specificity, a mutation of DNA binding elements and/or a deletion or addition of DNA binding elements." The terminator (or terminator fragment) to be modified can be a terminator (or terminator fragment) that is endogenous, artificial, pre-existing, or transgenic to the cell that is being edited. The replacement terminator (or replacement terminator fragment) can be a terminator (or terminator fragment) that is endogenous, artificial, pre-existing, or transgenic to the cell that is being edited.

The terminator (or terminator element) to be inserted can be a terminator (or terminator element) that is endogenous, artificial, pre-existing, or transgenic to the cell that is being edited.

In another embodiment, the guide polynucleotide/Cas endonuclease system can be used to allow for the deletion of a terminator or terminator element, wherein the terminator deletion (or terminator element deletion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements. The terminator or terminator fragment to be deleted can be endogenous, artificial, pre-existing, or transgenic to the cell that is being edited.

Modifications include 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target editing site, modified resistance to cellular degradation, and increased cellular permeability.

In some embodiments, the genomic sequence of interest to be modified is a polyubiquitination site, wherein the modification of the polyubiquitination sites results in a modified rate of protein degradation. The ubiquitin tag condemns proteins to be degraded by proteasomes or autophagy. Proteasome inhibitors are known to cause a protein overproduction. Modifications made to a DNA sequence encoding a protein of interest can result in at least one amino acid modification of the protein of interest, wherein said modification allows for the polyubiquitination of the protein (a post translational modification) resulting in a modification of the protein degradation.

In some embodiments, the target editing site is located in a gene coding region. In some embodiments, the target sequence is located in an intragenic region. In some embodiments, the target sequence is located in the telomeres.

In some embodiments, the method provided herein results of modification of one or more nucleotides at a target editing site.

In some embodiments, the modification to the target editing site is a substitution of one or more nucleotides. In some embodiments the modification to the target editing site is a substitution of 1, 2, 3, 4, 5, 6, 7, 8, 9, 10 or more nucleotides.

In some embodiments, the modification to the target editing site is a deletion of one or more nucleotides. In some embodiments the modification to the target editing site is a substitution of 1, 2, 3, 4, 5, 6, 7, 8, 9, 10 or more nucleotides.

In some embodiments, the modification to the target editing site is an insertion of one or more nucleotides. In some embodiments the modification to the target editing site is a substitution of 1, 2, 3, 4, 5, 6, 7, 8, 9, 10 or more nucleotides.

In some embodiments, a target editing site is modified by a donor sequence that has one or more insertions, deletions, or substitutions compared to the target editing site. In some embodiments, the target editing site is replaced by the donor sequence.

By manipulation of a target sequence, Applicants also mean the epigenetic manipulation of a target editing site. This may be of the chromatin state of a target sequence, such as by modification of the methylation state of the target editing site (i.e. addition or removal of methylation or methylation patterns or CpG islands), histone modification, increasing or reducing accessibility to the target editing site, or by promoting 3D folding.

Also provided is a method of interrogating function of one or more genes in one or more animal or plant cells, comprising introducing a genetic perturbation using the methods provided herein and determining changes in expression of the one or more genes in the altered cells, thereby interrogating the function of the one or more genes. In some embodiments, the genetic perturbation is a loss of function mutation.

In some embodiments, the method comprises using multiple donor DNAs with different modifications (i.e., insertions, deletions, or substitutions) to the same target. In some embodiments, the multiple donor DNAs target promoger regions or coding sequences. In some embodiments, cells with different modifications can be subsequently screened for a particular phenotype.

ii. Genetic Engineering of Mammals

Also provided herein are methods of genetic editing of a mammalian cell. In some embodiments, the genetic editing is of a genetic locus involved in a genetic condition or disease. In some embodiments, the disease or disorder is caused by a mutation in an enzyme. In some embodiments, the genetic condition is a metabolic disorder.

Exemplary conditions and genes are Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRHIA, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). Other preferred targets include any one or more of include one or more of: PCSK9; Hmgcr; SERPINAl; ApoB; LDL; Huntington disease (Huntington), Hemochromatosis (HEF), Duchenne muscular dystrophy (Dystrophin), Sickle cell anemia (Beta Globin), and Tay-Sachs (hexosaminidase A)

It will be appreciated that where reference is made to a method of modifying an organism or mammal including human or a non-human mammal or organism by manipulation of a target editing site in a genomic locus of interest, this may apply to the organism (or mammal) as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

The method may be ex vivo or in vitro, for instance in a cell culture or in an ex vivo or in vitro model (such as an organoid or 'animal or plant cell on a chip'). Alternatively, the method may be in vivo, in which case it may also include isolating the first population of cells from the subject, and transplanting the second population of cells (back) into the subject. Gene perturbation may be for one or more, or two or more, or three or more, or four or more genes.

In some embodiments of the present invention a knock out model can be produced.

In some embodiments, delivery is in the form of a vector which may be a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell. While in herein methods the vector may be a viral vector and this is advantageously an AAV, other viral vectors as herein discussed can be employed, such as lentivirus. For example, baculoviruses may be used for expression in insect cells. These insect cells may, in turn be useful for producing large quantities of further vectors, such as AAV or lentivirus vectors adapted for delivery of the present invention.

iii. Genetic Engineering of Plants

In some embodiments provided herein is a method of genetically engineering a plant. Polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, fatty acids, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with other traits.

Agronomically important traits such as oil starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J Biochem.* 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) *J. Bacteriol.* 170:5837-5847) facilitate expression of poly bydroxyalkanoates (PHAs)

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) Gene 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) *Nature* 400:256-261), and those that increase plant growth, such as ammonium-inducible glutamate dehydrogenase Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268 See, U.S. Pat. No. 7,361,811, herein incorporated by reference.

These polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) *Science* 266:789; Martin et al. (1993) Science 262:1432; and Mindrinos et al. (1994) *Cell* 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5.736, 514; 5,723,756; 5,593,881; and Geiser et at. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g., the HPPD gene) or other such genes known in the art. See, for example, U.S. Pat. Nos. 7,626,077, 5,310,667, 5,866,775, 6,225,114, 6,248,876, 7, 69,970, 6,867,293, and U.S. Provisional Application No. 61/40 1,456, each of which is herein incorporated by reference. The bar gene encodes resistance to the herbicide basta, the nptII gene encodes resistance to the antibiotics kanamycin and geneticin, and the ALS-gene mutants encode resistance to the herbicide chlorsulfuron.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) Cell 49:603-12; Figge et al., (1988) Cell 52:713-22; Deuschle et al., (1989) Proc. *Natl. Acad. Sci. USA* 86:5400-4; Fuerst et al., (1989) Proc. Natl. Acad. Sci. USA 86:2549-53; Deuschle et al., (1990) *Science* 248:480-3; Gossen, (1993) *Ph.D. Thesis, University of Heidelberg*; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) Biochemistry 27:1094-104; Bonin, (1993) *Ph.D. Thesis, University of Heidelberg*; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4. Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as O-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

In some embodiments, the eukaryotic cell is engineered to produce one or more exogenous proteins in a biosynthetic pathway In some embodiments, the biosynthetic pathway is for biofuel production. In some embodiments, the biosynthetic pathway is for an alcohol. In some embodiments, the biosynthetic pathway is for ethanol In some embodiments, the biosynthetic pathway is for production of a small molecule. In some embodiments, the biosynthetic pathway is for production of a drug. In some embodiments, the biosynthetic pathway is for production of a sterol, In some embodiments, the biosynthetic pathway is for a hormone. In some embodiments, the biosynthetic pathway is for production of a peptide. In some embodiments, the biosynthetic pathway is for a terpene.

In some embodiments, the eukaryotic cell is engineered such that is its progeny can no longer replicate. In some embodiments, the eukaryotic cell is a pathogenic cell.

The transgenes, recombinant DNA molecules, DNA sequences of interest, and polynucleotides of interest can be comprise one or more DNA sequences for gene silencing Methods for gene silencing involving the expression of DNA sequences in plant are known in the art include, but are not limited to, cosuppression, antisense suppression, double-stranded RNA (dsRNA) interference, hairpin RNA (bpRNA) interference, intron-containing hairpin RNA (ihpRNA) interference, transcriptional gene silencing, and micro RNA (miRNA) interference.

iv. Detection

One of ordinary skill in the art will appreciate that the genetic modification of the target editing site can be detected by various means. In some embodiments, the method further comprises sequencing a cell. In some embodiments, the method comprises detecting a reporter gene. In some embodiments, the method comprises selecting a cell using a selectable marker.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) Cell 71:63-72; Reznikoff, (1992) *Mol Microbiol* 6:2419-22; Hu et al., (1987) Cell 48:555-66; Brown et al., (1987) *Cell* 49:603-12; Figge et al., (1988) Cell 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) Biochemistry 27:1094-104; Bonin, (1993) *Ph.D. Thesis, University of Heidelberg*; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) Nature 334:721-4.

C. Nucleic acids

In one aspect, the present disclosure provides a nucleic acid that encodes an HDR promoting agent. In some embodiments, provided herein is a composition comprising nucleic acids encoding one or more of i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB). In some embodiments, the nucleic acids are in one or more vectors. In some embodiments, the nucleic acids are in one vector.

In some embodiments, the nucleic acid encodes at least one sequence-specific endonuclease. In some embodiments, the nucleic acid comprises a donor template DNA molecule having homology to the target editing site. In some embodiments, the nucleic acid encodes an HDR promoting agent. In some embodiments, the nucleic acid encodes a single-stranded DNA annealing protein (SSAP). In some embodiments, the nucleic acid encodes an exonuclease which can at least partially convert a double stranded DNA substrate to a single stranded DNA product. In some embodiments, the nucleic acid encodes a single stranded DNA binding protein (SSB). In some embodiments, the nucleic acid is an expression construct or a vector. In some embodiments, an expression construct or a vector comprises the nucleic acid.

In some embodiments, the nucleic acid encodes a gene-editing molecule. In some embodiments, the nucleic acid encodes a sequence-specific endonuclease. In some embodiments, the nucleic acid encodes a sequence-specific endonuclease comprises an RNA-guided nuclease or a polynucleotide encoding an RNA-guided nuclease and a guide RNA or a polynucleotide encoding a guide RNA. In some embodiments, nucleic acid encodes an RNA-guided DNA endonuclease, a type II Cas nuclease, a Cas9 nuclease, a type V Cas nuclease, a Cas12a nuclease, a Cas12b nuclease, a Cas12c nuclease, a CasY nuclease, a CasX nuclease, or an engineered nuclease. In some embodiments, the nucleic acid encodes a zinc-finger nuclease (ZFN), a transcription activator-like effector nuclease (TAL-effector nuclease), Argonaute, a meganuclease, or engineered meganuclease. In some embodiments, the nucleic acid encodes one or more sequence-specific endonucleases or sequence-specific endonucleases and guide RNAs that cleave a single DNA strand at two distinct DNA sequences in the target editing site. In some embodiments, the nucleic acid encodes a sequence-specific endonuclease that comprises at least one Cas9 nickase, Cas12a nickase, Cas12i, a zinc finger nickase, a TALE nickase, or a combination thereof. In some embodiments, the nucleic acid encodes a sequence-specific endonuclease that comprises Cas9 and/or Cas12a and the guide RNA molecules have at least one base mismatch to DNA sequences in the target editing site.

In some embodiments, the nucleic acid comprises a donor DNA molecule. In some embodiments, the nucleic acid comprises a donor template DNA. In some embodiments, the donor DNA molecule is provided on a circular DNA vector, geminivirus replicon, or as a linear DNA fragment. In some embodiments, the donor DNA molecule is flanked by an endonuclease recognition sequence.

In some embodiments, the donor DNA molecule comprises a modified sequence of a genomic DNA target editing site. In some embodiments, the donor DNA molecule comprises a substitution of one or more nucleotides compared to the target editing site. In some embodiments the donor DNA molecule comprises a substitution of 1, 2, 3, 4, 5, 6, 7, 8, 9, 10 or more nucleotides.

In some embodiments, the donor DNA molecule comprises a deletion of one or more nucleotides compared to the genomic target editing site. In some embodiments the donor DNA molecule comprises a deletion of 1, 2, 3, 4, 5, 6, 7, 8, 9, 10 or more nucleotides.

In some embodiments, the donor DNA molecule comprises an insertion of one or more nucleotides compared to the genomic target editing site. In some embodiments the insertion is 1, 2, 3, 4, 5, 6, 7, 8, 9, 10 or more nucleotides.

In some embodiments, the nucleic acid encodes a sequence-specific endonuclease comprises an RNA-guided nuclease and the target editing site comprises a PAM sequence and a sequence that is complementary to the guide RNA and located immediately adjacent to a protospacer adjacent motif (PAM) sequence. In some embodiments, the nucleic acid encodes a sequence-specific endonuclease that provides a 5' overhang at the target-editing site following cleavage. In some embodiments, the nucleic acid encodes a SSAP that provides for DNA strand exchange and base pairing of complementary DNA strands of homologous DNA molecules. In some embodiments, the nucleic acid encodes a SSAP that comprises a RecT/Redβ-, ERF-, or RAD52-family protein. In some embodiments, the nucleic acid encodes a RecT/Redβ-family protein comprising a Rac bacterial prophage RecT protein, a bacteriophage a beta protein, a bacteriophage SPP1 35 protein, a related protein with equivalent SSAP activity, or a protein having at least 70%, 75%, 80%, 85%, 90%, 95%, or 99% sequence identity to SEQ ID NO: 1, 2, or 3. In some embodiments, the nucleic acid encodes a ERF-family protein that comprises a bacteriophage P22 ERF protein, a functionally related protein, or a protein having at least 70%, 75%, 80%, 85%, 90%, 95%, or 99% sequence identity to SEQ ID NO: 4. In some embodiments, the nucleic acid encodes a RAD52-family protein that comprises a *Saccharomyces cerevisiae* Rad52 protein, a *Schizosaccharomyces pombe* Rad22 protein, *Kluyveromyces lactis* Rad52 protein, a functionally related protein, or a protein having at least 70%, 75%, 80%, 85%, 90%, 95%, or 99% sequence identity to SEQ ID NO: 5, 6, or 7.

In some embodiments, the nucleic acid encodes an exonuclease. In some embodiments, the nucleic acid encodes an exonuclease wherein a linear dsDNA molecule is a preferred substrate of the exonuclease. In some embodiments, a linear dsDNA molecule comprising a phosphorylated 5' terminus is a preferred substrate of the exonuclease. In some embodiments, the exonuclease has 5' to 3' exonuclease activity and can recognize a blunt ended dsDNA substrate, a dsDNA substrate having an internal break in one strand, a dsDNA substrate having a 5' overhang, and/or a dsDNA substrate having a 3' overhang. In some embodiments, the exonuclease has 3' to 5' exonuclease activity and can recognize a blunt ended dsDNA substrate, a dsDNA substrate having an internal break in one strand, a dsDNA substrate having a 5' overhang, and/or a dsDNA substrate having a 3' overhang. In some embodiments, the exonuclease comprises a bacteriophage lambda exo protein, an Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, Exonuclease III, a Trex2 exonuclease, a related protein with equivalent exonuclease activity, or a protein having at least 70%, 75%, 80%, 85%, 90%, 95%, or 99% sequence identity to SEQ ID NO: 8, 9, 136, 137, 138, 139, 140, 141, 142, 143, 144, or 145. In some embodiments, the exonuclease comprises a T7 phage exonuclease, *E. coli* Exonuclease III, a related protein with equivalent exonuclease activity, or a protein having at least 70%, 75%, 80%, 85%, 90%, 95%, or 99% sequence identity to SEQ ID NO: 143 or 144.

In some embodiments, the nucleic acid encodes a single stranded DNA binding protein (SSB). In some embodiments, the nucleic acid encodes an SSB and a SSAP. In some embodiments, the nucleic acid encodes a single stranded DNA binding protein (SSB) and a SSAP obtained from the same host organism. In some embodiments, the single stranded DNA binding protein (SSB) is a bacterial SSB or optionally an Enterobacteriaceae sp. SSB. In some embodiments, the SSB is an *Escherichia* sp., a *Shigella* sp., an *Enterobacter* sp., a *Klebsiella* sp., a *Serratia* sp., a *Pantoea* sp., or a *Yersinia* sp. SSB. In some embodiments, the SSB comprises a protein having at least 70%, 75%, 80%, 85%, 90%, 95%, or 99% sequence identity to SEQ ID NO: 31, 34-131, or 132.

In some embodiments, the nucleic acid encodes a SSAP, exonuclease, and/or SSB protein further comprising an operably linked nuclear localization signal (NLS) and/or a cell-penetrating peptide (CPP). In some embodiments, the nucleic acid encodes proteins for expression in a plant cell. In some embodiments, the SSAP, the exonuclease, and/or the single stranded DNA binding protein further comprise an operably linked nuclear localization signal (NLS) selected from the group consisting of SEQ ID NO: 10, SEQ ID NO: 11, SEQ ID NO: 12, SEQ ID NO: 13, SEQ ID NO: 14, SEQ ID NO: 15, and SEQ ID NO: 16.

In some embodiments, the nucleic acids provided herein encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB) are each operably linked to a promoter. In some embodiments, the promoter is a constitutively active promoter. In some embodiments, the promoter is an inducible promoter. In some embodiments, the promoter is a plants-specific promoter. In some embodiments, the promoter is a mammalian promoter. In some embodiments, the promoter is a viral promoter. In some embodiments, the promoter is a 35S promoter. In some embodiments, the promoter is ubiquitin promoter. In some embodiments the promoter is an actin promoter. In some embodiments, the promoter is a mammalian promoter. In some embodiments, the promoter is a CAG promoter. In some embodiments, the promoter is the U6 promoter. In some embodiments, the promoter is the EF1a promoter. In some embodiments the promoter is the human ACTB promoter some embodiments, the promoter is a CMV promoter. In some embodiments, the promoter is a U6 promoter. In some embodiments, the promoter is a T7 promoter. In some embodiments, the site specific nuclease, and/or its guide RNA for CRISPR/Cas-based nucleases, are expressed under the control of an inducible promoter. In this configuration, the onset of the genomic editing process can be induced at a time when the concentration of the other components of the system is not rate limiting.

In some embodiments, the nucleic acids provided herein are provided in one or more vectors. In some embodiments, the nucleic acids provided herein are provided in one vector. In some embodiments, the nucleic acids provided herein are provided in two vectors. In some embodiments, the nucleic acids provided herein are provided in three vectors. In some embodiments, the nucleic acids provided herein are provided in four vectors. In some embodiments, the nucleic acids provided herein are provided in five vectors.

In some embodiments, provided herein is a vector encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB). In some embodiments, provided herein is a vector encoding HDR promoting elements. In some embodiments, provided herein is a vector encoding a single-stranded DNA annealing protein (SSAP), an exonuclease which can at least partially convert a double stranded DNA substrate to a single stranded DNA product, and a single stranded DNA binding protein (SSB). In some embodiments, provided herein is a vector encoding at least one sequence-specific endonuclease and a donor template.

Also provided herein is a first vector comprising a single-stranded DNA annealing protein (SSAP), an exonuclease which can at least partially convert a double stranded DNA substrate to a single stranded DNA product, and a single stranded DNA binding protein (SSB) and a second vector comprising a donor template DNA and a guide RNA.

In some embodiments, the nucleic acid is optimized for expression in a particular cell type. In some embodiments, the nucleic acid is optimized for expression in a particular species. In some embodiments, the nucleic acid is optimized for expression in a plant cell. In some embodiments, the nucleic acid is optimized for expression in a mammalian cell. In some embodiments, the nucleic acid comprises a protein coding sequence, such as an exonuclease, a SSB protein, and/or a SSAP. In some embodiments, the protein coding sequence is codon-optimized for translation in a plant cell. In some embodiments, the protein coding sequence is codon-optimized for translation in a mammalian cell.

In certain embodiments, a donor DNA template homology arm can be about 20, 50, 100, 200, 400, or 600 to about 800, or 1000 base pairs in length. For example, a donor DNA template homology arm can be between about 20 to about 1000, about 50 to about 1000, about 100 to about 1000, about 200 to about 1000, or about 600 to 1000 base pairs in length. In some embodiments the donor DNA template homology arm is between about 400 to about 800 base pairs in length. In some embodiments, the donor DNA template homology arms are less than 250 base pairs in length. In some embodiments, the donor DNA template homology arms are less than 100 base pair in length.

In certain embodiments, the GC content of the donor DNA template homology arm is modified. In some embodiments, the GC content is maximized.

In some embodiments, the nucleic acids provided herein are modified for expression in a certain cell type. In some embodiments, the nucleic acids provided herein are modified for expression in eukaryotic cells. In some embodiments, the nucleic acids are modified for expression in plant or animal cells. In some embodiments, the nucleic acids are modified for mammalian cells. In some embodiments, the nucleic acids are modified for murine or primate cells. In some embodiments, the nucleic acids are modified for human cells. In some embodiments the nucleic acids are modified for mouse cells.

Methods of modification of nucleic acid compositions for expression particular cell types are well known in the art. In some embodiments, the GC (guanine-cytosine) content of a nucleotide provided herein is modified. In some embodiments, nucleic acids provided herein are codon optimized for a particular cell type, for example for eukaryotic cells.

i. Viral Vectors

In one aspect, the present disclosure provides vectors that comprises any of the nucleic acids disclosed herein for expression in a mammalian cell. In some embodiments, the vector comprises an expression construct. In some embodiments, the vector comprises a nucleic acid that encodes an HDR-promoting agent (e.g., an SSAP, an exonuclease, and/or an SSB protein), a sequence-specific endonuclease, and/or a donor template DNA molecule.

In some embodiments provided herein is a vector comprising nucleic acids encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and/or v) a single stranded DNA binding protein (SSB).

In some embodiments, a first vector encodes one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB). In some embodiments, a second vector encodes one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB). In some embodiments, the first vector does not encode at least one of the sequence-specific endonuclease, the donor template DNA molecule, the SSAP, the exonuclease, and the SSB protein. In some embodiments, the at least one of the sequence-specific endonuclease, the donor template DNA molecule, the SSAP, the exonuclease, and the SSB protein that is not encoded by the first vector is encoded by the second vector. In some embodiments, the components are encoded by a first and second vector as shown in Table 2, below.

TABLE 2

Combinations of components encoded by a first and second vector

| Combination Number | Component(s) Encoded by First Vector | Component(s) Encoded by Second Vector |
|---|---|---|
| 1 | Donor template DNA molecule<br>SSAP<br>Exonuclease<br>SSB | Sequence-specific endonuclease |
| 2 | Sequence-specific endonuclease<br>SSAP<br>Exonuclease<br>SSB | Donor template DNA molecule |
| 3 | Sequence-specific endonuclease<br>Donor template DNA molecule<br>Exonuclease<br>SSB | SSAP |
| 4 | Sequence-specific endonuclease<br>Donor template DNA molecule<br>SSAP<br>SSB | Exonuclease |
| 5 | Sequence-specific endonuclease<br>Donor template DNA molecule<br>SSAP<br>Exonuclease | SSB |
| 6 | SSAP<br>Exonuclease<br>SSB | Sequence-specific endonuclease<br>Donor template DNA molecule |
| 7 | Donor template DNA molecule<br>Exonuclease<br>SSB | Sequence-specific endonuclease<br>SSAP |
| 8 | Donor template DNA molecule<br>SSAP<br>SSB | Sequence-specific endonuclease<br>Exonuclease |
| 9 | Donor template DNA molecule<br>SSAP<br>Exonuclease | Sequence-specific endonuclease<br>SSB |
| 10 | SSAP<br>Exonuclease<br>SSB | Donor template DNA molecule<br>Sequence-specific endonuclease |

TABLE 2-continued

Combinations of components encoded by a first and second vector

| Combination Number | Component(s) Encoded by First Vector | Component(s) Encoded by Second Vector |
|---|---|---|
| 11 | Sequence-specific endonuclease<br>Exonuclease<br>SSB | Donor template DNA molecule<br>SSAP |
| 12 | Sequence-specific endonuclease<br>SSAP<br>SSB | Donor template DNA molecule<br>Exonuclease |
| 13 | Sequence-specific endonuclease<br>SSAP<br>Exonuclease | Donor template DNA molecule<br>SSB |
| 14 | Donor template DNA molecule<br>Exonuclease<br>SSB | SSAP<br>Sequence-specific endonuclease |
| 15 | Sequence-specific endonuclease<br>Exonuclease<br>SSB | SSAP<br>Donor template DNA molecule |
| 16 | Sequence-specific endonuclease<br>Donor template DNA molecule<br>SSB | SSAP<br>Exonuclease |
| 17 | Sequence-specific endonuclease<br>Donor template DNA molecule<br>Exonuclease | SSAP<br>SSB |
| 18 | Donor template DNA molecule<br>SSAP<br>SSB | Exonuclease<br>Sequence-specific endonuclease |
| 19 | Sequence-specific endonuclease<br>SSAP<br>SSB | Exonuclease<br>Donor template DNA molecule |
| 20 | Sequence-specific endonuclease<br>Donor template DNA molecule<br>SSB | Exonuclease<br>SSAP |
| 21 | Sequence-specific endonuclease<br>Donor template DNA molecule<br>SSAP | Exonuclease<br>SSB |
| 22 | Donor template DNA molecule<br>SSAP<br>Exonuclease | SSB<br>Sequence-specific endonuclease |
| 23 | Sequence-specific endonuclease<br>SSAP<br>Exonuclease | SSB<br>Donor template DNA molecule |
| 24 | Sequence-specific endonuclease<br>Donor template DNA molecule<br>Exonuclease | SSB<br>SSAP |
| 25 | Sequence-specific endonuclease<br>Donor template DNA molecule<br>SSAP | SSB<br>Exonuclease |
| 26 | Sequence-specific endonuclease<br>Donor template DNA molecule | SSAP<br>Exonuclease<br>SSB |
| 27 | Sequence-specific endonuclease<br>SSAP | Donor template DNA molecule<br>Exonuclease<br>SSB |
| 28 | Sequence-specific endonuclease<br>Exonuclease | Donor template DNA molecule<br>SSAP<br>SSB |
| 29 | Sequence-specific endonuclease<br>SSB | Donor template DNA molecule<br>SSAP<br>Exonuclease |
| 30 | Donor template DNA molecule<br>Sequence-specific endonuclease | SSAP<br>Exonuclease<br>SSB |
| 31 | Donor template DNA molecule<br>SSAP | Sequence-specific endonuclease<br>Exonuclease<br>SSB |
| 32 | Donor template DNA molecule<br>Exonuclease | Sequence-specific endonuclease<br>SSAP<br>SSB |
| 33 | Donor template DNA molecule<br>SSB | Sequence-specific endonuclease<br>SSAP<br>Exonuclease |
| 34 | SSAP<br>Sequence-specific endonuclease | Donor template DNA molecule<br>Exonuclease<br>SSB |

TABLE 2-continued

Combinations of components encoded by a first and second vector

| Combination Number | Component(s) Encoded by First Vector | Component(s) Encoded by Second Vector |
|---|---|---|
| 35 | SSAP<br>Donor template DNA molecule | Sequence-specific endonuclease<br>Exonuclease<br>SSB |
| 36 | SSAP<br>Exonuclease | Sequence-specific endonuclease<br>Donor template DNA molecule<br>SSB |
| 37 | SSAP<br>SSB | Sequence-specific endonuclease<br>Donor template DNA molecule<br>Exonuclease |
| 38 | Exonuclease<br>Sequence-specific endonuclease | Donor template DNA molecule<br>SSAP<br>SSB |
| 39 | Exonuclease<br>Donor template DNA molecule | Sequence-specific endonuclease<br>SSAP<br>SSB |
| 40 | Exonuclease<br>SSAP | Sequence-specific endonuclease<br>Donor template DNA molecule<br>SSB |
| 41 | Exonuclease<br>SSB | Sequence-specific endonuclease<br>Donor template DNA molecule<br>SSAP |
| 42 | SSB<br>Sequence-specific endonuclease | Donor template DNA molecule<br>SSAP<br>Exonuclease |
| 43 | SSB<br>Donor template DNA molecule | Sequence-specific endonuclease<br>SSAP<br>Exonuclease |
| 44 | SSB<br>SSAP | Sequence-specific endonuclease<br>Donor template DNA molecule<br>Exonuclease |
| 45 | SSB<br>Exonuclease | Sequence-specific endonuclease<br>Donor template DNA molecule<br>SSAP |
| 46 | Sequence-specific endonuclease | Donor template DNA molecule<br>SSAP<br>Exonuclease<br>SSB |
| 47 | Donor template DNA molecule | Sequence-specific endonuclease<br>SSAP<br>Exonuclease<br>SSB |
| 48 | SSAP | Sequence-specific endonuclease<br>Donor template DNA molecule<br>Exonuclease<br>SSB |
| 49 | Exonuclease | Sequence-specific endonuclease<br>Donor template DNA molecule<br>SSAP<br>SSB |
| 50 | SSB | Sequence-specific endonuclease<br>Donor template DNA molecule<br>SSAP<br>Exonuclease |
| 51 | Sequence-specific endonuclease<br>Donor template DNA molecule<br>SSAP<br>Exonuclease<br>SSB | |

In some embodiments, the sequence-specific endonuclease, the donor template DNA molecule, SSAP, exonuclease, and SSB are provided in three vectors in various combinations. For example, a first vector comprising the sequence-specific endonuclease, a second vector comprising the donor template DNA, and a third vector comprising the SSA-P, exonuclease, and SSB or a first vector comprising the sequence-specific endonuclease, the donor template DNA, and the SSAP, a second vector comprising the exonuclease, and a third vector comprising the SSB.

In some embodiments, the sequence-specific endonuclease, the donor template DNA molecule, SSAP, exonuclease, and SSB are provided in four vectors in various combinations. For example a first vector comprising the sequence-specific endonuclease, a second vector comprising the donor template DNA, a third vector comprising the SSAP, and a fourth vector comprising the exonuclease and SSB or a first vector comprising the sequence-specific endonuclease and the donor template DNA, a second vector comprising the SSAP, a third vector comprising the exonuclease, and a fourth vector comprising the SSB.

In some embodiments, the sequence-specific endonuclease, the donor template DNA molecule, SSAP, exonuclease, and SSB are provided in five vectors In some embodiments, the vector is a viral vector. In some embodiments, the vector is a parvoviral vector. In some embodiments, the vector is an adeno-associated virus (AAV) vector. In some embodiments, the vector is a recombinant AAV (rAAV) vector. In some embodiments, the vector is an adenoviral vector. In some embodiments, the vector is a retroviral vector. In some embodiments, the vector is a lentiviral vector. In some embodiments, the vector is a herpesviral vector. In some embodiments, the vector is baculoviral vector.

In some embodiments, the recombinant adenoviral vector is derived from adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHuSO, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD 114 or variants therein. In some embodiments, the vector is an rHSV vector. In some embodiments, the rHSV vector is derived from rHSV-1 or rHSV-2.

In some embodiments of the above methods, the vector is a rAAV vector. In some embodiments, an expression construct encoding an HDR-promoting agent (e.g., an SSAP, an exonuclease, and/or an SSB protein), a sequence-specific endonuclease, and/or a donor template DNA molecule is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffier nucleic acid. In some embodiments, the stuffier nucleic acid is located between the promoter and the nucleic acid encoding the expression construct. In some embodiments, the vector is a self-complementary rAAV vector. In some embodiments, the vector comprises first nucleic acid sequence encoding an HDR-promoting agent (e.g., an SSAP, an exonuclease, and/or an SSB protein), a sequence-specific endonuclease, and/or a donor template DNA molecule, and a second nucleic acid sequence encoding an HDR-promoting agent (e.g., an SSAP, an exonuclease, and/or an SSB protein), a sequence-specific endonuclease, and/or a donor template DNA molecule. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the invention provides a cell comprising any of vectors (e.g., rAAV vectors) described herein.

In some embodiments of the above methods, the vector encoding an HDR-promoting agent (e.g., an SSAP, an exonuclease, and/or an SSB), a sequence-specific endonuclease, and/or a donor template DNA molecule is in a viral particle, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu3, AdHu4, AdHu24, AdHu26, AdHu34, AdHu35, AdHu36, AdHu37, AdHu41, AdHu48, AdHu49, AdHuSO, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype S capsid. In some embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD 114 or variants therein. In some embodiments, the viral particle is a HSV particle. In some embodiments, the HSV particle is a rHSV-1 particle or a rHSV-2 particle.

In some embodiments of the above methods, the invention provides a recombinant AAV particle comprising any of the rAAV vectors described herein. In some embodiments, the AAV viral particle comprises an AAV1, AAV2, AAV3, AAV4, AAV5, AAV6, AAV7, AAV8, AAVrh8, AAVrh8R, AAV9, AAV 10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoVl serotype capsid. In some embodiments, the ITR and the capsid of the rAAV viral particle are derived from the same AAV serotype. In some embodiments, the ITR and the capsid of the rAAV viral particle are derived from different AAV serotypes. In some embodiments, the ITR is derived from AAV2 and the capsid of the rAAV particle is derived from AAV1. The invention provides a vector comprising the expression construct of any one of the embodiments described herein. In some embodiments, the expression construct encodes an HDR-promoting agent (e.g., an SSAP, an exonuclease, and/or an SSB), a sequence-specific endonuclease, and/or a donor template DNA molecule. In some embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype S. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD 114 or variants therein. In some embodiments, the vector is an rHSV vector. In some embodiments, the rHSV vector is derived from rHSV-1 or rHSV-2.

In some embodiments, the vector comprises a selectable marker.

In some embodiments of the above methods, the viral particle is in a composition (e.g., a pharmaceutical composition). In some embodiments, the composition further comprises a pharmaceutically acceptable carrier.

ii. Other Vectors

In some embodiments, the vector is a non-viral vector. In some embodiments, the vector is a plasmid. In some embodiments, the vector is a plant transformation vector. In some embodiments, the vector is a vector for *Agrobacterium*-mediated transient expression or stable transformation in tissue cultures or plant tissues.

Exemplary systems of using recombinant plasmid vectors that are compatible with the present invention include, but are not limited to the "cointegrate" and "binary" systems. In the "cointegrate" system, the shuttle vector containing the gene of interest is inserted by genetic recombination into a non-oncogenic plasmid that contains both the cis-acting and trans-acting elements required for plant cell transformation as, for example, in the pMILJ1 shuttle vector and the non-oncogenic plasmid pGV3850. The second system is called the "binary" system in which two plasmids are used; the gene of interest is inserted into a shuttle vector containing the cis-acting elements required for plant transformation. The other necessary functions are provided in trans by the non-oncogenic plasmid as exemplified by the pBIN19 shuttle vector and the non-oncogenic plasmid PAL4404. These and other vectors useful for these systems are commercially available.

D. Cells

In one aspect, the present disclosure provides a eukaryotic cell comprising an HDR promoting agent. In some embodiments, the eukaryotic cell comprises genome-editing molecules and an HDR promoting agent. In some embodiments the cell is a host cell. In some embodiments, the cell is a cell to be modified according to the present methods. In some embodiments, the genome editing molecules comprise (i) at least one sequence-specific endonuclease which cleaves a DNA sequence in the target editing site or at least one polynucleotide encoding the sequence-specific endonuclease; and (ii) a donor template DNA molecule having homology to the target editing site. In some embodiments, the HDR promoting agents comprise a single-stranded DNA annealing protein (SSAP), an exonuclease which can at least partially convert a double stranded DNA substrate to a single stranded DNA product, and a single stranded DNA binding protein (SSB).

In another aspect, the present disclosure provides a eukaryotic cell produced by the methods provided herein. In some embodiments, modification of a target editing site of a eukaryotic cell genome comprises providing genome-editing molecules and HDR promoting agents to a eukaryotic cell, wherein the genome editing molecules comprise (i) at least one sequence-specific endonuclease which cleaves a DNA sequence in the target editing site or at least one polynucleotide encoding the sequence-specific endonuclease, and (ii) a donor template DNA molecule having homology to the target editing site; and wherein the HDR promoting agents comprise a SSAP, an exonuclease which can at least partially convert a double stranded DNA substrate to a single stranded DNA product, and a SSB protein. In some embodiments, the cell has a genomic signature produced by modification according to the present methods. In some embodiments, a nuclease cleavage site is removed. In some embodiments, a nucleic acid sequence tag is interested.

In some embodiments, provided herein is a host cell comprising one or more vectors comprising i) nucleic acid encoding at least one sequence-specific endonuclease, ii) a donor template DNA molecule having homology to a target editing site in the eukaryotic cell, iii) nucleic acid encoding a single-stranded DNA annealing protein (SSAP), iv) nucleic acid encoding an exonuclease which can at least partially convert a double stranded DNA substrate to a single stranded DNA product, and v) nucleic acid encoding a single stranded DNA binding protein (SSB). In some embodiments, the host cell comprises one vector encoding i) nucleic acid encoding at least one sequence-specific endonuclease, ii) a donor template DNA molecule having homology to a target editing site in the eukaryotic cell, iii) nucleic acid encoding a single-stranded DNA annealing protein (SSAP), iv) nucleic acid encoding an exonuclease which can at least partially convert a double stranded DNA substrate to a single stranded DNA product, and v) nucleic acid encoding a single stranded DNA binding protein (SSB). In some embodiments, the cell comprises a first vector comprising i) nucleic acid encoding at least one sequence-specific endonuclease, ii) a donor template DNA molecule having homology to a target editing site in the eukaryotic cell and a second vector comprising, iii) nucleic acid encoding a single-stranded DNA annealing protein (SSAP), iv) nucleic acid encoding an exonuclease which can at least partially convert a double stranded DNA substrate to a single stranded DNA product, and v) nucleic acid encoding a single stranded DNA binding protein (SSB).

Further, the methods of the present disclosure may be used to increase HDR-mediated genome modification in a eukaryotic cell, make a eukaryotic cell having a genomic modification, and/or genetically engineer a eukaryotic cell as described herein.

In some embodiments, the cell is an isolated cell. In some embodiments the cell is in cell culture. In some embodiments, the cell is ex vivo. In some embodiments, the cell is obtained from a living organism, and maintained in a cell culture. In some embodiments, the cell is a single-celled organism. In some embodiments, the cell is inside of an organism. In some embodiments, the cell is an organism. In some embodiments, the cell is a cell of a single-celled eukaryotic organism, a protozoa cell, a cell from a plant, an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some embodiments, the cell is a cell that does not originate from a natural organism (e.g., the cell can be a synthetically made cell; also referred to as an artificial cell). In some embodiments, the cell is in a cell culture (e.g., in vitro cell culture). In some embodiments, the cell is one of a collection of cells. In some embodiments, the cell is a eukaryotic cell or derived from a eukaryotic cell. In some embodiments, the cell is a plant cell or derived from a plant cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is rodent cell or derived from a rodent cell. In some embodiments, the cell is a human cell or derived from a human cell. In some embodiments, the cell is a non-human animal cell or derived from a non-human animal cell. In some embodiments, the cell is a non-human mammalian cell or derived from a non-human mammalian cell. In some embodiments, the cell is a fungal cell or derived from a fungal cell. In some embodiments, the cell is an insect cell. In some embodiments, the cell is an arthropod cell. In some embodiments, the cell is a protozoan cell. In some embodiments, the cell is a helminth cell. In some embodiments, the cell is a non-mammal animal cell. In some embodiments, the cell is a fish cell. In some embodiments, the cell is an insect cell. In some embodiments, the cell is a fruit fly cell. In some embodiments, the cell is a *Drosophila melanogaster* cell. In some embodiments, the cell is a nematode cell. In some embodiments, the cell is a *Caenorhabditis elegans* cell. In some embodiments, the cell is a roundworm cell.

In some embodiments, the cell is a progenitor cell that comprises one or more of i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB), wherein the progenitor cell does not comprise at least one of i)-v), and wherein the at least one of i)-v) that is not comprised by the progenitor cell is subsequently provided by delivering a polypeptide, a DNA, or an mRNA to the progenitor cell and/or sexual crossing of the progenitor cell. For example, in some embodiments, the progenitor cell is lacking one or more components of i)-v) and is transformed with the components which are lacking.

i. Plant Cells

In some embodiments, the eukaryotic cell is a plant cell. In some embodiments, the eukaryotic cell comprising an HDR promoting agent is a plant cell. Further, the methods of the present disclosure may be used to increase HDR-mediated genome modification in a plant cell, make a plant cell having a genomic modification, and/or genetically engineer a plant cell. In some embodiments, the methods disclosed herein comprise editing a plant cell. In some embodiments, the methods disclosed herein comprise performing a genome modification in a plant cell. In some embodiments, the methods disclosed herein comprise modifying a target locus in a plant cell genome. In some embodiments, the methods disclosed herein comprise increasing HDR-mediated genome modification in a plant cell.

In certain embodiments, the cell is an isolated plant cells or plant protoplasts (i.e., are not located in undissociated or intact plant tissues, plant parts, or whole plants). In certain embodiments, the plant cells are obtained from any plant part or tissue or callus. In certain embodiments, the culture includes plant cells obtained from a plant tissue, a cultured plant tissue explant, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, callus, or plant cell suspension. In certain embodiments, the plant cell is derived from the L1 or L2 layer of an immature or mature embryo of a monocot plant (e.g., maize, wheat, sorghum, or rice).

In certain embodiments, the plant cell is located in undissociated or intact plant tissues, plant parts, plant explants, or whole plants. In certain embodiments, the plant cell can be located in an intact nodal bud, a cultured plant tissue explant, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, or callus. In certain embodiments, the explants used include immature embryos. Immature embryos (e.g., immature maize embryos) include 1.8-2.2 mm embryos, 1-7 mm embryos, and 3-7 mm embryos. In certain embodiments, the aforementioned embryos are obtained from mature ear-derived seed, leaf bases, leaves from mature plants, leaf tips, immature inflorescences, tassels, immature ears, and silks. In various aspects, the plant-derived explant used for transformation includes immature embryos, 1.8-2.2 mm embryos, 1-7 mm embryos, and 3.5-7 mm embryos. In an aspect, the embryos can be derived from mature ear-derived seed, leaf bases, leaves from mature plants, leaf tips, immature inflorescences, tassel, immature ear, or silks. In certain embodiments, the plant cell is a pluripotent plant cell (e.g., a stem cell or meristem cell). In certain embodiments, the plant cell is located within the L1 or L2 layer of an immature or mature embryo of a monocot plant (e.g., maize, wheat, sorghum, or rice).

In certain embodiments, the plant cell is a haploid, diploid, or polyploid plant cell or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications,* 5:5334, doi: 10.1038/ncomms6334). Haploids can also be obtained in a wide variety of monocot plants (e.g., maize, wheat, rice, sorghum, barley) or dicot plants (e.g., soybean, *Brassica* sp. including canola, cotton, tomato) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e. homozygosity) in the least possible time. Doubled haploid production can be particularly advantageous in slow-growing plants, such as fruit and other trees, or for producing hybrid plants that are offspring of at least one doubled-haploid plant.

In certain embodiments, the plant cell is obtained from or located in any monocot or dicot plant species of interest, for example, row crop plants, fruit-producing plants and trees, vegetables, trees, and ornamental plants including ornamental flowers, shrubs, trees, groundcovers, and turf grasses. In certain non-limiting embodiments, the plant cells are obtained from or located in alfalfa (*Medicago sativa*), almonds (*Prunus dulcis*), apples (Malus x *domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus* caryophyllus), carrots (*Daucus carota sativus*), cassava (*Manihot esculentum*), cherry (*Prunus avium*), chickpea (Cider *arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), *eucalyptus* (*Eucalyptus* spp.), flax (*Linum usitatissumum* L.), geraniums (*Pelargonium* spp.), grapefruit (*Citrus* x *paradisi*), grapes (*Vitus* spp.) including wine grapes (*Vitus vinfera*), guava (*Psidium guajava*), hemp and *cannabis* (e.g., *Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), *papaya* (*Caricapapaya*), peaches and nectarines (*Prunus persica*), pear (*Pyrus* spp.), pea (Pisa *sativum*), peanut (*Arachis hypogaea*), peonies (*Paeonia* spp.), petunias (*Petunia* spp.), pineapple (*Ananas comosus*), plantains (Musa spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius L*), sesame seed (*Sesame indium*), sorghum (*Sorghum bicolor*), soybean (*Glycine max* L.), squash (*Cucurbita pepo*), strawberries (*Fragaria* spp., Fragaria x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum L.*), tomato (*Lycopersicon esculentum*), tulips (*Tulipa* spp.), turnip (*Brassica rapa rapa*), walnuts (*Juglans* spp. *L.*), watermelon (*Citrulus lanatus*), wheat (*Tritium aestivum*), or yams (*Discorea* spp.).

ii. Mammalian Cells

In some embodiments, the eukaryotic cell comprising an HDR promoting agent is an animal cell. In some embodiments, the animal cell is a mammalian cell. Further, the methods of the present disclosure may be used to increase HDR-mediated genome modification in an animal cell, make an animal cell having a genomic modification, and/or genetically engineer an animal cell. In some embodiments, the methods may be used to increase HDR-mediated genome modification, make a cell having a genomic modification, and/or genetically engineer a mammalian cell. In some embodiments, the methods disclosed herein comprise editing an animal cell, e.g., a mammalian cell. In some embodiments, the methods disclosed herein comprise performing a genome modification in an animal cell, e.g., a mammalian cell. In some embodiments, the methods disclosed herein comprise modifying a target locus in an animal cell, e.g., a mammalian cell. In some embodiments, the methods disclosed herein comprise increasing HDR-mediated genome modification in an animal cell, e.g., a mammalian cell.

In some embodiments, the cell is an animal cell from any multicellular vertebrate or invertebrate animal. In some embodiments, the animal is a model organism used for biological, physiological, or genetic research. Accordingly, in some embodiments, the animal is selected from: mouse (*Mus musculus*), zebrafish (*Danio rerio*), fruit fly (*Drosophila melanogaster*), cat (*Felis sylvestris catus*), chicken (*Gallus gallus*), dog (*Canis lupus familiaris*), guinea pig (*Cavia porcellus*), rat (*Rattus norvegicus*) and nematode (*Caenorhabditis elegans*). In some embodiments, the animal is a domesticated or farmed animal. Accordingly, in some embodiments the animal is selected from: goat (*Capra aegagrus hircus*), pig (*Sus scrofa domesticus*), sheep (*Ovis aries*), cattle (*Bos taurus*), cat (*Felis catus*), donkey (*Equus africanus asinus*), duck (*Anas platyrhynchos domesticus*), water buffalo, including Bubalus bubalis bubalis and Bubalus *bubalis carabenesis*, the Western honey bee (*Apis mellfera*), including the subspecies Italian bee (*A. mellifera ligustica*), European dark bee (*A. melbfera melhfera*), Carniolan honey bee (*A. mellfera carnica*), Caucasian honey bee (*A. mellfera caucasia*), and Greek bee (*A. mellfera cecropia*), dromedary camel (*Camelus dromedarius*), horse (*Equus ferns caballus*), silkmoth (*Bombyx mori*), pigeon (*Columba livia*), goose (*Anser domesticus* and *Anser cygnoides domesticus*), yak (*Bos grunniens*), bactrian camel (*Camelus bactrianus*), llama (*Lama glama*), alpaca (*Vicugna pacos*), guineafowl (*Numida meleagris*), ferret (*Mustela putoriusfuro*), turkey (*Meleagris gallopavo*) grass carp, silver carp, common carp, nile tilapia, bighead carp, catla (indian carp), crucian carp, atlantic salmon, roho labeo, milkfish, rainbow trout, wuchang bream, black carp, northern snakehead and amur catfish.

In some embodiments, the cell is derived from a cell line, e.g., a mammalian cell line or a human cell line. A wide variety of cell lines for tissue culture are known in the art. Examples of cell lines include, but are not limited to, A549, HEK-293, 293T, MF7, K562, Caco-2, HeLa cells, and transgenic varieties thereof. In some embodiments, the cell is a HEK-293 cell. In some embodiments, the cell is a Chinese hamster ovary (CHO) cell. Cell lines are available from a variety of sources known to those with skill the art (see, e.g., the American Type Culture Collection (ATCC) (Manassas, Va.)). In some embodiments, a cell transfected with one or more nucleic acids (such as a vector encoding HDR promoting agents) as described herein is used to establish a new cell line comprising one or more vector-derived sequences to establish a new cell line comprising modification to a target nucleic acid.

In some embodiments, the cell is a primary cell, e.g., a mammalian primary cell or a human primary cell. For example, cultures of primary cells can be passaged 0 times, 1 time, 2 times, 4 times, 5 times, 10 times, 15 times or more. In some embodiments, the primary cells are harvest from an individual by any known method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

In some embodiments, the cell is a human cell. In some embodiments, the cell is a germline cell. In some embodiments, the cell is a somatic cell. In some embodiments, the cell is a post-mitotic cell. In some embodiments, the cell is an immune cell, such as a T cell, Natural killer (NK) cell, or a macrophage. In some embodiments, the cell is a human T cell obtained from a patient or a donor. The methods provided herein can be used to modify a target nucleic acid in a primary T cell for use in immunotherapy. In some embodiments, the methods provided herein are used to generate a CAR-T cell, e.g., by editing the genome of the T cell to introduce an expression construct that expresses a chimeric antigen receptor (CAR). In some embodiments, the methods provided herein are used to ex vivo modify an immune cell. In some embodiments, the methods provided herein are used to ex vivo generate a CAR-T cell. In some embodiments, the methods disclosed herein comprise editing a human cell. In some embodiments, the methods disclosed herein comprise performing a genome modification in a human cell. In some embodiments, the methods disclosed herein comprise modifying a target locus in a human cell. In some embodiments, the methods disclosed herein comprise increasing HDR-mediated genome modification in a human cell.

In some embodiments, the cell is a stem cell or progenitor cell. In some embodiments, the cell is an un-differentiated cell. In some embodiments, the cell is a human stem cell or progenitor cell. In some embodiments, the cell is a mammalian stem cell or progenitor cell. In some embodiments, the cell is an adult stem cell, an embryonic stem cell, an induced pluripotent (iPS) cell, or a progenitor cell (e.g., a cardiac progenitor cell, neural progenitor cell, etc.). In some embodiments, the cell is a hematopoietic stem cell (HSC). In some embodiments, the cell is a mesenchymal stem cell (MSC). In some embodiments, the cell is a neural stem cell. In some embodiments, the cell is an epithelial stem cell. Cells can include mammalian stem cells and progenitor cells, including rodent stem cells, rodent progenitor cells, human stem cells, human progenitor cells, etc.

In some embodiments, the cell is a diseased cell, e.g., a diseased mammalian cell or a diseased human cell. A diseased cell can have altered metabolic, gene expression, and/or morphologic features. In some embodiments, the cell has a genome with a genetic variant associated with disease. In some embodiments, the cell has a SNP associated with a disease. In some embodiments, the genome of the cell has a genetic marker associated with a disease. In some embodiments, the cell has a deleterious mutation. In some embodiments, the cell has a mutation that causes a disease. In some embodiments, the cell has a mutant allele associated with a disease. In some embodiments, the cell has a loss-of-function mutation. In some embodiments, the cell has a disease genotype. In some embodiments, the cell has a disease phenotype. In some embodiments, the cell has a genetic defect. In some embodiments, the cell has an oncogenic mutation. In some embodiments, the cell has an integrated and/or stably maintained virus. In some embodiments, a retrovirus is integrated into the genome of the cell. In some embodiments, a lentivirus is integrated into the genome of the cell. In some embodiments, the cell has a persistent viral infection. In some embodiments, the cell has HIV. In some embodiments, the cell has an integrated copy of the HIV genome. In some embodiments, the cell is infected with a virus. In some embodiments, the cell has a latent viral infection. In some embodiments, the cell is infected by a herpesvirus. In some embodiments, the cell is infected by a Human Herpesviruses 6 or 7. In some embodiments, the cell is infected by Herpes Simplex Virus Types 1 or 2. In some embodiments, the cell is infected by Varicella-Zoster Virus. In some embodiments, the cell is infected by a Human Papovavirus. In some embodiments, the cell is infected by an Epstein-Barr Virus. A diseased cell can be a cancer cell, a diabetic cell, or an apoptotic cell. A diseased cell can be a cell from a diseased subject. Exemplary diseases can include genetic disorders, infectious diseases, blood disorders, cancers, metabolic disorders, eye disorders, organ disorders, musculoskeletal disorders, cardiac disease, and the like. In some embodiments, the cell is derived from a patient. In some embodiments, the cell is modified ex vivo. In some embodiments, the cell is a cancer cell. In some embodiments, the cell is an embryonic cell. In some embodiments, the cell is an embryonic stem cell.

In some embodiments, the methods provided herein are used to genetically modify a diseased cell, e.g., a diseased mammalian cell or a diseased human cell. In some embodiments, the methods provided herein are used to genetically modify a diseased cell. In some embodiments, the methods provided herein are used to insert a wild-type allele of a gene into a diseased cell. In some embodiments, the methods provided herein are used to correct a deleterious mutation in a diseased cell. In some embodiments, the methods provided herein are used to genetically modify an oncogene. In some embodiments, the methods provided herein are used to genetically modify an allele of a gene associated with disease. In some embodiments, the methods provided herein are used to insert a healthy allele of a gene. In some embodiments, the methods provided herein are used to insert an allele of a gene that is not associated with disease. In some embodiments, the methods provided herein are used to remove an integrated or stably maintained virus, such as a lentivirus, a retrovirus, or a herpesvirus, from the genome of the cell.

iii. Fungal Cells

In some embodiments, the eukaryotic cell is a fungal cell. In some embodiments, the eukaryotic cell comprising an HDR promoting agent is a fungal cell. Further, the methods of the present disclosure may be used to increase HDR-mediated genome modification in a fungal cell, make a fungal cell having a genomic modification, and/or genetically engineer a fungal cell. In some embodiments, the methods disclosed herein comprise editing a fungal cell. In some embodiments, the methods disclosed herein comprise performing a genome modification in a fungal cell. In some embodiments, the methods disclosed herein comprise modifying a target locus in a fungal cell. In some embodiments, the methods disclosed herein comprise increasing HDR-mediated genome modification in a fungal cell.

In some embodiments, the fungal cell is a cell derived from a multicellular fungus. In some embodiments, the cell is an ascomycete cell. In some embodiments, the cell is a single-celled fungus. In some embodiments, the cell is a yeast cell. In some embodiments, the cell is a fungal cell of the genus *Aspergillus, Candida, Cochlobolus, Cryphonectria, Cryptococcus, Epidermophyton, Fusarium, Kluyveromyces, Lachancea, Mucor, Neurospora, Ophiostoma, Penicillium, Pichia, Pneumocystis, Pullularia, Saccharomyces, Schizosaccharomyces, Tolypocladium, Trichoderma, Rhodotorula*, or *Yarrowia*. In some embodiments, the cell is a *Candida* sp. cell, such as a *C. albicans, C. auris, C. dubliniensis, C. glabrata, C. guilliermondii*, or a *C. tropicalis* cell. In some embodiments, the cell is a chytrid fungal cell, i.e., a Chytridiomycota cell. In some embodiments, the cell is a Batrachochytrium sp. cell, such as a *Batrachochytrium dendrobatidis* cell. In some embodiments, the cell is a *Microsporidia* cell, such as a *Glugea* sp. or *Nosema* sp. cell. In some embodiments, the fungal cell is a parasite. In some embodiments, the cell is a *Trichophyton* sp. or *Microsporum* sp. cell, i.e., a member of the genera of fungi that includes the parasitic varieties that cause tinea. In some embodiments, the cell is a filamentous fungal cell, i.e., a cell from a filamentous fungus. In some embodiments, the cell is a *Cryptococcus* sp. cell, such as a *Cryptococcus neoformans* cell. In some embodiments, the cell is a *Botrytis* sp. cell, such as a *Botrytis cinerea, Botrytis allii, Botrytis anthophila, Botrytis elliptica, Botrytis fabae, Botrytis squamosal*, or a *Botrytis tracheiphila* cell.

iv. Other Eukaryotic Cells

In some embodiments, the eukaryotic cell comprising an HDR promoting agent is a microbial eukaryotic cell. Further, the methods of the present disclosure may be used to increase HDR-mediated genome modification in a microbial eukaryotic cell, make a microbial eukaryotic cell having a genomic modification, and/or genetically engineer a microbial eukaryotic cell. In some embodiments, the methods disclosed herein comprise editing a microbial eukaryote. In some embodiments, the methods disclosed herein comprise performing a genome modification in a microbial eukaryote. In some embodiments, the methods disclosed herein comprise modifying a target locus in a microbial eukaryote. In some embodiments, the methods disclosed herein comprise increasing HDR-mediated genome modification in a microbial eukaryote. In some embodiments, the cell is a microbial eukaryote. In some embodiments, the cell is a cell of a single-celled eukaryotic organism. In some embodiments, the cell is a protozoa cell. In some embodiments, the cell is a protist. In some embodiments, the cell is an infectious microbial eukaryote. In some embodiments, the cell is a parasitic microbial eukaryote. In some embodiments, the cell is a Giardia sp. cell, such as a *G. lamblia, G. muris, G. ardeae, G. psittaci, G. agilis* or *G. microti* cell. In some embodiments, the cell is a *Plasmodium* sp. cell, such as a *P. vivax, P. falciparum, P. malariae, P. ovale*, or *P. knowlesi* cell. In some embodiments, the cell is a kinetoplastid cell. In some embodiments, the cell is a *Trypanosoma* sp. cell, such as a *Trypanosoma cruzi* or *Trypanosoma brucei* cell.

In some embodiments, the cell is an algal cell. In some embodiments, the algal cell is of a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Fragilaropsis, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria, or Volvox*. In some embodiments, the cell is diatom. Diatoms include members of the genera *Achnanthes, Amphora, Chaetoceros, Coscinodiscus, Cylindrotheca, Cyclotella, Cymbella, Fragilaria, Fragilaropsis, Hantzschia, Navicula, Nitzschia, Pseudo-Nitzschia, Phaeodactylum, Psammodictyon, Skeletonema, Thalassionema, and Thalassiosira*. In some embodiments, the cell is a eustigmatophyte such as a *Nannochloropsis* species or a species of *Monodus, Pseudostaurastrum, Vischeria*, and *Eustigmatos*. In some embodiments, the cell is an algal cell of the genus *Nannochloropsis* such as, but are not limited to, *N. gaditana, N. granulata, N. limnetica, N. oceanica, N. oculata*, and *N. salina*.

In some embodiments, the cell is a heterokont. For example, heterokonts include not only eustigmatophytes and diatoms such as those listed above but also chytrid species, including labrinthulids and thraustochytrids. In some embodiments, the cell is of a heterokont species including, but are not limited to, *Bacillariophytes, Eustigmatophytes, Labrinthulids*, and *Thraustochytrids*. In some embodiments, the cell is of a species of Labryinthula, *Labryinthuloides, Thraustochytrium, Schizochytrium, Aplanochytrium, Aurantiochytrium, Japonochytrium, Diplophrys, or Ulkenia*. For example, the strain may be a species of *Thraustochytrium, Schizochytrium, Oblongichytrium, or Aurantiochytrium*. In some embodiments, the cell is an opisthokont. In some embodiments, the cell is a choanoflagellate. In some embodiments, the cell is amesomycetozoea (e.g., Sphaeroforma). In some embodiments, the cell is a unikont. In some embodiments, the cell is an amoebozoa. In some embodiments, the cell is of the genus *Acanthamoeba, Amoeba, Chaos, Dictyostelium Entamoeba*, or *Pelomyxa*.

v. Compositions of Cells

Provided herein are compositions of cells. In one aspect, the methods provided herein may be used to produce a composition of eukaryotic cells. In some embodiments, the composition of eukaryotic cells may be comprised of any of the cells described herein, e.g., plant, animal, fungal, or other eukaryotic cells. In some embodiments, the methods disclosed herein comprise editing a population of cells. In some embodiments, the methods disclosed herein comprise producing an edited population of cells. In some embodiments, the methods disclosed herein comprising producing an edited population of cells, wherein the proportion of edited cells in the population is about any one of 2-, 3—, 4-, 5-, 6-, 7-, 8-, 9-, 10-, 11-, 12-, 13-, 14-, 15-, 16-, 17-, 18-, 20-, 25-, 30-fold higher than that of a population of cells edited in the absence of HDR promoting agents, including any value or range between these values. In some embodiments, the methods disclosed herein comprising producing an edited population of cells, wherein the proportion of edited cells in the population is 10-fold higher than that of a population of cells edited in the absence of HDR promoting agents.

In some embodiments, provided herein are compositions clonal subpopulations of cells used in the methods provided herein. In some embodiments, the clonal subpopulation is a subpopulation of a cell line. In some embodiments, the clonal subpopulation is a subpopulation of cells derived from an individual. In some embodiments, the clonal cell subpopulation is a population of cells derived from a single cell. In some embodiments, the clonal cell subpopulation has the same genetic and epigenetic profile.

In some embodiments, the methods disclosed herein comprise performing a genome modification in a population of cells. In some embodiments, the methods disclosed herein comprise producing a composition of cells with a genome modification. In some embodiments, the methods disclosed herein comprising producing a composition of cells with a genome modification, wherein the proportion of cells in the population with the genome modification is 2-, 3-, 4-, 5-, 6-, 7-, 8-, 9-, 10-, 11-, 12-, 13-, 14-, 15-, 16-, 17-, 18-, 20-, 25-, 30-fold higher than that of a population of cells modified in the absence of HDR promoting agents, including any value or range between these values. In some embodiments, the methods disclosed herein comprise modifying a target locus in a population of cells. In some embodiments, the methods disclosed herein comprise producing a population of cells with a modified target locus. In some embodiments, the methods disclosed herein comprise producing a population of cells with a modified target locus, wherein the proportion of cells in the population with the modified target locus is 2-, 3-, 4-, 5-, 6-, 7-, 8-, 9-, 10-, 11-, 12-, 13-, 14-, 15-, 16-, 17-, 18-, 20-, 25-, 30-fold higher than that of a population of cells modified in the absence of HDR promoting agents, including any value or range between these values.

E. Kits

The methods of this invention can be provided in the form of a kit. In some embodiments, the kit comprises a nucleic acid encoding an HDR promoting agent. In some embodiments, the kit comprises nucleic acids encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB) and instructions for use. In some embodiments, the kit provides a vector comprising the nucleic acids. In some embodiments, the kit is used to modify a target editing site of the cell using the donor template DNA molecule. In some embodiments, the kit comprises any of the vectors described herein. In some embodiments, the kit comprises vectors for increasing HDR-mediated genome modification of a target editing site of a eukaryotic cell genome, such as a plant or mammalian cell genome. In some embodiments, the kit comprises vectors for increasing HDR-mediated genome modification of a target editing site in a plant cell. In some embodiments, the kit comprises vectors for increasing HDR-mediated genome modification of a target editing site in a mammalian cell.

In some embodiments, the kit comprises instructions. In some embodiments, the instructions include instructions on transforming a cell with the nucleic acids. In some embodiments, the instructions include instructions on detecting the presence of the nucleic acids in the cell. In some embodiments, the instructions include instructions on assessing the effects of the nucleic acids in the cell.

In some embodiments, the kit comprises an agent for detecting genetically engineered cells. In some embodiments, the kit comprises instructions for using the agent to detect genetically engineered cells. In some embodiments, the agent for detecting genetically engineered cells is an assay to assess the genome of the cells, such as a PCR assay, an RT-qPCR assay, a Southern blot, or a sequencing assay. In some embodiments, the agent for detecting genetically engineered cells is a set of oligonucleotide primers, wherein certain pairs of primers specifically amplify the genetic modification, or the wild-type target locus. In some embodiments, detection of the genetically engineered cells is performed using a reporter, such as a fluorescent reporter, a transcriptional reporter, a colorimetric reporter, or a chemiluminescent reporter. Accordingly, in some embodiments, the agent for detecting genetically engineered cells is a means for detecting the reporter.

In some embodiments, provided herein is a kit for increasing Homology Directed Repair (HDR)-mediated genome modification of a target editing site of a eukaryotic cell genome, such as a plant or mammalian cell genome. In some embodiments, the kit comprises nucleic acids encoding genome-editing molecules and HDR promoting agents. In some embodiments, the genome editing molecules comprise: (i) at least one sequence-specific endonuclease which cleaves a DNA sequence in the target editing site or at least one polynucleotide encoding the sequence-specific endonuclease; and (ii) a donor template DNA molecule having homology to the target editing site. In some embodiments, the HDR promoting agents comprise a single-stranded DNA annealing protein (SSAP), an exonuclease which can at least partially convert a double stranded DNA substrate to a single stranded DNA product, and a single stranded DNA binding protein (SSB). In some embodiments, the genome editing molecules and HDR promoting agents provide for modification of the target editing site of the eukaryotic cell genome with the donor template polynucleotide by HDR at a frequency that is increased in comparison to a control. In some embodiments, the kit comprises an agent for measuring the level of HDR-mediated genome modification of the target editing site.

In some embodiments, provided herein is a kit for making a eukaryotic cell having a genomic modification. In some embodiments, the kit comprises nucleic acids encoding genome editing molecules and Homology Directed Repair (HDR) promoting agents, wherein the genome editing molecules comprise: (i) at least one sequence-specific endonuclease which cleaves a DNA sequence in the target editing site or at least one polynucleotide encoding the sequence-specific endonuclease and a donor template DNA molecule having homology to the target editing site; and wherein the HDR promoting agents comprise a single-stranded DNA annealing protein (SSAP), an exonuclease which can at least partially convert a double stranded DNA substrate to a single stranded DNA product, and a single stranded DNA binding protein (SSB);whereby the genome editing molecules and HDR promoting agents provide for modification of the target editing site of the eukaryotic cell genome with the donor template polynucleotide by HDR at a frequency that is increased in comparison to a control. In some embodiments, the kit provides a means of isolating or propagating a eukaryotic cell comprising the genome modification, thereby making the eukaryotic cell having a genomic modification. In some embodiments, the kit comprises an agent for detecting the presence of the genome modification of the target editing site.

In some embodiments, provided herein is a kit for a method of genetic engineering of a eukaryotic cell. In some embodiments, the kit comprises nucleic acids encoding: i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB). In some embodiments, the kit comprises an agent for detecting genetic engineering of the target editing site.

EMBODIMENTS

Various embodiments of the eukaryotic cells (e.g., plant cells and mammalian cells), systems, and methods provided herein are included in the following non-limiting list of embodiments.

1. A method for increasing Homology Directed Repair (HDR)-mediated genome modification of a target editing site of a eukaryotic cell genome, comprising:
   providing genome-editing molecules and HDR promoting agents to a eukaryotic cell, wherein the genome editing molecules comprise: (i) at least one sequence-specific endonuclease which cleaves a DNA sequence in the target editing site or at least one polynucleotide encoding the sequence-specific endonuclease; and (ii) a donor template DNA molecule having homology to the target editing site; and wherein the HDR promoting agents comprise a single-stranded DNA annealing protein (SSAP), an exonuclease which can at least partially convert a double stranded DNA substrate to a single stranded DNA product, and a single stranded DNA binding protein (SSB);
   whereby the genome editing molecules and HDR promoting agents provide for modification of the target editing site of the eukaryotic cell genome with the donor template polynucleotide by HDR at a frequency that is increased in comparison to a control.

2. The method of embodiment 1, wherein the sequence-specific endonuclease comprises an RNA-guided nuclease or a polynucleotide encoding an RNA-guided nuclease and a guide RNA or a polynucleotide encoding a guide RNA.
3. The method of embodiment 2, wherein the RNA-guided nuclease comprises an RNA-guided DNA endonuclease, a type II Cas nuclease, a Cas9 nuclease, a type V Cas nuclease, a Cas12a nuclease, a Cas12b nuclease, a Cas12c nuclease, a CasY nuclease, a CasX nuclease, or an engineered nuclease.
4. The method of embodiment 1, wherein the sequence-specific endonuclease comprises a zinc-finger nuclease (ZFN), a transcription activator-like effector nuclease (TAL-effector nuclease), Argonaute, a meganuclease, or engineered meganuclease.
5. The method of embodiment 1, wherein the genome editing molecules comprise one or more sequence-specific endonucleases or sequence-specific endonucleases and guide RNAs that cleave a single DNA strand at two distinct DNA sequences in the target editing site.
6. The method of embodiment 5, wherein the sequence-specific endonucleases comprise at least one Cas9 nickase, Cas12a nickase, Cas12i, a zinc finger nickase, a TALE nickase, or a combination thereof.
7. The method of embodiment 5, wherein the sequence-specific endonucleases comprise Cas9 and/or Cas12a and the guide RNA molecules have at least one base mismatch to DNA sequences in the target editing site.
8. The method of embodiment 1, wherein the donor DNA molecule is provided on a circular DNA vector, geminivirus replicon, or as a linear DNA fragment.
9. The method of any one of embodiments 1 to 8, wherein the donor DNA molecule is flanked by copies of an endonuclease recognition sequence.
10. The method of any one of embodiments 1 to 9, wherein the sequence-specific endonuclease comprises an RNA-guided nuclease and the target editing site comprises a PAM sequence and a sequence that is complementary to the guide RNA and located immediately adjacent to a protospacer adjacent motif (PAM) sequence.
11. The method of any one of embodiments 1 to 10, wherein the sequence-specific endonuclease provides a 5' overhang at the target editing site following cleavage.
12. The method of any one of embodiments 1 to 11, wherein the SSAP provides for DNA strand exchange and base pairing of complementary DNA strands of homologous DNA molecules.
13. The method of any one of embodiments 1 to 12, wherein the SSAP comprises an RecT/Redβ-, ERF-, or RAD52-family protein.
14. The method of embodiment 13, wherein the RecT/Redβ-family protein comprises a Rac bacterial prophage RecT protein, a bacteriophage λ beta protein, a bacteriophage SPP1 35 protein, a related protein with equivalent SSAP activity, or a protein having at least 70%, 75%, 80%, 85%, 90%, 95%, or 99% sequence identity to SEQ ID NO: 1, 2, or 3.
15. The method of embodiment 13, wherein the ERF-family protein comprises a bacteriophage P22 ERF protein, a functionally related protein, or a protein having at least 70%, 75%, 80%, 85%, 90%, 95%, or 99% sequence identity to SEQ ID NO: 4.
16. The method of embodiment 13, wherein the RAD52-family protein comprises a *Saccharomyces cerevisiae* Rad52 protein. a *Schizosaccharomyces pombe* Rad22 protein, *Kluyveromyces lactis* Rad52 protein, a functionally related protein, or a protein having at least 70%, 75%, 80%, 85%, 90%, 95%, or 99% sequence identity to SEQ ID NO: 5, 6, or 7.
17. The method of any one of embodiments 1 to 16, wherein a linear dsDNA molecule is a preferred substrate of the exonuclease.
18. The method of embodiment 17, wherein a linear dsDNA molecule comprising a phosphorylated 5' terminus is a preferred substrate of the exonuclease.
19. The method of any one of embodiments 1 to 16, wherein the exonuclease has 5' to 3' exonuclease activity and can recognize a blunt ended dsDNA substrate, a dsDNA substrate having an internal break in one strand, a dsDNA substrate having a 5' overhang, and/or a dsDNA substrate having a 3' overhang.
20. The method of any one of embodiments 1 to 16, wherein the exonuclease has 3' to 5' exonuclease activity and can recognize a blunt ended dsDNA substrate, a dsDNA substrate having an internal break in one strand, a dsDNA substrate having a 5' overhang, and/or a dsDNA substrate having a 3' overhang.
21. The method of any one of embodiments 1 to 16, wherein the exonuclease comprises a bacteriophage lambda exo protein, an Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, Exonuclease III, a Trex2 exonuclease, a related protein with equivalent exonuclease activity, or a protein having at least 70%, 75%, 80%, 85%, 90%, 95%, or 99% sequence identity to SEQ ID NO: 8, 9, 136, 137, 138, 139, 140, 141, 142, 143, 144, or 145.
22. The method of any one of embodiments 1, 5, or 6, wherein the exonuclease comprises a T7 phage exonuclease, *E. coli* Exonuclease III, a related protein with equivalent exonuclease activity, or a protein having at least 70%, 75%, 80%, 85%, 90%, 95%, or 99% sequence identity to SEQ ID NO: 143 or 144.
23. The method of any one of embodiments 1 to 22, wherein the single stranded DNA binding protein (SSB) and the SSAP are obtained from the same host organism.
24. The method of any one of embodiments 1 to 23, wherein the single stranded DNA binding protein (SSB) is a bacterial SSB or optionally an Enterobacteriaceae sp. SSB.
25. The method of embodiment 24, wherein the SSB is an *Escherichia* sp., a *Shigella* sp., an *Enterobacter* sp., a *Klebsiella* sp., a *Serratia* sp., a *Pantoea* sp., or a *Yersinia* sp. SSB.
26. The method of any one of embodiments 1 to 23, wherein the SSB comprises a protein having at least 70%, 75%, 80%, 85%, 90%, 95%, or 99% sequence identity to SEQ ID NO:31, 34-131, or 132.
27. The method of any one of embodiments 1 to 26, wherein the frequency of HDR is increased by at least 2-fold in comparison to a control method wherein a control eukaryotic cell is provided with the genome editing molecules but is not exposed to at least one of said HDR promoting agents.
28. The method of any one of embodiments 1 to 26, wherein the frequency of non-homologous end-joining (NHEJ) is maintained or decreased by at least 2-fold in comparison to a control method wherein a control eukaryotic cell is provided with the genome editing molecules but is not exposed to at least one of said HDR promoting agents.

29. The method of any one of embodiments 1 to 28, wherein the SSAP, the exonuclease, and/or the SSB protein further comprise an operably linked nuclear localization signal (NLS) and/or a cell-penetrating peptide (CPP).

30. The method of any one of embodiments 1 to 29, wherein the SSAP, the exonuclease, and/or the SSB are provided to the cell as polyproteins comprising protease recognition sites or self-processing protein sequences inserted between the SSAP, the exonuclease, and/or the SSB.

31. The method of any one of embodiments 1 to 30, where the eukaryotic cell is a mammalian cell or a plant cell.

32. The method of embodiment 31, wherein the plant cell is haploid, diploid, or polyploid.

33. The method of embodiment 32, wherein the plant cell is in a culture medium, in a plant, or in a plant tissue.

34. The method of any one of embodiments 31-33, wherein the cell is a plant cell and the SSAP, the exonuclease, and/or the single stranded DNA binding protein further comprise an operably linked nuclear localization signal (NLS) selected from the group consisting of SEQ ID NO: 10, SEQ ID NO: 11, SEQ ID NO: 12, SEQ ID NO: 13, SEQ ID NO: 14, SEQ ID NO: 15, and SEQ ID NO: 16.

35. The method of any one of embodiments 31 to 34, further comprising the step of isolating and/or growing a plant cell, propagule, or plant obtained from the plant cell comprising the genome modification, wherein the genome of the plant cell, propagule, or plant comprises the genome modification.

36. A system for increasing Homology Directed Repair (HDR)-mediated genome modification of a target editing site of a eukaryotic cell genome, comprising:

(a) a eukaryotic cell;

(b) HDR promoting agents comprising a single-stranded DNA annealing protein (SSAP), an exonuclease which can at least partially convert a double stranded DNA substrate to a single stranded DNA product, and a single stranded DNA binding protein (SSB); and (c) genome editing molecule(s) comprising at least one sequence-specific endonuclease which cleaves a DNA sequence in the target editing site or at least one polynucleotide encoding the sequence-specific endonuclease and a donor template DNA molecule having homology to the target editing site;

wherein the eukaryotic cell is associated with, contacts, and/or contains and effective amount of the HDR promoting agents and the genome editing molecule (s).

37. The system of embodiment 36, wherein the genome editing molecules and/or sequence-specific endonuclease comprise an RNA-guided nuclease or a polynucleotide encoding an RNA-guided nuclease and a guide RNA or a polynucleotide encoding a guide RNA.

38. The system of embodiment 37, wherein the RNA-guided nuclease comprises an RNA-guided DNA endonuclease, a type II Cas nuclease, a Cas9 nuclease, a type V Cas nuclease, a Cas12a nuclease, a Cas12b nuclease, a Cas12c nuclease, a CasY nuclease, a CasX nuclease, or an engineered nuclease.

39. The system of embodiment 36, wherein the sequence-specific endonuclease comprises a zinc-finger nuclease (ZFN), a transcription activator-like effector nuclease (TAL-effector nuclease), Argonaute, a meganuclease, or engineered meganuclease.

40. The system of embodiment 36, wherein the genome editing molecules comprise one or more sequence-specific endonucleases or sequence-specific endonucleases and guide RNAs that cleave a single DNA strand at two distinct DNA sequences in the target editing site.

41. The system of embodiment 40, wherein the sequence-specific endonucleases comprise at least one Cas9 nickase, Cas12a nickase, Cas12i, a zinc finger nickase, a TALE nickase, or a combination thereof.

42. The system of embodiment 40, wherein the sequence-specific endonucleases comprise Cas9 and/or Cas12a and the guide RNA molecules have at least one base mismatch to DNA sequences in the target editing site.

43. The system of embodiment 36, wherein the donor DNA molecule is provided on a plasmid or a geminivirus genome.

44. The system of any one of embodiments 36 to 43, wherein the donor DNA molecule is flanked by an endonuclease recognition sequence.

45. The system of any one of embodiments 36 to 44, wherein the sequence-specific endonuclease comprises an RNA-guided nuclease and the target editing site comprises a PAM sequence and a sequence that is complementary to the guide RNA and located immediately adjacent to the PAM sequence.

46. The system of any one of embodiments 36 to 45, wherein the sequence-specific endonuclease provides a 5' overhang at the target editing site following cleavage.

47. The system of any one of embodiments 36 to 46, whereby the genome editing molecules and HDR promoting agents provide for modification of the target editing site of the eukaryotic cell genome with the donor template polynucleotide by HDR at a frequency that is increased by at least 2-fold in comparison to a control.

48. The system of any one of embodiments 36 to 47, wherein the SSAP provides for DNA strand exchange and base pairing of complementary DNA strands of homologous DNA molecules.

49. The system of embodiment 36 or 48, wherein the SSAP comprises an RecT/Redβ-, ERF-, or RAD52-family protein.

50. The system of embodiment 49, wherein the RecT/Redβ-family protein comprises a Rac bacterial prophage RecT protein, a bacteriophage λ beta protein, a bacteriophage SPP1 35 protein, or related protein with equivalent SSAP activity.

51. The system of embodiment 49, wherein the RecT/Redβ-family protein comprises a bacteriophage λ beta protein, a bacteriophage SPP1 35 protein, a Rac bacterial prophage RecT protein, or related protein with equivalent SSAP activity.

52. The system of embodiment 49 wherein the RecT/Redβ-family protein comprises a protein having at least 70%, 75%, 80%, 85%, 90%, 95%, or 99% sequence identity to SEQ ID NO: 1, 2, or 3.

53. The system of embodiment 49, wherein the ERF-family protein comprises a bacteriophage P22 ERF protein, a functionally related protein, or a protein having at least 70%, 75%, 80%, 85%, 90%, 95%, or 99% sequence identity to SEQ ID NO: 4.

54. The system of embodiment 49, wherein the RAD52-family protein comprises a *Saccharomyces cerevisiae*

Rad52 protein. a *Schizosaccharomyces pombe* Rad22 protein, *Kluyveromyces lactis* Rad52 protein, a functionally related protein, or a protein having at least 70%, 75%, 80%, 85%, 90%, 95%, or 99% sequence identity to SEQ ID NO: 5, 6, or 7.

55. The system of any one of embodiments 36 to 54, wherein a linear dsDNA molecule is a preferred substrate of the exonuclease.

56. The system of any one of embodiments 36 to 54, wherein a linear dsDNA molecule comprising a phosphorylated 5' terminus is a preferred substrate of the exonuclease.

57. The system of any one of embodiments 36 to 54, wherein the exonuclease has 5' to 3' exonuclease activity and can recognize a blunt ended dsDNA substrate, a dsDNA substrate having an internal break in one strand, a dsDNA substrate having a 5' overhang, and/or a dsDNA substrate having a 3' overhang.

58. The system of any one of embodiments 36 to 54, wherein the exonuclease has 3' to 5' exonuclease activity and can recognize a blunt ended dsDNA substrate, a dsDNA substrate having an internal break in one strand, a dsDNA substrate having a 5' overhang, and/or a dsDNA substrate having a 3' overhang.

59. The system of any one of embodiments 36 to 58, wherein the exonuclease comprises a bacteriophage lambda exo protein, an Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, *E. coli* Exonuclease III, a mammalian Trex2 exonuclease, a related protein with equivalent exonuclease activity, or a protein having at least 70%, 75%, 80%, 85%, 90%, 95%, or 99% sequence identity to SEQ ID NO: 8, 9, 136, 137, 138, 139, 140, 141, 142, 143, 144, or 145.

60. The system of any one of embodiments 36, 40, or 41, wherein the exonuclease comprises a T7 phage exonuclease, *E. coli* Exonuclease III, a related protein with equivalent exonuclease activity, or a protein having at least 70%, 75%, 80%, 85%, 90%, 95%, or 99% sequence identity to SEQ ID NO: 143 or 144.

61. The system of any one of embodiments 36 to 60, wherein the single stranded DNA binding protein (SSB) and the SSAP are obtained from the same host organism.

62. The system of any one of embodiments 36 to 61, wherein the single stranded DNA binding protein (SSB) is a bacterial SSB or optionally an Enterobacteriaceae sp. SSB.

63. The system of embodiment 62, wherein the SSB is an *Escherichia* sp., a *Shigella* sp., an *Enterobacter* sp., a *Klebsiella* sp., a *Serratia* sp., a *Pantoea* sp., or a *Yersinia* sp. SSB.

64. The system of any one of embodiments 36 to 63, wherein the SSB comprises a protein having at least 70%, 75%, 80%, 85%, 90%, 95%, or 99% sequence identity to SEQ ID NO: 31, 34-131, or 132.

65. The system of any one of embodiments 36 to 64, wherein the frequency of HDR is increased by at least 2-fold in comparison to a control system wherein a control eukaryotic cell is provided with the genome editing molecules but is not exposed to at least one of said HDR promoting agents.

66. The system of any one of embodiments 36 to 64, wherein the frequency of non-homologous end-joining (NHEJ) is maintained or decreased by at least 2-fold in comparison to a control system wherein a control eukaryotic cell is provided with the genome editing molecules but is not exposed to at least one of said HDR promoting agents.

67. The system of any one of embodiments 36 to 66, wherein the SSAP, the exonuclease, and/or the single stranded DNA binding protein further comprise an operably linked nuclear localization signal (NLS) and/or a cell-penetrating peptide (CPP).

68. The system of any one of embodiments 36 to 64, wherein the SSAP, the exonuclease, and/or the SSB are provided to the cell as polyproteins comprising protease recognition sites or self-processing protein sequences inserted between the SSAP, the exonuclease, and/or the SSB.

69. The system of any one of embodiments 36 to 68, where the eukaryotic cell is a mammalian cell or a plant cell.

70. The system of embodiment 69, wherein the plant cell is haploid, diploid, or polyploid.

71. The system of embodiment 69 or 70, wherein the plant cell is in a culture medium, in a plant, or in a plant tissue.

72. The system of embodiment 69, 70, or 71, wherein the cell is a plant cell and the SSAP, the exonuclease, and/or the single stranded DNA binding protein further comprise an operably linked nuclear localization signal (NLS) selected from the group consisting of SEQ ID NO: 10, SEQ ID NO: 11, SEQ ID NO: 12, SEQ ID NO: 13, SEQ ID NO: 14, SEQ ID NO: 15, and SEQ ID NO: 16.

73. The system of any one of embodiments 69 to 72, wherein the system provides for isolating and/or growing a plant cell, propagule, or plant obtained from the plant cell comprising the genome modification, and wherein the genome of the plant cell, propagule, or plant comprises the genome modification.

74. A method for making a eukaryotic cell having a genomic modification, comprising:

(a) providing genome editing molecules and Homology Directed Repair (HDR) promoting agents to a eukaryotic cell, wherein the genome editing molecules comprise: (i) at least one sequence-specific endonuclease which cleaves a DNA sequence in the target editing site or at least one polynucleotide encoding the sequence-specific endonuclease and a donor template DNA molecule having homology to the target editing site; and wherein the HDR promoting agents comprise a single-stranded DNA annealing protein (SSAP), an exonuclease which can at least partially convert a double stranded DNA substrate to a single stranded DNA product, and a single stranded DNA binding protein (SSB);whereby the genome editing molecules and HDR promoting agents provide for modification of the target editing site of the eukaryotic cell genome with the donor template polynucleotide by HDR at a frequency that is increased in comparison to a control; and (b) isolating or propagating a eukaryotic cell comprising the genome modification, thereby making the eukaryotic cell having a genomic modification.

75. The method of embodiment 74, wherein the genome editing molecules and/or sequence-specific endonuclease comprise an RNA-guided nuclease or a polynucleotide encoding an RNA-guided nuclease and a guide RNA or a polynucleotide encoding a guide RNA.

76. The method of embodiment 75, wherein the RNA-guided nuclease comprises an RNA-guided DNA endonuclease, a type II Cas nuclease, a Cas9 nuclease, a type V Cas nuclease, a Cas12a nuclease, a Cas12b nuclease, a Cas12c nuclease, a CasY nuclease, a CasX nuclease, or an engineered nuclease 77. The method of embodiment 74, wherein the sequence-specific endonuclease comprises a zinc-finger nuclease (ZFN), a transcription activator-like effector nuclease (TAL-effector nuclease), Argonaute, a meganuclease, or engineered meganuclease.

78. The method of embodiment 74, wherein the genome editing molecules comprise one or more sequence-specific endonucleases or sequence-specific endonucleases and guide RNAs that cleave a single DNA strand at two distinct DNA sequences in the target editing site.

79. The method of embodiment 78, wherein the sequence-specific endonucleases comprise at least one Cas9 nickase, Cas12a nickase, Cas12i, a zinc finger nickase, a TALE nickase, or a combination thereof.

80. The method of embodiment 78, wherein the sequence-specific endonucleases comprise Cas9 and/or Cas12a and the guide RNA molecules have at least one base mismatch to DNA sequences in the target editing site.

81. The method of embodiment 74, wherein the donor DNA molecule is provided in a plasmid or a geminivirus genome.

82. The method of any one of embodiments 74 to 81, wherein the donor DNA molecule is flanked by an endonuclease recognition sequence.

83. The method of any one of embodiments 74 to 82, wherein the sequence-specific endonuclease comprises an RNA-guided nuclease and the target editing site comprises a PAM sequence and a sequence that is complementary to the guide RNA and located immediately adjacent to the PAM sequence.

84. The method of any one of embodiments 74 to 83, wherein the sequence-specific endonuclease provides a 5' overhang at the target editing site following cleavage.

85. The method of any one of embodiments 74 to 84, wherein the SSAP provides for DNA strand exchange and base pairing of complementary DNA strands of homologous DNA molecules.

86. The method of any one of embodiments 74 to 85, wherein the SSAP comprises an RecT/Redβ-, ERF-, or RAD52-family protein.

87. The method of embodiment 86, wherein the RecT/Redβ-family protein comprises a Rac bacterial prophage RecT protein, a bacteriophage λ beta protein, a bacteriophage SPP1 35 protein, or related protein with equivalent SSAP activity.

88. The method of embodiment 86, wherein the RecT/Redβ-family protein comprises a protein having at least 70%, 75%, 80%, 85%, 90%, 95%, or 99% sequence identity to SEQ ID NO: 1, 2, or 3.

89. The method of embodiment 86, wherein the ERF-family protein comprises a bacteriophage P22 ERF protein, a functionally related protein, or a protein having at least 70%, 75%, 80%, 85%, 90%, 95%, or 99% sequence identity to SEQ ID NO: 4.

90. The method of embodiment 86, wherein the RAD52-family protein comprises a *Saccharomyces cerevisiae* Rad52 protein. a *Schizosaccharomyces pombe* Rad22 protein, *Kluyveromyces lactis* Rad52 protein, a functionally related protein, or a protein having at least 70%, 75%, 80%, 85%, 90%, 95%, or 99% sequence identity to SEQ ID NO: 5, 6, or 7.

91. The method of any one of embodiments 74 to 90, wherein a linear dsDNA molecule is a preferred substrate of the exonuclease.

92. The method of any one of embodiments 74 to 91, wherein a linear dsDNA molecule comprising a phosphorylated 5' terminus is a preferred substrate of the exonuclease.

93. The method of any one of embodiments 74 to 92, wherein the exonuclease has 5' to 3' exonuclease activity and can recognize a blunt ended dsDNA substrate, a dsDNA substrate having an internal break in one strand, a dsDNA substrate having a 5' overhang, and/or a dsDNA substrate having a 3' overhang.

94. The method of any one of embodiments 74 to 92, wherein the exonuclease has 3' to 5' exonuclease activity and can recognize a blunt ended dsDNA substrate, a dsDNA substrate having an internal break in one strand, a dsDNA substrate having a 5' overhang, and/or a dsDNA substrate having a 3' overhang.

95. The method of any one of embodiments 74 to 90, wherein the exonuclease comprises a bacteriophage lambda exo protein, an Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, *E. coli* Exonuclease III, a mammalian Trex2 exonuclease, a related protein with equivalent exonuclease activity, or a protein having at least 70%, 75%, 80%, 85%, 90%, 95%, or 99% sequence identity to SEQ ID NO: 8, 9, 136, 137, 138, 139, 140, 141, 142, 143, 144, or 145.

96. The method of embodiment 74, 78, or 79, wherein the exonuclease comprises a T7 phage exonuclease, *E. coli* Exonuclease III, a related protein with equivalent exonuclease activity, or a protein having at least 70%, 75%, 80%, 85%, 90%, 95%, or 99% sequence identity to SEQ ID NO: 143 or 144.

97. The method of any one of embodiments 74 to 96, wherein the single stranded DNA binding protein (SSB) and the SSAP are obtained from the same host organism.

98. The method of any one of embodiments 74 to 97, wherein the single stranded DNA binding protein (SSB) is a bacterial SSB or optionally an Enterobacteriaceae sp. SSB.

99. The method of embodiment 98, wherein the SSB is an *Escherichia* sp., a *Shigella* sp., an *Enterobacter* sp., a *Klebsiella* sp., a *Serratia* sp., a *Pantoea* sp., or a *Yersinia* sp. SSB.

100. The method of any one of embodiments 74 to 99, wherein the SSB comprises a protein having at least 70%, 75%, 80%, 85%, 90%, 95%, or 99% sequence identity to SEQ ID NO: 31, 34-131, or 132.

101. The method of any one of embodiments 74 to 100, wherein the frequency of HDR is increased by at least 2-fold in comparison to a control method wherein a control eukaryotic cell is provided with the genome editing molecules but is not exposed to at least one of said HDR promoting agents.

102. The method of any one of embodiments 74 to 100, wherein the frequency of non-homologous end-joining (NHEJ) is maintained or decreased by at least 2-fold in comparison to a control method wherein a control eukaryotic cell is provided with the genome editing molecules but is not exposed to at least one of said HDR promoting agents.

103. The method of any one of embodiments 74 to 102, wherein the SSAP, the exonuclease, and/or the single stranded DNA binding protein further comprise an operably linked nuclear localization signal (NLS) and/or a cell-penetrating peptide (CPP).

104. The system of any one of embodiments 74 to 103, wherein the SSAP, the exonuclease, and/or the SSB are provided to the cell as polyproteins comprising protease recognition sites or self-processing protein sequences inserted between the SSAP, the exonuclease, and/or the SSB.

105. The method of any one of embodiments 74 to 104, where the eukaryotic cell is a mammalian cell or a plant cell.

106. The method of embodiment 105, wherein the plant cell is haploid, diploid, or polyploid.

107. The method of embodiment 105 or 106, wherein the plant cell is in a culture medium, in a plant, or in a plant tissue.

108. The method of embodiment 105, 106, or 107, wherein the SSAP, the exonuclease, and/or the SSB further comprise an operably linked nuclear localization signal (NLS) selected from the group consisting of SEQ ID NO: 10, SEQ ID NO: 11, SEQ ID NO: 12, SEQ ID NO: 13, SEQ ID NO: 14, SEQ ID NO: 15, and SEQ ID NO: 16.

109. The method of any one of embodiments 105 to 108, further comprising the step of isolating and/or growing a plant cell, propagule, or plant obtained from the plant cell comprising the genome modification, wherein the genome of the plant cell, propagule, or plant comprises the genome modification.

110. The method of any one of embodiments 1-30, the system of any one of embodiments 36 to 68, or the method of any one of embodiments 74-104, wherein the HDR promoting agents, genome-editing molecules and eukaryotic cell or eukaryotic cell comprising the genome modification, are provided in an array comprising a plurality of containers, compartments, or locations and wherein each container, compartment, or location includes the HDR promoting agents, genome-editing molecules and eukaryotic cell or eukaryotic cell comprising the genome modification.

111. A method of genetic engineering of a eukaryotic cell comprising providing to the eukaryotic cell: i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB), wherein the target editing site of the cell is modified by the donor template DNA molecule.

112. The method of embodiment 111, wherein the sequence-specific endonuclease comprise an RNA-guided nuclease or a polynucleotide encoding an RNA-guided nuclease and a guide RNA or a polynucleotide encoding a guide RNA.

113. The method of embodiment 112, wherein the RNA-guided nuclease comprises an RNA-guided DNA endonuclease, a type II Cas nuclease, a Cas9 nuclease, a type V Cas nuclease, a Cas12a nuclease, a Cas12b nuclease, a Cas12c nuclease, a CasY nuclease, a CasX nuclease, Cas12i, Cas14, or an engineered nuclease.

114. The method of embodiment 111, wherein the sequence-specific endonuclease comprises a zinc-finger nuclease (ZFN), a transcription activator-like effector nuclease (TAL-effector nuclease), Argonaute, a meganuclease, or engineered meganuclease.

115. The method of embodiment 111, further comprising a guide RNA, wherein the sequence-specific endonucleases and guide RNAs cleave a single DNA strand at two distinct DNA sequences in the target editing site.

116. The method of embodiment 115, wherein the sequence-specific endonucleases comprise at least one Cas9 nickase, Cas12a nickase, a zinc finger nickase, a TALE nickase, or a combination thereof, wherein the sequence-specific endonuclease is specific for an endonuclease recognition sequence in the target editing site.

117. The method of embodiment 115, wherein the sequence-specific endonucleases comprise Cas9 and/or Cas12a and the guide RNA molecules have at least one base mismatch to DNA sequences in the target editing site.

118. The method of embodiment 111, wherein the donor DNA molecule is provided in a plasmid or a geminivirus genome.

119. The method of embodiment 111, wherein the donor DNA molecule is flanked by an endonuclease recognition sequence.

120. The method of embodiment 111, wherein the SSAP comprises an RecT/Redβ-, ERF-, or RAD52-family protein.

121. The method of embodiment 120, wherein the RecT/Redβ-family protein comprises a Rac bacterial prophage RecT protein, a bacteriophage λ beta protein, a bacteriophage SPP1 35 protein, or related protein with equivalent SSAP activity.

122. The method of embodiment 111, wherein a linear dsDNA molecule is a preferred substrate of the exonuclease.

123. The method of embodiment 111, wherein a linear dsDNA molecule comprising a phosphorylated 5' terminus is a preferred substrate of the exonuclease.

124. The method of embodiment 111, wherein the exonuclease has 5' to 3' exonuclease activity and can recognize a blunt ended dsDNA substrate, a dsDNA substrate having an internal break in one strand, a dsDNA substrate having a 5' overhang, and/or a dsDNA substrate having a 3' overhang.

125. The method of embodiment 111, wherein the exonuclease has 3' to 5' exonuclease activity and can recognize a blunt ended dsDNA substrate, a dsDNA substrate having an internal break in one strand, a dsDNA substrate having a 5' overhang, and/or a dsDNA substrate having a 3' overhang.

126. The method of embodiment 111, wherein the exonuclease comprises a bacteriophage lambda exo protein, an Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, *E. coli* Exonuclease III, a mammalian Trex2 exonuclease, a related protein with equivalent exonuclease activity, or a protein having at least 70%, 75%, 80%, 85%, 90%, 95%, or 99% sequence identity to SEQ ID NO: 8, 9, 136, 137, 138, 139, 140, 141, 142, 143, 144, or 145.

127. The method of embodiment 111, wherein the exonuclease comprises a T7 phage exonuclease, *E. coli* Exonuclease III, a related protein with equivalent exonuclease activity, or a protein having at least 70%, 75%, 80%, 85%, 90%, 95%, or 99% sequence identity to SEQ ID NO: 143 or 144.

128. The method of embodiment 111, wherein the single stranded DNA binding protein (SSB) and the SSAP are obtained from the same host organism.

129. The method of any one of embodiments 111 to 128, where the eukaryotic cell is a mammalian cell or a plant cell.

130. The method of embodiment 129, wherein the plant cell is haploid, diploid, or polyploid.

131. The method of embodiment 130, wherein the plant cell is in a culture medium, in a plant, or in a plant tissue.

132. The method of embodiment 131, further comprising the step of isolating and/or growing a plant cell, propagule, or plant obtained from the plant cell comprising the genome modification, wherein the genome of the plant cell, propagule, or plant comprises the genome modification.

133. The method of any one of embodiments 111-132, wherein one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB) are provided in one or more vectors.

135. The method of embodiment 133, wherein the vector is an *agrobacterium* vector.

136. The method of any one of embodiments 111-132, wherein one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB) are provided by in a chromosome.

137. The method of any one of embodiments 111-132, wherein one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB) are provided by introducing a polypeptide, a DNA, an mRNA, and/or sexual crossing.

138. The method of any one of embodiments 111-132, wherein one or more of the i) at least one sequence-specific endonuclease, ii) the donor template DNA molecule having homology to a target editing site in the eukaryotic cell, iii) the single-stranded DNA annealing protein (SSAP), iv) the exonuclease which can at least partially convert a double stranded DNA substrate to a single stranded DNA product, and v) the single stranded DNA binding protein (SSB) are provided by a progenitor cell comprising one or more of i)-v), wherein the progenitor cell does not comprise at least one of i)-v), wherein the at least one of i)-v) that is not comprised by the progenitor cell is subsequently provided by delivering a polypeptide, a DNA, or an mRNA to the progenitor cell and/or sexual crossing of the progenitor cell.

139. The method of any one of embodiments 111-138, further comprising detecting the modification.

140. The method of embodiment 139, wherein detecting the modification comprises amplicon sequencing.

141. The method of any one of embodiments 111-140, wherein the target editing site is in a protein coding sequence or a promoter.

142. The method of any one of embodiments 111-141, wherein the modification of the target editing site is an insertion, a deletion, or a substitution.

143. The method of any one of embodiments 111-142, wherein the target editing site is a gene encoding an agronomically important trait or a gene involved in a mammalian disease.

144. A method for producing a eukaryotic cell with a genetically modified target editing site comprising:
- (a) providing at least one sequence-specific endonuclease which cleaves a DNA sequence at least one endonuclease recognition sequence in said target editing site or at least one polynucleotide encoding said at least one sequence-specific endonuclease, and
- (b) providing at least one donor molecule comprising at least one double-stranded DNA sequence, wherein (i) said DNA sequence has a homology of at least 90% over a length of at least 50 nucleotides to sequences flanking the target editing site and (ii) wherein said donor sequence comprises at least one modification in comparison to said target editing site; and
- (c) providing at least one Homology Directed Repair (HDR) promoting agent comprising
  - (i) at least one single-stranded DNA annealing protein (SSAP), and
  - (ii) at least one exonuclease which can at least partially convert a double stranded DNA substrate to a single stranded DNA product, and
  - (iii) at least one single stranded DNA binding protein (SSB);

and whereby the at least one sequence-specific endonucleases, the at least one donor molecule, and the at least one HDR promoting agent introduce said modification into said target editing site of said eukaryotic cell; and
- (d) isolating a eukaryotic cell comprising a modification in said target editing site.

145. The method of embodiment 144, wherein the modification in selected from the group consisting of an insertion of one or more nucleotides, a deletion of one or more nucleotides, or a substitution of one or more nucleotides.

146. The method of embodiment 144, wherein a portion of the target editing site is deleted by using two sequence specific cleavages in said target editing site, and is replaced by a sequence provide by the donor molecule.

147. The method any one of embodiments 144-146, wherein said donor sequence is in a vector flanked by endonuclease recognition sequences.

148. The method of any one of embodiments 144-147, further comprises propagating the eukaryotic cell comprising the modification.

149. A method of producing a genetically modified organism comprising the steps of
 (i) producing a genetically modified eukaryotic cell by any of embodiment 144-148, and
 (ii) regenerating said cell into an organism.

150. The organism of embodiment 149, wherein the organism is selected from the group consisting of plants and non-human animals.

151. A composition comprising nucleic acids encoding one or more of i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

152. The composition of embodiment 151, wherein the nucleic acids are in one or more vectors.

153. A vector comprising nucleic acids encoding one or more of i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

154. The vector of embodiment 153, wherein the vector comprises the donor template DNA, the sequence specific endonuclease and a polynucleotide encoding a guide RNA.

155. The vector of embodiment 153, wherein the vector comprises the single-stranded DNA annealing protein (SSAP), the exonuclease which can at least partially convert a double stranded DNA substrate to a single stranded DNA product, and the single stranded DNA binding protein (SSB).

156. The vector of embodiment 153, wherein the vector comprises nucleic acids encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

157. A kit comprising nucleic acids encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB) and instructions for use for genetically engineering a eukaryotic cell.

158. The kit of embodiment 157, wherein the kit comprises a first vector and a second vector, wherein
 i) the first vector comprises nucleic acids comprising the donor template DNA and the sequence specific endonuclease, wherein the sequence-specific endonuclease comprises a polynucleotide encoding an RNA-guided nuclease and a polynucleotide encoding a guide RNA; and
 ii) the second vector comprises the single-stranded DNA annealing protein (SSAP), the exonuclease which can at least partially convert a double stranded DNA substrate to a single stranded DNA product, and the single stranded DNA binding protein (SSB).

159. The kit of any one of embodiments 157-158, further comprising an agent for detecting genetically engineered cells.

160. A cell comprising i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

161. A cell comprising nucleic acids encoding i) at least one sequence-specific endonuclease, ii) a donor template DNA molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB).

162. The cell of embodiment 160 or 161, wherein the cell is a plant or mammalian cell.

163. The cell of any one of embodiments 160-162, wherein the cell is a host cell.

164. A genetically engineered cell produced by the method of any one of embodiments 1-35 or 74-149.

165. A progenitor eukaryotic cell or organism for genetic engineering at a target editing site, comprising a subset of i) at least one sequence-specific endonuclease, ii) a donor template molecule having homology to a target editing site in the eukaryotic cell, iii) a single-stranded DNA annealing protein (SSAP), iv) an exonuclease which can at least partially convert a double stranded DNA substrate to a single stranded DNA product, and v) a single stranded DNA binding protein (SSB), wherein the cell does not comprises at least one of i)-v), wherein providing the cell or organism with the at least one of i)-v) that is not comprised in the progenitor cell or organism results in modification of the target editing site by the donor template molecule.

166. The progenitor eukaryotic cell or organism of embodiment 165, wherein the donor template is a double-stranded DNA molecule.

167. The progenitor cell of embodiment 165, wherein the cell is a germline cell.

168. The progenitor eukaryotic cell or organism of embodiment 165, wherein the progenitor eukaryotic cell is a progenitor plant cell and the at least one of i)-v) that is not comprised by the progenitor plant cell or plant is supplied by transformation.

169. The progenitor organism of embodiment 165, wherein the organism is a plant and wherein the at least one of i)-v) that is not comprised by the progenitor plant is supplied by sexual crossing to a second plant comprising the at least one of i)-v) that is not comprised by the progenitor plant.

170. The progenitor eukaryotic cell of embodiment 165, wherein the progenitor eukaryotic cell is an animal cell, and wherein at least one of i)-v) that is not comprised by the progenitor cell is supplied by transfection.

171. The progenitor organism of embodiment 165, wherein the progenitor organism is a non-human animal and the at least one of i)-v) that is not comprised by the non-human animal is supplied by sexual crossing to a non-human animal comprising the at least one of i)-v) that is not comprised by the non-human animal.

172. The vector according to embodiment 153, wherein the sequence-specific nuclease is operably linked to an inducible promoter.

173. The method of embodiment 111, wherein the sequence-specific endonuclease is a nickase.

EXAMPLES

The examples below are intended to be purely exemplary of the invention and should therefore not be considered to limit the invention in any way. The following examples and detailed description are offered by way of illustration and not by way of limitation.

Example 1. Exonuclease, SSAP, and SSB Expression Vectors and Donor DNA Template Sequences This example describes the construction of plant expression vectors used to express a bacteriophage lambda exonuclease (SEQ ID NO:8), a bacteriophage lambda beta SSAP protein (SEQ ID NO:1), and an *E. coli* SSB (SEQ ID NO:31).

Figure 2:
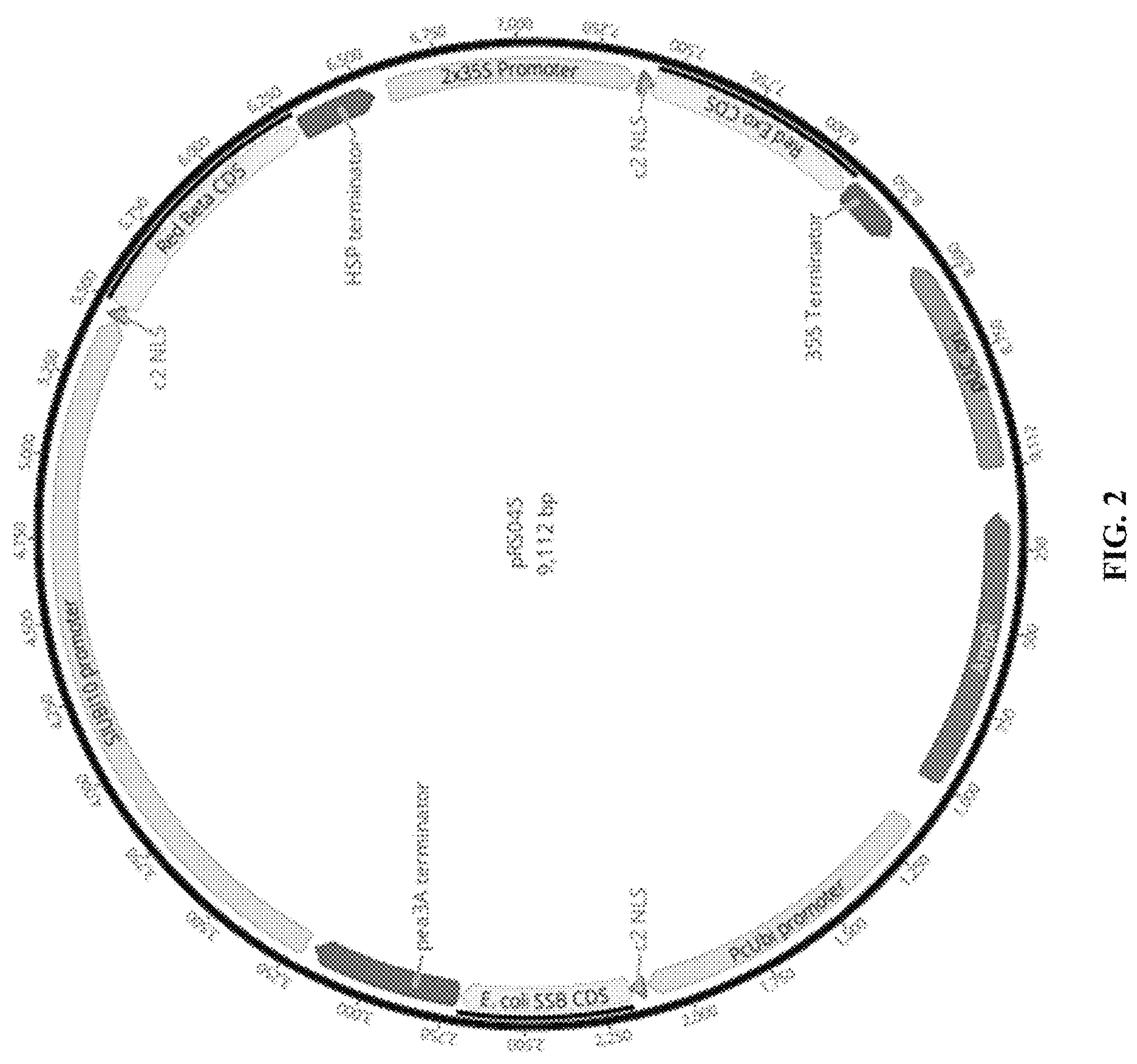
FIG. 2 shows a schematic diagram of the vector pRS045. Length in base pairs is indicated by the labels outside of the vector. Beginning at base pair 1, the vector includes an ampicillin resistance marker (AmpR), HDR promoting agents expression cassette (PcUbi promoter, c2 nuclear localization sequence (NLS) fused to an *E. coli* SSB coding sequence (*E. coli* SSB CDS), pea 3A terminator, tomato S1UBI10 promoter, c2 NLS fused to a SSAP coding sequence (Red Beta CDS), HSP terminator, 2x 35S promoter, c2 NLS fused to an exonuclease coding sequence (Red Exo CDS), and 35S terminator), and pUC origin of replication (pUC ori).

Plant expression constructs for expressing a Bacteriophage lambda exonuclease (SEQ ID NO:8), a bacteriophage lambda beta SSAP protein (SEQ ID NO: 1), and an *E. coli* SSB (SEQ ID NO:31) were constructed. A DNA sequence encoding a tobacco c2 nuclear localization signal (NLS) of SEQ ID NO:15 was operably linked to the DNA sequences encoding the exonuclease, the bacteriophage lambda beta SSAP protein, and the *E. coli* SSB to provide a DNA sequence encoding the c2 NLS-Exo (also known as Red-Exo), c2 NLS lambda beta SSAP (also known as Red-Beta), and c2 NLS-SSB fusion proteins that are set forth in SEQ ID NO: 135, SEQ ID NO: 134, and SEQ ID NO: 133, respectively. DNA sequences encoding the c2 NLS-Exo, c2 NLS lambda beta SSAP, and c2NLSf-SSB fusion proteins were operably linked to a 2x35S, SlUBI10, PcUBI4 promoter and a 35S, AtHSP, pea3A polyadenylation site respectively, to provide the exonuclease, SSAP, and SSB plant cell gene expression cassettes (see FIG. 2).

DNA donor template plasmids that targeted the promoter region of the tomato Antl gene for insertion of a 42 base pair heterologous sequence by HDR were constructed (FIG. 1). The circular DNA donor plasmid included a replacement template with desired insertion region (42 base pairs long) flanked on both sides by homology arms about 600-800 bp in length. The homology arms matched (i.e., were homologous to) gDNA (genomic DNA) regions flanking the target gDNA insertion site. The replacement template region comprising the donor DNA was flanked at each end by DNA sequences identical to the target gDNA sequence recognized by an RNA-guided nuclease. Plant expression cassettes that provided for expression of the RNA-guided sequence-specific endonuclease and a guide RNA complementary to sequences adjacent to the insertion site were also constructed (FIG. 1).

Example 2. Genome Editing Experiments with Tomato Protoplasts

This example describes gene editing in tomato protoplasts with both blunt- and staggered end cutting CAS nucleases in the presence and absence of an exonuclease, SSB, and SSAP.

Tomato protoplasts were isolated, cultivated, and subject to PEG-mediated transfection essentially according to published procedures (Čermák et al. 2017). The transfected materials included plasmids having the donor DNA template region described in Example 1, as well as expressing the gRNAs and Cas polynucleotides as indicated (FIG. 1). Cas polynucleotides were fused to a nuclear localization signal. The gRNA both targets a double strand break into the intended genomic DNA target and releases the replacement template from the donor plasmid (see FIG. 1). Some experiments were carried out with a Cas nuclease which is representative of a CAS nuclease that leaves a blunt end following cleavage of the endonuclease recognition sequence and referred to herein as a CasB nuclease. Other experiments were carried out with Cas nuclease which is representative of a CAS nuclease that leaves a staggered single stranded DNA overhanging end following cleavage of the endonuclease recognition sequence and referred to herein as a CasS nuclease.

After 48 hour of incubation of the protoplasts following transfection, gDNA was extracted from transfected samples and the target locus was amplified with primers complementary to genomic sequences flanking the introduced replacement sequence and the homology arm of the replacement template, and analyzed by amplicon sequencing.

Amplicons were sequenced using paired-end Illumina sequencing. Due to the size of the amplicon, only one read end (Read 1) of the paired-end reads covered the site of interest containing the targeted sequence insertion. Reads of interest (Read 1) were trimmed for quality and aligned to the reference amplicon. The reads had a unique molecular identifier (UMI) tag to distinguish them from some kinds of PCR duplicates, and these reads were de-duplicated from the alignment. The read that mapped to the un-edited genomic sequence (Read 2) was then checked for correct mapping to the genome. Alignments generated from Read Is were analyzed with CrispRVariants, which described and tallied all of the sequence alleles which differed within a 100 bp window centered on the cut site (Lindsay, H. et al. *Nature Biotechnology* 2016 34: 701-702). CrispRVariants reported the frequency of reads of each allele in number of reads of the total alignment. Different sequence alleles were categorized as 1) wildtype sequence, SNPs, or sequencing artifacts, 2) indel mutations, or 3) precise insertion events. CrispRVariants automatically detected SNPs based on the type of mutation and its distance from the defined cut site, an additional filtering steps were used to remove any other sequence aberration that did not involve bases within 5 bp on either side of the predicted cut site. These alleles were placed in category 1. All sequencing alleles which had an insertion or deletion mutation that involved any base within 5 bp on either side of the cut site were determined to be indels and were placed in category 2. Successful precise gene targeting yielded a single CrispRVariants sequence allele which was identifiable by an insertion of the expected size and sequence. In Tables 3-5, below, the frequencies reported for % indel are the sum of all frequencies of all sequencing alleles determined to be indels. The frequencies reported for % o precise are the frequency of the single precise insertion sequencing allele. The denominator for both frequencies is the sum of all reads which aligned to the reference amplicon.

Results of average measurements are summarized in Table 3 below. CasS (1) and CasS (2), were similar treatments, except that 2-fold increase of guide RNA was used in (2) when compared to (1). "Lambda RED" refers to all three HDR promoting agents (the exonuclease, lambda beta SSAP protein, and the SSB). SD=standard deviation.

TABLE 3

| Transfection Components | % indel (NHEJ) | % precise (HDR) | SD indel | SD precise |
|---|---|---|---|---|
| CasB, gRNA, GFP, donor DNA template plasmid + Lambda RED plasmid (all—CasB) | 8.25 | 3.68 | 1.19 | 0.39 |
| CasS (1), 1X gRNA, GFP, donor DNA template plasmid + Lambda RED plasmid (all CasS 1x) | 0.53 | 1.94 | 0.28 | 0.22 |
| CasS (2), 2X gRNA, GFP, donor DNA template plasmid + Lambda RED plasmid (all CasS 2x) | 0.43 | 1.91 | 0.38 | 0.33 |
| CasB, gRNA, GFP, donor DNA template plasmid (no Lambda Red—CasB) (Baseline control) | 29.2 | 0.3 | 1.1 | 0.07 |
| CasS (1), 1X gRNA, GFP, donor DNA template plasmid (no Lambda Red—CasS 1x) (Baseline control) | 6.43 | 0.1 | 0.27 | 0.05 |
| CasS (2), 2X gRNA, GFP, donor DNA template plasmid (no Lambda Red—CasS 2x) (Baseline control) | 5.42 | 0.13 | 0.98 | 0.06 |
| Lambda RED plasmid + donor DNA template, GFP plasmid (no nuclease) | 0.17 | 0.27 | 0.15 | 0.19 |
| Donor DNA template, GFP plasmid (donor only) | 0.54 | 0.22 | 0.62 | 0.18 |
| Lambda RED plasmid + GFP plasmid (Lambda Red only) | 0.51 | 0 | 0.34 | 0 |
| Green fluorescent protein plasmid (GFP only) | 0.02 | 0 | 0.04 | 0 |

Transfection of all three HDR promoting agents (i.e., the SSB, the exonuclease, and the SSAP) greatly enhanced (about 10-fold) the occurrence of THDR for both the CasB blunt end nuclease experiments and the CasS staggered end cutting nuclease. The baseline was measured in the absence of all three HDR promoting agents, when the donor template (DR) was incorporated in only 0.1-0.22% of the genome editing edits. As indicated in Table 3, the samples that did not contain the HDR promoting agents served as the baseline controls.

Eliminating any one or two of the three HDR promoting agents significantly diminished HDR occurrence, although in all cases it was still measurable above the baseline (Table 4).

TABLE 4

| Transfection Components | % indel (NHEJ) | % precise (HDR) | SD indel | SD precise |
|---|---|---|---|---|
| CasB, gRNA, GFP, donor DNA template plasmid + Lambda RED plasmid (all—CasB) | 9.16 | 2.89 | 0.50 | 0.19 |
| Lambda RED plasmid + donor DNA template, GFP plasmid (no nuclease) | 0.04 | 2.11 | 0.03 | 0.78 |
| Red-Beta, Red-Exo, Hyg plasmid + CasB, gRNA, GFP, donor DNA template plasmid (no SSB) | 5.99 | 0.52 | 1.72 | 0.51 |
| Red-Beta, SSB, Hyg plasmid + CasB, gRNA, GFP, donor DNA template plasmid (no Exo) | 11.63 | 0.26 | 0.99 | 0.02 |
| Red-Exo, SSB, GFP plasmid + CasB, gRNA, GFP, donor DNA template plasmid (no Beta) | 10.49 | 0.97 | 1.20 | 0.33 |
| SSB, GFP, Hyg plasmid + CasB, gRNA, GFP, donor DNA template plasmid (SSB only) | 6.71 | 0.27 | 0.29 | 0.13 |
| Red-Exo, GFP plasmid + CasB, gRNA, GFP, donor DNA template plasmid (Exo only) | 12.83 | 0.56 | 1.73 | 0.17 |
| Red-Beta, mCherry, Hyg plasmid + CasB, gRNA, GFP, donor DNA template plasmid (Beta only) | 14.23 | 0.28 | 1.20 | 0.04 |
| mCherry, GFP, Hyg plasmid + CasB, gRNA, GFP, donor DNA template plasmid (CasB + no Lambda Red) (Baseline control) | 14.15 | 0.24 | 1.07 | 0.02 |
| CasB, gRNA, GFP, donor DNA template plasmid (CasB + no Lambda Red) (Baseline control) | 21.17 | 0.41 | 0.39 | 0.12 |
| No transformation | 0.00 | 0.00 | 0.00 | 0.00 |

CasS nuclease-mediated editing with staggered ends at target editing sites produced a higher proportion of precise editing events (HIDR) than CasB nuclease-mediated editing with blunt ends at target editing sites. Accordingly, about 8000 of CasS nuclease-mediated and 30% o of CasB nuclease-mediated editing events were precise HIDR events versus NT-EJ events. The rate of generating NHEJ events was significantly decreased by the presence of the HIDR promoting agents.

Example 3. Genome Editing Experiments with Maize Protoplasts

This example describes gene editing in maize protoplasts in the presence and absence of an exonuclease, SSB, and SSAP, with blunt end cutting CAS nucleases inducing two double strand breaks in close proximity, to induce sequence replacement rather than insertion.

DNA donor template plasmids are constructed that target the coding region of the maize PYL-E gene for HIDR-mediated replacement of a 110 base pair sequence to introduce 7 base edits resulting in synonymous mutations and disruption of the two PAM sites targeted by the two gRNAs and 1 base edit resulting in an amino acid change. The circular DNA donor plasmid includes a replacement template with the desired modification (110 base pairs long region with 8 base modifications) flanked on both sides by homology arms about 500 bp in length. The homology arms match (i.e., are homologous to) gDNA (genomic DNA) regions flanking the two gRNA target sites. The replacement template region comprising the donor DNA is flanked at each end by DNA sequence identical to one of the two target gDNA sequences recognized by an RNA-guided nuclease.

Maize protoplasts are isolated, cultivated, and subjected to PEG-mediated transfection. The transfected materials includes plasmids expressing the c2 NLS-Exo, c2 NLS lambda beta SSAP, and c2 NLS-SSB fusion proteins that are set forth in SEQ ID NO: 135, SEQ ID NO: 134, and SEQ ID NO: 133, and are operably linked to a 2x35S, ZmUBI1, OsACT1 promoter and a 35S, AtHSP, pea3A polyadenylation site respectively. The plasmids also has the donor DNA template region described above, and expressing the two gRNAs and Cas polynucleotides as indicated. Cas polynucleotides are fused to a nuclear localization signal. Each of the two gRNAs both target a double strand break into the intended genomic DNA target and a sequence flanking the replacement template on one end in order to release the replacement template from the donor plasmid. Experiments are carried out with a Cas nuclease which leaves a blunt end following cleavage of the endonuclease recognition sequence and referred to herein as a CasB nuclease.

After 48 hour of incubation of the protoplasts following transfection, gDNA is extracted from transfected samples and the target locus was amplified with primers complementary to genomic sequences flanking the introduced base modifications and the homology arm of the replacement template, and analyzed by amplicon sequencing. HDR is observed at increased levels in protoplasts transfected with the plasmids expressing the c2 NLS-Exo, c2 NLS lambda beta SSAP, and c2 NLS-SSB fusion proteins, gRNAs, and polynucleotides encoding the Cas nuclease in comparison to the controls transfected with only the gRNAs and polynucleotides encoding the Cas nuclease.

Example 4. Biological Sequences

This example provides non-limiting embodiments of protein and nucleic acid sequences referred to herein. Biological sequences and their SEQ ID NOs are set forth in Table 5.

TABLE 5

Biological Sequences

| SEQ ID NO: | DESCRIPTION | SEQUENCE | COMMENTS |
|---|---|---|---|
| 1 | Bacteriophage Lambda beta protein | MSTALATLAGKLAERVGMDSVDPQELITTLRQTAFKGDASDAQFI ALLIVANQYGLNPWTKEIYAFPDKQNGIVPVVGVDGWSRIINENQ QFDGMDFEQDNESCICRIYRKDRNHPICVIEWMDECRREPFKIRE GREITGPWQSHPKRMLRHKAMIQCARLAFGFAGIYDKDEAERIVE NTAYTAERQPERDITPVNDETMQEINTLLIALDKTWDDDLLPLCS QIFRRDIRASSELTQAEAVKALGFLKQKAAEQKVAA | NCBI Reference Sequence: WP_ 000100844.1 |
| 2 | Rac bacterial prophage RecT protein | MTKQPPIAKADLQKTQGNRAPAAVKNSDVISFINQPSMKEQLAAA LPRHMTAERMIRIATTEIRKVPALGNCDTMSFVSAIVQCSQLGLE PGSALGHAYLLPFGNKNEKSGKKNVQLIIGYRGMIDLARRSGQIA SLSARVVREGDEFSFEFGLDEKLIHRPGENEDAPVTHVYAVARLK DGGTQFEVMTRKQIELVRSLSKAGNNGPWVTHWEEMAKKTAIRRL FKYLPVSIEIQRAVSMDEKEPLTIDPADSSVLTGEYSVIDNSEE | NCBI Reference Sequence: NP_415865.1 |
| 3 | Bacteriophage SPP1 35 protein | MATKKQEELKNALAQQNGAVPQTPVKPQDKVKGYLERMMPAIKDV LPKHLDADRLSRIAMNVIRTNPKLLECDTASLMGAVLESAKLGVE PGLLGQAYILPYTNYKKKTVEAQFILGYKGLLDLVRRSGHVSTIS AQTVYKNDTFEYEYGLDDKLVHRPAPFGTDRGEPVGYYAVAKMKD GGYNFLVMSKQDVEKHRDAFSKSKNREGVVYGPWADHFDAMAKKT VLRQLINYLPISVEQLSGVAADERTGSELHNQFADDDNIINVDIN TGEIIDHQEKLGGETNE | UniProtKB: locus Q38143_ BPSPP, accession Q38143; |
| 4 | Bacteriophage P22 ERF protein | MSKEFYARLAEIQEHLNAPKNQYNSFGKYKYRSCEDILEGVKPLL KGLFLSISDEIVLIGDRYYVKATATITDGENSHSASAIAREEENK KGMDAAQVTGATSSYARKYCLNGLFGIDDAKDADTEEHKQQQNAA RAKQTKSSPSSPAPEQVLKAFSEYAATETDKKKLIERYQHDWQLL TGHDDEQTKCVQVMNIRINELKQVA | NCBI Reference Sequence: NP_059596.1; mutations in ERF are complemented by Bacteriophage Lambda Red beta protein (Poteete AR, Fenton AC. Lambda red-dependent growth and recombination of phage P22. Virology. 1984 Apr 15;134(1): 161-7.) ERF-family motif underlined in bold |
| 5 | *Saccharomyces cerevisiae* RAD52 protein | MNEIMDMDEKKPVFGNHSEDIQTKLDKKLGPEYISKRVGFGTSRI AYIEGWRVINLANQIFGYNGWSTEVKSVVIDFLDERQGKFSIGCT AIVRVTLTSGTYREDIGYGTVENERRKPAAFERAKKSAVTDALKR SLRGFGNALGNCLYDKDFLAKIDKVKFDPPDFDENNLFRPTDEIS ESSRTNTLHENQEQQQYPNKRRQLTKVTNTNPDSTKNLVKIENTV SRGTPMMAAPAEANSKNSSNKDTDLKSLDASKQDQDDLLDDSLMF SDDFQDDDLINMGNTNSNVLTTEKDPVVAKQSPTASSNPEAEQIT FVTAKAATSVQNERYIGEESIFDPKYQAQSIRHTVDQTTSKHIPA SVLKDKTMTTARDSVYEKFAPKGKQLSMKNNDKELGPHMLEGAGN QVPRETTPIKTNATAFPPAAAPRFAPPSKVVHPNGNGAVPAVPQQ RSTRREVGRPKINPLHARKPT | NCBI Reference Sequence: NP_013680.2 |

TABLE 5-continued

Biological Sequences

| SEQ ID NO: | DESCRIPTION | SEQUENCE | COMMENTS |
|---|---|---|---|
| 6 | *Schizo-saccharomyces pombe* Rad22 | MSFEQKQHVASEDQGHFNTAYSHEEFNFLQSSLTRKLGPEYVSRR SGPGGFSVSYIESWKAIELANEIFGFNGWSSSIRSINVDFMDENK ENGRISLGLSVIVRVTIKDGAYHEDIGYGSIDNCRGKASAFEKCK KEGTTDALKRALRNFGNSLGNCMYDKYYLREVGKMKPPTYHFDSG DLFRKTDPAARESFIKKQKTLNSTRTVNNQPLVNKGEQLAPRRAA ELNDEQTREIEMYADEELDNIFVEDDIIAHLAVAEDTAHPAANNH HSEKAGTQINNKDKGSHNSAKPVQRSHTYPVAVPQNTSDSVGNAV TDTSPKTLFDPLKPNTGTPSPKFISARAAAAAEGVVSAPFTNNFN PRLDSPSIRKTSIIDHSKSLPVQRASVLPIIKQSSQTSPVSNNSM IRDSESIINERKENIGLIGVKRSLHDSTTSHNKSDLMRTNSDPQS AMRSRENYDATVDKKAKKG | UniProtKB/ Swiss-Prot: P36592.2 |
| 7 | *Kluyveromyces lactis* Rad52 | MEDTGSGKNGKDDIQTKLDKKLGPEYISKRVGFGSSRVAYIEGWK AINLANQIFGYDGWSTEVKNVTIDFLDERQGRFSIGCTAIVRVSL ADGTFREDIGYGTVENERRKASAFERAKKSAVTDALKRSLRGFGN ALGNCLYDKDFLAKIDKVKFDPPDFDEGNLFRPADELSEMSRSNM VGDAHTEGPSLKKRSLTNEDRNAVPSAPAQQTYRSNNHTTQKRAP KAQAVTASASPNEETSNQQQDPDDLLDDSFMESDEIQDDDLLNMN TTTNNKNSTNSSTTTTTISDEATGIISPVTFVTAKAATSLQHKDP IPSGSMFDPKFQAQSIRHTVDQSVSTPVRATILKEKGLDSDRSSI YSKFAPKGKELSGTTTNSEPYVAAPQTSATESNRSTPTRSNAQLA GPQPAPQLQGPQRTQLGRPRMLQQPNRRNVS | UniProtKB/ Swiss-Prot: P41768.2 |
| 8 | Bacteriophage Lambda exonuclease | MTPDIILQRTGIDVRAVEQGDDAWHKLRLGVITASEVHNVIAKPR SGKKWPDMKMSYFHTLLAEVCTGVAPEVNAKALAWGKQYENDART LFEFTSGVNVTESPIIYRDESMRTACSPDGLCSDGNGLELKCPFT SRDFMKFRLGGFEAIKSAYMAQVQYSMWVTRKNAWYFANYDPRMK REGLHYVVIERDEKYMASFDEIVPEFIEKMDEALAEIGFVFGEQW R | NCBI Reference Sequence: WP_ 000186853.1 |
| 9 | Rac bacterial prophage RecE exonuclease | MSTKPLFLLRKAKKSSGEPDVVLWASNDFESTCATLDYLIVKSGK KLSSYFKAVATNFPVVNDLPAEGEIDFTWSERYQLSKDSMTWELK PGAAPDNAHYQGNTNVNGEDMTEIEENMLLPISGQELPIRWLAQH GSEKPVTHVSRDGLQALHIARAEELPAVTALAVSHKTSLLDPLEI RELHKLVRDTDKVFPNPGNSNLGLITAFFEAYLNADYTDRGLLTK EWMKGNRVSHITRTASGANAGGGNLTDRGEGFVHDLTSLARDVAT GVLARSMDLDIYNLHPAHAKRIEETIAENKPPFSVFRDKFITMPG GLDYSRAIVVASVKEAPIGIEVIPAHVTEYLNKVLTETDHANPDP EIVDIACGRSSAPMPQRVTEEGKQDDEEKPQPSGTTAVEQGEAET MEPDATEHHQDTQPLDAQSQVNSVDAKYQELRAELHEARKNIPSK NPVDDDKLLAASRGEFVDGISDPNDPKWVKGIQTRDCVYQNQPET EKTSPDMNQPEPVVQQEPEIACNACGQTGGDNCPDCGAVMGDATY QETFDEESQVEAKENDPEEMEGAEHPHNENAGSDPHRDCSDETGE VADPVIVEDIEPGIYYGISNENYHAGPGISKSQLDDIADTPALYL WRKNAPVDTTKTKTLDLGTAFHCRVLEPEEFSNRFIVAPEFNRRT NAGKEEEKAFLMECASTGKTVITAEEGRKIELMYQSVMALPLGQW LVESAGHAESSIYWEDPETGILCRCRPDKIIPEFHWIMDVKTTAD IQRFKTAYYDYRYHVQDAFYSDGYEAQFGVQPTFVFLVASTTIEC GRYPVEIFMMGEEAKLAGQQEYHRNLRTLSDCLNTDEWPAIKTLS LPRWAKEYAND | NCBI Reference Sequence: AIN31810.1 |
| 10 | maize opaque-2 nuclear localization signal | RKRKESNRESARRSRRSRYRKKV | |
| 11 | SV40 large T antigen NLS | PKKKRKV | |
| 12 | Class II monopartite NLS consensus | K(K/R)*X*(K/R) | |
| 13 | Bipartite NLS consensus | (K/R)(K/R)$X_{10-12}$(K/R)$_{3/5}$ | where K/R)$_{3/5}$ represents at least three of either lysine or arginine |

TABLE 5-continued

| Biological Sequences | | | |
|---|---|---|---|
| SEQ ID NO: | DESCRIPTION | SEQUENCE | COMMENTS |
| | | | of five consecutive amino acids |
| 14 | Class 5 Plant NLS | LGKR(K/R)(W/F/Y) | |
| 15 | tobacco c2 NLS | QPSLKRMKIQPSSQP | |
| 16 | Extended SV40 Nuclear Localization Domain | ASPKKKRKVEASGS | |
| 17 | cell-penetrating peptide (CPP) | YGRKKRRQRRR | |
| 18 | cell-penetrating peptide (CPP) | RRQRRTSKLMKR | |
| 19 | cell-penetrating peptide (CPP) | GWTLNSAGYLLGKINLKALAALAKKIL | |
| 20 | cell-penetrating peptide (CPP) | KALAWEAKLAKALAKALAKHLAKALAKALKCEA | |
| 21 | cell-penetrating peptide (CPP) | RQIKIWFQNRRMKWKK | |
| 22 | cell-penetrating peptide (CPP) | YGRKKRRQRRR | |
| 23 | cell-penetrating peptide (CPP) | RKKRRQRR | |
| 24 | cell-penetrating peptide (CPP) | YARAAARQARA | |
| 25 | cell-penetrating peptide (CPP) | THRLPRRRRRR | |
| 26 | cell-penetrating peptide (CPP) | GGRRARRRRRR | |
| 27 | As Cpf1 (wild type) | MTQFEGFINLYQVSKTLRFELIPQGKILKHIQEQGFIEEDKARND HYKELKPIIDRIYKTYADQCLQLVQLDWENLSAAIDSYRKEKTEE TRNALIEEQATYRNAIHDYFIGRIDNLIDAINKRHAEIYKGLFKA ELFNGKVLKQLGTVTTTEHENALLRSFDKFTTYFSGFYENRKNVF SAEDISTAIPHRIVQDNFPKFKENCHIFTRLITAVPSLREHFENV KKAIGIFVSTSIEEVESFPFYNQLLTQTQIDLYNQLLGGISREAG TEKIKGLNEVLNLAIQKNDETAHIIASLPHRFIPLFKQILSDRNT LSFILEEFKSDEEVIQSFCKYKTLLRNENVLETAEALFNELNSID LTHIFISHKKLETISSALCDHWDTLRNALYERRISELIGKITKSA KEKVQRSLKHEDINLQEIISAAGKELSEAFKQKTSEILSHAHAAL DQPLPTTLKKQEEKEILKSQLDSLLGLYHLLDWFAVDESNEVDPE FSARLIGIKLEMEPSLSFYNKARNYAIKKPYSVEKFKLNFQMPTL ASGWDVNKEKNNGAILFVKNGLYYLGIMPKQKGRYKALSFEPTEK TSEGFDKMYYDYFPDAAKMIPKCSTQLKAVTAHFQTHTTPILLSN NFIEPLEITKEIYDLNNPEKEPKKFQTAYAKKTGDQKGYREALCK WIDFIRDFLSKYTKITSIDLSSLRPSSQYKDLGEYYAELNPLLYH ISFQRIAEKEIMDAVETGKLYLFQIYNKDFAKGHHGKPNLHTLYW TGLFSPENLAKTSIKLNGQAELFYRPKSRMKRMAHRLGEKMLNKK LKDQKTPIPDTLYQELYDYVNHRLSHDLSDEARALLPNVITKEVS | *Acidaminococcus* sp. (As) Cpf1 |

TABLE 5-continued

| SEQ ID NO: | DESCRIPTION | SEQUENCE | COMMENTS |
|---|---|---|---|
| Biological Sequences | | | |
| | | HEIIKDRRFTSDKEFFHVPITLNYQAANSPSKENQRVNAYLKEHP ETPIIGIDRGERNLIYITVIDSTGKILEQRSLNTIQQFDYQKKLD NREKERVAARQAWSVVGTIKDLKQGYLSQVIHEIVDLMIHYQAVV VLENLNFGEKSKRIGIAEKAVYQQFEKMLIDKLNCLVLKDYPAEK VGGVLNPYQLTDQFTSFAKMGTQSGFLFYVPAPYISKIDPLIGFV DPFVWKTIKNHESRKHFLEGFDFLHYDVKTGDFILHFKMNRNLSF QRGLPGFMPAWDIVFEKNETQFDAKGTPFIAGKRIVPVIENHRFT GRYRDLYPANELIALLEEKGIVFRDGSNILPKLLENDDSHAIDTM VALIRSVLQMRNSNAATGEDYINSPVRDLNGVCFDSRFQNPEWPM DADANGAYHIALKGQLLLNHLKESKDLKLQNGISNQDWLAYIQEL RN | |
| 28 | LbCpf1 (wild type) | MSKLEKFINCYSLSKTLRFKAIPVGKTQENIDNKRLLVEDEKRAE DYKGVKKLLDRYYLSFINDVLHSIKLKNLNNYISLFRKKTRTEKE NKELENLEINLRKEIAKAFKGNEGYKSLFKKDIIETILPEFLDDK DEIALVNSENGETTAFTGFEDNRENMESEEAKSTSIAFRCINENL TRYISNMDIFEKVDAIFDKHEVQEIKEKILNSDYDVEDFFEGEFF NFVLTQEGIDVYNAIIGGFVTESGEKIKGLNEYINLYNQKTKQKL PKFKPLYKQVLSDRESLSFYGEGYISDEEVLEVERNTLNKNSEIF SSIKKLEKLFKNFDEYSSAGIFVKNGPAISTISKDIFGEWNVIRD KWNAEYDDIHLKKKAVVTEKYEDDRRKSFKKIGSFSLEQLQEYAD ADLSVVEKLKEIIIQKVDEIYKVYGSSEKLFDADFVLEKSLKKND AVVAIMKDLLDSVKSFENYIKAFFGEGKETNRDESFYGDFVLAYD ILLKVDHIYDAIRNYVTQKPYSKDKFKLYFQNPQFMGGWDKDKET DYRATILRYGSKYYLAIMDKKYAKCLQKIDKDDVNGNYEKINYKL LPGPNKMLPKVFFSKKWMAYYNPSEDIQKIYKNGTFKKGDMFNLN DCHKLIDFFKDSISRYPKWSNAYDFNFSETEKYKDIAGFYREVEE QGYKVSFESASKKEVDKLVEEGKLYMFQIYNKDFSDKSHGTPNLH TMYFKLLFDENNHGQIRLSGGAELFMRRASLKKEELVVHPANSPI ANKNPDNPKKITTLSYDVYKDKRFSEDQYELHIPIAINKCPKNIF KINTEVRVLLKHDDNPYVIGIDRGERNLLYIVVVDGKGNIVEQYS LNEIINNFNGIRIKTDYHSLLDKKEKERFEARQNWTSIENIKELK AGYISQVVHKICELVEKYDAVIALEDLNSGFKNSRVKVEKQVYQK FEKMLIDKLNYMVDKKSNPCATGGALKGYQIINKFESFKSMSTQN GFIFYIPAWLISKIDPSTGFVNLLKIKYTSIADSKKFISSFDRIM YVPEEDLFEFALDYKNFSRTDADYIKKWKLYSYGNRIRIFRNPKK NNVEDWEEVCLISAYKELENKYGINYQQGDIRALLCEQSDKAFYS SFMALMSLMLQMRNSITGRTDVDFLISPVKNSDGIFYDSRNYEAQ ENAILPKNADANGAYNIARKVLWAIGQFKKAEDEKLDKVKIAISN KEWLEYAQTSVKH | *Lachnospiraceae bacterium* (Lb) Cpf1 |
| 29 | Fn Cpf1 (wild type) | MSIYQEFVNKYSLSKTLRFELIPQGKILENIKARGLILDDEKRAK DYKKAKQIIDKYHQFFIEEILSSVCISEDLLQNYSDVYFKLKKSD DDNLQKDFKSAKDTIKKQISEYIKDSEKFKNLFNQNLIDAKKGQE SDLIL WLKQSKDNGIELFKANSDITDIDEALEIIKSFKGWITYFKGEHEN RKNVYSSNDIPTSIIYRIVDDNLPKFLENKAKYESLKDKAPEAIN YEQIKKDLAEELTFDIDYKTSEVNQRVFSLDEVFEIANFNNYLNQ SGITKENTIIGGKFVNGENTKRKGINEYINLYSQQINDKILKKYK MSVLFKQILSDIESKSFVIDKLEDDSDVVITMQSFYEQIAAFKTV EEKSIKETLSLLFDDLKAQKLDLSKIYEKNDKSLIDLSQQVFDDY SVIGTAVLEYITQQIAPKNLDNPSKKEQELIAKKTEKAKYLSLET IKLALEEFNKHRDIDKQCRFEEILANFAAIPMIFDEIAQNKDNLA QISIKYQNQGKKDLLQASAEDDVKAIKDLLDQINNLLHKLKIFHI SQSEDKANILDKDEHFYLVFEECYFELANIVPLYNKIRNYITQKP YSDEKFKLNFENSTLANGWDKNKEPDNTAILFIKDDKYYLGVMNK KNNKIFDDKAIKENKGEGYKKIVYKLLPGANKMLPKVFFSAKSIK FYNPSEDILRIRNHSTHTKNGSPQKGYEKFEFNIEDCRKFIDFYK QSISKHPEWKDFGFRFSDIQRYNSIDEFYREVENQGYKLIFENIS ESYIDSVVNQGKLYLFQIYNKDFSAYSKGRPNLHTLYWKALFDER NLQDVVYKLNGEAELFYRKQSIPKKITHPAKEAIANKNKDNPKKE SVFEYDLIKDKRFTEDKFFFHCPITINFKSSGANKFNDEINLLLK EKANDVHILSIDRGERHLAYYTLVDGKGNIIKQDTFNIIGNDRMK TNYHDKLAAIEKDRDSARKDWKKINNIKEMKEGYLSQVVHEIAKL VIEYNAIVVFEDLNFGFKRGRFKVEKQVYQKLEKMLIEKLNYLVF KDNEFDKIGGVLRAYQLTAPFETFKKMGKQTGIIYYVPAGFTSKI CPVTGFVNQLYPKYESVSKSQEFFSKFDKICYNLDKGYFEFSFDY KNEGDKAAKGKWTIASEGSRLINFRNSDKNHNWDTREVYPTKELE KLLKDYSIEYGHGECIKAAICGESDKKFFAKLTSVLNTILQMRNS KTGTELDYLISPVADVNGNFFDSRQAPKNMPQDADANGAYHIGLK GLMLLGRIKNNQEGKKLNLVIKNEEYFEFVQNRNN | *Francisella novicida* (Fn) Cpf1 |

TABLE 5-continued

| SEQ ID NO: | DESCRIPTION | SEQUENCE | COMMENTS |
|---|---|---|---|
| | | Biological Sequences | |
| 30 | CasJ (wild type) | MQQYQVSKTVRFGLILKNSEKKHATHLLLKDLVNVSEERIKNEIT KDDKNQSELSFFNEVIETLDLMDKYIKDWENCFYRTDQIQLTKEY YKVIAKKACEDWFWINDRGMKEPTSSIISENSLKSSDKSKTSDNL DRKKKILDYWKGNIFKTQKAIKDVLDITEDIQKAIEEKKSHREIN RVNHRKMGIHLIHLINDTLVPLCNGSIFFGNISKLDFCESENEKL IDFASTEKQDERKFLLSKINEIKQYFEDNGGNVPFARATLNRHTA NQKPDRYNEEIKKLVNELGVNSLVRSLKSKTIEEIKTHFEFENKN KINELKNSFVLSIVEKIQLFKYKTIPASVRFLLADYFEEQKLSTK EEALTIFEEIGKPQNIGFDYIQLKEKDNFTLKKYPLKQAFDYAWE NLARLDQNPKANQFSVDECKRFFKEVFSMEMDNINFKTYALLLAL KEKTTAFDKKGEGAAKNKSEIIEQIKGVFEELDQPFKIIANTLRE EVIKKEDELNVLKRQYRETDRKIKTLQNEIKKIKNQIKNLENSKK YSFPEIIKWIDLTEQEQLLDKNKQAKSNYQKAKGDLGLIRGSQKT SINDYFYLTDKVYRKLAQDFGKKMADLREKLLDKNDVNKIKYLSY IVKDNQGYQYILLKPLEDKNAEIIELKSEPNGDLKLFEIKSLISK TLNKFIKNKGAYKEFHSAEFEHKKIKEDWKNYKYNSDFIVKLKKC LSHSDMANTQNWKAFGWDLDKCKSYETIEKEIDQKSYQLVEIKLS KITIEKWVKENNYLLLPIVNQDITAEKLKVNINQFTKDWQHIFEK NPNHRLHPEFNIAYRQPIKDYAKEGEKRYSRFQLTGQFMYEYIPQ DANYISRKEQITLFNDKEEQKIQVETFNNQIAKILNAEDFYVIGI DRGITQLATLCVLNKNGVIQGGFEIFTREFDYINKQWKHTKLKEN RNILDISNLKVETTVNGEKVLVDLSEVKTYLRDENGEPMKNEKGV ILTKDNLQKIKLKQLAYDRKLQYKMQHEPELVLSFLDRLENKEQI PNLLASTKLISAYKEGTAYADIDIEQFWNILQTFQTIVDKFGGIE NAKKTMEFRQYTELDASFDLKNGVVANMVGVVKFIMEKYNYKTFI ALEDLTFAFGQSIDGINGERLRSTKEDKEVDFKEQENSTLAGLGT YHFFEMQLLKKLSKTQIGNEIKHFVPAFRSTENYEKIVRKDKNVK AKIVSYPFGIVSFVNPRNTSISCPNCKNANKSNRIKKENDRILCK HNIEKTKGNCGFDTANFDENKLRAENKGKNFKYISSGDANAAYNI AVKLLEDKIFEINKK | CasJ |
| 31 | *E. coli* single stranded DNA binding polypeptide (SSB) | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | NCBI Reference Sequence: WP_ 000168305.1 |
| 32 | ERF protein motif | G(G/S/A)XX(S/T)Y(A/V/L/I/M/F)(K/R/E,/D/N/T/S) (K/R)YX(A/V/L/I/M/F)XX(A/V/L/I/M/F) A/V/L/I/M/F) | |
| 33 | FMDV 2A self-processing peptide sequence | QLLNFDLLKLAGDVESNPGP | |
| 34 | single strand DNA-binding protein [*Escherichia coli* APEC O1] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 35 | single strand DNA-binding protein [*Escherichia coli* UTI89] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 36 | ssDNA-binding protein [*Proteo-bacteria*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 37 | ssDNA-binding protein [*Escherichia*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNVGGGQPQGG WGQPQQPQGGNQFSGGAQSRPQQSAPAAPSNEPPMDFDDDIPF | |
| 38 | ssDNA-binding protein [*Shigella flexneri*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNKFSGGAQSRPQQSAPAAPSNEPPMDFDDDIPF | |

TABLE 5-continued

| Biological Sequences | | | |
|---|---|---|---|
| SEQ ID NO: | DESCRIPTION | SEQUENCE | COMMENTS |
| 39 | ssDNA-binding protein [*Escherichia coli*] | MASKGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 40 | single-stranded DNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYLEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 41 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSAQDRYTTEVVVNVGGTMQMLGGRQGGGAPAGGNIGGGQPQGG WGQPQQPQGGNQFSGGAQSRPQQSAPAAPSNEPPMDFDDDIPF | |
| 42 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAAGNIGGGQPQGG WGQPQQPQGGNQFSGGAQSRPQQSAPAAPSNEPPMDFDDDIPF | |
| 43 | ssDNA-binding protein [*Escherichia coli*] | MASRGVNKVILVGNLGHDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 44 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQSG WGQPQQPQGGNQFSGGAQSRPQQSAPAAPSNEPPMDFDDDIPF | |
| 45 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGS WGQPQQPQGGNQFSGGAQSRPQQSAPAAPSNEPPMDFDDDIPF | |
| 46 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGSAQSRPQQSAPAAPSNEPPMDFDDDIPF | |
| 47 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGSNQFSGGAQSRPQQSAPAAPSNEPPMDFDDDIPF | |
| 48 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGSNIGGGQPQGG WGQPQQPQGGNQFSGGAQSRPQQSAPAAPSNEPPMDFDDDIPF | |
| 49 | ssDNA-binding protein [*Escherichia coli*] | MASRGVNKVILVGNLGQDPEVRYMPNSGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 50 | ssDNA-binding protein [*Escherichia*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQSGGAPAGGNIGGGQPQGG WGQPQQPQGGNQFSGGAQSRPQQSAPAAPSNEPPMDFDDDIPF | |
| 51 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSTPAAPSNEPPMDFDDDIPF | |
| 52 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGQPQGGW GQSQQPQGGNQFSGGAQSRPQQSAPAAPSNEPPMDFDDDIPF | |

TABLE 5-continued

| SEQ ID NO: | DESCRIPTION | SEQUENCE | COMMENTS |
|---|---|---|---|
| Biological Sequences | | | |
| 53 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSCGAQSRPQQSAPAAPSNEPPMDFDDDIPF | |
| 54 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMXMLGGRQGGGAPAGGNIGGGQPQGG WGQPQQPQGGNQFSGGAQSRPQQSAPAAPSNEPPMDFDDDIPF | |
| 55 | ssDNA-binding protein [*Escherichia coli*] | MASRGVNKVILVGNLGQDPEVRYMPNGGAYANITLATSESWRDKA TGEMKEQTEWHRVVLFGKLAEVVSEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 56 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGVQSRPQQSAPAAPSNEPPMDFDDDIPF | |
| 57 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGDAPAGGNIGGGQPQGG WGQPQQPQGGNQFSGGAQSRPQQSAPAAPSNEPPMDFDDDIPF | |
| 58 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQDGNQFSGGAQSRPQQSAPAAPSNEPPMDFDDDIPF | |
| 59 | ssDNA-binding protein [*Escherichia coli*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYITEVVVNVGGTMQMLGGRQGGGAPAGGNIGGGQPQGG WGQPQQPQGGNQFSGGAQSRPQQSAPAAPSNEPPMDFDDDIPF | |
| 60 | Single-strand DNA binding protein [*Shigella dysenteriae* 1617] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQLQGG WGQPQQPQGGNQFSGGAQSRPQQSAPAAPSNEPPMDFDDDIPF | |
| 61 | single-stranded DNA-binding protein [*Escherichia albertii*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGLDRYTTEVVVNVGGTMQMLGGRQGGGAPAGGNIGGGQPQGG WGQPQQPQGGNQFSGGAQSRPQQSAPAAPSNEPPMDFDDDIPF | |
| 62 | Single-stranded DNA-binding protein [*Escherichia coli*] | MASRGVNKVILVGNLGQDPEVRYMPNGGAYANITLATSESWRDKA TGEMKEQTEWHRVVLFGKLAEVASEYLCKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 63 | ssDNA-binding protein [*Escherichia coli*] | MASRGVNKVILVGNLGLDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQSAPAAPSNEPPMDFDDDIPF | |
| 64 | ssDNA-binding protein [*Escherichia coli*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQGG WGQPQQPQGGNQFSGGAQSRPQQPAPAAPSNEPPMDFDDDIPF | |
| 65 | ssDNA-binding protein *Entero-bacteriaceae*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQLQGG WGQPQQPQGGNQFSGGAQSRPQQSAPAAPSNEPPMDFDDDIPF | |

TABLE 5-continued

| Biological Sequences | | | |
|---|---|---|---|
| SEQ ID NO: | DESCRIPTION | SEQUENCE | COMMENTS |
| 66 | ssDNA-binding protein [*Escherichia coli*] | MASRGVNKVILVGNLGQDPEVRYMPNGGAVANITLATSESWRDKATGEMKDQTEWHRVVLFGKLAEVASEYLRKGSQVYIEGQLRTRKWTDQSGQDRYTTEVVVNVGGTMQMLGGRQGGGAPAGGNIGGGQPQGGWGQPQQPQGGNQFSGGAQSRPQQSTPAAPSNEPPMDFDDDIPF | |
| 67 | ssDNA-binding protein [*Escherichia coli*] | MASRGVNKVILVGNLGQDPEVRYMPNGGAVANITLATSESWRDKATGEMKEQTEWHRVVLFGKLAEVASEYLRKGSQVYIEGQLRTRKWTDQSGQDRYTTEVVVNVGGTMQMLGGRQGGGAPAGGNIGGGQPQGGWGQPQQPQGGNQFSGGAQSRLQQSAPAAPSNEPPMDFDDDIPF | |
| 68 | ssDNA-binding protein [*Escherichia coli*] | MASRGVNKVILVGNLGQDPEVRYMPNGGAVANITLATSESWRDKATGEMKEQTEWHRVVLFGKLAEVASEYLRKGSQVYIEGQLRTRKWTDQSGQDRYTTEVVVNVGGTMQMLGGRQGGGAPAGGNIGGGQPQGGWGQPQQLQGGNQFSGGAQSRPQQSAPAAPSNEPPMDFDDDIPF | |
| 69 | ssDNA-binding protein [*Escherichia*] | MASRGVNKVILVGNLGQDPEVRYMPNGGAVANITLATSESWRDKATGEMKEQTEWHRVVLFGKLAEVASEYLRKGSQVYIEGQLRTRKWTDQSGQDRYTTEVVVNVGGTMQMLGGRQSGGAPTGGNIGGGQPQGGWGQPQQPQGGNQFSGGAQSRPQQSAPAAPSNEPPMDFDDDIPF | |
| 70 | ssDNA-binding protein [*Escherichia coli*] | MASRGVNKVILVGNLGQDPEVRYMPNGGAVANITLATSESWRDKATGEMKEQTEWHRVVLFGKLAEVASEYLRKGSQGYIEGQLRTRKWTDQSGQDRYTTEVVVNVGGTMQMLGGRQGGGAPAGGNIGGGQPQGGWGQPQQPQGGNQFSGGAQSRPQQSAPAAPSNEPPMDFDDDIPF | |
| 71 | ssDNA-binding protein [*Escherichia coli*] | MASRGVNKVILVGNLGQDPEVRYMPNGGAVANITLATSESWRDKATGEMKEQTEWHRVVLFGKLAEGASEYLRKGSQVYIEGQLRTRKWTDQSGQDRYTTEVVVNVGGTMQMLGGRQGGGAPAGGNIGGGQPQGGWGQPQQPQGGNQFSGGAQSRPQQSAPAAPSNEPPMDFDDDIPF | |
| 72 | single-stranded DNA-binding protein [*Escherichia albertii*] | MASRGVNKVILVGNLGQDPEVRYMPNGGAVANITLATSESWRDKATGEMKEQTEWHRVVLFGKLAEVASEYLRKGSLVYIEGQLRTRKWTDQSGQDRYTTEVVVNVGGTMQMLGGRQSGGAPAGGNIGGGQPQGGWGQPQQPQGGNQFSGGAQSRPQQSAPAAPSNEPPMDFDDDIPF | |
| 73 | ssDNA-binding protein [*Escherichia albertii*] | MASRGVNKVILVGNLGQDPEVRYMPNGGAYANITLATSEFWRDKATGEMKEQTEWHRVVLFGKLAEVASEYLRKGSQVYIEGQLRTRKWTDQSGQDRYTTEVVVNVGGTMQMLGGRQSGGAPAGGNIGGGQPQGGWGQPQQPQGGNQFSGGAQSRPQQSAPAAPSNEPPMDFDDDIPF | |
| 74 | ssDNA-binding protein [*Escherichia coli*] | MASRGVNKVILVGNLGQDPEVRYMPNGGAYANITLATSESWRDKATGEMKEQTEWHRVVLFGKLAEVASEYLRKGSQVYIEGQLRTRKWTDQSGQDRYTTEVVVNVGGTMQMLGGRQGGGAPAGGNIGGGQPQGGWGQPQQPQGGWGQPQQPQGGNQFSGGAQSRPQQSAPAAPSNEPPMDFDDDIPF | |
| 75 | ssDNA-binding protein [*Citrobacter*] | MASRGVNKVILVGNLGQDPEVRYMPNGGAYANITLATSESWRDKATGEMKEQTEWHRVVLFGKLAEVASEYLRKGSQVYIEGQLRTRKWTDQSGVEKYTTEVVVNVGGTMQMLGGRQGGGAPAGGNAGGGQQGGWGQPQQPQGGNQFSGGAQSRPQQSAPAAPSNEPPMDFDDDIPF | |
| 76 | ssDNA-binding protein [*Citrobacter koseri*] | MASRGVNKVILVGNLGQDPEVRYMPNGGAYANITLATSESWRDKQTGEMKEQTEWHRVVLFGKLAEVASEYLRKGSQVYIEGQLRTRKWTDQSGQDKYTTEVVVNVGGTMQMLGGRQGGGAPAGGNMGGGQQQGGWGQPQQPQGGNQFSGGAQSRPQQQSAPAPSNEPPMDFDDDIPF | |
| 77 | single-stranded DNA-binding protein [*Escherichia coli* ECC-1470] | MASRGVNKVILVGNLGQDPEVRYMPNGGAYANITLATSESWRDKATGEMKEQTEWHRVVLFGKLAEVASEYLRKGSQVYIEGQLRTRKWTDQSGQDRYTTEVVVNVGGTMQMLGGRQGGGAPAGGNIGGGQPQGGWGQPQQPQGGNQFSGGAQSRPQQSAPAAPSNEPPMD | |
| 78 | ssDNA-binding protein [*Citrobacter koseri*] | MASRGVNKVILVGNLGQDPEVRYMPNGGAYANITLATSESWRDKQTGEMKEQTEWHRVVLFGKLAEVASEYLRKGSQVYIEGQLRTRKWTDQSGQDKYTTEVVVNVGGTMQMLGGRQGGGVPAGGNMGGGQQQGGWGQPQQPQGGNQFSGGAQSRPQQQSAPAPSNEPPMDFDDDIPF | |
| 79 | single-stranded DNA- | MASRGVNKVILVGNLGQDPEVRYMPNGGAYANITLATSESWRDKQTGEMKEQTEWHRVVLFGKLAEVASEYLRKGSQVYIEGQLRTRKWT | |

TABLE 5-continued

| SEQ ID NO: | DESCRIPTION | SEQUENCE | COMMENTS |
|---|---|---|---|
| Biological Sequences | | | |
| | binding protein [*Citrobacter koseri*] | DQSGQDKYITEVVVNVGGTMQMLGGRQGGGAPAGGNMGGGQQQGG WGQPQQPQGGNQFSGGAQSRPQQQSAPAPSNEPPMDFDDDIPF | |
| 80 | ssDNA-binding protein [*Shigella*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGQDRYTTEVVVNVGGTMQMLGGRQGGGAPAGGNIGGGQPQQP QGGNQFSGGAQSRPQQSAPAAPSNEPPMDFDDDIPF | |
| 81 | ssDNA-binding protein *Entero-bacteriaceae*] | MASRGVNKVILVGNLGQDPEVRYMPNGGAYANITLATSESWRDKA TGEMKEQTEWHRVVLFGKLAEVASEYLRKGSQVYIEGQLRTRKWT DQSGVEKYTTEVVVNVGGTMQMLGGRQGGGAPAGGGQQQGGWGQP QQPQGGNQFSGGAQSRPQQSAPAAPSNEPPMDFDDDIPF | |
| 82 | ssDNA-binding protein [*Citrobacter freundii* complex] | MASRGVNKVILVGNLGQDPEVRYMPNGGAVANITLATSESWRDKA TGEMKEQTEWHRVVLFGKLAEVASEYLRKGSQVYIEGQLRTRKWT DQSGVEKYTTEVVVNVGGTMQMLGGRQGGGAPAGGGQQQGGWGQP QQPQGGNQFSGGGQSRPQQSAPAAPSNEPPMDFDDDIPF | |
| 83 | ssDNA-binding protein [*Citrobacter*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGVEKYTTEVVVNVGGTMQMLGGRQGGGAPAGGGQQQGGWGQP QQPQGGNQFSGGEQSRPQQSAPAAPSNEPPMDFDDDIPF | |
| 84 | ssDNA-binding protein [*Citrobacter youngae*] | MASRGVNKVILVGNLGQDPEVRYMPNGGAVANITLATSESWRDKA TGEMKEQTEWHRVVLFGKLAEVAGEYLRKGSQVYIEGQLRTRKWT DQSGVEKYTTEVVVNVGGTMQMLGGRQGGGAPAGGGQQQGGWGQP QQPQGGNQFSGGAQSRPQQSAPAAPSNEPPMDFDDDIPF | |
| 85 | single-stranded DNA-binding protein [*Citrobacter werkmanii*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGVEKYTTEVVVNVGGTMQMLGGRQGGGAPAGGGQQQGGWGQP QQPQGGNQFSGGAQSRPQQSAPAAPSNEPSMDFDDDIPF | |
| 86 | ssDNA-binding protein [*Citrobacter* sp. MGH109] | MASRGVNKVILVGNLGQDPEVRYMPNGGAVANITLATSESWRDKA TGEMKEQTEWHRVVLFGKLAEVASEYLRKGSQVYIEGQLRTRKWT DQSGVEKYTTEVVVNVGGTMQMLGGRQGGGAPAGGGQQQGGWGQP QQPQGGNQFSGGAQSRLQQSAPAAPSNEPPMDFDDDIPF | |
| 87 | ssDNA-binding protein *Entero-bacteriaceae*] | MASRGVNKVILVGNLGQDPEVRYMPNGGAVANITLATSESWRDKA TGEMKEQTEWHRVVLFGKLAEVASEYLRKGSQVYIEGQLRTRKWT DQSGVEKYTTEVVVNVGGTMQMLGGRQGGGAPAGGGQQQGGWGQP QQPQGGNQFSGGAQSRPQQQSAPAAPSNEPPMDFDDDIPF | |
| 88 | ssDNA-binding protein [*Citrobacter*] | MASRGVNKVILVGNLGQDPEVRYMPNGGAVANITLATSESWRDKQ TGEMKEQTEWHRVVLFGKLAEVASEYLRKGSQVYIEGQLRTRKWT DQSGQDKYTTEVVVNVGGTMQMLGGRQGGGAPAGGQQQQGGWGQP QQPQGGNQFSGGAQSRPQQQSAPAPSNEPPMDFDDDIPF | |
| 89 | ssDNA-binding protein [*Proteo-bacteria*] | MASRGVNKVILVGNLGQDPEVRYMPSGGAVANITLATSESWRDKA TGEMKEQTEWHRVVLFGKLAEVAGEYLRKGSQVYIEGQLRTRKWT DQSGQEKYTTEVVVNVGGTMQMLGGRQGGGAPAGGGQQQGGWGQP QQPQGGNQFSGGAQSRPQQQSAPAPSNEPPMDFDDDIPF | |
| 90 | single-stranded DNA-binding protein [*Escherichia coli* PA5] | MPNGGAVANITLATSESWRDKATGEMKEQTEWHRVVLFGKLAEVA SEYLRKGSQVYIEGQLRTRKWTDQSGQDRYTTEVVVNVGGTMQML GGRQGGGAPAGGNIGGGQPQGGWGQPQQPQGGNQFSGGAQSRPQQ SAPAAPSNEPPMDFDDDIPF | |
| 91 | ssDNA-binding protein [*Enterobacter aerogenes*] | MASRGVNKVILVGNLGQDPEVRYMPSGGAYANFTLATSESWRDKQ TGEMKEQTEWHRVVLFGKLAEVAGEYLRKGSQVYIEGQLRTRKWT DQSGQDKYTTEIVVNVGGTMQMLGGRQGGGAPASGGQQQGGWGQP QQPQGGNQFSGGAQSRPQQQAPAAPSNEPPMDFDDDIPF | |
| 92 | ssDNA-binding protein [*Enterobacter cloacae*] | MASKGVNKVILVGNLGQDPEVRYLPSGGAVCSVTLATSESWRDKA TGELKEQTEWHRVVLFGKLAEVAGEYLRKGSQVYIEGQLRTRKWT DQSGQEKYTTEVVVNVGGTMQMLGGRQGGGAPTGGSQNQQQGGWG RHQQPQGGNQFSGGAQSRPQQQSAPAPSNEPPMDLDDDIPF | |

TABLE 5-continued

| SEQ ID NO: | DESCRIPTION | SEQUENCE | COMMENTS |
|---|---|---|---|
| Biological Sequences | | | |
| 93 | ssDNA-binding protein [*Enterobacter cloacae*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGAEKYTTEVVVNVGGTMQMLGGRQGGGAPAGGSQQQGGWGQP QQPQGGNQFSGGAQSRPQQQSAPAPSNEPPMDFDDDIPF | |
| 94 | single-stranded DNA-binding protein [*Klebsiella* sp. G5] | MASRGVNKVILVGNLGQDPEVRYMPSGGAYANITLATSESWRDKQ TGEMKEQTEWHRVVLFGKLAEVAGEYLRKGSQVYIEGQLRTRKWT DQSGQEKYTTEVVVNVGGTMQMLGGRQGGGAPAGGNMGGGQQQGG WGQPQQPQGGNQFSGGAQSRPQQQSAPAPSNEPPMDFDDDIPF | |
| 95 | ssDNA-binding protein [*Klebsiella oxytoca*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEVVVNVGGTMQMLGGRQGASAPAGGGQQQGGWGQ PQQPQGGNQFSGGAQSRPQQQAPAAPSNEPPMDFDDDIPF | |
| 96 | ssDNA-binding protein [*Entero-bacteriaceae*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGAEKYTTEVVVNVGGTMQMLGGRQGGGAPAGGNMGGGQGQQG GWGQPQQPQGGNQFSGGAQSRPQQSAPAPSNEPPMDFDDDIPF | |
| 97 | ssDNA-binding protein [*Enterobacter lignolyticus*] | MASRGVNKVILVGNLGQDPEVRYMPSGGAYANITLATSESWRDKQ TGEMKEQTEWHRVVLFGKLAEVAGEYLRKGSQVYIEGQLRTRKWT DQSGQEKYTTEVVVNVGGTMQMLGGRQGGGASAGGNMGGGQQQGG WGQPQQPQGGNQFSGGAQSRPQQQSAPAPSNEPPMDFDDDIPF | |
| 98 | ssDNA-binding protein [*Serratia marcescens*] | MASRGVNKVILVGNLGQDPEVRYMPNGGAYANITLATSESWRDKA TGEQKEKTEWHRVVLFGKLAEVAGEYLRKGSQVYIEGSLQTRKWQ DQSGQDRYTTEIVVNVGGTMQMLGGRQGGGAPAGQSAGGQSGWGQ PQQPQGGNQFSGGQQQSRPAQNSAPATSNEPPMDFDDDIPF | |
| 99 | ssDNA-binding protein [*Enterobacter cloacae* complex] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEVVVNVGGTMQMLGGRQGSGAPAGGGQQQGGWGQP QQPQGGNQFSGGAQSRPQQQSAPAPSNEPPMDFDDDIPF | |
| 100 | ssDNA-binding protein [*Enterobacter cloacae* complex] | MASKGVNKVILVGNLGQDPEVRYLPSGGAVCSVTLATSESWRDKA TGELKEQTEWHRVVLFGKLAEVAGEYLRKGSQVYIEGQLRTRKWT DQSGQEKYTTEVVVNVGGTMQMLGGRQGGGAPAGGSQNQQQGGWG QPQQPQGGNQFSGGAQSRPQQQSAPAPSNEPPMDFDDDIPF | |
| 101 | ssDNA-binding protein [*Entero-bacteriaceae*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEVVVNVGGTMQMLGGRQGAGAPAGGGQQQGGWGQ PQQPQGGNQFSGGAQSRPQQQAPAAPSNEPPMDFDDDIPF | |
| 102 | ssDNA-binding protein [*Entero-bacteriaceae*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEIVVNVGGTMQMLGGRQGAGAPAGGGQQQGGWGQ PQQPQGGNQFSGGAQSRPQQQAPAAPSNEPPMDFDDDIPF | |
| 103 | single-stranded DNA-binding protein [*Enterobacter cloacae*] | MASKGVNKVILVGNLGQDPEVRYLPSGSAVCSVTLATSESWRDKA TGELKEQTEWHRVVLFGKLAEVAGEYLRKGSQVYIEGQLRTRKWT DQSGQEKYTTEVVVNVGGTMQMLGGRQGGGAPAGGSQNQQQGGWG QPQQPQGGNQFSGGAQSRPQQQSAPAPSNEPPMDFDDDIPF | |
| 104 | ssDNA-binding protein [*Klebsiella oxytoca*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEVVVNVGGTMQMLGGRQGAGAPAGGGQQQGGWGQ PQQPQGGNQYSGGAQSRPQQQAPAAPSNEPPMDFDDDIPF | |
| 105 | ssDNA-binding protein [*Klebsiella oxytoca*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEVVVNVGGTMQMLGGRQGAGAPAGGGQQQGGWGQ PQQPQGGNQFSGGAQSRPQQQTPAAPSNEPPMDFDDDIPF | |

TABLE 5-continued

Biological Sequences

| SEQ ID NO: | DESCRIPTION | SEQUENCE | COMMENTS |
|---|---|---|---|
| 106 | ssDNA-binding protein [*Pantoea*] | MASRGVNKVILVGNLGQDPEVRYMPNGGAYANITLATSESWRDKQ TGENKEITEWHRVVLFGKLAEVAGEYLRKGSQVYIEGQLRTRKWQ DQGGQDRYTTEVVVNVGGTMQMLGGRQQGGASAGGAPMGGGQQSG GNNNGWGQPQQPQGGNQFSGGAQSRPQPQSAPASNNNEPPMDFDD DIPF | |
| 107 | single-stranded DNA-binding protein [*Klebsiella oxytoca*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGQEKYTTEVVVNVGGTMQMLGGRQQGAGAPAGGGQQQGGWGQ PQQPQGGNQFSGGAQSRPQQQAPAAPSNETPMDFDDDIPF | |
| 108 | ssDNA-binding protein [*Entero-bacteriaceae*] | MASRGVNKVILVGNLGQDPEVRYMPNGGAYANITLATSESWRDKA TGEQKEKTEWHRVVLFGKLAEVAGEYLRKGSQVYIEGSLQTRKWQ DQSGQDRYTTEIVVNVGGTMQMLGGRQGGGAPAGQSAGGQGGWGQ PQQPQSGNQFSGGQQQSRPAQNSAPATSNEPPMDFDDDIPF | |
| 109 | ssDNA-binding protein [*Klebsiella pneumoniae*] | MASRGVNKVILVGNLGQDPEVRYMPSGGAYANFTLATSESWRDKH TGEMKEQTEWHRVVLFGKLAEVAGEYLRKGSQVYIEGQLRTRKWT DQSGQDKYTTEVVVNVGGTMQMLGGRQGGGAPAGGGQQQGGWGQP QQPQGGNQFSGGAQSRPQQQAPAAPSNEPPMDFDDDIPF | |
| 110 | single-stranded DNA-binding protein [*Klebsiella pneumoniae*] | MASRGVNKVILVGNLGQDPEVRYMPSGGAYANFTLATSESWRDKQ TGEMKEQTEWHRVVLFGKLAEVAGEYLRKGSQVYIEGQLRTRKWT DQSGQDKYTTEVVVNVGGTMQMLGGRQGGGAPAGGGQQQGGWGQP QGGNQFSGGAQSRPQQQAPAAPSNEPPMDFDDDIPF | |
| 111 | ssDNA-binding protein [*Entero-bacteriaceae*] | ASRGVNKVILVGNLGQDPEVRYMPSGGAYANFTLATSESWRDKQT GEMKEQTEWHRVVLFGKLAEVAGEYLRKGSQVYIEGQLRTRKWTD QSGQDKYTTEVVVNVGGTMQMLGGRQGGGAPAGGGQQQGGWGQPQ QPQGGNQFSGGAQSRPQQQAPAAPSNEPPMDFDDDIPF | |
| 112 | ssDNA-binding protein [*Klebsiella pneumoniae*] | MASRGVNKVILVGNLGQDPEVRYMPSGGAYANFTLATSESWRDKQ TGEMKEQTEWHRVVLFGKLAEVAGEYLRKGSQVYIEGQLRTRKWT DQSGQDKYTTEVVVNVGGTMQMLGGRQGGGAPAGGGQQQGGWGQP QQPQGGNQFSGGAQSRPQQQAPAAPSNEPPMDFDDDIPF | |
| 113 | ssDNA-binding protein [*Gammaproteo-bacteria*] | MASRGVNKVILVGNLGQDPEVRYMPNGGAYANITLATSESWRDKQ TGEMKEQTEWHRVVLFGKLAEVASEYLRKGSQVYIEGQLRTRKWT DQSGVEKYTTEVVVNVGGTMQMLGGRQGGGAPAGGQQQQGGWGQP QQPQGGNQFSGGAQSRPQQQSAPAAPSNEPPMDFDDDIPF | |
| 114 | ssDNA-binding protein [*Enterobacter aerogenes*] | MASRGVNKVILVGNLGQDPEVRYMPSGGAYANFTLATSESWRDKQ TGEMKEQTEWHRVVLFGKLAEVAGEYLRKGSQVYIEGQLRTRKWT DQSGQDKYTTEIVVNVGGTMQMLGGRQGGGAPAGGQQQGGWGQPQ QPQGGNQFSGGAQSRPQQQAPAAPSNEPPMDFDDDIPF | |
| 115 | ssDNA-binding protein [*Enterobacter aerogenes*] | MASRGVNKVILVGNLGQDPEVRYMPSGGAYANFTLATSESWRDKQ TGEMKEQTEWHRVVLFGKLAEVAGEYLRKGSQVYIEGQLRTRKWT DQSGQDKYTTEIVVNVGGTMQMLGGRQGGGAPAGGGQQQGGWGQP QQPQGGNQFSGGAQSRPQQQAPAAPSNEPPMDFDDDIPF | |
| 116 | ssDNA-binding protein [*Serratia*] | MASRGVNKVILVGNLGQDPEVRYMPNGGAYANITLATSESWRDKA TGEQKEKTEWHRVVLFGKLAEVAGEYLRKGSQVYIEGSLQTRKWQ DQSGQDRYTTEIVVNVGGTMQMLGGRQGGGAPAGQSAGGQGGWGQ PQQPQGGNQFSGGQQQSRPAQNSAPAASSNEPPMDFDDDIPF | |
| 117 | ssDNA-binding protein [*Yokenella regensburgei*] | MASRGVNKVILVGNLGQDPEVRYMPNGGAVANITLATSESWRDKA TGEMKEQTEWHRVVLFGKLAEVAGEYLRKGSQVYIEGQLRTRKWT DQSGQEKYTTEIVVNVGGTMQMLGGRQQGGAPAGGGQQQGGWGQP QQPQGGNQFSGGAQSRPQQQSAPAPSNEPPMDFDDDIPF | |
| 118 | ssDNA-binding protein [*Raoultella terrigena*] | MASRGVNKVILVGNLGQDPEVRYMPSGGAVANFTLATSESWRDKQ TGEMKEQTEWHRVVLFGKLAEVAGEYLRKGSQVYIEGQLRTRKWT DQSGAEKYTTEIVVNVGGTMQMLGGRQGGGAPAGGGQQQGGWGQP QQPQQQPQGGNQFSGGAQSRPQQQAPAAPSNEPPMDFDDDIPF | |
| 119 | ssDNA-binding protein | MASRGVNKVILVGNLGQDPEVRYMPSGGAVANFTLATSESWRDKQ TGEMKEQTEWHRVVLFGKLAEVAGEYLRKGSQVYIEGQLRTRKWT | |

TABLE 5-continued

| SEQ ID NO: | DESCRIPTION | SEQUENCE | COMMENTS |
|---|---|---|---|
| Biological Sequences | | | |
| | [*Klebsiella pneumoniae*] | DQSGQDKYTTEVVVNVGGTMQMLGGRQGGGAPAGGGQQQGGWGQP QQPQGGNQFSGGAQSRPQQQAPSAPSNEPPMDFDDDIPF | |
| 120 | ssDNA-binding protein [*Yersinia*] | MASRGVNKVILVGNLGQDPEVRYMPNGGAVANITLATSESWRDKA TGEQKEKTEWHRVVLFGKLAEVAGEYLRKGSQVYIEGALQTRKWQ DQSGQERYTTEVVVNVGGTMQMLGGRQGGGAPAGGSQQDGGAQGG WGQPQQPQGGNQFSGGQTSRPAQSAPAAQPQGGNEPPMDFDDDIP F | |
| 121 | ssDNA-binding protein [*Klebsiella pneumoniae*] | MASRGVNKVILVGNLGQDPEVRYMPSGGAVANFTLATSESWRDKQ TGEMKEQTEWHRVVLFGKLAEVAGEYLRKGSQVYIEGQLRTRKWT DQSGQDKYTTEVVVNVSGTMQMLGGRQGGGAPAGGGQQQGGWGQP QQPQGGNQFSGGAQSRPQQQAPAAPSNEPPMDFDDDIPF | |
| 122 | ssDNA-binding protein [*Cronobacter condimenti*] | MASRGVNKVILVGNLGQDPEVRYMPNGGAVANLRLATSESWRDKQ TGEMKEVTEWHSVVLYGKLAEVAGEYLRKGSQIYIEGQLRTRKWQ DQSGQDRYSTEVVVNVGGTMQMLGGRQGGGAPAGGNMGGGQQQGG WGQPQQPQQQSGGAQFSGGAQSRPQQQAPAPSNEPPMDFDDDIPF | |
| 123 | ssDNA-binding protein [*Klebsiella* sp. 10982] | MASRGVNKVILVGNLGQDPEVRYMPSGGAVANFTLATSESWRDKQ TGEMKEQTEWHRVVLFGKLAEVAGEYLRKGSQVYIEGQLRTRKWT DQSGQDKYTTEVVVNVGGTMQMLGGRQGGGAPAGGGQQQGGWGQP QQPQGGSQFSGGAQSRPQQQAPAAPSNEPPMDFDDDIPF | |
| 124 | single-stranded DNA-binding protein [*Klebsiella pneumoniae*] | MASRGVNKVILVGNLGQDPEVRYMPSGGAVANFTLATSESWRDKQ TGEMKEQTEWHRVVLFGKLAEVAGEYLRKGSQVYIEGQLRTRKWT DQSGQDKYTTEVVVNVGGTMQMLGGRQGGGAPAGGGQQQGGWGQP QQPQGGNQFSGGAQSRPQQQAPAAPSNETPMDFDDDIPFMASRGV NKVILVGNLGQDPEVRYMPSGGAVANFTLATSESWRDKQTGEMKE QTEWHRVVLFGKLAEVAGEYLRKGSQVYIEGQLRTRKWTDQSGQD KYTTEVVVNVGGTMQMLGGRQGGGAPAGGGQQQGGWGQPQQPQGG NQFSGGAQSRPQQQAPAAPSNETPMDFDDDIPFAEVAGEYLRKGS QVYIEGQLRTRKWTDQSGQDKYTTEVVVNVGGTMQMLGGRQGGGA RAGGGQQQGGWGQPQQPQGGNQFSGGAQSRPQQQAPAAPSNETPM DFDDDIPF | |
| 125 | ssDNA-binding protein [*Trabulsiella guamensis*] | MASRGVNKVILVGNLGQDPEVRYMPNGGAVANITLATSESWRDKQ TGEMKEQTEWHRVVLFGKLAEVASEYLRKGSQVYIEGQLRTRKWT DQSGVEKYTTEVVVNVGGTMQMLGGRQGGAGAPAGGGQQQQGGWG QPQQPQGGAQFSGGAQSRPQQQSAPAPSNEPPMDFDDDIPF | |
| 126 | ssDNA-binding protein [*Enterobacter cloacae*] | MASKGVNKVILVGNLGQDPEVRYLPSGGAVCSVTLATSESWRDKA TGELKEQTEWHRIVLFGKLAEVAGEYLRKGSQVYIEGQLRTRKWT DQSGQEKYTTEVVVNVGGTMQMLGGRQGGGAPAGGGQSQQHGGWG QYQHPQVGNQFSGGAQSRPQQQSAPAPSNEPPMDFDDDIPF | |
| 127 | ssDNA-binding protein [*Trabulsiella* odontotermitis | MASRGVNKVILVGNLGQDPEVRYMPNGGAYANITLATSESWRDKQ TGEMKEQTEWHRVVLFGKLAEVASEYLRKGSQVYIEGQLRTRKWT DQSGVEKYTTEVVVNVGGTMQMLGGRQGGAGAPAGGGQPQQQGGW GQPQQPQGGAQFSGGAQSRPQQQSAPAPSNEPPMDFDDDIPF | |
| 128 | ssDNA-binding protein [*Trabulsiella odontotermitis*] | MASRGVNKVILVGNLGQDPEVRYMPNGGAYANITLATSESWRDKQ TGEMKEQTEWHRVVLFGKLAEVASEYLRKGSQVYIEGQLRTRKWT DQSGVEKYTTEVVVNVGGTMQMLGGRQGGAGAPAGGGQQQGGWGQ PQQPQQQGGAQFSGGAQSRPQQQSAPAPSNEPPMDFDDDIPF | |
| 129 | ssDNA-binding protein [*Kosakonia radicincitans*] | MASRGVNKVILVGNLGQDPEVRYMPSGGAYANITLATSESWRDKQ TGEMKEQTEWHRVVLFGKLAEVAGEYLRKGSQVYIEGQLRTRKWT DQSGQEKYTTEVVVNVGGTMQMLGGRQGGGAPAGGGQQQGGWGQP QQPQGGNQFSGGAQSRPQQSSAPAPSNEPPMDFDDDIPF | |
| 130 | single-stranded DNA-binding protein [*Serratia marcescens*] | MASRGVNKVILVGNLGQDPEVRYMPNGGAYANITLATSESWRDKA TGEQKEKTEWHRVVLFGKLAEVAGEYLRKGSQVYIEGSLQTRKWT DQAGVEKYTTEVVVNVGGTMQMLGGRQGGGAPAGQSAGGQGGWGQ PQQPQGGNQFSGGQQQSRPAQNSAPAASSNEPPMDFDDDIPF | |
| 131 | ssDNA-binding protein [*Kluyvera*] | MASRGVNKVILVGNLGQDPEVRYMPNGGAYANITLATSESWRDKA TGEMKEQTEWHRVVLFGKLAEVAGEYLRKGSQVYIEGQLRTRKWT DQSGAEKYTTEVVVNVGGTMQMLGGRQGGGAPAGGGQQQQGGWGQ PQQPQGGNQFSGGAQSRPQQQSAPAPSNEPPMDFDDDIPF | |

TABLE 5-continued

| SEQ ID NO: | DESCRIPTION | SEQUENCE | COMMENTS |
|---|---|---|---|
| Biological Sequences | | | |
| 132 | ssDNA-binding protein [*Enterobacter asburiae*] | MASRGVNKVILVGNLGQDPEVRYMPSGGAYANITLATSESWRDKA TGEMKEQTEWHRVVLFGKLAEVAGEYLRKGSQVYIEGQLRTRKWT DQSGAEKYTTEVVVNVGGTMQMLGGRQGGGTPAGGGQQQQGGWGQ PQQPQGGNQFSGGAQSRPQQQSAPAPSNEPPMDFDDDIPF | |
| 133 | c2 NLS-SSB fusion protein | MQPSLKRMKIQPSSQPASRGVNKVILVGNLGQDPEVRYMPNGGAV ANITLATSESWRDKATGEMKEQTEWHRVVLFGKLAEVASEYLRKG SQVYIEGQLRTRKWTDQSGQDRYTTEVVVNVGGTMQMLGGRQGGG APAGGNIGGGQPQGGWGQPQQPQGGNQFSGGAQSRPQQSAPAAPS NEPPMDFDDDIPF | |
| 134 | c2 NLS-Bacteriophage Lambda Red beta SSAP-fusion protein | MQPSLKRMKIQPSSQPMSTALATLAGKLAERVGMDSVDPQELITT LRQTAFKGDASDAQFIALLIVANQYGLNPWTKEIYAFPDKQNGIV PVVGVDGWSRIINENQQFDGMDFEQDNESCTCRIYRKDRNHPICV TEWMDECRREPFKTREGREITGPWQSHPKRMLRHKAMIQCARLAF GFAGIYDKDEAERIVENTAYTAERQPERDITPVNDETMQEINTLL IALDKTWDDDLLPLCSQIERRDIRASSELTQAEAVKALGELKQKA AEQKVAA | |
| 135 | c2 NLS-Bacteriophage Lambda Red Exonuclease-fusion protein | MQPSLKRMKIQPSSQPTPDIILQRTGIDVRAVEQGDDAWHKLRLG VITASEVHNVIAKPRSGKKWPDMKMSYFHILLAEVCIGVAPEVNA KALAWGKQYENDARTLFEFTSGVNVTESPIIYRDESMRTACSPDG LCSDGNGLELKCPFTSRDFMKFRLGGFEAIKSAYMAQVQYSMWVT RKNAWYFANYDPRMKREGLHYVVIERDEKYMASFDEIVPEFIEKM DEALAEIGFVFGEQWR | |
| 136 | Artemis | MSSFEGQMAEYPTISIDRFDRENLRARAYELSHCHKDHMKGLRAP ILKRRLECSLKVYLYCSPVIKELLLTSPKYRFWKKRIISIEIETP TQISLVDEASGEKEEIVVILLPAGHCPGSVMFLFQGNNGTVLYTG DFRLAQGEAARMELLHSGGRVKDIQSVYLDTTFCDPRFYQIPSRE ECLSGVLELVRSWITRSPYHVVWLNCKAAYGYEYLFTNLSEELGV QVHVNKLDMERNMPEILHHLTTDRNIQIHACRHPKAEEYFQWSKL PCGITSRNRIPLHIISIKPSTMWFGERSRKINVIVRTGESSYRAC FSFHSSYSEIKDFLSYLCPVNAYPNVIPVGITMDK VVEILKPLCRSSQSTEPKYKPLGKLKRARTVHRDSEEEDDYLFDD PLPIPLRHKVPYPETFHPEVFSMTAVSEKQPEKLRQTPGCCRAEC MQSSRFINFVDCEESNSESEEEVGIPASLQGDLGSVLHLQKADGD VPQWEVFFKRNDEITDESLENFPSSTVAGGSQSPKLFSDSDGEST HISSQNSSQSTHITEQGSQGWDSQSDTVLLSSQERNSGDITSLDK ADYRPTIKENIPASLMEQNVICPKDTYSDLKSRDKDVTIVPSTGE PTILSSETHIPEEKSLLNLSTNADSQSSSDFEVPSTPEAELPKRE HLQYLYEKLATGESIAVKKRKCSLLDT | NCBI Reference Sequence: NP_ 001029027.1 |
| 137 | Apollo (*Actinidia chinensis* var. *chinensis*) | MGIQGLLPLLKSIMVPIHIKDLEDCCVAIDTYSWLHKGALSCSKD LCKGQSTSKHIDYCMNRVNLLQHYGIRPILVFDGGPLPMKSEQES KRARSRKENLACAIENESNGNNASAYKCYQKAVVISPSVAYELIQ VLKKENVYYVVAPYEADAQMTFLAVSKQVDAVITEDSDLIAFGCP RIIYKMDKLEQGVEFRYSMLQQNKELNFTGFTKRMLLEMCILSGC DYLQSLPGIGLKKAHALVKKFKSYDKVIKHLKYSTASVSSSYEES FRKAIMTFQHQRVYDPTIEDIVHLSDLPQYVGDDLDFLGPAILQH LAKGIARGDLDPFTKMPIQGVNNGAGLVDEGMYKLNNEKSEGFAS LEAKRRFMAPRSTPKHRNPITETCSTVEHITEDADACKINCSLES LLDSRYFDVASPSEGYVKHGVAAKSPESKSPSHGSHDKEEILGEG DNRSPQDPLLQQFKHSIPKLCMTLQKERAKSVADSGQDKIRKENT KVIVRSSYFQHKLVKENDKENIKEDVITDKGENINPKREHKSASD GGEAKTRIKNRKTIVRSSYFLHKSVNENDQDNRHEKLIINDDFTT HTHENGIPESASGDGYFNNSIVKRKVSPVDSVQMEKTNYKCMRMD ASLPIESSSISTLNNTIMETKAEGGKEGSNISHLKNYSDIAEKSI ERFVSVISSFKCSSSGSSASGLRAPLRNTEHMY | GenBank: PSS29025.1 |
| 138 | DNA2 exonuclease (*Mus musculus*) | MEPLDELDLLLLEEDGGAEAVPRVELLRKKADALFPETVLSRGVD NRYLVLAVETSQNERGAEEKRLHVTASQDREHEVLCILRNGWSSV PVEPGDIVHLEGDCTSEPWIIDDDFGYFILYPDMMISGTSVASSI RCLRRAVLSETFRGSDPATRQMLIGTILHEVFQKAISESFAPERL QELALQTLREVRHLKEMYRLNLSQDEILCEVEEYLPSFSKWAEDF MRKGPSSEFPQMQLSLPSDGSNRSSPCNIEVVKSLDIEESIWSPR FGLKGKIDVTVGVKIHRDCKMKYKVMPLELKIGKESNSIEHRSQV VLYTLLSQERREDPEAGWLLYLKTGQMYPVPANHLDKRELLKLRN WLAASLLHRVSRAAPGEEARLSALPQIIEEEKTCKYCSQIGNCAL YSRAVEEQGDDASIPEAMLSKIQEETRHLQLAHLKYFSLWCLMLT LESQSKDNRKTHQSIWLTPASELEESGNCVGNLVRTEPVSRVCDG QYLHNFQRKNGPMPATNLMAGDRIILSGEERKLFALSKGYVKKMN KAAVICLLDRNLSTLPATIVERLDREERHGDISTPLGNLSKLMES TDPSKRLRELIIDFREPQFIAYLSSVLPHDAKDTVANILKGLNKP | NCBI Reference Sequence: NP_796346.2 |

TABLE 5-continued

| SEQ ID NO: | DESCRIPTION | SEQUENCE | COMMENTS |
|---|---|---|---|
| Biological Sequences | | | |
| | | QRQAMKRVLLSKDYTLIVGMPGIGKITTICALVRILSACGFSVLL TSYTHSAVDNILLKLAKFKVGFLRLGQSHKVHPDIQKFTEEEICR SRSIASLAHLEELYNSHPIVATTCMGINHPIFSRKTFDFCIVDEA SQISQPVCLGPLFFSRRFVLVGDHQQLPPLVVNREARALGMSESL FKRLERNESAVVQLTVQYRMNRKIMSLSNKLTYAGKLECGSDRVA NAVLALPNLKDARLSLQLYADYSDSPWLAGVLEPDNPVCFLNTDK VPAPEQVENGGVSNVTEARLIVFLTSTFIKAGCSPSDIGVIAPYR QQLRIISDLLARSSVGMVEVNTVDKYQGRDKSLILVSEVRSNEDG TLGELLKDWRRLNVALTRAKHKLILLGSVSSLKRFPPLGTLFDHL NAEQLILDLPSREHESLSHILGDCQRD | |
| 139 | Exo1 exonuclease (*Saccharomyces cerevisiae*) | MGIQGLLPQLKPIQNAVSLRRYEGEVLAIDGYAWLHRAACSCAYE LAMGKPIDKYLQFFIKRFSLLKTFKVEPYLVFDGDAIPVKKSTES KRRDKRKENKAIAERLWACGEKKNAMDYFQKCVDITPEMAKCIIC YCKLNGIRYIVAPFEADSQMVYLEQKNIVQGIISEDSDLLVFGCR RLITKLNDYGECLEICRDNFIKLPKKFPLGSLTNEEIITMVCLSG CDYINGIPKVGLITAMKLVRRENTIERIILSIQREGKLMIPDTYI NEYEAAVLAFQFQRVFCPIRKKIVSLNEIPLYLKDTESKRKRLYA CIGFVIHRETQKKQIVHFDDDIDHHLHLKIAQGDLNPYDFHQPLA NREHKLQLASKSNIEFGKINSINSEAKVKPIESFFQKMTKLDHYP KVANNIHSLRQAEDKLIMAIKRRKLSNANVVQETLKDIRSKFFNK PSMTVVENFKEKGDSTQDFKEDINSQSLEEPVSESQLSTQIPSSF ITTNLEDDDNLSEEVSEVVSDTEEDRKNSEGKIIGNEIYNTDDDG DGDISEDYSETAESRVPISSITSFPGSSQRSISGCTKVLQKFRYS SSFSGVNANRQPLFPRHVNQKSRGMVYVNQNRDDDCDDNDGKNQI MQRPLLRKSLIGARSQRIVIDMKSVDERKSFNSSPILHEESKKRD IETTKSSQARPAVRSISLLSQFVYKGK | GenBank: KZV07919.1 |
| 140 | SOX (herpesvirus) | MEATPTPADLFSEDYLVDTLDGLTVDDQQAVLASLSFSKFLKHAK VRDWCAQAKIQPSMPALRMAYNYFLFSKVGEFIGSEDVCNFFVDR VEGGVRLLDVASVYAACSQMNAHQRHHICCLVERATSSQSLNPVW DALRDGIISSSKFHWAVKQQNTSKKIFSPWPITNNHFVAGPLAFG LRCEEVVKILLAILLHPDEANCLDYGFMQSPQNGIFGVSLDFAAN VKIDTEGRLQFDPNCKVYEIKCRFKYTFAKMECDPIYAAYQRLYE APGKLALKDFFYSISKPAVEYVGLGKLPSESDYLVAYDQEWEACP RKKRKLIPLHNLIRECILHNSTTESDVYVLIDPQDTRGQISIKAR FKANLFVNVRHSYFYQVLLQSSIVEEYIGLDSGIPRLGSPKYYIA TGFFRKRGYQDPVNCTIGGDALDPHVEIPILLIVIPVYFPRGAKH RLLHQAANFWSRSAKDTFPYIKWDFSYLSANVPHSP | UniProtKB/ Swiss- Prot: Q2HR95.1 |
| 141 | UL12 exonuclease | MELEPVGKKYRPEREDSSKGRKILIVSVNSQLQGASPILGTRAHP PHSELTDYTFSRYILYHLAPSELKEAIHPLYHRLNYIADVIKRGT SEGRWLGYPYSCILDTEDELRNESRRNTSSPSDHALRWCLLVESF TIEQANCDLWHIFRQSLLTASSVKWTDDGKLDTVGIMSDNSTAYV ETCSVAFGKHNEPLAKSLVTMFCLNHSRHVHNTSPRRENVFVFED VSDRTIQSESDYSCGLMIDTRIGMVGASLDMLVCERDPFGLLQPD SENQAIETYEIKCRAKYAFCPDKRSELSQCYERLLNVRTMGSLRL FISAIQRPCVDYFQPGNVPRSKEALITSNEEWKVGNSAYHAAQSR IRCNAFDKCHLELNSNVQSRVWLFGEPDLETDTIYPLPWDIGKLS LDVPIFSNPRHPNFKQIYLQTYVAAGYFGERRTTPFLVTFIGRWR KRREFGKKFSLIADSGLGKPISTVHADQAIPVLLIVTPVIVDEAF YGEIESAGCRAFGELVKQLWAKQPHT | GenBank: AAG30051.1 |
| 142 | *E. coli* exonuclease VIII | MSKVFICAAIPDELATREEGAVAVATAIEAGDERRARAKFHWQFL EHYPAAQDCAYKFIVCEDKPGIPRPALDSWDAEYMQENRWDEESA SFVPVETESDPMNVIFDKLAPEVQNAVMVKFDICENITVDMVISA QELLQEDMATFDGHIVEALMKMPEVNAMYPELKLHAIGWVKHKCI PGAKWPEIQAEMRIWKKRREGERKETGKYTSVVDLARARANQQYT ENSIGKISPVIAAIHREYKKQTWKILDDELAYALWPGDVDAGNIDG SIHRWAKKEVIDNDREDWKRISASMRKQPDALRYDRQTIFGLVRE RPIDIHKDPIALNKYICEYLITKGVFENEETDLGTVDVLQSSETQ TDAVETEVSDIPKNETAPEAEPSVEREGPFYFLFADKDGEKYGRA NKLSGLDKALAAGATEITKEEYFARKNGTYTGLPQNVDTAEDSEQ PEPIKVTADEVNKIMQAANISQPDADKLLAASRGEFVEEISDPND PKWVKGIQTRDSVNQNQHESERNYQKAEQNSTNALQNEPETKQPE PVAQQEVEKVCTACGQTGGGNCPDCGAVMGDATYQETFDEEYQVE VQEDDPEEMEGAEHPHKENTGGNQHHNSDNETGETADHSIKVNGH HEITSTSRAGIHLMIDLETMGKNPDAPIICNRLI | NCBI Reference Sequence: WP_ 077887717.1 |
| 143 | T7 phage exonuclease (Enterobacteria phage T7) | MALLDLKQFYELREGCDDKGILVMDGDWLVFQAMSAAEFDASWEE EIWHRCCDHAKARQILEDSIKSYETRKKAWAGAPIVLAFTDSVNW RKELVDPNYKANRKAVKKPVGYFEFLDALFEREEFYCIREPMLEG DDVMGVIASNPSAFGARKAVIISCDKDFKTIPNCDFLWCTIGNIL | NCBI Reference Sequence: NP_041988.1 |

TABLE 5-continued

Biological Sequences

| SEQ ID NO: | DESCRIPTION | SEQUENCE | COMMENTS |
|---|---|---|---|
| | | TQTEESADWWHLFQTIKGDITDGYSGIAGWGDTAEDFLNNPFITE PKTSVLKSGKNKGQEVIKWVKRDPEPHETLWDCIKSIGAKAGMTE EDIIKQGQMARILRFNEYNFIDKEIYLWRP | |
| 144 | Exonuclease III (*E. coli*) | MKFVSFNINGLRARPHQLEAIVEKHQPDVIGLQETKVHDDMFPLE EVAKLGYNVFYHGQKGHYGVALLTKETPIAVRRGFPGDDEEAQRR IIMAEIPSLLGNVTVINGYFPQGESRDHPIKFPAKAQFYQNLQNY LETELKRDNPVLIMGDMNISPTDLDIGIGEENRKRWLRTGKCSFL PEEREWMDRLMSWGLVDTFRHANPQTADRFSWFDYRSKGFDDNRG LRIDLLLASQPLAECCETGIDYEIRSMEKPSDHAPVWATFRR | GenBank: BAA15540.1 |
| 145 | Trex2 exonuclease (mouse) | MSEPPRAETFVFLDLEATGLPNMDPEIAEISLFAVHRSSLENPER DDSGSLVLPRVLDKLTLCMCPERPFTAKASEITGLSSESLMHCGK AGFNGAVVRTLQGFLSRQEGPICLVAHNGFDYDFPLLCTELQRLG AHLPQDTVCLDTLPALRGLDRAHSHGTRAQGRKSYSLASLFHRYF QAEPSAAHSAEGDVHTLLLIFLHRAPELLAWADEQARSWAHIEPM YVPPDGPSLEA | NCBI Reference Sequence: NP_036037.1 |
| 146 | Hammerhead ribozyme | AAATTACTGATGAGTCCGTGAGGACGAAACGAGTAAGCTCGTC | |
| 147 | Hepatitis delta virus (HDV) ribozyme | GGCCGGCATGGTCCCAGCCTCCTCGCTGGCGCCGGCTGGGCAACA TGCTTCGGCATGGCGAATGGGAC | |
| 148 | Amino acid linker | MAPKKKRKVGGSGS | For linking SV40 NLS to HDR promoting agent proteins in human cells |
| 149 | Tomato SlUBI10 promoter | atcgtatccagtgcaccatatttttggcgattaccactcatatt attgtgtttagtagatattttaggtgcataattgatctcttcttt aaaactaggggcacttattattatacatccacttgacacttgctt tagttggctatttttttatttttatttttgtcaactacccca atttaaattttatttgattaagatatttttatggacctactttat aattaaaaatattttctatttgaaaaggaaggacaaaaatcatac aattttggtccaactactcctctctttttttttttggctttataa aaaaggaaagtgattagtaataaataattaaataatgaaaaaagg aggaaataaaattttcgaattaaaatgtaaaagagaaaaaggaga gggagtaatcattgtttaactttatctaaagtaccccaattcgat tttacatgtatatcaaattatacaaatattttattaaaatataga tattgaataattttattattcttgaacatgtaaataaaaaattatc tattatttcaatttttatataaactattatttgaaatctcaatta tgatttttttaatatcactttctatccatgataatttcagcttaaa aagttttgtcaataattacattaattttgttgatgaggatgacaa gatttcggtcatcaattacatatacacaaattgaaatagtaagca acttgatttttttctcataatgataatgacaaagacacgaaaag acaattcaatattcacattgatttattttatatgataataatta caataataatattcttataaagaaagagatcaattttgactgatc caaaaatttatttattttttactataccaacgtcactaattatatc taataatgtaaaacaattcaatcttacttaaatattaatttgaaa taaactatttttataacgaaattactaaatttatccaataacaaa aaggtcttaagaagacataaattctttttttgtaatgctcaaata aatttgagtaaaaaagaatgaaattgagtgattttttttaatca taagaaaataaataattaatttcaatataataaaacagtaatata atttcataaatggaattcaatacttacctcttagatataaaaaat aaatataaaaataaagtgtttctaataaacccgcaatttaaataa aatatttaatattttcaatcaaatttaaataattatattaaaata tcgtagaaaaagagcaatatataatacaagaaagaagatttaagt acaattatcaactattattatactctaattttgttatatttaatt tcttacggttaaggtcatgttcacgataaactcaaaatacgctgt atgaggacatattttaaattttaaccaataataaaactaagttat ttttagtatattttttttgtttaacgtgacttaatttttcttttct agaggagcgtgtaagtgtcaacctcattctcctaattttcccaac cacataaaaaaaaaataaaggtagcttttgcgtgttgatttggta cactacacgtcattattacacgtgttttcgtatgattggttaatc catgaggcggtttcctctagagtcggccataccatctataaaata aagctttctgcagctcatttttttcatcttctatctgatttctatt | |

TABLE 5-continued

| Biological Sequences | | | |
|---|---|---|---|
| SEQ ID NO: | DESCRIPTION | SEQUENCE | COMMENTS |
| | | ataatttctctgaattgccttcaaatttctctttcaaggttagaa<br>tttttctctatttttggtttttgtttgtttagattctgagttta<br>gttaatcaggtgctgttaaagccctaaattttgagttttttcgg<br>ttgttttgatggaaaatacctaacaattgagtttttcatgttgt<br>tttgtcggagaatgcctacaattggagttcctttcgttgttttga<br>tgagaaagcccctaatttgagtgtttttccgtcgatttgattta<br>aaggtttatattcgagttttttcgtcggtttaatgagaaggcct<br>aaaataggagttttctggttgatttgactaaaaaagccatggaa<br>ttttgtgtttttgatgtcgctttggttctcaaggcctaagatctg<br>agtttctccggttgttttgatgaaaaagccctaaaattggagttt<br>ttatcttgtgttttaggttgttttaatccttataatttgagtttt<br>ttcgttgttctgattgttgttttatgaatttcctgca | |

Example 5. Genome Editing in Tomato Protoplasts

The following example describes experiments assessing gene editing in tomato protoplasts using a Cas nuclease in the presence and absence of HDR promoting agents (i.e., an exonuclease, SSB protein, and SSAP). Specifically, experiments to test the effects of modifying the form and delivery method of the template donor DNA, HDR promoting agents, and nuclease reagents on genome editing were performed.

Materials and Methods

Tomato protoplasts were isolated, cultivated, and transfected as described in Example 2. Genome editing was assessed using amplicon sequencing, as described in Example 2.

Design of Plasmids for Transfection

Figure 3:
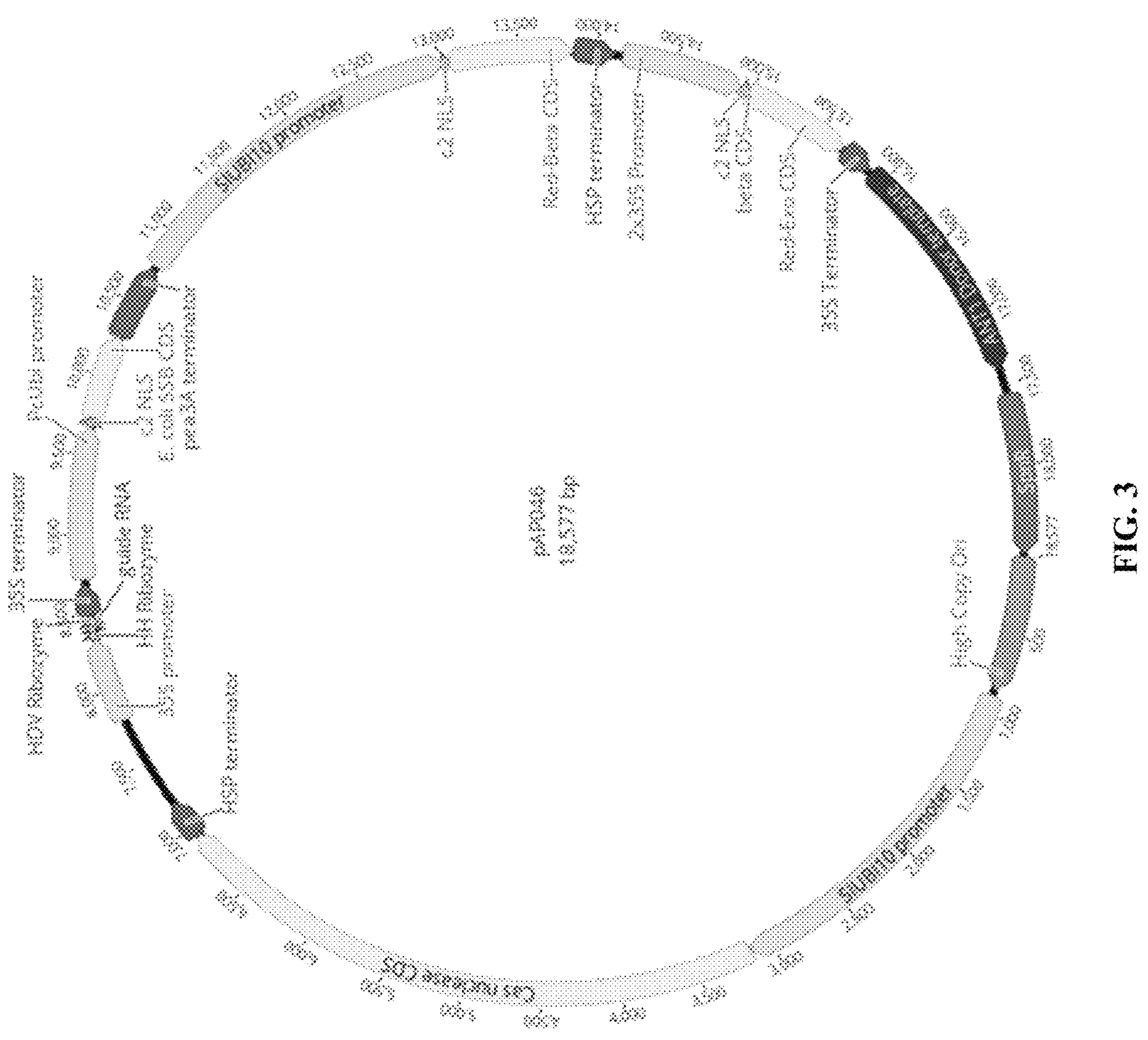
FIG. 3 shows a schematic diagram of the vector pAPO46. Length in base pairs is indicated by the labels outside of the vector. Beginning at base pair 1, the vector includes a high copy number origin of replication (High Copy Ori), Cas expression cassette (tomato S1UBI10 promoter, Cas nuclease coding sequence (Cas nuclease CDS), and HSP terminator), guide RNA and ribozyme expression cassette (35S promoter, sequence encoding a hammerhead (HH) ribozyme, sequence encoding a guide RNA, sequence encoding a hepatitis delta virus (HDV) ribozyme, and 35S terminator), HDR promoting agents expression cassette (PcUbi promoter, c2 NLS fused to an *E. coli* SSB coding sequence (*E. coli* SSB CDS), pea 3A terminator, tomato S1UBI10 promoter, c2 NLS fused to a SSAP coding sequence (Red Beta CDS), HSP terminator, 2x 35S promoter, c2 NLS fused to an exonuclease coding sequence (Red Exo CDS), and 35S terminator), ANTi donor template, and spectinomycin resistance marker (SpnR).
Figure 4:
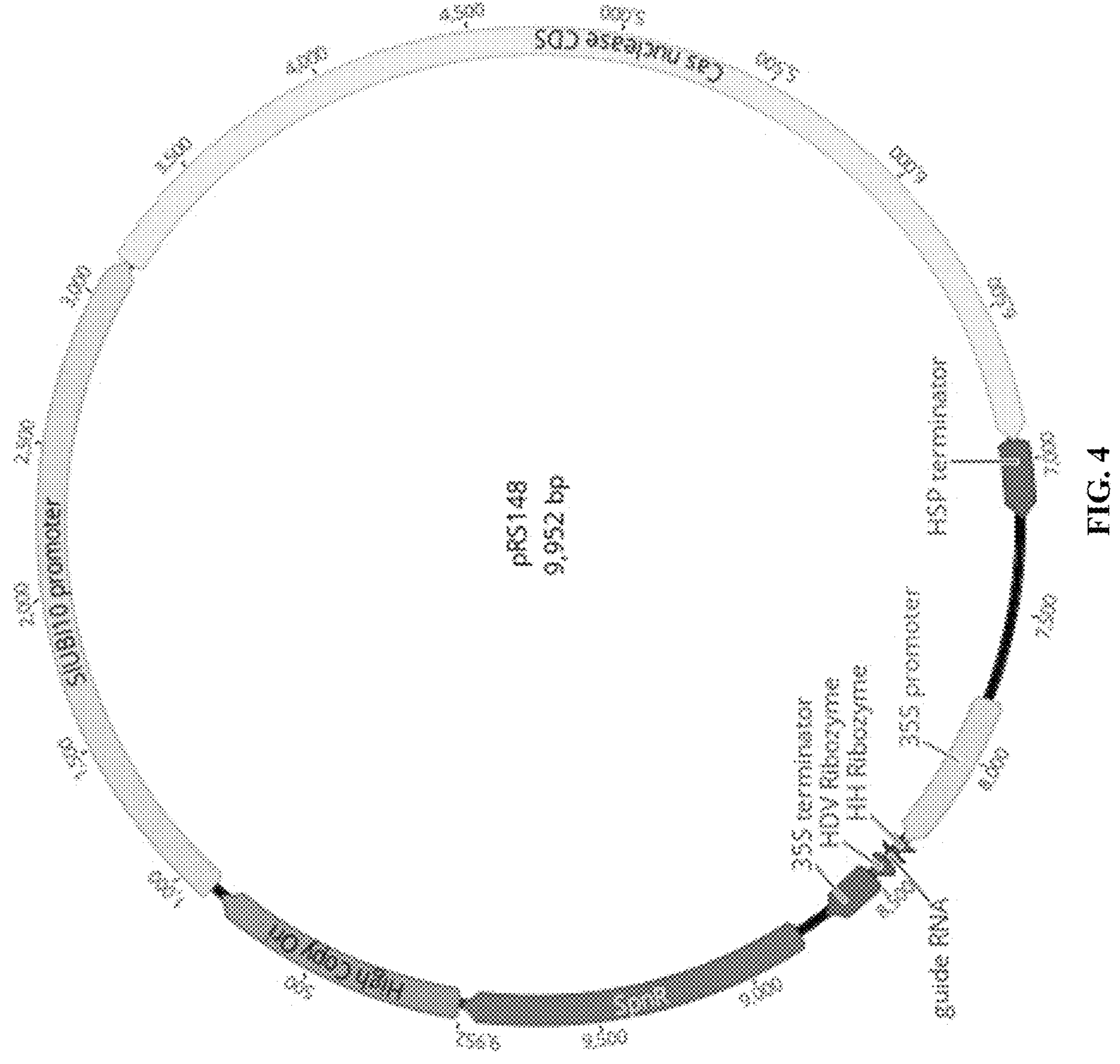
FIG. 4 shows a schematic diagram of the vector pRS148. Length in base pairs is indicated by the labels outside of the vector. Beginning at base pair 1, the vector includes a high copy number origin of replication (High Copy Ori), Cas expression cassette (tomato S1UBI10 promoter, Cas nuclease coding sequence (Cas nuclease CDS), and HSP terminator), guide RNA and ribozyme expression cassette (35S promoter, sequence encoding a hammerhead (HH) ribozyme, sequence encoding a guide RNA, sequence encoding a hepatitis delta virus (HDV) ribozyme, and 35S terminator), and spectinomycin resistance marker (SpnR).
Figure 5:
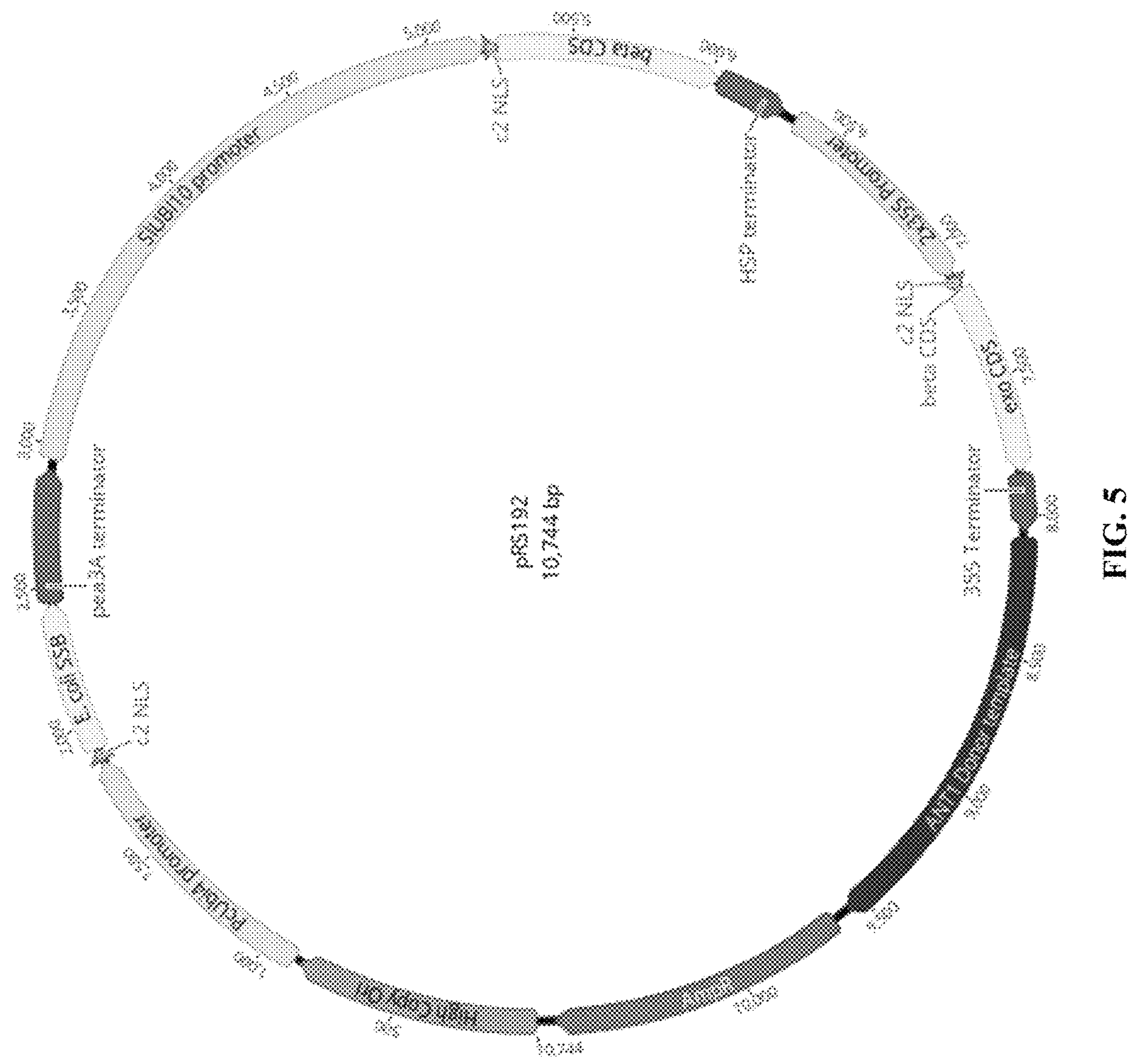
FIG. 5 shows a schematic diagram of the vector pRS192. Length in base pairs is indicated by the labels outside of the vector. Beginning at base pair 1, the vector includes a high copy number origin of replication (High Copy Ori), HDR promoting agent expression cassette (PcUbi promoter, c2 NLS fused to an *E. coli* SSB coding sequence (*E. coli* SSB CDS), pea 3A terminator, tomato S1UBI10 promoter, c2 NLS fused to a SSAP coding sequence (Red Beta CDS), HSP terminator, 2x 35S promoter, c2 NLS fused to an exonuclease coding sequence (Red Exo CDS), and 35S terminator), ANTi donor template, and ampicillin resistance marker (AmpR).

Plasmids were constructed comprising either all the components as part of a single vector (plasmid, see FIG. 3), or with components separated on two different plasmids for co-transfection (see FIGS. 4-5). In particular, a first vector encoded CasS nuclease and its corresponding guide RNA, and a second vector all three HDR promoting agents (i.e., the SSB protein, exonuclease, and SSAP). In addition, the donor template flanked by endonuclease recognition sequences was present in either the first or second vector.

DNA donor templates to target the promoter region of the tomato Ant1 gene for insertion of a 42 base pair heterologous sequence and deletion of 3 base pairs by HDR were constructed.

Linearized Donor DNA

Donor template DNA was added either as a linear double stranded DNA molecule, or as part of a circular vector flanked by specific nuclease recognition sequences.

Presence of gRNA Recognition Sites on DNA Template

The effect of the presence of the gRNA-recognized cut sites that flanked the donor DNA template was tested by eliminating them from a transfection vector.

Results

Tomato protoplasts were transformed with one or two plasmid vectors encoding a Cas nuclease, a guide RNA, and a donor DNA in the presence and absence of HDR promoting agents (i.e., an exonuclease, a SSB protein, and a SSAP) (see FIGS. 3-5). Tables 6A-6C, below, provide a summary of data from tomato protoplast gene editing experiments.

Co-transformation of two vectors consistently showed a significant increase in precise genome editing attributable to HIDR, and a decrease in insertion and deletion (indel) editing attributable to non-homologous end joining (NHEJ), as shown in Table 6A, below. There was a high proportion (e.g. ~~70-80%) of precise to indel edits in the presence of HDR promoting agents (i.e., the SSB, the exonuclease, and the SSA-P). When the donor template DNA and Cas nuclease were co-transformed on separate vectors (FIGS. 4-5), inclusion of the donor template in the absence of HDR promoting agents significantly decreased NHEJ editing without significantly promoting precise editing. When the donor template DNA and Cas nuclease were on a single vector (FIG. 3), the presence of the HIDR promoting agents decreased NHEJ editing to a lesser extent. When the gRNA-recognized cut sites flanking the donor template DNA were eliminated, the presence of the HIDR promoting agents did not decrease the level of NHEJ editing. Co-transformation of components on different vectors did not significantly improve the HIDR efficiency over the efficiency described in Example 2.

TABLE 6A

| Tomato protoplast gene editing with one vs. two vectors (Experiment LR-16) | | | | |
|---|---|---|---|---|
| Transfection Components | % indel (NHEJ) | % precise (HDR) | SD indel | SD precise |
| Lambda RED, CasS, gRNA, donor DNA template plasmid (all—1 vector) | 4.37 | 13.22 | 0.72 | 1.71 |
| CasS, gRNA, donor DNA template plasmid + Lambda Red plasmid (all—2 vectors) | 1.92 | 7.98 | 0.84 | 1.57 |
| CasS, gRNA plasmid + Lambda RED, donor DNA template plasmid (all—2 vectors) | 4.60 | 2.91 | 0.57 | 0.13 |
| CasS, gRNA plasmid + donor DNA template plasmid (no Lambda Red) | 6.31 | 0.48 | 0.52 | 0.17 |
| CasS, gRNA plasmid (CasS only) | 32.89 | 0.00 | 1.37 | 0.00 |
| Donor DNA template plasmid (donor only) | 0.27 | 0.16 | 0.13 | 0.09 |

TABLE 6A-continued

| Tomato protoplast gene editing with one vs. two vectors (Experiment LR-16) | | | | |
|---|---|---|---|---|
| Transfection Components | % indel (NHEJ) | % precise (HDR) | SD indel | SD precise |
| Lambda Red plasmid (Lambda Red only) | 0.14 | 0.00 | 0.11 | 0.00 |
| GFP plasmid | 0.12 | 0.00 | 0.04 | 0.00 |

The linear template DNA was as effective in promoting precise (HIDR) editing and decreased indel (NHEJ) editing as the circular vector flanked by specific nuclease recognition sequences, as used in Example 2 (Table 6B).

TABLE 6B

| Tomato protoplast gene editing with linear vs. circular donor DNA template (Experiment LR-18) | | | | |
|---|---|---|---|---|
| Transfection Components | % indel (NHEJ) | % precise (HDR) | SD indel | SD precise |
| Lambda RED, CasS, gRNA, donor DNA template plasmid (all—1 vector) | 2.46 | 8.74 | 0.19 | 0.75 |
| CasS, gRNA, donor DNA template plasmid + Lambda Red plasmid (all—2 vectors) | 1.15 | 3.12 | 0.08 | 0.07 |
| CasS, gRNA plasmid + Lambda RED, donor DNA template plasmid (all—2 vectors) | 6.95 | 4.24 | 0.36 | 0.31 |
| CasS, gRNA plasmid + Lambda Red plasmid + Linear donor DNA template (linear donor) | 0.47 | 2.75 | 0.11 | 0.31 |
| CasS, gRNA plasmid + donor DNA template plasmid (no Lambda Red—2 vectors) | 6.64 | 0.21 | 0.24 | 0.11 |
| CasS, gRNA, donor DNA template plasmid (no Lambda Red—1 vector) | 12.21 | 0.09 | 0.16 | 0.05 |
| CasS, gRNA plasmid (CasS only) | 25.64 | 0.00 | 0.50 | 0.00 |
| Donor DNA template plasmid (donor only) | 0.08 | 0.22 | 0.07 | 0.06 |
| Lambda Red plasmid (Lambda Red only) | 0.01 | 0.00 | 0.01 | 0.00 |
| GFP plasmid | 0.00 | 0.00 | 0.00 | 0.00 |
| no transfection | 0.01 | 0.00 | 0.02 | 0.00 |

The effect of the DNA template flanking cut sites was tested by eliminating them from a transfection vector. The number and percentage of precise edits was greater than that of negative controls that had no HIDR promoting agents, but were less than that of positive controls having the DNA template flanking cut sites as in Example 2 (Table 6C). Similarly, the indel frequency was less than that of negative controls, and slightly higher than positive controls.

TABLE 6C

| Tomato protoplast gene editing with donor template with or without flanking cut sites (FCS) (Experiment LR-21) | | | | |
|---|---|---|---|---|
| Transfection Components | % indel (NHEJ) | % precise (HDR) | SD indel | SD precise |
| Lambda RED, CasS, gRNA, donor DNA template with FCS plasmid (all—FCS) | 4.03 | 17.30 | 0.27 | 0.82 |
| Lambda RED, CasS, gRNA, donor DNA template without FCS plasmid (all—no FCS) | 6.06 | 3.86 | 0.16 | 0.18 |
| Lambda RED, donor DNA template with FCS plasmid (no nuclease—FCS) | 0.00 | 0.01 | 0.00 | 0.01 |
| Lambda RED, donor DNA template without FCS plasmid (no nuclease—no FCS) | 0.02 | 0.18 | 0.02 | 0.09 |
| CasS, gRNA, donor DNA template with FCS plasmid (no Lambda Red—FCS) | 27.99 | 0.24 | 1.90 | 0.12 |
| CasS, gRNA, donor DNA template without FCS plasmid (no Lambda Red—no FCS) | 39.46 | 0.27 | 0.88 | 0.04 |
| CasS, gRNA plasmid (CasS only) | 36.57 | 0.00 | 1.27 | 0.00 |
| Donor DNA template with FCS plasmid (donor only—FCS) | 0.02 | 0.42 | 0.02 | 0.16 |
| Donor DNA template with FCS plasmid (donor only—no FCS) | 0.02 | 0.55 | 0.01 | 0.06 |
| no transfection | 0.00 | 0.00 | 0.01 | 0.00 |

Example 6. Genomic Replacement of SPX in Maize

The following example describes editing of a miRNA binding site at the SPXlocus in maize protoplasts using HDR promoting agents (i.e., the exonuclease, lambda beta SSAP, and *E. coli* SSB protein).

Materials and Methods

Design of Plasmid Constructs

Two gRNAs are used to target regions surrounding the miRNA binding site at the SPXlocus in maize for CasS-mediated cleavage, to thereby mediate replacement of the site. A donor DNA fragment is used as a template for HDR repair/editing mediated by HDR promoting agents.

Plasmid constructs are designed to replace the miRNA binding site at the SPXlocus in maize and its flanking regions with a fragment containing SNPs every three base pairs within the miRNA binding site. In addition, SNPs are introduced to mutate the two PAM sites, and thereby prevent cutting of the locus after editing has occurred. One of the SNPs introduced into the miRNA binding site acts as a SNP for both the miRNA binding site and one of the PAM sequences.

Figure 6:
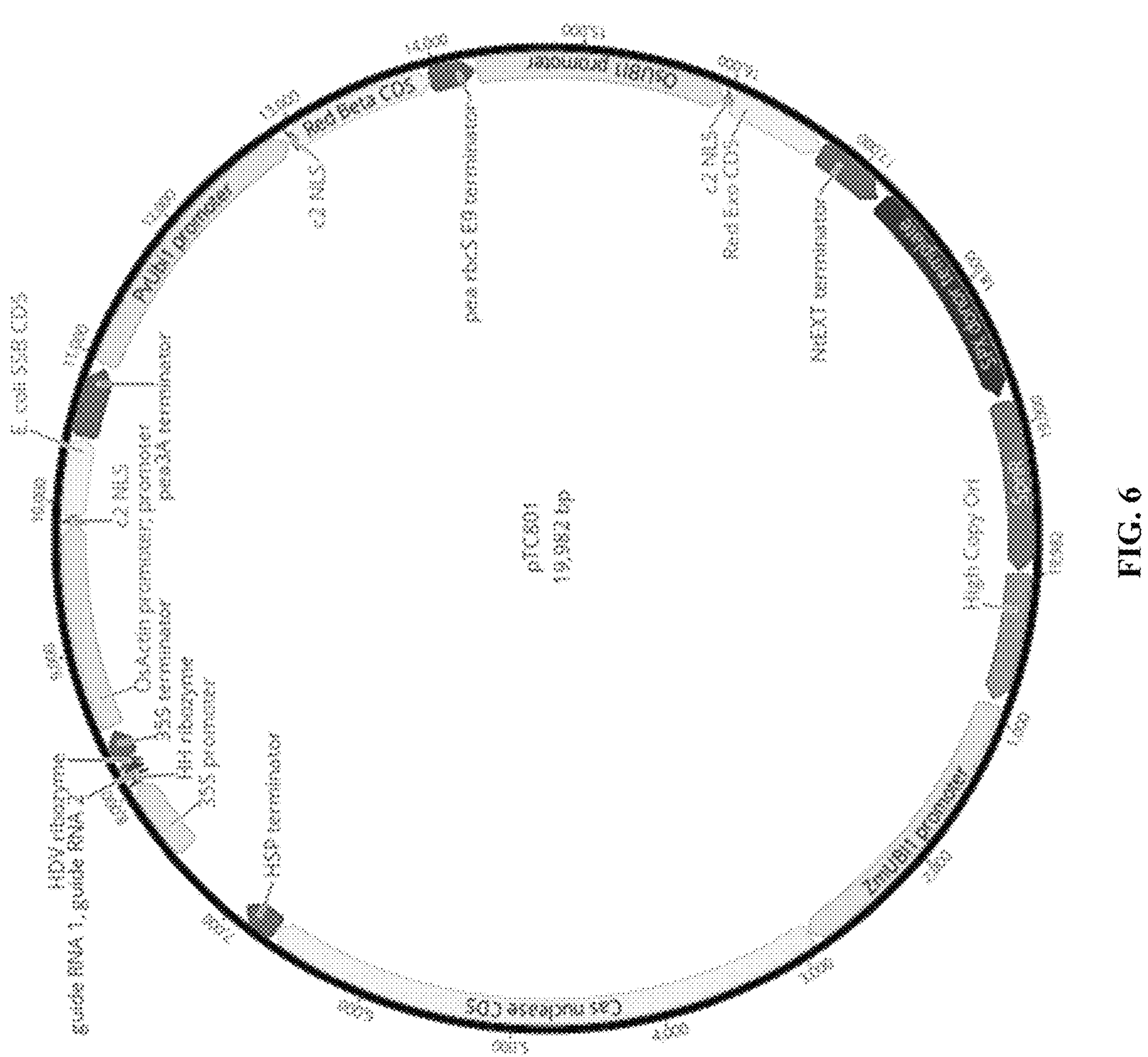
FIG. 6 shows a schematic diagram of the vector pTC801. Length in base pairs is indicated by the labels outside of the vector. Beginning at base pair 1, the vector includes a high copy number origin of replication (High Copy Ori), Cas expression cassette (maize ubiquitin (ZmUbi) promoter, Cas nuclease coding sequence (Cas nuclease CDS), and HSP terminator), a guide RNA and ribozyme expression cassette (35S promoter, sequence encoding a hammerhead (HH) ribozyme, sequences encoding a guide RNA 1 and 2, sequence encoding a hepatitis delta virus (HDV) ribozyme, and 35S terminator), a HDR promoting agents expression cassette (*Oryza sativa* actin (OsActin) promoter, c2 NLS fused to an *E. coli* SSB coding sequence (*E. coli* SSB CDS), pea 3A terminator, *Panicum virgatum* ubiquitin (PvUbil) promoter, c2 NLS fused to a SSAP coding sequence (Red Beta CDS), pea rbcS E9 terminator, *O. sativa* ubiquitin (OsUBI) promoter, c2 NLS fused to an exonuclease coding sequence (Red Exo CDS), and tobacco extensin (NtEXT) terminator), SPX donor template, and spectinomycin resistance marker (SpnR).

A system with a CasS nuclease with two gRNAs specific to the target, the HDR promoting agents (exonuclease, lambda beta SSAP, and the *E. coli* SSB protein), and a donor template with the replacement fragment and ~700 base pair homology arms which are homologous to the target editing site is used. The vectors expressing Cas9 and the HDR promoting agents were designed as described in Example 6. The homology arms were designed to be ~700 base pairs, because previous experiments have shown that ~500-750 base pair arms are functional (see Example 6). In addition, GC content of the homology arms was also considered and maximized, which, without wishing to be bound by theory, may help with annealing and promoting precise editing. Each of the two gRNA target sequences were also present at the ends of the donor in order for the donor to be cleaved and released from the plasmid for subsequent editing mediated by HDR promoting agents. A single plasmid expressed all necessary components for editing (see FIG. 6). Each expressed component was driven by its own promoter.

Maize Cultivation and Transfection, and Amplicon Sequencing

Each individual plasmid is transfected into maize protoplasts in four separate replicates. Cells are incubated for 48 hours. Genomic DNA is then extracted, and of amplicon sequencing libraries are prepared. Insertion and deletion (indel) frequencies and replacement efficiency are quantified from the amplicon sequencing data as described in Example 2, above.

Results

The miRNA binding site at the SPXlocus in maize is edited using a CasS nuclease targeted by two gRNAs in the presence or absence of HDR promoting agents. In addition to this experimental sample, baseline controls as well as several other controls are included in the experiment. As shown in Table 7, vectors encoding CasS with the two gRNAs and the donor, CasS with the two gRNAs, CasS with the individual gRNAs, and the donor only serve as controls.

TABLE 7

Summary of samples in maize protoplast SPX locus editing experiment

| Transfection Components |
| --- |
| CasS + Lambda Red + 2 gRNAs + donor DNA |
| CasS + 2 gRNAs + donor DNA |
| CasS + 2 gRNAs |
| CasS + 1 gRNA |
| CasS + 1 gRNA |
| Donor DNA |
| CasS + 2 gRNAs + Lambda Red |
| CasS + 1st gRNA + Lambda Red + donor |
| CasS + 2nd gRNA + Lambda Red + donor |
| CasS + 1st gRNA |
| CasS + 2nd gRNA |
| Lambda Red only control |
| GFP control |
| No transfection control |

Precise editing and indels are measured by sequencing and compared between the different samples.

Example 7. Enhanced HDR in *Nicotiana benthamiana*

The following example describes genome editing in *Nicotiana benthamiana* leaves. In particular, the efficiency of editing in planta is measured by repairing the coding sequence of GFP in a *N. benthamiana* reporter line with a mutant allele of GFP, in the presence or absence of HDR promoting agents (i.e., the exonuclease, lambda beta SSAP, and the *E. coli* SSB protein).

Materials and Methods

*N. benthamiana* Cultivation and Transfection

Figure 7:
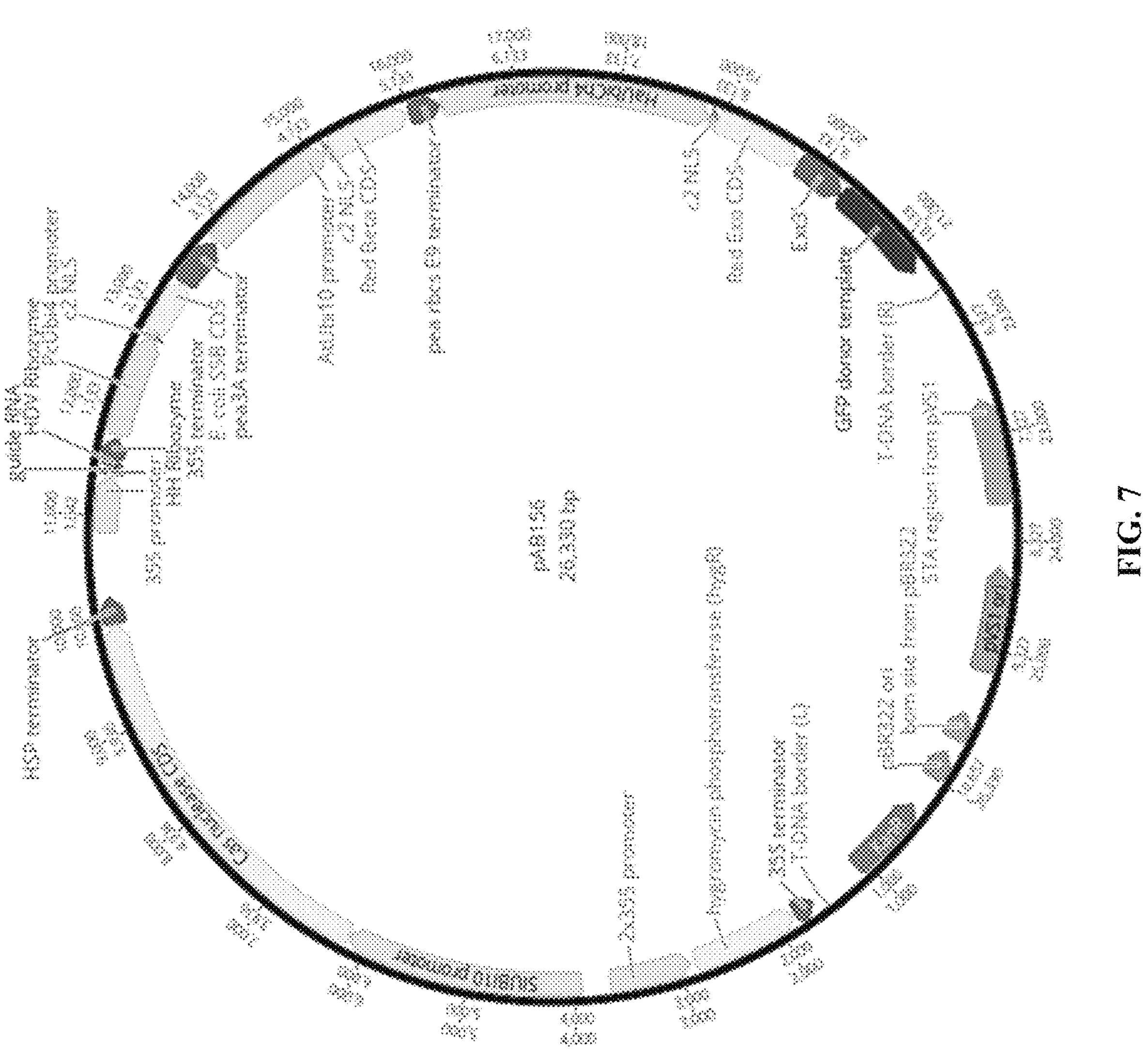
FIG. 7 shows a schematic diagram of the vector pAB156. Length in base pairs is indicated by the labels outside of the vector. Beginning at base pair 1, the vector includes a kanamycin resistance marker (KanR), left T-DNA border, a hygromycin resistance cassette (2x 35S promoter, hygromycin phosphotransferase (hygR) coding sequence, and 35S terminator), a Cas expression cassette (tomato S1UBI10 promoter, Cas nuclease coding sequence (Cas nuclease CDS), and HSP terminator), a guide RNA and ribozyme expression cassette (35S promoter, sequence encoding a guide RNA, sequence encoding a hammerhead (HH) ribozyme, sequence encoding a hepatitis delta virus (HDV) ribozyme, and 35S terminator), a HDR promoting agents expression cassette (PcUbi4 promoter, c2 NLS fused to an *E. coli* SSB coding sequence (*E. coli* SSB CDS), pea 3A terminator, AtUbil0 promoter, c2 NLS fused to a SSAP coding sequence (Red Beta CDS), pea rbcS E9 terminator, HaUbiCh4 promoter, c2 NLS fused to an exonuclease coding sequence (Red Exo CDS), and Ext3' terminator), GFP donor template, right T-DNA border, and STA region from pVS1.

Seeds of *N. benthamiana* with a loss-of-function allele of GFP are germinated on kanamycin selection media (50 mg/mL) for two weeks before being transferred to soil and grown in a Conviron growth chamber (12 h/12 h/75 mol/$m^2s$", day:night:light) for two weeks. *N. benthamiana* leaves are syringe-infiltrated with *Agrobacterium tumefaciens* (strain GV3101) expressing a T-DNA vector that contains the CasS and HDR promoting agents expression cassettes, as well as a donor template that has the GFP-repair template (see FIG. 7). Leaf samples are then taken for genotyping to confirm the presence of the reporter transgene via PCR. Plants are incubated with the growth lid on for 3 days before being evaluated and harvested. Treated leaves are transferred to tissue culture and whole plants are regenerated from tissue culture. All samples are tested in triplicate.

Assessment of GFP Coding Sequence Repair

The repair of the GFP coding sequence is assessed using one of a number of methods. The proportion and number of leaf cells containing the targeted insertion is quantified by the visualization of GFP signal using fluorescence microscopy 3 days after infiltration.

The frequency of target insertion within infiltrated leaves is quantified using amplicon sequencing, as described in Example 2, of the right genome/donor border to estimate the overall efficiency of precise editing.

Regenerated whole plants are qualitatively compared to confirm stable expression of the targeted insertion by visualization of GFP signal using fluorescence microscopy.

The frequency of targeted insertion within regenerated whole plants is quantified by Sanger sequencing of the right-hand genome/donor border to estimate the overall efficiency of precise editing.

Results

*N. benthamiana* leaves are transformed to express a CasS system for genetically modifying a mutant GFP gene, with and without HDR promoting agents. Table 8, below, provides a summary of the components transformed into *N. benthamiana* leaves. "Lambda RED" refers to all three HDR promoting agents (the exonuclease, lambda beta SSAP protein, and the SSB).

TABLE 8

Summary of samples in *N. benthamiana* GFP reporter editing experiment

| Transfection Components |
| --- |
| CasS + Lambda Red + gRNA + donor DNA |
| CasS + gRNA + donor DNA |
| CasS + gRNA |
| GFP (positive infiltration control) |
| GUS (negative infiltration control) |
| No treatment |

Repair of the mutant GFP is measured and compared between the samples.

Example 8. Enhanced HDR in Dividing Tomato and Maize Tissue

The following example describes experiments testing gene editing mediated by HDR promoting agents in dividing plant tissues. In particular, tomato cotyledon explants were editing using a Cas nuclease in the presence and absence of HDR promoting agents. In addition, maize embryo explants are edited using a Cas nuclease in the presence and absence of HDR promoting agents.

Maize Explant Transformation

Materials and Methods

Design of Plasmid for Maize Transformation

This example describes the construction of plant expression vectors for *Agrobacterium* mediated maize transformation. Two plant gene expression vectors were prepared. Plant expression cassettes for expressing a Bacteriophage lambda exonuclease (SEQ ID NO:8), a bacteriophage lambda beta SSAP protein (SEQ ID NO: 1), and an *E. coli* SSB (SEQ ID NO:31) were constructed. A DNA sequence encoding a tobacco c2 nuclear localization signal (NLS) of SEQ ID NO:15 was fused to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133, respectively. DNA sequences encoding the c2 NLS-Exo, c2 NLS lambda beta SSAP, and c2NLS-SSB fusion proteins were operably linked to a OsUBI1, S1UBI1, OsACT promoter and a pea3A, pea rbcs E9, NtEXT polyadenylation site respectively, to provide the exonuclease, SSAP, and SSB plant expression cassettes.

A DNA donor sequence that targets the promoter region of the maize gln1-3 gene for insertion of a 36 base pair heterologous sequence by HDR was constructed. The DNA donor sequence includes a replacement template with desired insertion region (36 base pairs long) flanked on both sides by homology arms about 500-635 bp in length. The homology arms match (i.e., are homologous to) gDNA (genomic DNA) regions flanking the target gDNA insertion site. The replacement template region comprising the donor DNA is flanked at each end by DNA sequences identical to the gln1-3 gene sequence recognized by an RNA-guided nuclease.

A plant expression cassette that provides for expression of the RNA-guided sequence-specific (CasB cutting type) endonuclease was constructed. A plant expression cassette that provides for expression of a guide RNA complementary to sequences adjacent to the insertion site was constructed. An *Agrobacterium* superbinary plasmid transformation vector containing a cassette that provides for the expression of the phosphinothricin N-acetyltransferasesynthase (PAT) protein was constructed. Once the cassettes, donor sequence and *Agrobacterium* superbinary plasmid transformation vector are constructed, they were combined to generate two maize transformation plasmids.

Figure 8:
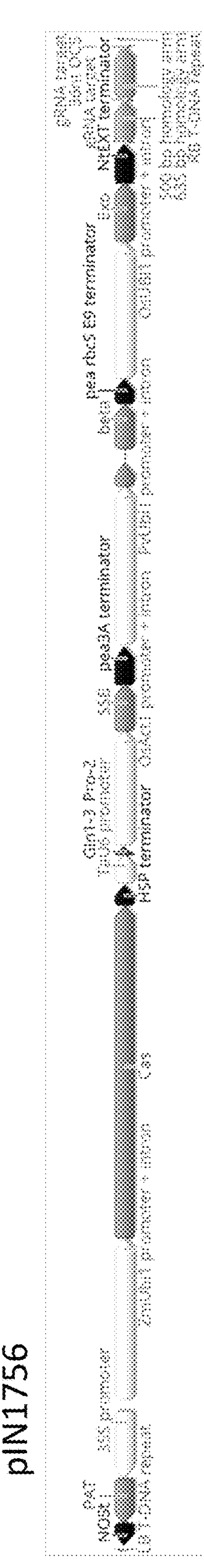
FIG. 8 shows a schematic diagram of the designed insertion regions of superbinary T-DNA vectors p1N1757 (lower) and pIN1576 (upper). p1N1757 includes a left T-DNA border, NOS terminator, PAT for glufosinate selection, 35S promoter, a Cas expression cassette (maize ubiquitin (ZmUbi) promoter, Cas nuclease coding sequence (Cas nuclease CDS), and HSP terminator), a guide RNA expression cassette (wheat U6 (TaU6) promoter, sequence encoding a guide RNA (Gln1-3 Pro-2), and Pol III terminator), Gln1-3 donor template, and right T-DNA border. Additionally, vector pIN1756 includes an HDR promoting agents expression cassette (*O. sativa* actin (OsActin promoter+intron) promoter, *E. coli* SSB coding sequence (SSB), pea 3A terminator; *P. virgatum* ubiquitin (PvUbil promoter+intron) promote, an SSAP coding sequence (beta), pea rbcS E9 terminator; *O. sativa* ubiquitin (OsUB1) promoter, an exonuclease coding sequence (Exo), and tobacco extensin (NtEXT) terminator).
Figure 8:
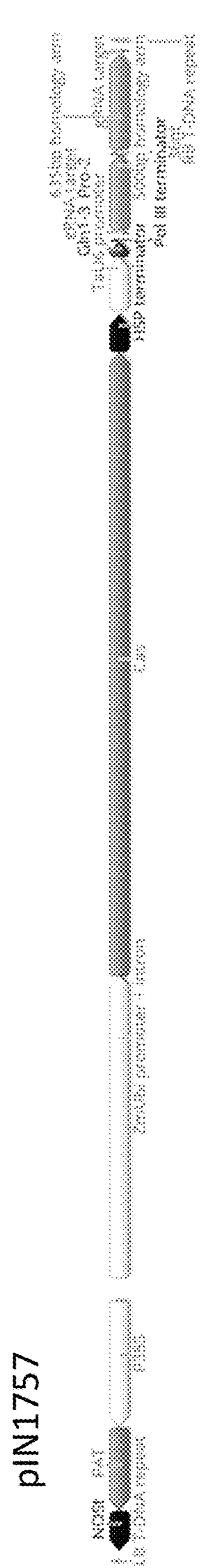

Maize transformation plasmid pIN1757 was constructed with the PAT cassette, the RNA-guided sequence-specific endonuclease cassette, the guide RNA cassette, and the gln1-3 DNA donor sequence into the *Agrobacterium* superbinary plasmid transformation vector (FIG. 8).

Maize transformation plasmid pIN1756 was constructed with the PAT cassette, the RNA-guided sequence-specific endonuclease cassette, the guide RNA cassette, the SSB cassette, the lambda beta SSAP cassette, the Exo cassette, and the gln1-3 DNA donor sequence into the *Agrobacterium* superbinary plasmid transformation vector (FIG. 8).

Maize Transformation

All constructs were delivered from superbinary vectors in *Agrobacterium* strain LBA4404.

Maize transformations were performed based on published methods (Ishida et. al, Nature Protocols 2007; 2, 1614-1621). Briefly, immature embryos from inbred line GIBE0104, approximately 1.8-2.2 mm in size, were isolated from surface sterilized ears 10-14 days after pollination. Embryos were placed in an *Agrobacterium* suspension made with infection medium at a concentration of $OD_{600}$=1.0. Acetosyringone (200 μM) was added to the infection medium at the time of use. Embryos and *Agrobacterium* were placed on a rocker shaker at slow speed for 15 minutes. Embryos were then poured onto the surface of a plate of co-culture medium. Excess liquid media was removed by tilting the plate and drawing off all liquid with a pipette. Embryos were flipped as necessary to maintain a scutelum up orientation. Co-culture plates were placed in a box with a lid and cultured in the dark at 22° C. for 3 days. Embryos were then transferred to resting medium, maintaining the scutellum up orientation. Embryos remain on resting medium for 7 days at 27-28° C. Embryos that produced callus were transferred to Selection 1 medium with 7.5 mg/L phosphinothricin (PPT) and cultured for an additional 7 days. Callused embryos were placed on Selection 2 medium with 10 mg/L PPT and cultured for 14 days at 27-28° C. Growing calli resistant to the selection agent were transferred to Pre-Regeneration media with 10 mg/L PPT to initiate shoot development. Calli remained on Pre-Regeneration media for 7 days. Calli beginning to initiate shoots were transferred to Regeneration medium with 7.5 mg/L PPT in Phytatrays and cultured in light at 27-28° C. Shoots that reached the top of the Phytatray with intact roots were isolated into Shoot Elongation medium prior to transplant into soil and gradual acclimatization to greenhouse conditions.

Results

The number of explants in each experimental condition is provided in Table 9A, below. Regenerated shoots were sampled and gDNA was extracted from 45 regenerated plants from 16 embryos (“events”) for pIN1757 and from 201 regenerated plants from 53 embryos for pIN1756. The ZmGln1.3 locus was amplified from gDNA using primers designed to generate an amplicon of about 835 base pairs; the forward primer is about 130 bp 5' of the endonuclease cut site, and the reverse primer is outside of the 3' homology arm, so that only the endogenous locus is amplified. After bead clean-up, the amplicons were analyzed by next-generation sequencing.

The numbers reported in Table 9A, #Indel and #HDR columns, represent samples with at least 5,000 mapped reads to the target sequence and at least 50% full alignment to the amplicon. After filtering for samples with at least 5,000 reads mapping to the target sequence and at least 50% full alignment to the amplicon, 2 independent events (5 plants) were identified out of 53 events (201 plants) with targeted insertion (3.77%) when the HDR promoting agents were present, compared to 0 out of 16 events when the HDR promoting agents were not present.

TABLE 9A

Summary of transformed maize embryos

| Construct | # embryos treated | Shoots recovered/ events | # Indel | # HDR |
|---|---|---|---|---|
| pIN1757 | 397 | 45/16 | 40/43 | 0/43 |
| pIN1756 | 472 | 201/53 | 112/137 | 105/137 |

Tomato Explant Transformation

Materials and Methods

Design of plasmids for tomato transformation

Plant expression cassettes for expressing a Bacteriophage lambda exonuclease (SEQ ID NO:8), a bacteriophage lambda beta SSAP protein (SEQ ID NO: 1), and an *E. coli* SSB (SEQ ID NO:31) were constructed. A DNA sequence encoding a tobacco c2 nuclear localization signal (NLS) of SEQ ID NO:15 was operably linked to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133, respectively. DNA sequences encoding the c2 NLS-Exo, c2 NLS lambda beta SSAP, and c2NLS-SSB fusion proteins were operably linked to a 2x35S, SlUBI10, PcUBI4 promoter and a 35S, AtHSP, pea3A polyadenylation site respectively, to provide the exonuclease, SSAP, and SSB plant expression cassettes.

In addition, a DNA donor sequence that targeted the promoter region of the tomato Ant1 gene (S1Ant1) for insertion of a 42 base pair heterologous sequence by HDR was constructed. The DNA donor sequences included a replacement template with desired insertion region (42 base pairs long) flanked on both sides by homology arms about 600-800 bp in length. The homology arms matched (i.e., were homologous to) endogenous DNA regions flanking the target gDNA insertion site. The replacement template region comprising the donor DNA was flanked at each end by DNA sequences identical to the endogeneous target editing site sequence recognized by an RNA-guided nuclease.

Further, a plant expression cassette that provides for expression of the RNA-guided sequence-specific endonuclease was constructed. A plant expression cassette that provides for expression of a guide RNA complementary to sequences adjacent to the insertion site was constructed. A plant expression cassette that provides for expression of the green fluorescent protein (GFP) was constructed. An *Agrobacterium* binary plasmid transformation vector containing a cassette that provides for the expression of the 5-enolpyruvylshikimate-3-phosphate (EPSPS) synthase was constructed.

Once the cassettes, donor sequence and *Agrobacterium* transformation plasmid vector were constructed, they were combined to generate three tomato transformation plasmids.

Figure 9A:
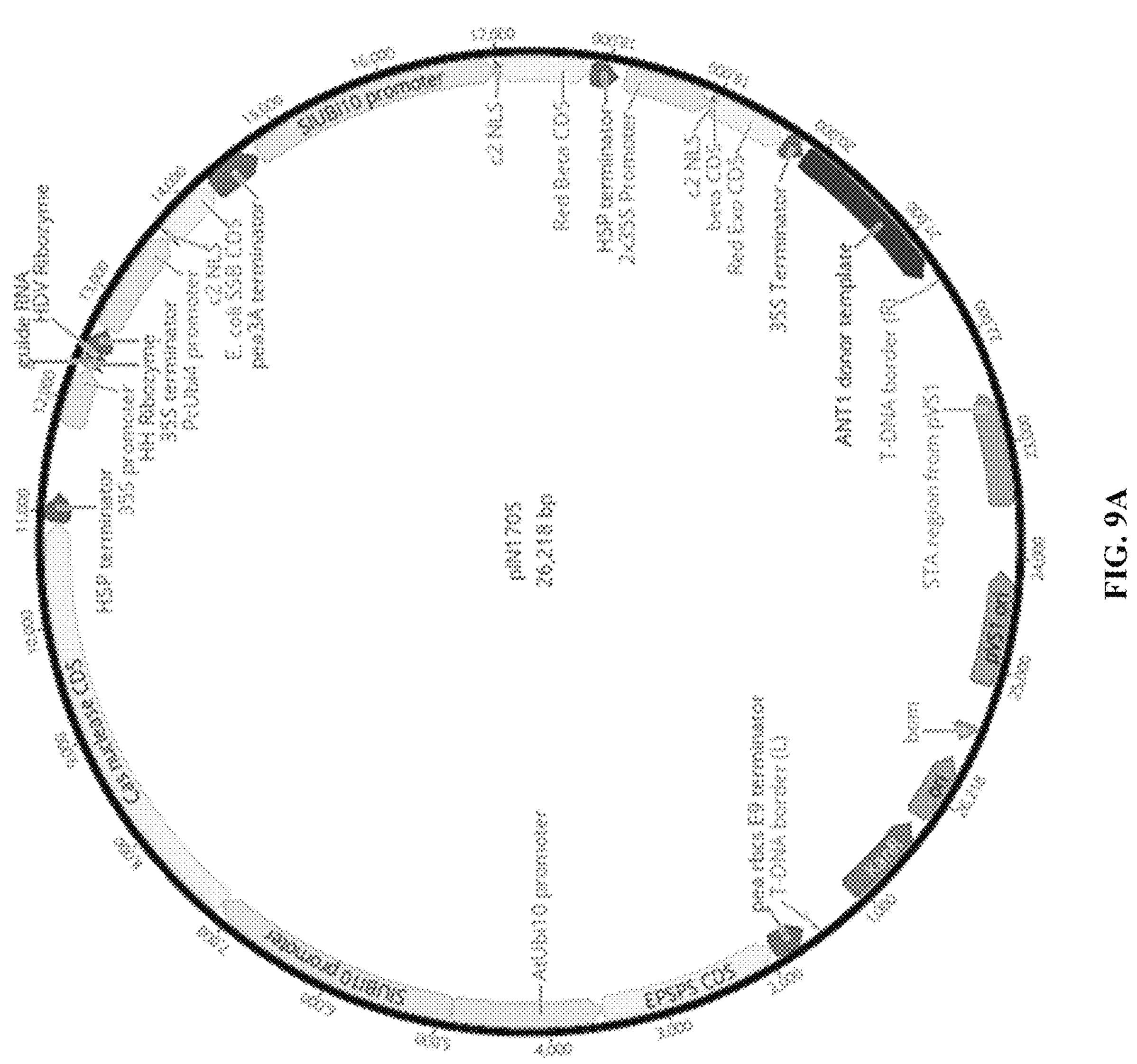
FIG. 9A-9B show schematic diagrams of vectors and expression cassettes for transforming tomato cotyledons.
Figure 9B:
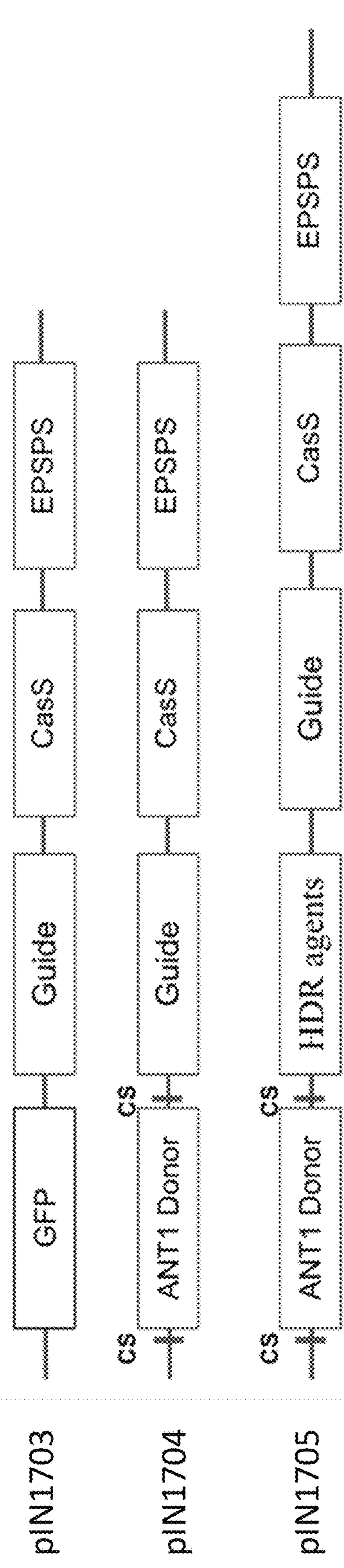

Tomato transformation plasmid pIN1703 was constructed with the RNA-guided sequence-specific endonuclease cassette, the guide RNA cassette and the GFP cassette cloned into the *Agrobacterium* transformation plasmid vector (FIG. 9B). Tomato transformation plasmid pIN1704 was constructed with the RNA-guided sequence-specific endonuclease cassette, the guide RNA cassette and Ant1 DNA donor sequence cloned into the *Agrobacterium* transformation plasmid vector (FIG. 9B). Tomato transformation plasmid pIN1705 was constructed with the RNA-guided sequence-specific endonuclease cassette, the guide RNA cassette, the SSB cassette, the lambda beta SSAP cassette, the exonuclease cassette and Antl DNA donor sequence cloned into the *Agrobacterium* transformation plasmid vector (FIGS. 9A-9B).

All vectors were delivered to tomato using the *Agrobacterium* strain EHA105.

Tomato Explant Transformation

The vectors described above were used to transform tomato (cv. Moneymaker) explants to regenerated stably transformed transgenic shoots with the above mentioned components. Tomato transformations were performed based on previously published methods (Van Eck J., Keen P., Tjahjadi M. (2019) *Agrobacterium tumefaciens-Mediated Transformation of Tomato*. In: Kumar S., Barone P., Smith M. (eds) *Transgenic Plants. Methods in Molecular Biology*, vol 1864. Humana Press, New York, NY). Briefly, tomato seeds were sterilized with 50% commercial bleach for 10 minutes and germinated on ½ strength MSO media. Before the true leaf has emerged, cotyledonary leaves were dissected to collect the middle 3-5 mm section of the leaves. These leaves were transformed with *Agrobacterium* and then placed on resting regeneration media for two weeks. After two weeks, explants were moved to regeneration media supplemented with 2 mg/L glyphosate as a selection agent. Explants were subcultured every two weeks. In about 6-7 weeks, shoots began regenerating from these explants.

Samples were collected from well-elongated shoots, and shoots were moved to rooting media supplemented with 2 mg/L glyphosate. For small shoots, entire shoot masses were collected (i.e., destructive sampling) for molecular analysis.

Assessment of Tomato Explant Transformation

Regenerated shoots were first identified as transgene positive by a TaqMan qPCR assay to detect the presence of the nuclease sequence. Further, the qPCR assay was used to estimate whether the transgene insertion occurred in low (1-2 copies) or high (>2 copies) copy numbers, as shown in Table 9B, below. To assess the level of HDR-mediated editing events, the S1Ant1 locus was amplified from the same gDNA source extracted from the previously confirmed nuclease sequence positive explants, and analyzed via next generation sequencing.

Results

A system was designed with a CRISPR endonuclease (CasS), a guide RNA for site-specific cleavage and the HDR promoting agents (exonuclease, lambda beta SSAP protein, and *E. coli* SSB), as described above. A donor DNA molecule featuring the sequence to be integrated flanked by homology arms that matched the targeted genomic locus was also included. The donor DNA was flanked by a cut site matching the guide RNA on either side so that the donor molecule can be excised, and released from the genomic insertion site in which the transgene was inserted. To test the effectiveness of this system in improving targeted integrations into the genome of dividing plant tissues, the full system described above was delivered via *Agrobacterium* to explants of tomato.

The system's effectiveness was measured by comparing the efficiency of precise targeted integration from the HDR promoting agents system (FIG. 9A) compared to a baseline experimental condition composed of just the CasS nuclease, guide RNA, and DNA donor (see pIN1704 in FIG. 9B). Efficiency of precise targeted integration was calculated based on DNA sequencing of shoots regenerated from the transformed explants. The percentage of tomato shoots that contained the integrated donor sequence out of the total number of regenerated shoots is shown in Table 9B, below, for each construct. The sampled tissues were chimeric rather than genetically uniform due to the nature of tomato transformation system, and the sequencing results reflected some independent editing occurrences within individual plants. In Table 9B, indel refers to both NHEJ-type and HDR-type of mutation at the target location in the S1Ant1 promoter. HDR mutations were considered likely heritable when more than 30% of the sequencing reads from an individual sample were precise edits, i.e. insertions of the template DNA. The the level of precise editing did not correlate with number of transgene copies. The percentage of heritable HDR-mediated editing events was highest in the shoots transformed with the vector encoding the HDR promoting agents (pIN1705). A few edited plants were further characterized by long read sequencing. Of six pIN1704-transformed plant samples, some scarless editing was detected in only one. Of fifteen pIN1705-transformed plant samples, some scarless editing was detected in ten, of which at least four had biallelic 100% scarless editing. As a result of the targeted sequence insertion, edited plants showed different levels of anthocyanin accumulation. Altogether, the vector encoding the HDR promoting agents significantly improved the HDR-mediated precise editing.

TABLE 9B

| Summary of gene editing in tomato explants | | | | | |
|---|---|---|---|---|---|
| Construct | Number of low copy (1-2 copy) events | Number of high copy (>2) events | % mutation freq. (% Indel > 30%) | % heritable HDR (>30% HDR) events | Normalized % heritable HDR (>30% HDR) events |
| pIN1703 | 20 | 10 | 100% (30/30) | 0% (0/30) | 0% |
| pIN1704 | 124 | 6 | 75.3% (98/130) | 0.7% (1/130) | 0.93% |
| pIN1705 | 190 | 10 | 74% (148/200) | 4% (8/200) | 5.4% |

Tomato editing experiments as described above were repeated, and the results are shown in Table 9C. Again, the percentage of heritable HDR-mediated editing events was highest in the shoots transformed with the vector encoding the HDR promoting agents (pIN1705); the same trend was observed.

TABLE 9C

| Summary of gene editing in tomato explants | | | |
|---|---|---|---|
| Construct | % mutation freq. (% Indel > 30%) | % heritable HDR (>30% HDR) events | Normalized % heritable HDR (>30% HDR) events |
| pIN1704 | 54% (54/100) | 2% (2/100) | 3.7% |
| pIN1705 | 75.6% (189/250) | 6.8% (17/250) | 8.9% |

Example 9. Enhanced HDR in Mammalian Cells

The following example describes the precise editing of loci in human embryonic kidney 293 (HEK-293) cells in the presence or absence of HDR promoting agents. An FRT site and a minimal AAVS1 site are inserted into the EMX1 and GRIN2b genes, respectively. Plasmids expressing the editing machinery are transfected into cell lines in order to induce targeted insertions at specific target editing sites in these genes.

Materials and Methods

Design of Plasmid for Transfection

A single plasmid is generated encoding a CasS nuclease with a gRNA specific to the EMX1 or GRIN2b target locus, the HDR promoting agents (exonuclease, lambda beta SSAP, and the *E. coli* SSB protein), and a donor template with the insertion sequence and ~700 base pair homology arms that are homologous to the target editing site. Each component is driven by a separate promoter. The gene cassettes are first synthesized in three separate intermediary plasmids called module A, B and C and then assembled into a single expression plasmid.

Figure 10:
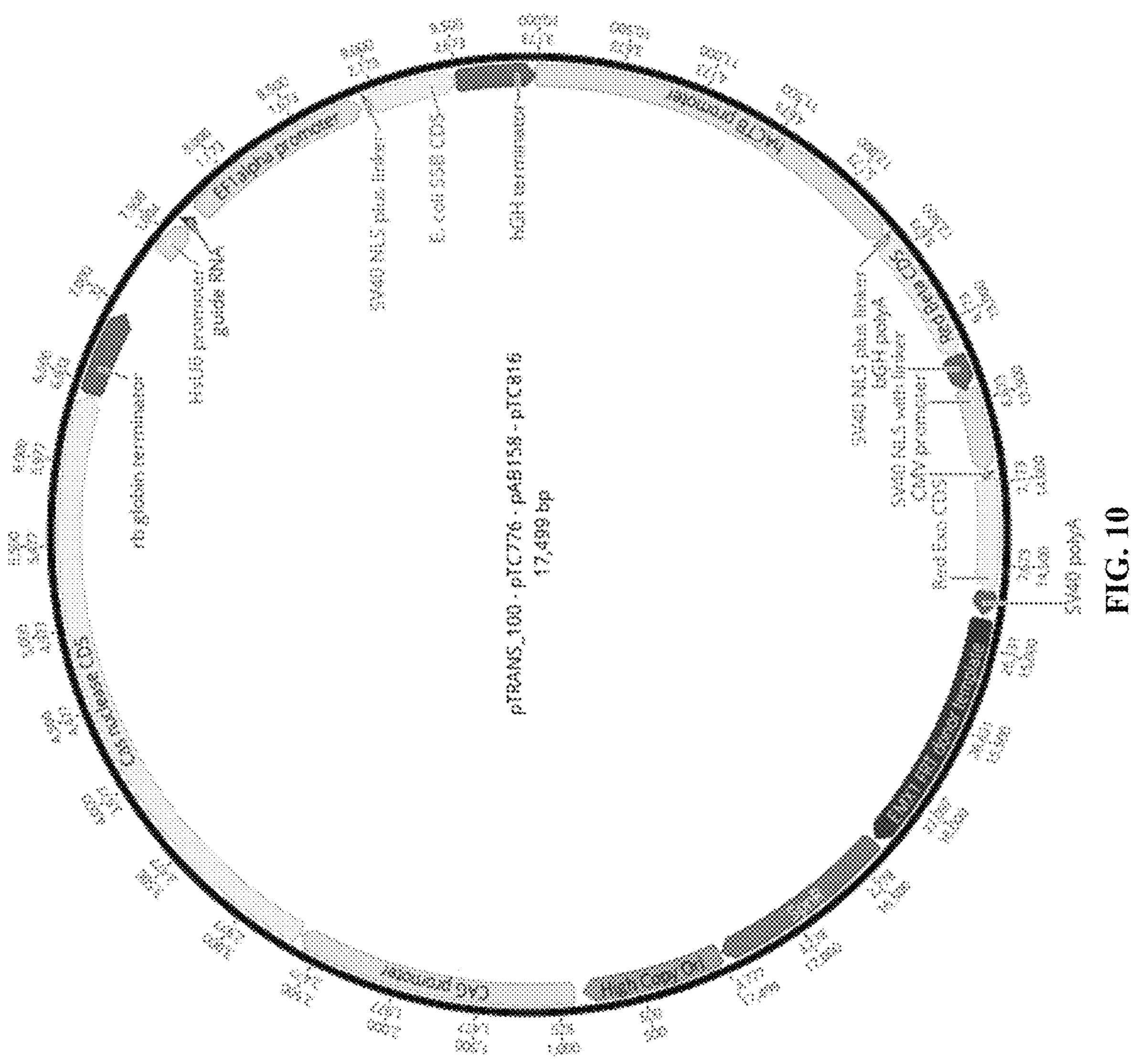
FIG. 10 shows a schematic diagram of a vector for expression in humans. Length in base pairs is indicated by the labels outside of the vector. Beginning at base pair 1, the vector includes a high copy number origin of replication (High Copy Ori), a Cas expression cassette (CAG promoter, Cas nuclease coding sequence (Cas nuclease CDS), and rabbit beta-globin (rb globin) terminator), a guide RNA expression cassette (*H sapiens* U6 (HsU6) promoter, sequence encoding a guide RNA), a HDR promoting agents expression cassette (*H sapiens* EFla promoter, SV40 NLS linked to an *E. coli* SSB coding sequence (*E. coli* SSB CDS), human growth hormone (hGH) terminator, *H. sapiens* ACTB (hACTB) promoter, SV40 NLS linked to a SSAP coding sequence (Red Beta CDS), bovine growth hormone (bGH) terminator, CMV promoter, SV40 NLS linked to a exonuclease coding sequence (Red Exo CDS), and SV40 polyA signal), EMX1 FRT donor template, and spectinomycin resistance marker (SpnR).

The amino acid sequences of CasS and the HDR promoting agents are as described in Example 1, except for the NLS for the HDR promoting agents. In particular, the HDR promoting agents are fused to the SV40 NLS with an amino acid linker (SEQ ID NO: 148, MAPKKKRKVGGSGS). All coding-sequences are codon-optimized for expression in humans. As shown in FIG. 10, CasB is under control of the CAG promoter and the rabbit beta-globin terminator (CAGp- CasS -rb_globin_t), the gRNA is under control of the *H. sapiens* U6 promoter (HsU6p-gRNA), the SSB protein is under control of the *H. sapiens* EF1a promoter and the human growth hormone (hGH) terminator (HsEF lap-SSB-hGHt), the SSAP is under control of the *H. sapiens* ACTB promoter and the bovine growth hormone (bGH) terminator (HsACTB-Beta-bGHt), and the exonuclease is under control of the CMV promoter and the SV40 terminator (CMVp-Exo-SV40t).

In addition, the donor is also flanked by the same gRNA target sequence as the one present in the genomic target, thus leading to the release of the donor from the delivered plasmid, and subsequent editing mediated by HDR promoting agents (see FIG. 10).

A separate plasmid is constructed for each sample shown in Table 10, below.

Transfection of HEK-293 cells

The plasmid is transfected into HEK-293 cells. Three separate transfections per plasmid serve as replicates.

After transfections, the cells are incubated for 48-72 hours, after which genomic DNA is extracted from all samples for subsequent preparation of amplicon sequencing libraries.

Amplicon Sequencing

The targets are amplified with a primer annealing to the sequence directly adjacent to the insertion site and a primer annealing to the genomic sequence outside of the homology region present in the donor (to prevent amplification of the donor from the plasmid). The insertion efficiencies at the target loci are then quantified using the amplicon sequencing data from the read coming from the primer adjacent to the insertion sequence.

HEK-293 cells are edited in the presence or absence of HDR promoting agents. In particular, a 34 base pair FRT site is inserted into the EMX1 locus, and a 33 base pair minimal AAVS1 site is inserted into GRIN2b locus using the plasmids described above.

In addition to the sample containing CasS, all three HDR promoting agents ("Lambda Red"), a gRNA, and a donor DNA, several controls are included in order to compare the editing efficiency of the samples with HDR promoting agents to baseline controls, as shown in Table 10. "Lambda RED" refers to all three HDR promoting agents (the exonuclease, lambda beta SSAP protein, and the SSB).

TABLE 10

| Summary of samples in HEK-293 cells gene editing experiment |
| --- |
| Transfection Components |
| CasS + Lambda Red + gRNA + donor DNA |
| CasS + gRNA + donor DNA |
| CasS + gRNA |
| Donor DNA |
| No transfection |

In particular, samples containing CasS with the gRNA and donor (the baseline control without HDR promoting agents), the Lambda Red genes and the donor (no nuclease control to confirm the nuclease-mediated cleavage of target DNA is important), the donor only, and CasS with the gRNA (cleavage control to make sure we are getting efficient cleavage of the target) are transfected individually as controls. The sample with CasS with the gRNA and donor is the baseline sample that the samples with the HDR promoting agents are compared to. In addition, no transfection controls are also evaluated.

The breadth and scope of the present disclosure should not be limited by any of the above-described Examples, but should be defined only in accordance with the preceding embodiments, the following claims, and their equivalents.

REFERENCES

Bernad A, Blanco L, Lázaro JM, Martin G, Salas M. A conserved 3'-5' exonuclease active site in prokaryotic and eukaryotic DNA polymerases. *Cell.* 1989 Oct. 6; 59(1): 219-28.

Brettschneider, R., D. Becker, and H. Lorz. 1997. "Efficient Transformation of Scutellar Tissue of Immature Maize Embryos." *Theoretical and Applied Genetics* 94 (6-7): 737-48. doi: 10.1007/s001220050473.

Čermák, Tomis, Shaun J. Curtin, Javier Gil-Humanes, Radim Čegan, Thomas J. Y. Kono, Eva Konečná, Joseph J. Belanto, et al. 2017. "A Multipurpose Toolkit to Enable Advanced Genome Engineering in Plants." *The Plant Cell Online* 29 (6): 1196-1217. doi: 10.1 105/tpc.16.00922.

Dotson S B, Lanahan M B, Smith A G, Kishore G M. A phosphonate monoester hydrolase from Burkholderia caryophilli PG2982 is useful as a conditional lethal gene in plants. *Plant J.* 1996 August;10(2):383-92.

Clark, R. M., Tavaré, S., Doebley, J. Estimating a Nucleotide Substitution Rate for Maize from Polymorphism at a Major Domestication Locus, *Molecular Biology and Evolution*, Volume 22, Issue 11, November 2005, Pages 2304-2312, doi: 10.1093/molbev/msi228.

Dasgupta S, Collins G B, Hunt A G. Co-ordinated expression of multiple enzymes in different subcellular compartments in plants. *Plant J.* 1998 October; 16(1):107-16.

Frame, Bronwyn, Marcy Main, Rosemarie Schick, and Kan Wang. 2011. "Genetic Transformation Using Maize Immature Zygotic Embryos." *Methoads in Molecular Biology* (Clifton, N.J.) 710: 327-41. doi: 10.1007/978-1-61737-988-8_22.

Fu BXH, Smith J D, Fuchs R T, Mabuchi M, Curcuru J, Robb G B, Fire AZ. Target-dependent nickase activities of the CRISPR-Cas nucleases Cpf1 and Cas9. *Nat Microbiol.* 2019 May; 4(5):888-897. doi: 10.1038/s41564-019-0382-0. March 4. PubMed PMID: 30833733; PubMed Central PMCID: PMC6512873.

Gao, Caixia, Jin-Long Qiu, Jinxing Liu, Kunling Chen, Yanpeng Wang, Yi Zhang, Yuan Zong, and Zhen Liang. 2016. "Efficient and Transgene-Free Genome Editing in Wheat through Transient Expression of CRISPR/Cas9 DNA or RNA." *Nature Communications* 7 (August): 12617. doi: 10.1038/ncomms12617.

Halpin C, Cooke SE, Barakate A, El Amrani A, Ryan MD. Self-processing 2A-polyproteins--a system for co-ordinate expression of multiple proteins in transgenic plants. *Plant J.* 1999 February; 17(4):453-9.

Hamada, Haruyasu, Yuelin Liu, Yozo Nagira, Ryuji Miki, Naoaki Taoka, and Ryozo Imai. 2018. "Biolistic-Delivery-Based Transient CRISPR/Cas9 Expression Enables in Planta Genome Editing in Wheat." *Scientific Reports* 8 (1): 14422. doi: 10.1038/s41598-018-32714-6.

Honig, Arik, Ira Marton, Michal Rosenthal, J. Jeff Smith, Michael G. Nicholson, Derek Jantz, Amir Zuker, and Alexander Vainstein. 2015. "Transient Expression of Virally Delivered Meganuclease In Planta Generates Inherited Genomic Deletions." Molecular Plant 8 (8): 1292-94. doi: 10.1016/j.molp.2015.04.001.

Ishida Y., Hiei Y., Komari T. 2007. *Agrobacterium*-mediated Transformation of Maize. *Nature Protocols* 2, 1614-1621.

Iyer L M, Koonin E V, Aravind L. 2002. Classification and evolutionary history of the single-strand annealing proteins, RecT, Redbeta, ERF and RAD52. *BMC Genomics* 3:8. doi:10.1186/1471-2164-3-8.

Jiang W, Bikard D, Cox D, Zhang F, Marraffini LA. RNA-guided editing of bacterial genomes using CRISPR-Cas systems. *Nat Biotechnol.* 2013 March; 31(3):233-9.doi: 10.1038/nbt.2508.

Jinek M, Chylinski K, Fonfara I, Hauer M, Doudna J A, Charpentier E. A programmable dual-RNA-guided DNA endonuclease in adaptive bacterial immunity. *Science.* 2012 Aug. 17; 337(6096):816-21. doi: 10.1126/science.1225829.

Kim E, Kim S, Kim D H, Choi B S, Choi IY, Kim JS. Precision genome engineering with programmable DNA-nicking enzymes. *Genome Res.* 2012 July; 22(7):1327-33. doi: 10.1101/gr.138792.112.

Kirienko D R, Luo A, Sylvester μW. Reliable transient transformation of intact maize leaf cells for functional genomics and experimental study. *Plant Physiol.* 2012 August; 159(4):1309-18. doi: 10.1 104/pp. 112.199737.

Kosugi S, Hasebe M, Matsumura N, Takashima H, Miyamoto-Sato E, Tomita M, Yanagawa H. Six classes of nuclear localization signals specific to different binding grooves of importin alpha. *J Biol Chem.* 2009 Jan. 2; 284(1):478-85. doi: 10.1074/jbc.M807017200.

Lindsay, H. et al. 2016. CrispRVariants Charts the Mutation Spectrum of Genome Engineering Experiments. Nature Biotechnology 34: 701-702. doi: 10.1038/nbt.3628.

Liu, Wusheng, Joshua S. Yuan, and C. Neal Stewart. 2013. "Advanced Genetic Tools for Plant Biotechnology." *Nature Reviews. Genetics* 14 (11): 781-93. doi: 10.1038/nrg3583.

Long L, Guo D D, Gao W, Yang W W, Hou L P, Ma X N, Miao Y C, Botella J R, Song C P. Optimization of CRISPR/Cas9 genome editing in cotton by improved sgRNA expression. *Plant Methods.* 2018 Oct. 3; 14:85. doi: 10.1186/s13007-018-0353-0.

Lynch M. Evolution of the mutation rate. *Trends Genet.* 2010 August; 26(8):345-52. doi: 10.1016/j.tig.2010.05.003

Martin-Ortigosa, Susana, and Kan Wang. 2014. "Proteolistics: A Biolistic Method for Intracellular Delivery of Proteins." *Transgenic Research* 23 (5): 743-56. doi: 10.1007/s11248-014-9807-y.

Murphy, K. 2016. λ Recombination and Recombineering, *EcoSal Plus* 2016. doi:10.1128/ecosalplus.

Nagle M, Déjardin A, Pilate G, Strauss SH. Opportunities for Innovation in Genetic Transformation of Forest Trees. *Front Plant Sci.* 2018 Oct. 2; 9:1443. doi: 10.3389/fpls.2018.01443.

Nussaume, L. Vincentz, M., and Caboche, M. 1991. Constitutive Nitrate Reductase: a dominant conditional marker for plant genetics. *The Plant J.* 1(2):267-274.

Nuccio M., Chen X., Conville J., Zhou A., Liu X. (2015) Plant Trait Gene Expression Cassette Design. In: Azhakanandam K., Silverstone A., Daniell H., Davey M. (eds) *Recent Advancements in Gene Expression and Enabling Technologies in Crop Plants*. Springer, New York, NY.

O'Reilly D, Kartje Z J, Ageely E A, Malek-Adamian E, Habibian M, Schofield A, Barkau C L, Rohilla K J, DeRossett L B, Weigle A T, Damha M J, Gagnon K T. Extensive CRISPR RNA modification reveals chemical compatibility and structure-activity relationships for Cas9 biochemical activity. *Nucleic Acids Res.* 2019 Jan. 25; 47(2):546-558. doi: 10.1093/nar/gkyl214.

Sivamani, E., Nalapalli, S., Prairie, A. et al. Mol Biol Rep (2019). doi.org/10.1007/s11033-019-04737-3.

Schindele P, Wolter F, Puchta H. Transforming plant biology and breeding with CRISPR/Cas9, Cas12 and Cas13. *FEBS Lett.* 2018 June; 592(12):1954-1967. doi:10.1002/1873-3468.13073.

Schlaman, H. R. M., and Hooykaas, P.J.J. (1997) Effectiveness of the bacterial gene codA encoding cytosine deaminase as a negative selectable marker in *Agrobacterium*-mediated plant transformation. *Plant Journal* 11(6):1377-1385.

Soda, Neelam, Lokesh Verma, and Jitender Giri. 2017. "CRISPR-Cas9 Based Plant Genome Editing: Significance, Opportunities and Recent Advances." *Plant Physiology and Biochemistry*, October. doi: 10.1016/j.plaphy.2017.10.024.

Urnov, Fyodor D., Edward J. Rebar, Michael C. Holmes, H. Steve Zhang, and Philip D. Gregory. 2010. "Genome Editing with Engineered Zinc Finger Nucleases." *Nature Reviews. Genetics* 11 (9): 636-46. doi: 10.1038/nrg2842.

Urwin P E, McPherson M J, Atkinson H J. Enhanced transgenic plant resistance to nematodes by dual proteinase inhibitor constructs. *Planta.* 1998 April; 204(4):472-9.

Van Eck J., Keen P., Tjahjadi M. (2019) *Agrobacterium tumefaciens-Mediated Transformation of Tomato*. In: Kumar S., Barone P., Smith M. (eds) *Transgenic Plants. Methods in Molecular Biology*, vol 1864. Humana Press, New York, NY.

Vidarsson G, Dekkers G, Rispens T. IgG subclasses and allotypes: from structure to effector functions. *Front Immunol.* 2014 Oct. 20; 5:520. doi: 10.3389/fimmu.2014.00520.

Wang K, Fredens J, Brunner S F, Kim S H, Chia T, Chin μW. Defining synonymous codon compression schemes by genome recoding. *Nature.* 2016 Nov. 3; 539(7627):59-64. doi: 10.1038/nature20124.

Wang, Kan, and Bronwyn Frame. 2009. "Biolistic Gun-Mediated Maize Genetic Transformation." *Methods in Molecular Biology* (Clifton, N.J.) 526: 29-45. doi: 10.1007/978-1-59745-494-0_3.

Wang, Wei, Qianli Pan, Fei He, Alina Akhunova, Shiaoman Chao, Harold Trick, and Eduard Akhunov. 2018. "Transgenerational CRISPR-Cas9 Activity Facilitates Multiplex Gene Editing in Allopolyploid Wheat." *The CRISPR Journal* 1 (1): 65-74. doi: 10.1089/crispr.2017.0010.

Wu Y, Gao T, Wang X, Hu Y, Hu X, Hu Z, Pang J, Li Z, Xue J, Feng M, Wu L, Liang D. TALE nickase mediates high efficient targeted transgene integration at the human multi-copy ribosomal DNA locus. *Biochem Biophys Res Commun.* 2014 Mar. 28; 446(1):261-6. doi: 10.1016/j.bbrc.2014.02.099.

Yamano T, Nishimasu H, Zetsche B, Hirano H, Slaymaker I M, Li Y, Fedorova I, Nakane T, Makarova K S, Koonin E V, Ishitani R, Zhang F, Nureki O. Crystal Structure of Cpf1 in Complex with Guide RNA and Target DNA. *Cell.* 2016 May 5; 165(4):949-62. doi: 10.1016/j.cell.2016.04.003.

Yan W X, Hunnewell P, Alfonse L E, Carte J M, Keston-Smith E, Sothiselvam S,Garrity A J, Chong S, Makarova K S, Koonin E V, Cheng D R, Scott D A. Functionally diverse type V CRISPR-Cas systems. *Science.* 2019 Jan. 4; 363(6422):88-91. doi:10.1126/science.aav7271.

Yin H, Song C Q, Suresh S, Wu Q, Walsh S, Rhym L H, Mintzer E, Bolukbasi M F, Zhu L J, Kauffman K, Mou H, Oberholzer A, Ding J, Kwan S Y, Bogorad R L, Zatsepin T, Koteliansky V, Wolfe S A, Xue W, Langer R, Anderson D G. Structure-guided chemical modification of guide RNA enables potent non-viral in vivo genome editing. *Nat. Biotechnol.* 2017 December; 35(12):1179-1187. doi: 10.1038/nbt.4005.

Zhang, Yi, Zhen Liang, Yuan Zong, Yanpeng Wang, Jinxing Liu, Kunling Chen, Jin-Long Qiu, and Caixia Gao. 2016. "Efficient and Transgene-Free Genome Editing in Wheat through Transient Expression of CRISPR/Cas9 DNA or RNA." *Nature Communications* 7 (August): 12617. doi: 10.1038/ncomms12617.

What is claimed is:

1. A system for increasing Homology Directed Repair (HDR)-mediated genome modification of a target editing site of a plant cell, comprising:

(a) a plant cell;

(b) heterologous HDR promoting agents comprising a single-stranded DNA annealing protein (SSAP), an exonuclease which can convert a double stranded DNA substrate to a single stranded DNA product, and a single stranded DNA binding protein (SSB); and (c) genome editing molecule(s) comprising at least one sequence-specific endonuclease which cleaves a DNA sequence in the target editing site or at least one polynucleotide encoding the sequence-specific endonuclease and a donor template DNA molecule having homology to the target editing site;

wherein the plant cell is associated with, contacts, or contains an effective amount of the HDR promoting agents and the genome editing molecule(s).

2. The system of claim 1, wherein the genome editing molecules or sequence-specific endonuclease is selected from the group consisting of an RNA-guided nuclease or a polynucleotide encoding an RNA-guided nuclease and a guide RNA or a polynucleotide encoding a guide RNA.

3. The system of claim 2, wherein the RNA-guided nuclease is selected from the group consisting of a type II Cas nuclease, a Cas9 nuclease, a type V Cas nuclease, a Cas12a nuclease, a Cas12b nuclease, a Cas12c nuclease, a CasY nuclease, a CasX nuclease, Cas12i, Cas14 and an engineered nuclease.

4. The system of claim 1, wherein the SSAP is selected from the group consisting of a RecT/Redβ-, ERF-, and a RAD52-family protein.

5. The system of claim 4, wherein the RecT/Redβ-family protein is selected from the group consisting of a Rac bacterial prophage RecT protein, a bacteriophage k beta protein, and a bacteriophage SPP1 35 protein.

6. The system of claim 4 wherein the exonuclease has 5' to 3' exonuclease activity and can recognize a blunt ended dsDNA substrate, a dsDNA substrate having an internal break in one strand, a dsDNA substrate having a 5' overhang, or a dsDNA substrate having a 3' overhang.

7. The system of claim 1, wherein the exonuclease is selected from the group consisting of bacteriophage lambda exo protein, a Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, *E. coli* Exonuclease III, a mammalian Trex2 exonuclease, and a protein having at least 70% sequence identity to SEQ ID NO: 8, 9, 136, 137, 138, 139, 140, 141, 142, 143, 144, or 145.

8. The system of claim 1, wherein the SSB has at least 70% sequence identity to SEQ ID NO: 31, 34-131, or 132.

9. The system of claim 1, wherein the SSAP is a bacteriophage lambda beta SSAP, the exonuclease is a bacteriophage lambda exonuclease, and the SSB is an *E. coli* SSB.

10. The system of claim 1, wherein the frequency of HDR is increased by at least 2-fold in comparison to a control system wherein a control plant cell is provided with the genome editing molecules but is not exposed to at least one of said HDR promoting agents.

11. The system of claim 1, wherein the SSAP, the exonuclease, and/or the single stranded DNA binding protein further comprise an operably linked nuclear localization signal (NLS) or a cell-penetrating peptide (CPP).

12. The system of claim 11, wherein the operably linked NLS is selected from the group consisting of SEQ ID NO: 10, SEQ ID NO: 11, SEQ ID NO: 12, SEQ ID NO: 13, SEQ ID NO: 14, SEQ ID NO: 15, and SEQ ID NO: 16.

13. The system of claim 1, wherein the plant cell is haploid, diploid, or polyploid.

14. The system of claim 1, wherein the plant cell is in a culture medium, in a plant, or in a plant tissue.

15. The system of claim 1, wherein the system provides for isolating and/or growing a plant cell, propagule, or plant obtained from the plant cell comprising the genome modification, and wherein the genome of the plant cell, propagule, or plant comprises the genome modification.

16. A method for making a eukaryotic cell having a genomic modification, comprising:

(a) providing genome editing molecules and heterologous Homology Directed Repair (HDR) promoting agents to a eukaryotic cell, wherein the genome editing molecules comprise: at least one sequence-specific endonuclease which cleaves a DNA sequence in the target editing site or at least one polynucleotide encoding the sequence-specific endonuclease and a donor template DNA molecule having homology to the target editing site;

and wherein the heterologous HDR promoting agents comprise a single-stranded DNA annealing protein (SSAP), an exonuclease which can convert a double stranded DNA substrate to a single stranded DNA product, and a single stranded DNA binding protein (SSB);

whereby the genome editing molecules and HDR promoting agents provide for modification of the target editing site of the eukaryotic cell genome with the donor template DNA by HDR at a frequency that is increased in comparison to a control; and (b) isolating or propagating a eukaryotic cell comprising the genome modification, thereby making the eukaryotic cell having a genomic modification.

17. The method of claim 16, wherein the sequence-specific endonuclease comprises an RNA-guided nuclease or a polynucleotide encoding an RNA-guided nuclease and a guide RNA or a polynucleotide encoding a guide RNA.

18. The method of claim 16, wherein the RNA-guided nuclease is selected from the group consisting of a type II Cas nuclease, a Cas9 nuclease, a type V Cas nuclease, a Cas12a nuclease, a Cas12b nuclease, a Cas12c nuclease, a CasY nuclease, a CasX nuclease, and an engineered nuclease.

19. The method of claim 16, wherein the donor DNA molecule is provided on a circular DNA vector, geminivirus replicon, or as a linear DNA fragment.

20. The method of claim 16, wherein the donor DNA molecule is flanked by an endonuclease recognition sequence.

21. The method of claim 16, wherein the SSAP is selected from the group consisting of a RecT/Redβ-, ERF-, and a RAD52-family protein.

22. The method of claim 21, wherein the RecT/Redβ-family protein is selected from the group consisting of a Rac bacterial prophage RecT protein, a bacteriophage k beta protein, a bacteriophage SPP1 35 protein, and a protein having at least 70% sequence identity to SEQ ID NO: 1, 2, or 3.

23. The method of claim 16, wherein the exonuclease has 5' to 3' exonuclease activity and can recognize a blunt ended dsDNA substrate, a dsDNA substrate having an internal break in one strand, a dsDNA substrate having a 5' overhang, or a dsDNA substrate having a 3' overhang.

24. The method of claim 16, wherein the exonuclease is selected from the group consisting of a bacteriophage lambda exo protein, a Rac prophage RecE exonuclease, an Artemis protein, an Apollo protein, a DNA2 exonuclease, an Exo1 exonuclease, a herpesvirus SOX protein, UL12 exonuclease, an enterobacterial exonuclease VIII, a T7 phage exonuclease, *E. coli* Exonuclease III, a mammalian Trex2 exonuclease, or a protein having at least 70% sequence identity to SEQ ID NO: 8, 9, 136, 137, 138, 139, 140, 141, 142, 143, 144, or 145.

25. The method of claim 16, wherein the SSB has at least 70% sequence identity to SEQ ID NO: 31, 34-131, or 132.

26. The method of claim 16, wherein the SSAP is a bacteriophage lambda beta SSAP, the exonuclease is a bacteriophage lambda exonuclease, and the SSB is an *E. coli* SSB.

27. The method of claim 16, wherein the frequency of HDR is increased by at least 2-fold in comparison to a control method wherein a control eukaryotic cell is provided with the genome editing molecules but is not exposed to at least one of said HDR promoting agents.

28. The method of claim 16, wherein the frequency of non-homologous end-joining (NHEJ) is maintained or decreased by at least 2-fold in comparison to a control method wherein a control eukaryotic cell is provided with the genome editing molecules but is not exposed to at least one of said HDR promoting agents.

29. The method of claim 16, wherein the eukaryotic cell is a mammalian cell or a plant cell.

30. A method for producing a eukaryotic cell with a genetically modified target editing site comprising:

(a) providing at least one sequence-specific endonuclease which cleaves a DNA sequence at least one endonuclease recognition sequence in said target editing site or at least one polynucleotide encoding said at least one sequence-specific endonuclease, and (b) providing at least one donor molecule comprising at least one double-stranded DNA sequence, wherein (i) said DNA sequence has a homology of at least 90% over a length of at least 50 nucleotides to sequences flanking the target editing site and (ii) wherein said donor sequence comprises at least one modification in comparison to said target editing site; and (c) providing at least one heterologous Homology Directed Repair (HDR) promoting agent comprising (i) at least one single-stranded DNA annealing protein (SSAP), and (ii) at least one exonuclease which can convert a double stranded DNA substrate to a single stranded DNA product, and (iii) at least one single stranded DNA binding protein (SSB);

and whereby the at least one sequence-specific endonucleases, the at least one donor molecule, and the at least one HDR promoting agent introduce said modification into said target editing site of said eukaryotic cell; and (d) isolating a eukaryotic cell comprising a modification in said target editing site.

31. The method of claim 30, wherein the modification is selected from the group consisting of an insertion of one or more nucleotides, a deletion of one or more nucleotides, or a substitution of one or more nucleotides.

32. The method of claim 30, wherein a portion of the target editing site is deleted by using two sequence specific cleavages in said target editing site, and is replaced by a sequence provided by the donor molecule.

33. The method of claim 30, wherein said donor sequence is in a vector flanked by endonuclease recognition sequences.

34. The method of claim 30, wherein the method further comprises propagating the eukaryotic cell comprising the modification.

35. The method of claim 30, wherein the at least one SSAP is a bacteriophage lambda beta SSAP, the at least one exonuclease is a bacteriophage lambda exonuclease, and the at least one SSB is an *E. coli* SSB.

36. A method of producing a genetically modified organism comprising the steps of (i) producing a genetically modified eukaryotic cell by the method of claim 30, and (ii) regenerating said cell into an organism.

37. The method of claim 36, wherein the organism is selected from the group consisting of plants and non-human animals.

* * * * *

SEQUENCE LISTING

```
<160> NUMBER OF SEQ ID NOS: 149

<210> SEQ ID NO 1
<211> LENGTH: 261
<212> TYPE: PRT
<213> ORGANISM: Unknown
<220> FEATURE:
<223> OTHER INFORMATION: Bacteria (eubacteria)

<400> SEQUENCE: 1

Met Ser Thr Ala Leu Ala Thr Leu Ala Gly Lys Leu Ala Glu Arg Val
1               5                   10                  15

Gly Met Asp Ser Val Asp Pro Gln Glu Leu Ile Thr Thr Leu Arg Gln
```

```
            20                  25                  30

Thr Ala Phe Lys Gly Asp Ala Ser Asp Ala Gln Phe Ile Ala Leu Leu
        35                  40                  45

Ile Val Ala Asn Gln Tyr Gly Leu Asn Pro Trp Thr Lys Glu Ile Tyr
    50                  55                  60

Ala Phe Pro Asp Lys Gln Asn Gly Ile Val Pro Val Val Gly Val Asp
65                  70                  75                  80

Gly Trp Ser Arg Ile Ile Asn Glu Asn Gln Gln Phe Asp Gly Met Asp
                85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
        115                 120                 125

Glu Pro Phe Lys Thr Arg Glu Gly Arg Glu Ile Thr Gly Pro Trp Gln
    130                 135                 140

Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
                165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
        195                 200                 205

Leu Ile Ala Leu Asp Lys Thr Trp Asp Asp Asp Leu Leu Pro Leu Cys
    210                 215                 220

Ser Gln Ile Phe Arg Arg Asp Ile Arg Ala Ser Ser Glu Leu Thr Gln
225                 230                 235                 240

Ala Glu Ala Val Lys Ala Leu Gly Phe Leu Lys Gln Lys Ala Ala Glu
                245                 250                 255

Gln Lys Val Ala Ala
            260


<210> SEQ ID NO 2
<211> LENGTH: 269
<212> TYPE: PRT
<213> ORGANISM: Escherichia coli str. K-12 substr. MG1655

<400> SEQUENCE: 2

Met Thr Lys Gln Pro Pro Ile Ala Lys Ala Asp Leu Gln Lys Thr Gln
1               5                   10                  15

Gly Asn Arg Ala Pro Ala Ala Val Lys Asn Ser Asp Val Ile Ser Phe
            20                  25                  30

Ile Asn Gln Pro Ser Met Lys Glu Gln Leu Ala Ala Ala Leu Pro Arg
        35                  40                  45

His Met Thr Ala Glu Arg Met Ile Arg Ile Ala Thr Thr Glu Ile Arg
    50                  55                  60

Lys Val Pro Ala Leu Gly Asn Cys Asp Thr Met Ser Phe Val Ser Ala
65                  70                  75                  80

Ile Val Gln Cys Ser Gln Leu Gly Leu Glu Pro Gly Ser Ala Leu Gly
                85                  90                  95

His Ala Tyr Leu Leu Pro Phe Gly Asn Lys Asn Glu Lys Ser Gly Lys
            100                 105                 110

Lys Asn Val Gln Leu Ile Ile Gly Tyr Arg Gly Met Ile Asp Leu Ala
        115                 120                 125
```

```
Arg Arg Ser Gly Gln Ile Ala Ser Leu Ser Ala Arg Val Val Arg Glu
    130                 135                 140

Gly Asp Glu Phe Ser Phe Glu Phe Gly Leu Asp Glu Lys Leu Ile His
145                 150                 155                 160

Arg Pro Gly Glu Asn Glu Asp Ala Pro Val Thr His Val Tyr Ala Val
                165                 170                 175

Ala Arg Leu Lys Asp Gly Gly Thr Gln Phe Glu Val Met Thr Arg Lys
            180                 185                 190

Gln Ile Glu Leu Val Arg Ser Leu Ser Lys Ala Gly Asn Asn Gly Pro
        195                 200                 205

Trp Val Thr His Trp Glu Glu Met Ala Lys Lys Thr Ala Ile Arg Arg
    210                 215                 220

Leu Phe Lys Tyr Leu Pro Val Ser Ile Glu Ile Gln Arg Ala Val Ser
225                 230                 235                 240

Met Asp Glu Lys Glu Pro Leu Thr Ile Asp Pro Ala Asp Ser Ser Val
                245                 250                 255

Leu Thr Gly Glu Tyr Ser Val Ile Asp Asn Ser Glu Glu
            260                 265


<210> SEQ ID NO 3
<211> LENGTH: 287
<212> TYPE: PRT
<213> ORGANISM: Unknown
<220> FEATURE:
<223> OTHER INFORMATION: Bacteriophage SPP1 35 protein

<400> SEQUENCE: 3

Met Ala Thr Lys Lys Gln Glu Glu Leu Lys Asn Ala Leu Ala Gln Gln
1               5                   10                  15

Asn Gly Ala Val Pro Gln Thr Pro Val Lys Pro Gln Asp Lys Val Lys
            20                  25                  30

Gly Tyr Leu Glu Arg Met Met Pro Ala Ile Lys Asp Val Leu Pro Lys
        35                  40                  45

His Leu Asp Ala Asp Arg Leu Ser Arg Ile Ala Met Asn Val Ile Arg
    50                  55                  60

Thr Asn Pro Lys Leu Leu Glu Cys Asp Thr Ala Ser Leu Met Gly Ala
65                  70                  75                  80

Val Leu Glu Ser Ala Lys Leu Gly Val Glu Pro Gly Leu Leu Gly Gln
                85                  90                  95

Ala Tyr Ile Leu Pro Tyr Thr Asn Tyr Lys Lys Lys Thr Val Glu Ala
            100                 105                 110

Gln Phe Ile Leu Gly Tyr Lys Gly Leu Leu Asp Leu Val Arg Arg Ser
        115                 120                 125

Gly His Val Ser Thr Ile Ser Ala Gln Thr Val Tyr Lys Asn Asp Thr
    130                 135                 140

Phe Glu Tyr Glu Tyr Gly Leu Asp Asp Lys Leu Val His Arg Pro Ala
145                 150                 155                 160

Pro Phe Gly Thr Asp Arg Gly Glu Pro Val Gly Tyr Tyr Ala Val Ala
                165                 170                 175

Lys Met Lys Asp Gly Gly Tyr Asn Phe Leu Val Met Ser Lys Gln Asp
            180                 185                 190

Val Glu Lys His Arg Asp Ala Phe Ser Lys Ser Lys Asn Arg Glu Gly
        195                 200                 205

Val Val Tyr Gly Pro Trp Ala Asp His Phe Asp Ala Met Ala Lys Lys
    210                 215                 220
```

```
Thr Val Leu Arg Gln Leu Ile Asn Tyr Leu Pro Ile Ser Val Glu Gln
225                 230                 235                 240

Leu Ser Gly Val Ala Ala Asp Glu Arg Thr Gly Ser Glu Leu His Asn
                245                 250                 255

Gln Phe Ala Asp Asp Asp Asn Ile Ile Asn Val Asp Ile Asn Thr Gly
            260                 265                 270

Glu Ile Ile Asp His Gln Glu Lys Leu Gly Gly Glu Thr Asn Glu
        275                 280                 285


<210> SEQ ID NO 4
<211> LENGTH: 205
<212> TYPE: PRT
<213> ORGANISM: Salmonella virus P22

<400> SEQUENCE: 4

Met Ser Lys Glu Phe Tyr Ala Arg Leu Ala Glu Ile Gln Glu His Leu
1               5                   10                  15

Asn Ala Pro Lys Asn Gln Tyr Asn Ser Phe Gly Lys Tyr Lys Tyr Arg
            20                  25                  30

Ser Cys Glu Asp Ile Leu Glu Gly Val Lys Pro Leu Leu Lys Gly Leu
        35                  40                  45

Phe Leu Ser Ile Ser Asp Glu Ile Val Leu Ile Gly Asp Arg Tyr Tyr
    50                  55                  60

Val Lys Ala Thr Ala Thr Ile Thr Asp Gly Glu Asn Ser His Ser Ala
65                  70                  75                  80

Ser Ala Ile Ala Arg Glu Glu Glu Asn Lys Lys Gly Met Asp Ala Ala
                85                  90                  95

Gln Val Thr Gly Ala Thr Ser Ser Tyr Ala Arg Lys Tyr Cys Leu Asn
            100                 105                 110

Gly Leu Phe Gly Ile Asp Asp Ala Lys Asp Ala Asp Thr Glu Glu His
        115                 120                 125

Lys Gln Gln Gln Asn Ala Ala Pro Ala Lys Gln Thr Lys Ser Ser Pro
    130                 135                 140

Ser Ser Pro Ala Pro Glu Gln Val Leu Lys Ala Phe Ser Glu Tyr Ala
145                 150                 155                 160

Ala Thr Glu Thr Asp Lys Lys Lys Leu Ile Glu Arg Tyr Gln His Asp
                165                 170                 175

Trp Gln Leu Leu Thr Gly His Asp Asp Glu Gln Thr Lys Cys Val Gln
            180                 185                 190

Val Met Asn Ile Arg Ile Asn Glu Leu Lys Gln Val Ala
        195                 200                 205


<210> SEQ ID NO 5
<211> LENGTH: 471
<212> TYPE: PRT
<213> ORGANISM: Saccharomyces cerevisiae S288C

<400> SEQUENCE: 5

Met Asn Glu Ile Met Asp Met Asp Glu Lys Lys Pro Val Phe Gly Asn
1               5                   10                  15

His Ser Glu Asp Ile Gln Thr Lys Leu Asp Lys Lys Leu Gly Pro Glu
            20                  25                  30

Tyr Ile Ser Lys Arg Val Gly Phe Gly Thr Ser Arg Ile Ala Tyr Ile
        35                  40                  45

Glu Gly Trp Arg Val Ile Asn Leu Ala Asn Gln Ile Phe Gly Tyr Asn
    50                  55                  60
```

-continued

```
Gly Trp Ser Thr Glu Val Lys Ser Val Val Ile Asp Phe Leu Asp Glu
65                  70                  75                  80

Arg Gln Gly Lys Phe Ser Ile Gly Cys Thr Ala Ile Val Arg Val Thr
                85                  90                  95

Leu Thr Ser Gly Thr Tyr Arg Glu Asp Ile Gly Tyr Gly Thr Val Glu
            100                 105                 110

Asn Glu Arg Arg Lys Pro Ala Ala Phe Glu Arg Ala Lys Lys Ser Ala
        115                 120                 125

Val Thr Asp Ala Leu Lys Arg Ser Leu Arg Gly Phe Gly Asn Ala Leu
    130                 135                 140

Gly Asn Cys Leu Tyr Asp Lys Asp Phe Leu Ala Lys Ile Asp Lys Val
145                 150                 155                 160

Lys Phe Asp Pro Pro Asp Phe Asp Glu Asn Asn Leu Phe Arg Pro Thr
                165                 170                 175

Asp Glu Ile Ser Glu Ser Ser Arg Thr Asn Thr Leu His Glu Asn Gln
            180                 185                 190

Glu Gln Gln Gln Tyr Pro Asn Lys Arg Arg Gln Leu Thr Lys Val Thr
        195                 200                 205

Asn Thr Asn Pro Asp Ser Thr Lys Asn Leu Val Lys Ile Glu Asn Thr
    210                 215                 220

Val Ser Arg Gly Thr Pro Met Met Ala Ala Pro Ala Glu Ala Asn Ser
225                 230                 235                 240

Lys Asn Ser Ser Asn Lys Asp Thr Asp Leu Lys Ser Leu Asp Ala Ser
                245                 250                 255

Lys Gln Asp Gln Asp Asp Leu Leu Asp Asp Ser Leu Met Phe Ser Asp
            260                 265                 270

Asp Phe Gln Asp Asp Asp Leu Ile Asn Met Gly Asn Thr Asn Ser Asn
        275                 280                 285

Val Leu Thr Thr Glu Lys Asp Pro Val Val Ala Lys Gln Ser Pro Thr
    290                 295                 300

Ala Ser Ser Asn Pro Glu Ala Glu Gln Ile Thr Phe Val Thr Ala Lys
305                 310                 315                 320

Ala Ala Thr Ser Val Gln Asn Glu Arg Tyr Ile Gly Glu Glu Ser Ile
                325                 330                 335

Phe Asp Pro Lys Tyr Gln Ala Gln Ser Ile Arg His Thr Val Asp Gln
            340                 345                 350

Thr Thr Ser Lys His Ile Pro Ala Ser Val Leu Lys Asp Lys Thr Met
        355                 360                 365

Thr Thr Ala Arg Asp Ser Val Tyr Glu Lys Phe Ala Pro Lys Gly Lys
    370                 375                 380

Gln Leu Ser Met Lys Asn Asn Asp Lys Glu Leu Gly Pro His Met Leu
385                 390                 395                 400

Glu Gly Ala Gly Asn Gln Val Pro Arg Glu Thr Thr Pro Ile Lys Thr
                405                 410                 415

Asn Ala Thr Ala Phe Pro Pro Ala Ala Ala Pro Arg Phe Ala Pro Pro
            420                 425                 430

Ser Lys Val Val His Pro Asn Gly Asn Gly Ala Val Pro Ala Val Pro
        435                 440                 445

Gln Gln Arg Ser Thr Arg Arg Glu Val Gly Arg Pro Lys Ile Asn Pro
    450                 455                 460

Leu His Ala Arg Lys Pro Thr
465                 470
```

```
<210> SEQ ID NO 6
<211> LENGTH: 469
<212> TYPE: PRT
<213> ORGANISM: Schizosaccharomyces pombe

<400> SEQUENCE: 6

Met Ser Phe Glu Gln Lys Gln His Val Ala Ser Glu Asp Gln Gly His
1               5                   10                  15

Phe Asn Thr Ala Tyr Ser His Glu Glu Phe Asn Phe Leu Gln Ser Ser
            20                  25                  30

Leu Thr Arg Lys Leu Gly Pro Glu Tyr Val Ser Arg Arg Ser Gly Pro
        35                  40                  45

Gly Gly Phe Ser Val Ser Tyr Ile Glu Ser Trp Lys Ala Ile Glu Leu
    50                  55                  60

Ala Asn Glu Ile Phe Gly Phe Asn Gly Trp Ser Ser Ser Ile Arg Ser
65                  70                  75                  80

Ile Asn Val Asp Phe Met Asp Glu Asn Lys Glu Asn Gly Arg Ile Ser
                85                  90                  95

Leu Gly Leu Ser Val Ile Val Arg Val Thr Ile Lys Asp Gly Ala Tyr
            100                 105                 110

His Glu Asp Ile Gly Tyr Gly Ser Ile Asp Asn Cys Arg Gly Lys Ala
        115                 120                 125

Ser Ala Phe Glu Lys Cys Lys Lys Glu Gly Thr Thr Asp Ala Leu Lys
    130                 135                 140

Arg Ala Leu Arg Asn Phe Gly Asn Ser Leu Gly Asn Cys Met Tyr Asp
145                 150                 155                 160

Lys Tyr Tyr Leu Arg Glu Val Gly Lys Met Lys Pro Pro Thr Tyr His
                165                 170                 175

Phe Asp Ser Gly Asp Leu Phe Arg Lys Thr Asp Pro Ala Ala Arg Glu
            180                 185                 190

Ser Phe Ile Lys Lys Gln Lys Thr Leu Asn Ser Thr Arg Thr Val Asn
        195                 200                 205

Asn Gln Pro Leu Val Asn Lys Gly Glu Gln Leu Ala Pro Arg Arg Ala
    210                 215                 220

Ala Glu Leu Asn Asp Glu Gln Thr Arg Glu Ile Glu Met Tyr Ala Asp
225                 230                 235                 240

Glu Glu Leu Asp Asn Ile Phe Val Glu Asp Asp Ile Ile Ala His Leu
                245                 250                 255

Ala Val Ala Glu Asp Thr Ala His Pro Ala Ala Asn Asn His His Ser
            260                 265                 270

Glu Lys Ala Gly Thr Gln Ile Asn Asn Lys Asp Lys Gly Ser His Asn
        275                 280                 285

Ser Ala Lys Pro Val Gln Arg Ser His Thr Tyr Pro Val Ala Val Pro
    290                 295                 300

Gln Asn Thr Ser Asp Ser Val Gly Asn Ala Val Thr Asp Thr Ser Pro
305                 310                 315                 320

Lys Thr Leu Phe Asp Pro Leu Lys Pro Asn Thr Gly Thr Pro Ser Pro
                325                 330                 335

Lys Phe Ile Ser Ala Arg Ala Ala Ala Ala Ala Glu Gly Val Val Ser
            340                 345                 350

Ala Pro Phe Thr Asn Asn Phe Asn Pro Arg Leu Asp Ser Pro Ser Ile
        355                 360                 365

Arg Lys Thr Ser Ile Ile Asp His Ser Lys Ser Leu Pro Val Gln Arg
    370                 375                 380
```

```
Ala Ser Val Leu Pro Ile Ile Lys Gln Ser Ser Gln Thr Ser Pro Val
385                 390                 395                 400

Ser Asn Asn Ser Met Ile Arg Asp Ser Glu Ser Ile Ile Asn Glu Arg
                405                 410                 415

Lys Glu Asn Ile Gly Leu Ile Gly Val Lys Arg Ser Leu His Asp Ser
            420                 425                 430

Thr Thr Ser His Asn Lys Ser Asp Leu Met Arg Thr Asn Ser Asp Pro
        435                 440                 445

Gln Ser Ala Met Arg Ser Arg Glu Asn Tyr Asp Ala Thr Val Asp Lys
    450                 455                 460

Lys Ala Lys Lys Gly
465


<210> SEQ ID NO 7
<211> LENGTH: 436
<212> TYPE: PRT
<213> ORGANISM: Kluyveromyces lactis

<400> SEQUENCE: 7

Met Glu Asp Thr Gly Ser Gly Lys Asn Gly Lys Asp Asp Ile Gln Thr
1               5                   10                  15

Lys Leu Asp Lys Lys Leu Gly Pro Glu Tyr Ile Ser Lys Arg Val Gly
            20                  25                  30

Phe Gly Ser Ser Arg Val Ala Tyr Ile Glu Gly Trp Lys Ala Ile Asn
        35                  40                  45

Leu Ala Asn Gln Ile Phe Gly Tyr Asp Gly Trp Ser Thr Glu Val Lys
    50                  55                  60

Asn Val Thr Ile Asp Phe Leu Asp Glu Arg Gln Gly Arg Phe Ser Ile
65                  70                  75                  80

Gly Cys Thr Ala Ile Val Arg Val Ser Leu Ala Asp Gly Thr Phe Arg
                85                  90                  95

Glu Asp Ile Gly Tyr Gly Thr Val Glu Asn Glu Arg Arg Lys Ala Ser
            100                 105                 110

Ala Phe Glu Arg Ala Lys Lys Ser Ala Val Thr Asp Ala Leu Lys Arg
        115                 120                 125

Ser Leu Arg Gly Phe Gly Asn Ala Leu Gly Asn Cys Leu Tyr Asp Lys
    130                 135                 140

Asp Phe Leu Ala Lys Ile Asp Lys Val Lys Phe Asp Pro Pro Asp Phe
145                 150                 155                 160

Asp Glu Gly Asn Leu Phe Arg Pro Ala Asp Glu Leu Ser Glu Met Ser
                165                 170                 175

Arg Ser Asn Met Val Gly Asp Ala His Thr Glu Gly Pro Ser Leu Lys
            180                 185                 190

Lys Arg Ser Leu Thr Asn Glu Asp Arg Asn Ala Val Pro Ser Ala Pro
        195                 200                 205

Ala Gln Gln Thr Tyr Arg Ser Asn Asn His Thr Thr Gln Lys Arg Ala
    210                 215                 220

Pro Lys Ala Gln Ala Val Thr Ala Ser Ala Ser Pro Asn Glu Glu Thr
225                 230                 235                 240

Ser Asn Gln Gln Gln Asp Pro Asp Asp Leu Leu Asp Asp Ser Phe Met
                245                 250                 255

Phe Ser Asp Glu Ile Gln Asp Asp Asp Leu Leu Asn Met Asn Thr Thr
            260                 265                 270

Thr Asn Asn Lys Asn Ser Thr Asn Ser Ser Thr Thr Thr Thr Thr Ile
        275                 280                 285
```

```
Ser Asp Glu Ala Thr Gly Ile Ile Ser Pro Val Thr Phe Val Thr Ala
    290                 295                 300

Lys Ala Ala Thr Ser Leu Gln His Lys Asp Pro Ile Pro Ser Gly Ser
305                 310                 315                 320

Met Phe Asp Pro Lys Phe Gln Ala Gln Ser Ile Arg His Thr Val Asp
                325                 330                 335

Gln Ser Val Ser Thr Pro Val Arg Ala Thr Ile Leu Lys Glu Lys Gly
            340                 345                 350

Leu Asp Ser Asp Arg Ser Ser Ile Tyr Ser Lys Phe Ala Pro Lys Gly
        355                 360                 365

Lys Glu Leu Ser Gly Thr Thr Thr Asn Ser Glu Pro Tyr Val Ala Ala
    370                 375                 380

Pro Gln Thr Ser Ala Thr Glu Ser Asn Arg Ser Thr Pro Thr Arg Ser
385                 390                 395                 400

Asn Ala Gln Leu Ala Gly Pro Gln Pro Ala Pro Gln Leu Gln Gly Pro
                405                 410                 415

Gln Arg Thr Gln Leu Gly Arg Pro Arg Met Leu Gln Gln Pro Asn Arg
            420                 425                 430

Arg Asn Val Ser
        435


<210> SEQ ID NO 8
<211> LENGTH: 226
<212> TYPE: PRT
<213> ORGANISM: Unknown
<220> FEATURE:
<223> OTHER INFORMATION: Bacteria (eubacteria)

<400> SEQUENCE: 8

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205
```

```
Lys Met Asp Glu Ala Leu Ala Glu Ile Gly Phe Val Phe Gly Glu Gln
    210                 215                 220

Trp Arg
225
```

<210> SEQ ID NO 9
<211> LENGTH: 866
<212> TYPE: PRT
<213> ORGANISM: Unknown
<220> FEATURE:
<223> OTHER INFORMATION: Rac bacterial prophage RecE exonuclease

<400> SEQUENCE: 9

```
Met Ser Thr Lys Pro Leu Phe Leu Leu Arg Lys Ala Lys Lys Ser Ser
1               5                   10                  15

Gly Glu Pro Asp Val Val Leu Trp Ala Ser Asn Asp Phe Glu Ser Thr
            20                  25                  30

Cys Ala Thr Leu Asp Tyr Leu Ile Val Lys Ser Gly Lys Lys Leu Ser
        35                  40                  45

Ser Tyr Phe Lys Ala Val Ala Thr Asn Phe Pro Val Val Asn Asp Leu
    50                  55                  60

Pro Ala Glu Gly Glu Ile Asp Phe Thr Trp Ser Glu Arg Tyr Gln Leu
65                  70                  75                  80

Ser Lys Asp Ser Met Thr Trp Glu Leu Lys Pro Gly Ala Ala Pro Asp
                85                  90                  95

Asn Ala His Tyr Gln Gly Asn Thr Asn Val Asn Gly Glu Asp Met Thr
            100                 105                 110

Glu Ile Glu Glu Asn Met Leu Leu Pro Ile Ser Gly Gln Glu Leu Pro
        115                 120                 125

Ile Arg Trp Leu Ala Gln His Gly Ser Glu Lys Pro Val Thr His Val
    130                 135                 140

Ser Arg Asp Gly Leu Gln Ala Leu His Ile Ala Arg Ala Glu Glu Leu
145                 150                 155                 160

Pro Ala Val Thr Ala Leu Ala Val Ser His Lys Thr Ser Leu Leu Asp
                165                 170                 175

Pro Leu Glu Ile Arg Glu Leu His Lys Leu Val Arg Asp Thr Asp Lys
            180                 185                 190

Val Phe Pro Asn Pro Gly Asn Ser Asn Leu Gly Leu Ile Thr Ala Phe
        195                 200                 205

Phe Glu Ala Tyr Leu Asn Ala Asp Tyr Thr Asp Arg Gly Leu Leu Thr
    210                 215                 220

Lys Glu Trp Met Lys Gly Asn Arg Val Ser His Ile Thr Arg Thr Ala
225                 230                 235                 240

Ser Gly Ala Asn Ala Gly Gly Gly Asn Leu Thr Asp Arg Gly Glu Gly
                245                 250                 255

Phe Val His Asp Leu Thr Ser Leu Ala Arg Asp Val Ala Thr Gly Val
            260                 265                 270

Leu Ala Arg Ser Met Asp Leu Asp Ile Tyr Asn Leu His Pro Ala His
        275                 280                 285

Ala Lys Arg Ile Glu Glu Ile Ile Ala Glu Asn Lys Pro Pro Phe Ser
    290                 295                 300

Val Phe Arg Asp Lys Phe Ile Thr Met Pro Gly Gly Leu Asp Tyr Ser
305                 310                 315                 320

Arg Ala Ile Val Val Ala Ser Val Lys Glu Ala Pro Ile Gly Ile Glu
                325                 330                 335
```

```
Val Ile Pro Ala His Val Thr Glu Tyr Leu Asn Lys Val Leu Thr Glu
            340                 345                 350

Thr Asp His Ala Asn Pro Asp Pro Glu Ile Val Asp Ile Ala Cys Gly
        355                 360                 365

Arg Ser Ser Ala Pro Met Pro Gln Arg Val Thr Glu Glu Gly Lys Gln
    370                 375                 380

Asp Asp Glu Glu Lys Pro Gln Pro Ser Gly Thr Thr Ala Val Glu Gln
385                 390                 395                 400

Gly Glu Ala Glu Thr Met Glu Pro Asp Ala Thr Glu His His Gln Asp
                405                 410                 415

Thr Gln Pro Leu Asp Ala Gln Ser Gln Val Asn Ser Val Asp Ala Lys
            420                 425                 430

Tyr Gln Glu Leu Arg Ala Glu Leu His Glu Ala Arg Lys Asn Ile Pro
        435                 440                 445

Ser Lys Asn Pro Val Asp Asp Asp Lys Leu Leu Ala Ala Ser Arg Gly
    450                 455                 460

Glu Phe Val Asp Gly Ile Ser Asp Pro Asn Asp Pro Lys Trp Val Lys
465                 470                 475                 480

Gly Ile Gln Thr Arg Asp Cys Val Tyr Gln Asn Gln Pro Glu Thr Glu
                485                 490                 495

Lys Thr Ser Pro Asp Met Asn Gln Pro Glu Pro Val Val Gln Gln Glu
            500                 505                 510

Pro Glu Ile Ala Cys Asn Ala Cys Gly Gln Thr Gly Gly Asp Asn Cys
        515                 520                 525

Pro Asp Cys Gly Ala Val Met Gly Asp Ala Thr Tyr Gln Glu Thr Phe
    530                 535                 540

Asp Glu Glu Ser Gln Val Glu Ala Lys Glu Asn Asp Pro Glu Glu Met
545                 550                 555                 560

Glu Gly Ala Glu His Pro His Asn Glu Asn Ala Gly Ser Asp Pro His
                565                 570                 575

Arg Asp Cys Ser Asp Glu Thr Gly Glu Val Ala Asp Pro Val Ile Val
            580                 585                 590

Glu Asp Ile Glu Pro Gly Ile Tyr Tyr Gly Ile Ser Asn Glu Asn Tyr
        595                 600                 605

His Ala Gly Pro Gly Ile Ser Lys Ser Gln Leu Asp Asp Ile Ala Asp
    610                 615                 620

Thr Pro Ala Leu Tyr Leu Trp Arg Lys Asn Ala Pro Val Asp Thr Thr
625                 630                 635                 640

Lys Thr Lys Thr Leu Asp Leu Gly Thr Ala Phe His Cys Arg Val Leu
                645                 650                 655

Glu Pro Glu Glu Phe Ser Asn Arg Phe Ile Val Ala Pro Glu Phe Asn
            660                 665                 670

Arg Arg Thr Asn Ala Gly Lys Glu Glu Glu Lys Ala Phe Leu Met Glu
        675                 680                 685

Cys Ala Ser Thr Gly Lys Thr Val Ile Thr Ala Glu Glu Gly Arg Lys
    690                 695                 700

Ile Glu Leu Met Tyr Gln Ser Val Met Ala Leu Pro Leu Gly Gln Trp
705                 710                 715                 720

Leu Val Glu Ser Ala Gly His Ala Glu Ser Ser Ile Tyr Trp Glu Asp
                725                 730                 735

Pro Glu Thr Gly Ile Leu Cys Arg Cys Arg Pro Asp Lys Ile Ile Pro
            740                 745                 750
```

```
Glu Phe His Trp Ile Met Asp Val Lys Thr Thr Ala Asp Ile Gln Arg
        755                 760                 765

Phe Lys Thr Ala Tyr Tyr Asp Tyr Arg Tyr His Val Gln Asp Ala Phe
    770                 775                 780

Tyr Ser Asp Gly Tyr Glu Ala Gln Phe Gly Val Gln Pro Thr Phe Val
785                 790                 795                 800

Phe Leu Val Ala Ser Thr Thr Ile Glu Cys Gly Arg Tyr Pro Val Glu
                805                 810                 815

Ile Phe Met Met Gly Glu Glu Ala Lys Leu Ala Gly Gln Gln Glu Tyr
            820                 825                 830

His Arg Asn Leu Arg Thr Leu Ser Asp Cys Leu Asn Thr Asp Glu Trp
        835                 840                 845

Pro Ala Ile Lys Thr Leu Ser Leu Pro Arg Trp Ala Lys Glu Tyr Ala
    850                 855                 860

Asn Asp
865


<210> SEQ ID NO 10
<211> LENGTH: 23
<212> TYPE: PRT
<213> ORGANISM: Unknown
<220> FEATURE:
<223> OTHER INFORMATION: Maize opaque-2 nuclear localization signal

<400> SEQUENCE: 10

Arg Lys Arg Lys Glu Ser Asn Arg Glu Ser Ala Arg Arg Ser Arg Arg
1               5                   10                  15

Ser Arg Tyr Arg Lys Lys Val
            20


<210> SEQ ID NO 11
<211> LENGTH: 7
<212> TYPE: PRT
<213> ORGANISM: Unknown
<220> FEATURE:
<223> OTHER INFORMATION: SV40 large T antigen NLS

<400> SEQUENCE: 11

Pro Lys Lys Lys Arg Lys Val
1               5


<210> SEQ ID NO 12
<211> LENGTH: 4
<212> TYPE: PRT
<213> ORGANISM: Artificial Sequence
<220> FEATURE:
<223> OTHER INFORMATION: Class II monopartite NLS consensus
<220> FEATURE:
<221> NAME/KEY: VARIANT
<222> LOCATION: 2, 4
<223> OTHER INFORMATION: Xaa = Lys or Arg
<220> FEATURE:
<221> NAME/KEY: VARIANT
<222> LOCATION: 3
<223> OTHER INFORMATION: Xaa = Any Amino Acid

<400> SEQUENCE: 12

Lys Xaa Xaa Xaa
1


<210> SEQ ID NO 13
<211> LENGTH: 19
<212> TYPE: PRT
<213> ORGANISM: Artificial Sequence
```

<220> FEATURE:
<223> OTHER INFORMATION: Bipartite NLS consensus
<220> FEATURE:
<221> NAME/KEY: VARIANT
<222> LOCATION: 1, 2
<223> OTHER INFORMATION: Xaa = Lys or Arg
<220> FEATURE:
<221> NAME/KEY: VARIANT
<222> LOCATION: 3, 4, 5, 6, 7, 8, 9, 10, 11, 12, 13, 14
<223> OTHER INFORMATION: Xaa = Any Amino Acid, and up to two can be present or absent
<220> FEATURE:
<221> NAME/KEY: VARIANT
<222> LOCATION: 15, 16, 17, 18, 19
<223> OTHER INFORMATION: Xaa = Any Amino Acid, and at least three are either Lys or Arg

<400> SEQUENCE: 13

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

<210> SEQ ID NO 14
<211> LENGTH: 6
<212> TYPE: PRT
<213> ORGANISM: Unknown
<220> FEATURE:
<223> OTHER INFORMATION: Class 5 Plant NLS
<220> FEATURE:
<221> NAME/KEY: VARIANT
<222> LOCATION: 5
<223> OTHER INFORMATION: Xaa = Lys or Arg
<220> FEATURE:
<221> NAME/KEY: VARIANT
<222> LOCATION: 6
<223> OTHER INFORMATION: Xaa = Trp, Phe, or Tyr

<400> SEQUENCE: 14

```
Leu Gly Lys Arg Xaa Xaa
1               5
```

<210> SEQ ID NO 15
<211> LENGTH: 15
<212> TYPE: PRT
<213> ORGANISM: Unknown
<220> FEATURE:
<223> OTHER INFORMATION: tobacco c2 NLS

<400> SEQUENCE: 15

```
Gln Pro Ser Leu Lys Arg Met Lys Ile Gln Pro Ser Ser Gln Pro
1               5                   10                  15
```

<210> SEQ ID NO 16
<211> LENGTH: 14
<212> TYPE: PRT
<213> ORGANISM: Unknown
<220> FEATURE:
<223> OTHER INFORMATION: Extended SV40 Nuclear Localization Domain

<400> SEQUENCE: 16

```
Ala Ser Pro Lys Lys Lys Arg Lys Val Glu Ala Ser Gly Ser
1               5                   10
```

<210> SEQ ID NO 17
<211> LENGTH: 11
<212> TYPE: PRT
<213> ORGANISM: Unknown
<220> FEATURE:
<223> OTHER INFORMATION: cell-penetrating peptide (CPP)

<400> SEQUENCE: 17

Tyr Gly Arg Lys Lys Arg Arg Gln Arg Arg Arg
1 5 10

<210> SEQ ID NO 18
<211> LENGTH: 12
<212> TYPE: PRT
<213> ORGANISM: Unknown
<220> FEATURE:
<223> OTHER INFORMATION: cell-penetrating peptide (CPP)

<400> SEQUENCE: 18

Arg Arg Gln Arg Arg Thr Ser Lys Leu Met Lys Arg
1 5 10

<210> SEQ ID NO 19
<211> LENGTH: 27
<212> TYPE: PRT
<213> ORGANISM: Unknown
<220> FEATURE:
<223> OTHER INFORMATION: cell-penetrating peptide (CPP)

<400> SEQUENCE: 19

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 20
<211> LENGTH: 33
<212> TYPE: PRT
<213> ORGANISM: Unknown
<220> FEATURE:
<223> OTHER INFORMATION: cell-penetrating peptide (CPP)

<400> SEQUENCE: 20

Lys Ala Leu Ala Trp Glu Ala Lys Leu Ala Lys Ala Leu Ala Lys Ala
1 5 10 15

Leu Ala Lys His Leu Ala Lys Ala Leu Ala Lys Ala Leu Lys Cys Glu
20 25 30

Ala

<210> SEQ ID NO 21
<211> LENGTH: 16
<212> TYPE: PRT
<213> ORGANISM: Unknown
<220> FEATURE:
<223> OTHER INFORMATION: cell-penetrating peptide (CPP)

<400> SEQUENCE: 21

Arg Gln Ile Lys Ile Trp Phe Gln Asn Arg Arg Met Lys Trp Lys Lys
1 5 10 15

<210> SEQ ID NO 22
<211> LENGTH: 11
<212> TYPE: PRT
<213> ORGANISM: Unknown
<220> FEATURE:
<223> OTHER INFORMATION: cell-penetrating peptide (CPP)

<400> SEQUENCE: 22

Tyr Gly Arg Lys Lys Arg Arg Gln Arg Arg Arg
1 5 10

<210> SEQ ID NO 23
<211> LENGTH: 8
<212> TYPE: PRT
<213> ORGANISM: Unknown
<220> FEATURE:
<223> OTHER INFORMATION: cell-penetrating peptide (CPP)

<400> SEQUENCE: 23

```
Arg Lys Lys Arg Arg Gln Arg Arg
1               5
```

<210> SEQ ID NO 24
<211> LENGTH: 11
<212> TYPE: PRT
<213> ORGANISM: Unknown
<220> FEATURE:
<223> OTHER INFORMATION: cell-penetrating peptide (CPP)

<400> SEQUENCE: 24

```
Tyr Ala Arg Ala Ala Ala Arg Gln Ala Arg Ala
1               5                   10
```

<210> SEQ ID NO 25
<211> LENGTH: 11
<212> TYPE: PRT
<213> ORGANISM: Unknown
<220> FEATURE:
<223> OTHER INFORMATION: cell-penetrating peptide (CPP)

<400> SEQUENCE: 25

```
Thr His Arg Leu Pro Arg Arg Arg Arg Arg Arg
1               5                   10
```

<210> SEQ ID NO 26
<211> LENGTH: 11
<212> TYPE: PRT
<213> ORGANISM: Unknown
<220> FEATURE:
<223> OTHER INFORMATION: cell-penetrating peptide (CPP)

<400> SEQUENCE: 26

```
Gly Gly Arg Arg Ala Arg Arg Arg Arg Arg Arg
1               5                   10
```

<210> SEQ ID NO 27
<211> LENGTH: 1307
<212> TYPE: PRT
<213> ORGANISM: Unknown
<220> FEATURE:
<223> OTHER INFORMATION: Acidaminococcus sp.

<400> SEQUENCE: 27

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95
```

```
Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
```

```
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940
```

Asp Asn Arg Glu Lys Glu Arg Val Ala Ala Arg Gln Ala Trp Ser Val
945 950 955 960

Val Gly Thr Ile Lys Asp Leu Lys Gln Gly Tyr Leu Ser Gln Val Ile
965 970 975

His Glu Ile Val Asp Leu Met Ile His Tyr Gln Ala Val Val Val Leu
980 985 990

Glu Asn Leu Asn Phe Gly Phe Lys Ser Lys Arg Thr Gly Ile Ala Glu
995 1000 1005

Lys Ala Val Tyr Gln Gln Phe Glu Lys Met Leu Ile Asp Lys Leu Asn
1010 1015 1020

Cys Leu Val Leu Lys Asp Tyr Pro Ala Glu Lys Val Gly Gly Val Leu
1025 1030 1035 1040

Asn Pro Tyr Gln Leu Thr Asp Gln Phe Thr Ser Phe Ala Lys Met Gly
1045 1050 1055

Thr Gln Ser Gly Phe Leu Phe Tyr Val Pro Ala Pro Tyr Thr Ser Lys
1060 1065 1070

Ile Asp Pro Leu Thr Gly Phe Val Asp Pro Phe Val Trp Lys Thr Ile
1075 1080 1085

Lys Asn His Glu Ser Arg Lys His Phe Leu Glu Gly Phe Asp Phe Leu
1090 1095 1100

His Tyr Asp Val Lys Thr Gly Asp Phe Ile Leu His Phe Lys Met Asn
1105 1110 1115 1120

Arg Asn Leu Ser Phe Gln Arg Gly Leu Pro Gly Phe Met Pro Ala Trp
1125 1130 1135

Asp Ile Val Phe Glu Lys Asn Glu Thr Gln Phe Asp Ala Lys Gly Thr
1140 1145 1150

Pro Phe Ile Ala Gly Lys Arg Ile Val Pro Val Ile Glu Asn His Arg
1155 1160 1165

Phe Thr Gly Arg Tyr Arg Asp Leu Tyr Pro Ala Asn Glu Leu Ile Ala
1170 1175 1180

Leu Leu Glu Glu Lys Gly Ile Val Phe Arg Asp Gly Ser Asn Ile Leu
1185 1190 1195 1200

Pro Lys Leu Leu Glu Asn Asp Asp Ser His Ala Ile Asp Thr Met Val
1205 1210 1215

Ala Leu Ile Arg Ser Val Leu Gln Met Arg Asn Ser Asn Ala Ala Thr
1220 1225 1230

Gly Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp Ala
1250 1255 1260

Asn Gly Ala Tyr His Ile Ala Leu Lys Gly Gln Leu Leu Leu Asn His
1265 1270 1275 1280

Leu Lys Glu Ser Lys Asp Leu Lys Leu Gln Asn Gly Ile Ser Asn Gln
1285 1290 1295

Asp Trp Leu Ala Tyr Ile Gln Glu Leu Arg Asn
1300 1305

<210> SEQ ID NO 28
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 28

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415
```

-continued

```
Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
```

```
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp Ser
    1010                1015                1020

Lys Lys Phe Ile Ser Ser Phe Asp Arg Ile Met Tyr Val Pro Glu Glu
1025                1030                1035                1040

Asp Leu Phe Glu Phe Ala Leu Asp Tyr Lys Asn Phe Ser Arg Thr Asp
                1045                1050                1055

Ala Asp Tyr Ile Lys Lys Trp Lys Leu Tyr Ser Tyr Gly Asn Arg Ile
            1060                1065                1070

Arg Ile Phe Arg Asn Pro Lys Lys Asn Asn Val Phe Asp Trp Glu Glu
        1075                1080                1085

Val Cys Leu Thr Ser Ala Tyr Lys Glu Leu Phe Asn Lys Tyr Gly Ile
    1090                1095                1100

Asn Tyr Gln Gln Gly Asp Ile Arg Ala Leu Leu Cys Glu Gln Ser Asp
1105                1110                1115                1120

Lys Ala Phe Tyr Ser Ser Phe Met Ala Leu Met Ser Leu Met Leu Gln
                1125                1130                1135

Met Arg Asn Ser Ile Thr Gly Arg Thr Asp Val Asp Phe Leu Ile Ser
            1140                1145                1150

Pro Val Lys Asn Ser Asp Gly Ile Phe Tyr Asp Ser Arg Asn Tyr Glu
        1155                1160                1165

Ala Gln Glu Asn Ala Ile Leu Pro Lys Asn Ala Asp Ala Asn Gly Ala
    1170                1175                1180

Tyr Asn Ile Ala Arg Lys Val Leu Trp Ala Ile Gly Gln Phe Lys Lys
1185                1190                1195                1200

Ala Glu Asp Glu Lys Leu Asp Lys Val Lys Ile Ala Ile Ser Asn Lys
                1205                1210                1215

Glu Trp Leu Glu Tyr Ala Gln Thr Ser Val Lys His
            1220                1225
```

<210> SEQ ID NO 29
<211> LENGTH: 1300
<212> TYPE: PRT
<213> ORGANISM: Francisella novicida

<400> SEQUENCE: 29

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
```

-continued

```
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830
```

```
Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val Tyr
    1010                1015                1020

Gln Lys Leu Glu Lys Met Leu Ile Glu Lys Leu Asn Tyr Leu Val Phe
1025                1030                1035                1040

Lys Asp Asn Glu Phe Asp Lys Thr Gly Gly Val Leu Arg Ala Tyr Gln
                1045                1050                1055

Leu Thr Ala Pro Phe Glu Thr Phe Lys Lys Met Gly Lys Gln Thr Gly
            1060                1065                1070

Ile Ile Tyr Tyr Val Pro Ala Gly Phe Thr Ser Lys Ile Cys Pro Val
        1075                1080                1085

Thr Gly Phe Val Asn Gln Leu Tyr Pro Lys Tyr Glu Ser Val Ser Lys
    1090                1095                1100

Ser Gln Glu Phe Phe Ser Lys Phe Asp Lys Ile Cys Tyr Asn Leu Asp
1105                1110                1115                1120

Lys Gly Tyr Phe Glu Phe Ser Phe Asp Tyr Lys Asn Phe Gly Asp Lys
                1125                1130                1135

Ala Ala Lys Gly Lys Trp Thr Ile Ala Ser Phe Gly Ser Arg Leu Ile
            1140                1145                1150

Asn Phe Arg Asn Ser Asp Lys Asn His Asn Trp Asp Thr Arg Glu Val
        1155                1160                1165

Tyr Pro Thr Lys Glu Leu Glu Lys Leu Leu Lys Asp Tyr Ser Ile Glu
    1170                1175                1180

Tyr Gly His Gly Glu Cys Ile Lys Ala Ala Ile Cys Gly Glu Ser Asp
1185                1190                1195                1200

Lys Lys Phe Phe Ala Lys Leu Thr Ser Val Leu Asn Thr Ile Leu Gln
                1205                1210                1215

Met Arg Asn Ser Lys Thr Gly Thr Glu Leu Asp Tyr Leu Ile Ser Pro
            1220                1225                1230

Val Ala Asp Val Asn Gly Asn Phe Phe Asp Ser Arg Gln Ala Pro Lys
        1235                1240                1245
```

```
Asn Met Pro Gln Asp Ala Asp Ala Asn Gly Ala Tyr His Ile Gly Leu
    1250                1255                1260

Lys Gly Leu Met Leu Leu Gly Arg Ile Lys Asn Asn Gln Glu Gly Lys
1265                1270                1275                1280

Lys Leu Asn Leu Val Ile Lys Asn Glu Glu Tyr Phe Glu Phe Val Gln
                1285                1290                1295

Asn Arg Asn Asn
            1300


<210> SEQ ID NO 30
<211> LENGTH: 1320
<212> TYPE: PRT
<213> ORGANISM: Unknown
<220> FEATURE:
<223> OTHER INFORMATION: CasJ (wild type)

<400> SEQUENCE: 30

Met Gln Gln Tyr Gln Val Ser Lys Thr Val Arg Phe Gly Leu Thr Leu
1               5                   10                  15

Lys Asn Ser Glu Lys Lys His Ala Thr His Leu Leu Leu Lys Asp Leu
            20                  25                  30

Val Asn Val Ser Glu Glu Arg Ile Lys Asn Glu Ile Thr Lys Asp Asp
        35                  40                  45

Lys Asn Gln Ser Glu Leu Ser Phe Phe Asn Glu Val Ile Glu Thr Leu
    50                  55                  60

Asp Leu Met Asp Lys Tyr Ile Lys Asp Trp Glu Asn Cys Phe Tyr Arg
65                  70                  75                  80

Thr Asp Gln Ile Gln Leu Thr Lys Glu Tyr Tyr Lys Val Ile Ala Lys
                85                  90                  95

Lys Ala Cys Phe Asp Trp Phe Trp Thr Asn Asp Arg Gly Met Lys Phe
            100                 105                 110

Pro Thr Ser Ser Ile Ile Ser Phe Asn Ser Leu Lys Ser Ser Asp Lys
        115                 120                 125

Ser Lys Thr Ser Asp Asn Leu Asp Arg Lys Lys Lys Ile Leu Asp Tyr
    130                 135                 140

Trp Lys Gly Asn Ile Phe Lys Thr Gln Lys Ala Ile Lys Asp Val Leu
145                 150                 155                 160

Asp Ile Thr Glu Asp Ile Gln Lys Ala Ile Glu Glu Lys Lys Ser His
                165                 170                 175

Arg Glu Ile Asn Arg Val Asn His Arg Lys Met Gly Ile His Leu Ile
            180                 185                 190

His Leu Ile Asn Asp Thr Leu Val Pro Leu Cys Asn Gly Ser Ile Phe
        195                 200                 205

Phe Gly Asn Ile Ser Lys Leu Asp Phe Cys Glu Ser Glu Asn Glu Lys
    210                 215                 220

Leu Ile Asp Phe Ala Ser Thr Glu Lys Gln Asp Glu Arg Lys Phe Leu
225                 230                 235                 240

Leu Ser Lys Ile Asn Glu Ile Lys Gln Tyr Phe Glu Asp Asn Gly Gly
                245                 250                 255

Asn Val Pro Phe Ala Arg Ala Thr Leu Asn Arg His Thr Ala Asn Gln
            260                 265                 270

Lys Pro Asp Arg Tyr Asn Glu Glu Ile Lys Lys Leu Val Asn Glu Leu
        275                 280                 285

Gly Val Asn Ser Leu Val Arg Ser Leu Lys Ser Lys Thr Ile Glu Glu
    290                 295                 300
```

```
Ile Lys Thr His Phe Glu Phe Glu Asn Lys Asn Lys Ile Asn Glu Leu
305                 310                 315                 320

Lys Asn Ser Phe Val Leu Ser Ile Val Glu Lys Ile Gln Leu Phe Lys
                325                 330                 335

Tyr Lys Thr Ile Pro Ala Ser Val Arg Phe Leu Leu Ala Asp Tyr Phe
            340                 345                 350

Glu Glu Gln Lys Leu Ser Thr Lys Glu Glu Ala Leu Thr Ile Phe Glu
        355                 360                 365

Glu Ile Gly Lys Pro Gln Asn Ile Gly Phe Asp Tyr Ile Gln Leu Lys
    370                 375                 380

Glu Lys Asp Asn Phe Thr Leu Lys Lys Tyr Pro Leu Lys Gln Ala Phe
385                 390                 395                 400

Asp Tyr Ala Trp Glu Asn Leu Ala Arg Leu Asp Gln Asn Pro Lys Ala
                405                 410                 415

Asn Gln Phe Ser Val Asp Glu Cys Lys Arg Phe Phe Lys Glu Val Phe
            420                 425                 430

Ser Met Glu Met Asp Asn Ile Asn Phe Lys Thr Tyr Ala Leu Leu Leu
        435                 440                 445

Ala Leu Lys Glu Lys Thr Thr Ala Phe Asp Lys Lys Gly Glu Gly Ala
    450                 455                 460

Ala Lys Asn Lys Ser Glu Ile Ile Glu Gln Ile Lys Gly Val Phe Glu
465                 470                 475                 480

Glu Leu Asp Gln Pro Phe Lys Ile Ile Ala Asn Thr Leu Arg Glu Glu
                485                 490                 495

Val Ile Lys Lys Glu Asp Glu Leu Asn Val Leu Lys Arg Gln Tyr Arg
            500                 505                 510

Glu Thr Asp Arg Lys Ile Lys Thr Leu Gln Asn Glu Ile Lys Lys Ile
        515                 520                 525

Lys Asn Gln Ile Lys Asn Leu Glu Asn Ser Lys Lys Tyr Ser Phe Pro
    530                 535                 540

Glu Ile Ile Lys Trp Ile Asp Leu Thr Glu Gln Glu Gln Leu Leu Asp
545                 550                 555                 560

Lys Asn Lys Gln Ala Lys Ser Asn Tyr Gln Lys Ala Lys Gly Asp Leu
                565                 570                 575

Gly Leu Ile Arg Gly Ser Gln Lys Thr Ser Ile Asn Asp Tyr Phe Tyr
            580                 585                 590

Leu Thr Asp Lys Val Tyr Arg Lys Leu Ala Gln Asp Phe Gly Lys Lys
        595                 600                 605

Met Ala Asp Leu Arg Glu Lys Leu Leu Asp Lys Asn Asp Val Asn Lys
    610                 615                 620

Ile Lys Tyr Leu Ser Tyr Ile Val Lys Asp Asn Gln Gly Tyr Gln Tyr
625                 630                 635                 640

Thr Leu Leu Lys Pro Leu Glu Asp Lys Asn Ala Glu Ile Ile Glu Leu
                645                 650                 655

Lys Ser Glu Pro Asn Gly Asp Leu Lys Leu Phe Glu Ile Lys Ser Leu
            660                 665                 670

Thr Ser Lys Thr Leu Asn Lys Phe Ile Lys Asn Lys Gly Ala Tyr Lys
        675                 680                 685

Glu Phe His Ser Ala Glu Phe Glu His Lys Lys Ile Lys Glu Asp Trp
    690                 695                 700

Lys Asn Tyr Lys Tyr Asn Ser Asp Phe Ile Val Lys Leu Lys Lys Cys
705                 710                 715                 720

Leu Ser His Ser Asp Met Ala Asn Thr Gln Asn Trp Lys Ala Phe Gly
```

```
                725                 730                 735

Trp Asp Leu Asp Lys Cys Lys Ser Tyr Glu Thr Ile Glu Lys Glu Ile
            740                 745                 750

Asp Gln Lys Ser Tyr Gln Leu Val Glu Ile Lys Leu Ser Lys Thr Thr
        755                 760                 765

Ile Glu Lys Trp Val Lys Glu Asn Asn Tyr Leu Leu Leu Pro Ile Val
    770                 775                 780

Asn Gln Asp Ile Thr Ala Glu Lys Leu Lys Val Asn Thr Asn Gln Phe
785                 790                 795                 800

Thr Lys Asp Trp Gln His Ile Phe Glu Lys Asn Pro Asn His Arg Leu
                805                 810                 815

His Pro Glu Phe Asn Ile Ala Tyr Arg Gln Pro Thr Lys Asp Tyr Ala
            820                 825                 830

Lys Glu Gly Glu Lys Arg Tyr Ser Arg Phe Gln Leu Thr Gly Gln Phe
        835                 840                 845

Met Tyr Glu Tyr Ile Pro Gln Asp Ala Asn Tyr Ile Ser Arg Lys Glu
    850                 855                 860

Gln Ile Thr Leu Phe Asn Asp Lys Glu Glu Gln Lys Ile Gln Val Glu
865                 870                 875                 880

Thr Phe Asn Asn Gln Ile Ala Lys Ile Leu Asn Ala Glu Asp Phe Tyr
                885                 890                 895

Val Ile Gly Ile Asp Arg Gly Ile Thr Gln Leu Ala Thr Leu Cys Val
            900                 905                 910

Leu Asn Lys Asn Gly Val Ile Gln Gly Gly Phe Glu Ile Phe Thr Arg
        915                 920                 925

Glu Phe Asp Tyr Thr Asn Lys Gln Trp Lys His Thr Lys Leu Lys Glu
    930                 935                 940

Asn Arg Asn Ile Leu Asp Ile Ser Asn Leu Lys Val Glu Thr Thr Val
945                 950                 955                 960

Asn Gly Glu Lys Val Leu Val Asp Leu Ser Glu Val Lys Thr Tyr Leu
                965                 970                 975

Arg Asp Glu Asn Gly Glu Pro Met Lys Asn Glu Lys Gly Val Ile Leu
            980                 985                 990

Thr Lys Asp Asn Leu Gln Lys Ile Lys Leu Lys Gln Leu Ala Tyr Asp
        995                 1000                1005

Arg Lys Leu Gln Tyr Lys Met Gln His Glu Pro Glu Leu Val Leu Ser
    1010                1015                1020

Phe Leu Asp Arg Leu Glu Asn Lys Glu Gln Ile Pro Asn Leu Leu Ala
1025                1030                1035                1040

Ser Thr Lys Leu Ile Ser Ala Tyr Lys Glu Gly Thr Ala Tyr Ala Asp
                1045                1050                1055

Ile Asp Ile Glu Gln Phe Trp Asn Ile Leu Gln Thr Phe Gln Thr Ile
            1060                1065                1070

Val Asp Lys Phe Gly Gly Ile Glu Asn Ala Lys Lys Thr Met Glu Phe
        1075                1080                1085

Arg Gln Tyr Thr Glu Leu Asp Ala Ser Phe Asp Leu Lys Asn Gly Val
    1090                1095                1100

Val Ala Asn Met Val Gly Val Val Lys Phe Ile Met Glu Lys Tyr Asn
1105                1110                1115                1120

Tyr Lys Thr Phe Ile Ala Leu Glu Asp Leu Thr Phe Ala Phe Gly Gln
                1125                1130                1135

Ser Ile Asp Gly Ile Asn Gly Glu Arg Leu Arg Ser Thr Lys Glu Asp
            1140                1145                1150
```

```
Lys Glu Val Asp Phe Lys Glu Gln Glu Asn Ser Thr Leu Ala Gly Leu
        1155                1160                1165

Gly Thr Tyr His Phe Phe Glu Met Gln Leu Leu Lys Lys Leu Ser Lys
    1170                1175                1180

Thr Gln Ile Gly Asn Glu Ile Lys His Phe Val Pro Ala Phe Arg Ser
1185                1190                1195                1200

Thr Glu Asn Tyr Glu Lys Ile Val Arg Lys Asp Lys Asn Val Lys Ala
                1205                1210                1215

Lys Ile Val Ser Tyr Pro Phe Gly Ile Val Ser Phe Val Asn Pro Arg
            1220                1225                1230

Asn Thr Ser Ile Ser Cys Pro Asn Cys Lys Asn Ala Asn Lys Ser Asn
        1235                1240                1245

Arg Ile Lys Lys Glu Asn Asp Arg Ile Leu Cys Lys His Asn Ile Glu
    1250                1255                1260

Lys Thr Lys Gly Asn Cys Gly Phe Asp Thr Ala Asn Phe Asp Glu Asn
1265                1270                1275                1280

Lys Leu Arg Ala Glu Asn Lys Gly Lys Asn Phe Lys Tyr Ile Ser Ser
                1285                1290                1295

Gly Asp Ala Asn Ala Ala Tyr Asn Ile Ala Val Lys Leu Leu Glu Asp
            1300                1305                1310

Lys Ile Phe Glu Ile Asn Lys Lys
        1315                1320


<210> SEQ ID NO 31
<211> LENGTH: 178
<212> TYPE: PRT
<213> ORGANISM: Escherichia coli

<400> SEQUENCE: 31

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 32
```

<211> LENGTH: 16
<212> TYPE: PRT
<213> ORGANISM: Artificial Sequence
<220> FEATURE:
<223> OTHER INFORMATION: ERF protein motif
<220> FEATURE:
<221> NAME/KEY: VARIANT
<222> LOCATION: 2
<223> OTHER INFORMATION: Xaa = Gly, Ser, or Ala
<220> FEATURE:
<221> NAME/KEY: VARIANT
<222> LOCATION: 3, 4
<223> OTHER INFORMATION: Xaa = Any Amino Acid
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 7
<223> OTHER INFORMATION: Xaa = Ala, Val, Leu, Ile, Met, or Phe
<220> FEATURE:
<221> NAME/KEY: VARIANT
<222> LOCATION: 8
<223> OTHER INFORMATION: Xaa = Lys, Arg, Glu, Asp, Asn, Thr, or Ser
<220> FEATURE:
<221> NAME/KEY: VARIANT
<222> LOCATION: 9
<223> OTHER INFORMATION: Xaa = Lys or Arg
<220> FEATURE:
<221> NAME/KEY: VARIANT
<222> LOCATION: 11
<223> OTHER INFORMATION: Xaa = Any Amino Acid
<220> FEATURE:
<221> NAME/KEY: VARIANT
<222> LOCATION: 12
<223> OTHER INFORMATION: Xaa = Ala, Val, Leu, Ile, Met, or Phe
<220> FEATURE:
<221> NAME/KEY: VARIANT
<222> LOCATION: 13, 14
<223> OTHER INFORMATION: Xaa = Any Amino Acid
<220> FEATURE:
<221> NAME/KEY: VARIANT
<222> LOCATION: 15, 16
<223> OTHER INFORMATION: Xaa = Ala, Val, Leu, Ile, Met, or Phe

<400> SEQUENCE: 32

```
Gly Xaa Xaa Xaa Xaa Tyr Xaa Xaa Xaa Tyr Xaa Xaa Xaa Xaa Xaa Xaa
1               5                   10                  15
```

<210> SEQ ID NO 33
<211> LENGTH: 20
<212> TYPE: PRT
<213> ORGANISM: Unknown
<220> FEATURE:
<223> OTHER INFORMATION: FMDV 2A self-processing peptide sequence

<400> SEQUENCE: 33

```
Gln Leu Leu Asn Phe Asp Leu Leu Lys Leu Ala Gly Asp Val Glu Ser
1               5                   10                  15

Asn Pro Gly Pro
            20
```

<210> SEQ ID NO 34
<211> LENGTH: 178
<212> TYPE: PRT
<213> ORGANISM: Escherichia coli APEC O1

<400> SEQUENCE: 34

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
```

```
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 35
<211> LENGTH: 178
<212> TYPE: PRT
<213> ORGANISM: Escherichia coli UTI89

<400> SEQUENCE: 35

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 36
<211> LENGTH: 178
<212> TYPE: PRT
<213> ORGANISM: Unknown
```

<220> FEATURE:
<223> OTHER INFORMATION: Proteobacteria

<400> SEQUENCE: 36

Met Ala Ser Arg Gly Val Asn Lys Val Ile Leu Val Gly Asn Leu Gly
1 5 10 15

Gln Asp Pro Glu Val Arg Tyr Met Pro Asn Gly Gly Ala Val Ala Asn
20 25 30

Ile Thr Leu Ala Thr Ser Glu Ser Trp Arg Asp Lys Ala Thr Gly Glu
35 40 45

Met Lys Glu Gln Thr Glu Trp His Arg Val Val Leu Phe Gly Lys Leu
50 55 60

Ala Glu Val Ala Ser Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Arg Tyr Thr Thr Glu Val Val Val Asn Val Gly Gly Thr Met Gln Met
100 105 110

Leu Gly Gly Arg Gln Gly Gly Gly Ala Pro Ala Gly Gly Asn Ile Gly
115 120 125

Gly Gly Gln Pro Gln Gly Gly Trp Gly Gln Pro Gln Gln Pro Gln Gly
130 135 140

Gly Asn Gln Phe Ser Gly Gly Ala Gln Ser Arg Pro Gln Gln Ser Ala
145 150 155 160

Pro Ala Ala Pro Ser Asn Glu Pro Pro Met Asp Phe Asp Asp Asp Ile
165 170 175

Pro Phe

<210> SEQ ID NO 37
<211> LENGTH: 178
<212> TYPE: PRT
<213> ORGANISM: Unknown
<220> FEATURE:
<223> OTHER INFORMATION: Escherichia

<400> SEQUENCE: 37

Met Ala Ser Arg Gly Val Asn Lys Val Ile Leu Val Gly Asn Leu Gly
1 5 10 15

Gln Asp Pro Glu Val Arg Tyr Met Pro Asn Gly Gly Ala Val Ala Asn
20 25 30

Ile Thr Leu Ala Thr Ser Glu Ser Trp Arg Asp Lys Ala Thr Gly Glu
35 40 45

Met Lys Glu Gln Thr Glu Trp His Arg Val Val Leu Phe Gly Lys Leu
50 55 60

Ala Glu Val Ala Ser Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Arg Tyr Thr Thr Glu Val Val Val Asn Val Gly Gly Thr Met Gln Met
100 105 110

Leu Gly Gly Arg Gln Gly Gly Gly Ala Pro Ala Gly Gly Asn Val Gly
115 120 125

Gly Gly Gln Pro Gln Gly Gly Trp Gly Gln Pro Gln Gln Pro Gln Gly
130 135 140

Gly Asn Gln Phe Ser Gly Gly Ala Gln Ser Arg Pro Gln Gln Ser Ala
145 150 155 160

```
Pro Ala Ala Pro Ser Asn Glu Pro Pro Met Asp Phe Asp Asp Asp Ile
                165                 170                 175

Pro Phe


<210> SEQ ID NO 38
<211> LENGTH: 178
<212> TYPE: PRT
<213> ORGANISM: Shigella flexneri

<400> SEQUENCE: 38

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Lys Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 39
<211> LENGTH: 178
<212> TYPE: PRT
<213> ORGANISM: Escherichia coli

<400> SEQUENCE: 39

Met Ala Ser Lys Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
```

```
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 40
<211> LENGTH: 178
<212> TYPE: PRT
<213> ORGANISM: Escherichia coli

<400> SEQUENCE: 40

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Leu
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 41
<211> LENGTH: 178
<212> TYPE: PRT
<213> ORGANISM: Escherichia coli

<400> SEQUENCE: 41

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80
```

```
Glu Gly Gln Leu Arg Thr Arg Lys Trp Thr Asp Gln Ser Ala Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 42
<211> LENGTH: 178
<212> TYPE: PRT
<213> ORGANISM: Escherichia coli

<400> SEQUENCE: 42

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Ala Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 43
<211> LENGTH: 178
<212> TYPE: PRT
<213> ORGANISM: Escherichia coli

<400> SEQUENCE: 43

Met Ala Ser Arg Gly Val Asn Lys Val Ile Leu Val Gly Asn Leu Gly
1               5                   10                  15

His Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45
```

```
Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 44
<211> LENGTH: 178
<212> TYPE: PRT
<213> ORGANISM: Escherichia coli

<400> SEQUENCE: 44

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Ser Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 45
<211> LENGTH: 178
<212> TYPE: PRT
<213> ORGANISM: Escherichia coli

<400> SEQUENCE: 45

Met Ala Ser Arg Gly Val Asn Lys Val Ile Leu Val Gly Asn Leu Gly
```

```
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Ser Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 46
<211> LENGTH: 178
<212> TYPE: PRT
<213> ORGANISM: Escherichia coli

<400> SEQUENCE: 46

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Ser Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 47
```

<211> LENGTH: 178
<212> TYPE: PRT
<213> ORGANISM: Escherichia coli

<400> SEQUENCE: 47

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Ser Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe
```

<210> SEQ ID NO 48
<211> LENGTH: 178
<212> TYPE: PRT
<213> ORGANISM: Escherichia coli

<400> SEQUENCE: 48

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Ser Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160
```

```
Pro Ala Ala Pro Ser Asn Glu Pro Pro Met Asp Phe Asp Asp Asp Ile
                165                 170                 175

Pro Phe


<210> SEQ ID NO 49
<211> LENGTH: 178
<212> TYPE: PRT
<213> ORGANISM: Escherichia coli

<400> SEQUENCE: 49

Met Ala Ser Arg Gly Val Asn Lys Val Ile Leu Val Gly Asn Leu Gly
1               5                   10                  15

Gln Asp Pro Glu Val Arg Tyr Met Pro Asn Ser Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 50
<211> LENGTH: 178
<212> TYPE: PRT
<213> ORGANISM: Unknown
<220> FEATURE:
<223> OTHER INFORMATION: Escherichia

<400> SEQUENCE: 50

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110
```

```
Leu Gly Gly Arg Gln Ser Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 51
<211> LENGTH: 178
<212> TYPE: PRT
<213> ORGANISM: Escherichia coli

<400> SEQUENCE: 51

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Thr
145                 150                 155                 160

Pro Ala Ala Pro Ser Asn Glu Pro Pro Met Asp Phe Asp Asp Asp Ile
                165                 170                 175

Pro Phe


<210> SEQ ID NO 52
<211> LENGTH: 177
<212> TYPE: PRT
<213> ORGANISM: Escherichia coli

<400> SEQUENCE: 52

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80
```

```
Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gln Pro Gln Gly Gly Trp Gly Gln Ser Gln Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asp Phe Asp Asp Asp Ile Pro
                165                 170                 175

Phe


<210> SEQ ID NO 53
<211> LENGTH: 178
<212> TYPE: PRT
<213> ORGANISM: Escherichia coli

<400> SEQUENCE: 53

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Cys Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 54
<211> LENGTH: 178
<212> TYPE: PRT
<213> ORGANISM: Escherichia coli
<220> FEATURE:
<221> NAME/KEY: VARIANT
<222> LOCATION: 111
<223> OTHER INFORMATION: Xaa = Any Amino Acid

<400> SEQUENCE: 54

Met Ala Ser Arg Gly Val Asn Lys Val Ile Leu Val Gly Asn Leu Gly
1               5                   10                  15
```

```
Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Xaa Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 55
<211> LENGTH: 178
<212> TYPE: PRT
<213> ORGANISM: Escherichia coli

<400> SEQUENCE: 55

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Val Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 56
<211> LENGTH: 178
<212> TYPE: PRT
```

<213> ORGANISM: Escherichia coli

<400> SEQUENCE: 56

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Val Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe
```

<210> SEQ ID NO 57
<211> LENGTH: 178
<212> TYPE: PRT
<213> ORGANISM: Escherichia coli

<400> SEQUENCE: 57

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Asp Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175
```

Pro Phe

<210> SEQ ID NO 58
<211> LENGTH: 178
<212> TYPE: PRT
<213> ORGANISM: Escherichia coli

<400> SEQUENCE: 58

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Asp
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe
```

<210> SEQ ID NO 59
<211> LENGTH: 178
<212> TYPE: PRT
<213> ORGANISM: Escherichia coli

<400> SEQUENCE: 59

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Ile Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
```

```
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 60
<211> LENGTH: 178
<212> TYPE: PRT
<213> ORGANISM: Shigella dysenteriae 1617

<400> SEQUENCE: 60

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Leu Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 61
<211> LENGTH: 178
<212> TYPE: PRT
<213> ORGANISM: Escherichia albertii

<400> SEQUENCE: 61

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Leu Asp
                85                  90                  95
```

```
Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 62
<211> LENGTH: 178
<212> TYPE: PRT
<213> ORGANISM: Escherichia coli

<400> SEQUENCE: 62

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Cys Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 63
<211> LENGTH: 178
<212> TYPE: PRT
<213> ORGANISM: Escherichia coli

<400> SEQUENCE: 63

Met Ala Ser Arg Gly Val Asn Lys Val Ile Leu Val Gly Asn Leu Gly
1               5                   10                  15

Leu Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60
```

Ala Glu Val Ala Ser Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Arg Tyr Thr Thr Glu Val Val Val Asn Val Gly Gly Thr Met Gln Met
100 105 110

Leu Gly Gly Arg Gln Gly Gly Gly Ala Pro Ala Gly Gly Asn Ile Gly
115 120 125

Gly Gly Gln Pro Gln Gly Gly Trp Gly Gln Pro Gln Gln Pro Gln Gly
130 135 140

Gly Asn Gln Phe Ser Gly Gly Ala Gln Ser Arg Pro Gln Gln Ser Ala
145 150 155 160

Pro Ala Ala Pro Ser Asn Glu Pro Pro Met Asp Phe Asp Asp Asp Ile
165 170 175

Pro Phe

<210> SEQ ID NO 64
<211> LENGTH: 178
<212> TYPE: PRT
<213> ORGANISM: Escherichia coli

<400> SEQUENCE: 64

Met Ala Ser Arg Gly Val Asn Lys Val Ile Leu Val Gly Asn Leu Gly
1 5 10 15

Gln Asp Pro Glu Val Arg Tyr Met Pro Asn Gly Gly Ala Val Ala Asn
20 25 30

Ile Thr Leu Ala Thr Ser Glu Ser Trp Arg Asp Lys Ala Thr Gly Glu
35 40 45

Met Lys Glu Gln Thr Glu Trp His Arg Val Val Leu Phe Gly Lys Leu
50 55 60

Ala Glu Val Ala Ser Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Arg Tyr Thr Thr Glu Val Val Val Asn Val Gly Gly Thr Met Gln Met
100 105 110

Leu Gly Gly Arg Gln Gly Gly Gly Ala Pro Ala Gly Gly Asn Ile Gly
115 120 125

Gly Gly Gln Pro Gln Gly Gly Trp Gly Gln Pro Gln Gln Pro Gln Gly
130 135 140

Gly Asn Gln Phe Ser Gly Gly Ala Gln Ser Arg Pro Gln Gln Pro Ala
145 150 155 160

Pro Ala Ala Pro Ser Asn Glu Pro Pro Met Asp Phe Asp Asp Asp Ile
165 170 175

Pro Phe

<210> SEQ ID NO 65
<211> LENGTH: 178
<212> TYPE: PRT
<213> ORGANISM: Unknown
<220> FEATURE:
<223> OTHER INFORMATION: Enterobacteriaceae

<400> SEQUENCE: 65

Met Ala Ser Arg Gly Val Asn Lys Val Ile Leu Val Gly Asn Leu Gly
1 5 10 15

```
Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Leu Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 66
<211> LENGTH: 178
<212> TYPE: PRT
<213> ORGANISM: Escherichia coli

<400> SEQUENCE: 66

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Asp Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Thr
145                 150                 155                 160

Pro Ala Ala Pro Ser Asn Glu Pro Pro Met Asp Phe Asp Asp Asp Ile
                165                 170                 175

Pro Phe


<210> SEQ ID NO 67
<211> LENGTH: 178
```

<212> TYPE: PRT
<213> ORGANISM: Escherichia coli

<400> SEQUENCE: 67

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Leu Gln Gln Ser Ala
145                 150                 155                 160

Pro Ala Ala Pro Ser Asn Glu Pro Pro Met Asp Phe Asp Asp Asp Ile
                165                 170                 175

Pro Phe
```

<210> SEQ ID NO 68
<211> LENGTH: 178
<212> TYPE: PRT
<213> ORGANISM: Escherichia coli

<400> SEQUENCE: 68

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Leu Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
```

```
                165                 170                 175

Pro Phe


<210> SEQ ID NO 69
<211> LENGTH: 178
<212> TYPE: PRT
<213> ORGANISM: Unknown
<220> FEATURE:
<223> OTHER INFORMATION: Escherichia

<400> SEQUENCE: 69

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Ser Gly Gly Ala Pro Thr Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 70
<211> LENGTH: 178
<212> TYPE: PRT
<213> ORGANISM: Escherichia coli

<400> SEQUENCE: 70

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Gly Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
```

```
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 71
<211> LENGTH: 178
<212> TYPE: PRT
<213> ORGANISM: Escherichia coli

<400> SEQUENCE: 71

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Gly Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 72
<211> LENGTH: 178
<212> TYPE: PRT
<213> ORGANISM: Escherichia albertii

<400> SEQUENCE: 72

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Leu Val Tyr Ile
65                  70                  75                  80
```

```
Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Ser Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 73
<211> LENGTH: 178
<212> TYPE: PRT
<213> ORGANISM: Escherichia albertii

<400> SEQUENCE: 73

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Phe Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Ser Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 74
<211> LENGTH: 188
<212> TYPE: PRT
<213> ORGANISM: Escherichia coli

<400> SEQUENCE: 74

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45
```

```
Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Trp Gly Gln Pro Gln Gln Pro Gln Gly Gly Asn Gln Phe Ser Gly
145                 150                 155                 160

Gly Ala Gln Ser Arg Pro Gln Gln Ser Ala Pro Ala Ala Pro Ser Asn
                165                 170                 175

Glu Pro Pro Met Asp Phe Asp Asp Asp Ile Pro Phe
            180                 185
```

<210> SEQ ID NO 75
<211> LENGTH: 177
<212> TYPE: PRT
<213> ORGANISM: Unknown
<220> FEATURE:
<223> OTHER INFORMATION: Citrobacter

<400> SEQUENCE: 75

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ala Gly
        115                 120                 125

Gly Gly Gln Gln Gly Gly Trp Gly Gln Pro Gln Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asp Phe Asp Asp Asp Ile Pro
                165                 170                 175

Phe
```

<210> SEQ ID NO 76
<211> LENGTH: 178
<212> TYPE: PRT
<213> ORGANISM: Citrobacter koseri

<400> SEQUENCE: 76

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Met Gly
        115                 120                 125

Gly Gly Gln Gln Gln Gly Gly Trp Gly Gln Pro Gln Gln Pro Gln Gly
    130                 135                 140

Gly Asn Gln Phe Ser Gly Gly Ala Gln Ser Arg Pro Gln Gln Gln Ser
145                 150                 155                 160

Ala Pro Ala Pro Ser Asn Glu Pro Pro Met Asp Phe Asp Asp Asp Ile
                165                 170                 175

Pro Phe
```

<210> SEQ ID NO 77
<211> LENGTH: 171
<212> TYPE: PRT
<213> ORGANISM: Escherichia coli ECC-1470

<400> SEQUENCE: 77

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Gln Pro Gln Gly
    130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp
                165                 170
```

```
<210> SEQ ID NO 78
<211> LENGTH: 178
<212> TYPE: PRT
<213> ORGANISM: Citrobacter koseri

<400> SEQUENCE: 78

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Val Pro Ala Gly Gly Asn Met Gly
        115                 120                 125

Gly Gly Gln Gln Gln Gly Gly Trp Gly Gln Pro Gln Gln Pro Gln Gly
    130                 135                 140

Gly Asn Gln Phe Ser Gly Gly Ala Gln Ser Arg Pro Gln Gln Gln Ser
145                 150                 155                 160

Ala Pro Ala Pro Ser Asn Glu Pro Pro Met Asp Phe Asp Asp Asp Ile
                165                 170                 175

Pro Phe


<210> SEQ ID NO 79
<211> LENGTH: 178
<212> TYPE: PRT
<213> ORGANISM: Citrobacter koseri

<400> SEQUENCE: 79

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Ile Thr Glu Val Val Val Asn Val Gly Gly Thr Met Gln Met
            100                 105                 110

Leu Gly Gly Arg Gln Gly Gly Gly Ala Pro Ala Gly Gly Asn Met Gly
        115                 120                 125

Gly Gly Gln Gln Gln Gly Gly Trp Gly Gln Pro Gln Gln Pro Gln Gly
    130                 135                 140

Gly Asn Gln Phe Ser Gly Gly Ala Gln Ser Arg Pro Gln Gln Gln Ser
145                 150                 155                 160
```

```
Ala Pro Ala Pro Ser Asn Glu Pro Pro Met Asp Phe Asp Asp Asp Ile
                165                 170                 175

Pro Phe


<210> SEQ ID NO 80
<211> LENGTH: 171
<212> TYPE: PRT
<213> ORGANISM: Unknown
<220> FEATURE:
<223> OTHER INFORMATION: Shigella

<400> SEQUENCE: 80

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gln Pro Gln Gly Gly Asn Gln Phe Ser Gly Gly
    130                 135                 140

Ala Gln Ser Arg Pro Gln Gln Ser Ala Pro Ala Ala Pro Ser Asn Glu
145                 150                 155                 160

Pro Pro Met Asp Phe Asp Asp Asp Ile Pro Phe
                165                 170


<210> SEQ ID NO 81
<211> LENGTH: 174
<212> TYPE: PRT
<213> ORGANISM: Unknown
<220> FEATURE:
<223> OTHER INFORMATION: Enterobacteriaceae

<400> SEQUENCE: 81

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110
```

```
Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Ser Ala Pro Ala Ala Pro
145                 150                 155                 160

Ser Asn Glu Pro Pro Met Asp Phe Asp Asp Asp Ile Pro Phe
                165                 170


<210> SEQ ID NO 82
<211> LENGTH: 174
<212> TYPE: PRT
<213> ORGANISM: Citrobacter freundii complex

<400> SEQUENCE: 82

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Gly Gln Ser Arg Pro Gln Gln Ser Ala Pro Ala Ala Pro
145                 150                 155                 160

Ser Asn Glu Pro Pro Met Asp Phe Asp Asp Asp Ile Pro Phe
                165                 170


<210> SEQ ID NO 83
<211> LENGTH: 174
<212> TYPE: PRT
<213> ORGANISM: Unknown
<220> FEATURE:
<223> OTHER INFORMATION: Citrobacter

<400> SEQUENCE: 83

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80
```

```
Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Glu Gln Ser Arg Pro Gln Gln Ser Ala Pro Ala Ala Pro
145                 150                 155                 160

Ser Asn Glu Pro Pro Met Asp Phe Asp Asp Asp Ile Pro Phe
                165                 170


<210> SEQ ID NO 84
<211> LENGTH: 174
<212> TYPE: PRT
<213> ORGANISM: Citrobacter youngae

<400> SEQUENCE: 84

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Ser Ala Pro Ala Ala Pro
145                 150                 155                 160

Ser Asn Glu Pro Pro Met Asp Phe Asp Asp Asp Ile Pro Phe
                165                 170


<210> SEQ ID NO 85
<211> LENGTH: 174
<212> TYPE: PRT
<213> ORGANISM: Citrobacter werkmanii

<400> SEQUENCE: 85

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60
```

```
Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Ser Ala Pro Ala Ala Pro
145                 150                 155                 160

Ser Asn Glu Pro Ser Met Asp Phe Asp Asp Asp Ile Pro Phe
                165                 170


<210> SEQ ID NO 86
<211> LENGTH: 174
<212> TYPE: PRT
<213> ORGANISM: Citrobacter sp. MGH109

<400> SEQUENCE: 86

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Leu Gln Gln Ser Ala Pro Ala Ala Pro
145                 150                 155                 160

Ser Asn Glu Pro Pro Met Asp Phe Asp Asp Asp Ile Pro Phe
                165                 170


<210> SEQ ID NO 87
<211> LENGTH: 175
<212> TYPE: PRT
<213> ORGANISM: Unknown
<220> FEATURE:
<223> OTHER INFORMATION: Enterobacteriaceae

<400> SEQUENCE: 87

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
```

```
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Ala
145                 150                 155                 160

Pro Ser Asn Glu Pro Pro Met Asp Phe Asp Asp Asp Ile Pro Phe
                165                 170                 175


<210> SEQ ID NO 88
<211> LENGTH: 174
<212> TYPE: PRT
<213> ORGANISM: Unknown
<220> FEATURE:
<223> OTHER INFORMATION: Citrobacter

<400> SEQUENCE: 88

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gln Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Pro
145                 150                 155                 160

Ser Asn Glu Pro Pro Met Asp Phe Asp Asp Asp Ile Pro Phe
                165                 170


<210> SEQ ID NO 89
<211> LENGTH: 174
<212> TYPE: PRT
<213> ORGANISM: Unknown
<220> FEATURE:
<223> OTHER INFORMATION: Proteobacteria

<400> SEQUENCE: 89
```

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Pro
145                 150                 155                 160

Ser Asn Glu Pro Pro Met Asp Phe Asp Asp Asp Ile Pro Phe
                165                 170


<210> SEQ ID NO 90
<211> LENGTH: 155
<212> TYPE: PRT
<213> ORGANISM: Escherichia coli PA5

<400> SEQUENCE: 90

Met Pro Asn Gly Gly Ala Val Ala Asn Ile Thr Leu Ala Thr Ser Glu
1               5                   10                  15

Ser Trp Arg Asp Lys Ala Thr Gly Glu Met Lys Glu Gln Thr Glu Trp
            20                  25                  30

His Arg Val Val Leu Phe Gly Lys Leu Ala Glu Val Ala Ser Glu Tyr
        35                  40                  45

Leu Arg Lys Gly Ser Gln Val Tyr Ile Glu Gly Gln Leu Arg Thr Arg
    50                  55                  60

Lys Trp Thr Asp Gln Ser Gly Gln Asp Arg Tyr Thr Thr Glu Val Val
65                  70                  75                  80

Val Asn Val Gly Gly Thr Met Gln Met Leu Gly Gly Arg Gln Gly Gly
                85                  90                  95

Gly Ala Pro Ala Gly Gly Asn Ile Gly Gly Gly Gln Pro Gln Gly Gly
            100                 105                 110

Trp Gly Gln Pro Gln Gln Pro Gln Gly Gly Asn Gln Phe Ser Gly Gly
        115                 120                 125

Ala Gln Ser Arg Pro Gln Gln Ser Ala Pro Ala Ala Pro Ser Asn Glu
    130                 135                 140

Pro Pro Met Asp Phe Asp Asp Asp Ile Pro Phe
145                 150                 155


<210> SEQ ID NO 91
<211> LENGTH: 174
<212> TYPE: PRT
<213> ORGANISM: Enterobacter aerogenes

<400> SEQUENCE: 91
```

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Ile Val Val Asn Val Gly Gly Thr Met Gln Met
            100                 105                 110

Leu Gly Gly Arg Gln Gly Gly Gly Ala Pro Ala Ser Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ala Pro Ala Ala Pro
145                 150                 155                 160

Ser Asn Glu Pro Pro Met Asp Phe Asp Asp Asp Ile Pro Phe
                165                 170
```

<210> SEQ ID NO 92
<211> LENGTH: 176
<212> TYPE: PRT
<213> ORGANISM: Enterobacter cloacae

<400> SEQUENCE: 92

```
Met Ala Ser Lys Gly Val Asn Lys Val Ile Leu Val Gly Asn Leu Gly
1               5                   10                  15

Gln Asp Pro Glu Val Arg Tyr Leu Pro Ser Gly Gly Ala Val Cys Ser
            20                  25                  30

Val Thr Leu Ala Thr Ser Glu Ser Trp Arg Asp Lys Ala Thr Gly Glu
        35                  40                  45

Leu Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Thr Gly Gly Ser Gln Asn
        115                 120                 125

Gln Gln Gln Gly Gly Trp Gly Arg His Gln Gln Pro Gln Gly Gly Asn
    130                 135                 140

Gln Phe Ser Gly Gly Ala Gln Ser Arg Pro Gln Gln Gln Ser Ala Pro
145                 150                 155                 160

Ala Pro Ser Asn Glu Pro Pro Met Asp Leu Asp Asp Asp Ile Pro Phe
                165                 170                 175
```

<210> SEQ ID NO 93
<211> LENGTH: 174
<212> TYPE: PRT
<213> ORGANISM: Enterobacter cloacae

<400> SEQUENCE: 93

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Ala Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Ser Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Pro
145                 150                 155                 160

Ser Asn Glu Pro Pro Met Asp Phe Asp Asp Asp Ile Pro Phe
                165                 170
```

<210> SEQ ID NO 94
<211> LENGTH: 178
<212> TYPE: PRT
<213> ORGANISM: Klebsiella sp. G5

<400> SEQUENCE: 94

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Met Gly
        115                 120                 125

Gly Gly Gln Gln Gln Gly Gly Trp Gly Gln Pro Gln Gln Pro Gln Gly
    130                 135                 140

Gly Asn Gln Phe Ser Gly Gly Ala Gln Ser Arg Pro Gln Gln Gln Ser
145                 150                 155                 160

Ala Pro Ala Pro Ser Asn Glu Pro Pro Met Asp Phe Asp Asp Asp Ile
                165                 170                 175

Pro Phe
```

<210> SEQ ID NO 95
<211> LENGTH: 175
<212> TYPE: PRT
<213> ORGANISM: Klebsiella oxytoca

<400> SEQUENCE: 95

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Ser Ala Pro Ala Gly Gly Gly Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Ala Pro Ala Ala
145                 150                 155                 160

Pro Ser Asn Glu Pro Pro Met Asp Phe Asp Asp Asp Ile Pro Phe
                165                 170                 175
```

<210> SEQ ID NO 96
<211> LENGTH: 178
<212> TYPE: PRT
<213> ORGANISM: Unknown
<220> FEATURE:
<223> OTHER INFORMATION: Enterobacteriaceae

<400> SEQUENCE: 96

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Ala Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Met Gly
        115                 120                 125

Gly Gly Gln Gly Gln Gln Gly Gly Trp Gly Gln Pro Gln Gln Pro Gln
    130                 135                 140

Gly Gly Asn Gln Phe Ser Gly Gly Ala Gln Ser Arg Pro Gln Gln Ser
```

145 150 155 160

Ala Pro Ala Pro Ser Asn Glu Pro Pro Met Asp Phe Asp Asp Asp Ile
165 170 175

Pro Phe

<210> SEQ ID NO 97
<211> LENGTH: 178
<212> TYPE: PRT
<213> ORGANISM: Enterobacter lignolyticus

<400> SEQUENCE: 97

Met Ala Ser Arg Gly Val Asn Lys Val Ile Leu Val Gly Asn Leu Gly
1 5 10 15

Gln Asp Pro Glu Val Arg Tyr Met Pro Ser Gly Gly Ala Val Ala Asn
20 25 30

Ile Thr Leu Ala Thr Ser Glu Ser Trp Arg Asp Lys Gln Thr Gly Glu
35 40 45

Met Lys Glu Gln Thr Glu Trp His Arg Val Val Leu Phe Gly Lys Leu
50 55 60

Ala Glu Val Ala Gly Glu Tyr Leu Arg Lys Gly Ser Gln Val Tyr Ile
65 70 75 80

Glu Gly Gln Leu Arg Thr Arg Lys Trp Thr Asp Gln Ser Gly Gln Glu
85 90 95

Lys Tyr Thr Thr Glu Val Val Val Asn Val Gly Gly Thr Met Gln Met
100 105 110

Leu Gly Gly Arg Gln Gly Gly Gly Ala Ser Ala Gly Gly Asn Met Gly
115 120 125

Gly Gly Gln Gln Gln Gly Gly Trp Gly Gln Pro Gln Gln Pro Gln Gly
130 135 140

Gly Asn Gln Phe Ser Gly Gly Ala Gln Ser Arg Pro Gln Gln Gln Ser
145 150 155 160

Ala Pro Ala Pro Ser Asn Glu Pro Pro Met Asp Phe Asp Asp Asp Ile
165 170 175

Pro Phe

<210> SEQ ID NO 98
<211> LENGTH: 176
<212> TYPE: PRT
<213> ORGANISM: Serratia marcescens

<400> SEQUENCE: 98

Met Ala Ser Arg Gly Val Asn Lys Val Ile Leu Val Gly Asn Leu Gly
1 5 10 15

Gln Asp Pro Glu Val Arg Tyr Met Pro Asn Gly Gly Ala Val Ala Asn
20 25 30

Ile Thr Leu Ala Thr Ser Glu Ser Trp Arg Asp Lys Ala Thr Gly Glu
35 40 45

Gln Lys Glu Lys Thr Glu Trp His Arg Val Val Leu Phe Gly Lys Leu
50 55 60

Ala Glu Val Ala Gly Glu Tyr Leu Arg Lys Gly Ser Gln Val Tyr Ile
65 70 75 80

Glu Gly Ser Leu Gln Thr Arg Lys Trp Gln Asp Gln Ser Gly Gln Asp
85 90 95

Arg Tyr Thr Thr Glu Ile Val Val Asn Val Gly Gly Thr Met Gln Met
100 105 110

```
Leu Gly Gly Arg Gln Gly Gly Gly Ala Pro Ala Gly Gln Ser Ala Gly
        115                 120                 125

Gly Gln Ser Gly Trp Gly Gln Pro Gln Gln Pro Gln Gly Gly Asn Gln
    130                 135                 140

Phe Ser Gly Gly Gln Gln Gln Ser Arg Pro Ala Gln Asn Ser Ala Pro
145                 150                 155                 160

Ala Thr Ser Asn Glu Pro Pro Met Asp Phe Asp Asp Asp Ile Pro Phe
                165                 170                 175


<210> SEQ ID NO 99
<211> LENGTH: 174
<212> TYPE: PRT
<213> ORGANISM: Enterobacter cloacae complex

<400> SEQUENCE: 99

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Ser Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Pro
145                 150                 155                 160

Ser Asn Glu Pro Pro Met Asp Phe Asp Asp Asp Ile Pro Phe
                165                 170


<210> SEQ ID NO 100
<211> LENGTH: 176
<212> TYPE: PRT
<213> ORGANISM: Enterobacter cloacae complex

<400> SEQUENCE: 100

Met Ala Ser Lys Gly Val Asn Lys Val Ile Leu Val Gly Asn Leu Gly
1               5                   10                  15

Gln Asp Pro Glu Val Arg Tyr Leu Pro Ser Gly Gly Ala Val Cys Ser
            20                  25                  30

Val Thr Leu Ala Thr Ser Glu Ser Trp Arg Asp Lys Ala Thr Gly Glu
        35                  40                  45

Leu Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95
```

```
Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Ser Gln Asn
        115                 120                 125

Gln Gln Gln Gly Gly Trp Gly Gln Pro Gln Gln Pro Gln Gly Gly Asn
    130                 135                 140

Gln Phe Ser Gly Gly Ala Gln Ser Arg Pro Gln Gln Gln Ser Ala Pro
145                 150                 155                 160

Ala Pro Ser Asn Glu Pro Pro Met Asp Phe Asp Asp Asp Ile Pro Phe
                165                 170                 175


<210> SEQ ID NO 101
<211> LENGTH: 175
<212> TYPE: PRT
<213> ORGANISM: Unknown
<220> FEATURE:
<223> OTHER INFORMATION: Enterobacteriaceae

<400> SEQUENCE: 101

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Ala Pro Ala Ala
145                 150                 155                 160

Pro Ser Asn Glu Pro Pro Met Asp Phe Asp Asp Asp Ile Pro Phe
                165                 170                 175


<210> SEQ ID NO 102
<211> LENGTH: 175
<212> TYPE: PRT
<213> ORGANISM: Unknown
<220> FEATURE:
<223> OTHER INFORMATION: Enterobacteriaceae

<400> SEQUENCE: 102

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60
```

```
Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Ile Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Ala Pro Ala Ala
145                 150                 155                 160

Pro Ser Asn Glu Pro Pro Met Asp Phe Asp Asp Asp Ile Pro Phe
                165                 170                 175


<210> SEQ ID NO 103
<211> LENGTH: 176
<212> TYPE: PRT
<213> ORGANISM: Enterobacter cloacae

<400> SEQUENCE: 103

Met Ala Ser Lys Gly Val Asn Lys Val Ile Leu Val Gly Asn Leu Gly
1               5                   10                  15

Gln Asp Pro Glu Val Arg Tyr Leu Pro Ser Gly Ser Ala Val Cys Ser
            20                  25                  30

Val Thr Leu Ala Thr Ser Glu Ser Trp Arg Asp Lys Ala Thr Gly Glu
        35                  40                  45

Leu Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Ser Gln Asn
        115                 120                 125

Gln Gln Gln Gly Gly Trp Gly Gln Pro Gln Gln Pro Gln Gly Gly Asn
    130                 135                 140

Gln Phe Ser Gly Gly Ala Gln Ser Arg Pro Gln Gln Gln Ser Ala Pro
145                 150                 155                 160

Ala Pro Ser Asn Glu Pro Pro Met Asp Phe Asp Asp Asp Ile Pro Phe
                165                 170                 175


<210> SEQ ID NO 104
<211> LENGTH: 175
<212> TYPE: PRT
<213> ORGANISM: Klebsiella oxytoca

<400> SEQUENCE: 104

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45
```

```
Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gly Gly Trp Gly Gln Pro Gln Gln Pro Gln Gly Gly Asn Gln
    130                 135                 140

Tyr Ser Gly Gly Ala Gln Ser Arg Pro Gln Gln Gln Ala Pro Ala Ala
145                 150                 155                 160

Pro Ser Asn Glu Pro Pro Met Asp Phe Asp Asp Asp Ile Pro Phe
                165                 170                 175


<210> SEQ ID NO 105
<211> LENGTH: 175
<212> TYPE: PRT
<213> ORGANISM: Klebsiella oxytoca

<400> SEQUENCE: 105

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Thr Pro Ala Ala
145                 150                 155                 160

Pro Ser Asn Glu Pro Pro Met Asp Phe Asp Asp Asp Ile Pro Phe
                165                 170                 175


<210> SEQ ID NO 106
<211> LENGTH: 184
<212> TYPE: PRT
<213> ORGANISM: Unknown
<220> FEATURE:
<223> OTHER INFORMATION: Pantoea

<400> SEQUENCE: 106

Met Ala Ser Arg Gly Val Asn Lys Val Ile Leu Val Gly Asn Leu Gly
1               5                   10                  15
```

```
Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Asn Lys Glu Ile Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Gln Asp Gln Gly Gly Gln Asp
                85                  90                  95

Arg Tyr Thr Thr Glu Val Val Val Asn Val Gly Gly Thr Met Gln Met
            100                 105                 110

Leu Gly Gly Arg Gln Gln Gly Gly Ala Ser Ala Gly Gly Ala Pro Met
        115                 120                 125

Gly Gly Gly Gln Gln Ser Gly Gly Asn Asn Asn Gly Trp Gly Gln Pro
    130                 135                 140

Gln Gln Pro Gln Gly Gly Asn Gln Phe Ser Gly Gly Ala Gln Ser Arg
145                 150                 155                 160

Pro Gln Pro Gln Ser Ala Pro Ala Ser Asn Asn Asn Glu Pro Pro Met
                165                 170                 175

Asp Phe Asp Asp Asp Ile Pro Phe
            180


<210> SEQ ID NO 107
<211> LENGTH: 175
<212> TYPE: PRT
<213> ORGANISM: Klebsiella oxytoca

<400> SEQUENCE: 107

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Ala Pro Ala Ala
145                 150                 155                 160

Pro Ser Asn Glu Thr Pro Met Asp Phe Asp Asp Asp Ile Pro Phe
                165                 170                 175


<210> SEQ ID NO 108
<211> LENGTH: 176
<212> TYPE: PRT
<213> ORGANISM: Unknown
```

<220> FEATURE:
<223> OTHER INFORMATION: Enterobacteriaceae

<400> SEQUENCE: 108

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Gln Lys Glu Lys Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Ser Leu Gln Thr Arg Lys Trp Gln Asp Gln Ser Gly Gln Asp
                85                  90                  95

Arg Tyr Thr Thr Glu Ile Val Val Asn Val Gly Gly Thr Met Gln Met
            100                 105                 110

Leu Gly Gly Arg Gln Gly Gly Gly Ala Pro Ala Gly Gln Ser Ala Gly
        115                 120                 125

Gly Gln Gly Gly Trp Gly Gln Pro Gln Gln Pro Gln Ser Gly Asn Gln
    130                 135                 140

Phe Ser Gly Gly Gln Gln Gln Ser Arg Pro Ala Gln Asn Ser Ala Pro
145                 150                 155                 160

Ala Thr Ser Asn Glu Pro Pro Met Asp Phe Asp Asp Asp Ile Pro Phe
                165                 170                 175
```

<210> SEQ ID NO 109
<211> LENGTH: 174
<212> TYPE: PRT
<213> ORGANISM: Klebsiella pneumoniae

<400> SEQUENCE: 109

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys His Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ala Pro Ala Ala Pro
145                 150                 155                 160

Ser Asn Glu Pro Pro Met Asp Phe Asp Asp Asp Ile Pro Phe
                165                 170
```

<210> SEQ ID NO 110
<211> LENGTH: 171
<212> TYPE: PRT
<213> ORGANISM: Klebsiella pneumoniae

<400> SEQUENCE: 110

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gly Gly Asn Gln Phe Ser Gly Gly
    130                 135                 140

Ala Gln Ser Arg Pro Gln Gln Gln Ala Pro Ala Ala Pro Ser Asn Glu
145                 150                 155                 160

Pro Pro Met Asp Phe Asp Asp Asp Ile Pro Phe
                165                 170
```

<210> SEQ ID NO 111
<211> LENGTH: 173
<212> TYPE: PRT
<213> ORGANISM: Unknown
<220> FEATURE:
<223> OTHER INFORMATION: Enterobacteriaceae

<400> SEQUENCE: 111

```
Ala Ser Arg Gly Val Asn Lys Val Ile Leu Val Gly Asn Leu Gly Gln
1               5                   10                  15

Asp Pro Glu Val Arg Tyr Met Pro Ser Gly Gly Ala Val Ala Asn Phe
            20                  25                  30

Thr Leu Ala Thr Ser Glu Ser Trp Arg Asp Lys Gln Thr Gly Glu Met
        35                  40                  45

Lys Glu Gln Thr Glu Trp His Arg Val Val Leu Phe Gly Lys Leu Ala
    50                  55                  60

Glu Val Ala Gly Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Lys
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Gly Gly Gln Gln Gln
        115                 120                 125

Gly Gly Trp Gly Gln Pro Gln Gln Pro Gln Gly Gly Asn Gln Phe Ser
    130                 135                 140

Gly Gly Ala Gln Ser Arg Pro Gln Gln Gln Ala Pro Ala Ala Pro Ser
```

```
145                 150                 155                 160

Asn Glu Pro Pro Met Asp Phe Asp Asp Asp Ile Pro Phe
                165                 170


<210> SEQ ID NO 112
<211> LENGTH: 174
<212> TYPE: PRT
<213> ORGANISM: Klebsiella pneumoniae

<400> SEQUENCE: 112

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ala Pro Ala Ala Pro
145                 150                 155                 160

Ser Asn Glu Pro Pro Met Asp Phe Asp Asp Asp Ile Pro Phe
                165                 170


<210> SEQ ID NO 113
<211> LENGTH: 175
<212> TYPE: PRT
<213> ORGANISM: Unknown
<220> FEATURE:
<223> OTHER INFORMATION: Gammaproteobacteria

<400> SEQUENCE: 113

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gln Gln Gln
        115                 120                 125
```

```
Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Ala
145                 150                 155                 160

Pro Ser Asn Glu Pro Pro Met Asp Phe Asp Asp Asp Ile Pro Phe
                165                 170                 175


<210> SEQ ID NO 114
<211> LENGTH: 173
<212> TYPE: PRT
<213> ORGANISM: Enterobacter aerogenes

<400> SEQUENCE: 114

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Ile Val Val Asn Val Gly Gly Thr Met Gln Met
            100                 105                 110

Leu Gly Gly Arg Gln Gly Gly Gly Ala Pro Ala Gly Gly Gln Gln Gln
        115                 120                 125

Gly Gly Trp Gly Gln Pro Gln Gln Pro Gln Gly Gly Asn Gln Phe Ser
    130                 135                 140

Gly Gly Ala Gln Ser Arg Pro Gln Gln Gln Ala Pro Ala Ala Pro Ser
145                 150                 155                 160

Asn Glu Pro Pro Met Asp Phe Asp Asp Asp Ile Pro Phe
                165                 170


<210> SEQ ID NO 115
<211> LENGTH: 174
<212> TYPE: PRT
<213> ORGANISM: Enterobacter aerogenes

<400> SEQUENCE: 115

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Ile Val Val Asn Val Gly Gly Thr Met Gln Met
            100                 105                 110
```

```
Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ala Pro Ala Ala Pro
145                 150                 155                 160

Ser Asn Glu Pro Pro Met Asp Phe Asp Asp Asp Ile Pro Phe
                165                 170


<210> SEQ ID NO 116
<211> LENGTH: 177
<212> TYPE: PRT
<213> ORGANISM: Unknown
<220> FEATURE:
<223> OTHER INFORMATION: Serratia

<400> SEQUENCE: 116

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Gln Lys Glu Lys Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Ser Leu Gln Thr Arg Lys Trp Gln Asp Gln Ser Gly Gln Asp
                85                  90                  95

Arg Tyr Thr Thr Glu Ile Val Val Asn Val Gly Gly Thr Met Gln Met
            100                 105                 110

Leu Gly Gly Arg Gln Gly Gly Gly Ala Pro Ala Gly Gln Ser Ala Gly
        115                 120                 125

Gly Gln Gly Gly Trp Gly Gln Pro Gln Gln Pro Gln Gly Gly Asn Gln
    130                 135                 140

Phe Ser Gly Gly Gln Gln Gln Ser Arg Pro Ala Gln Asn Ser Ala Pro
145                 150                 155                 160

Ala Ala Ser Ser Asn Glu Pro Pro Met Asp Phe Asp Asp Asp Ile Pro
                165                 170                 175

Phe


<210> SEQ ID NO 117
<211> LENGTH: 174
<212> TYPE: PRT
<213> ORGANISM: Yokenella regensburgei

<400> SEQUENCE: 117

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
```

```
65                  70                  75                  80

Glu Gly Gln Leu Arg Thr Arg Lys Trp Thr Asp Gln Ser Gly Gln Glu
                85                  90                  95

Lys Tyr Thr Thr Glu Ile Val Val Asn Val Gly Gly Thr Met Gln Met
            100                 105                 110

Leu Gly Gly Arg Gln Gln Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ser Ala Pro Ala Pro
145                 150                 155                 160

Ser Asn Glu Pro Pro Met Asp Phe Asp Asp Asp Ile Pro Phe
                165                 170


<210> SEQ ID NO 118
<211> LENGTH: 178
<212> TYPE: PRT
<213> ORGANISM: Raoultella terrigena

<400> SEQUENCE: 118

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Ala Glu
                85                  90                  95

Lys Tyr Thr Thr Glu Ile Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gln Gln Pro Gln Gly
    130                 135                 140

Gly Asn Gln Phe Ser Gly Gly Ala Gln Ser Arg Pro Gln Gln Gln Ala
145                 150                 155                 160

Pro Ala Ala Pro Ser Asn Glu Pro Pro Met Asp Phe Asp Asp Asp Ile
                165                 170                 175

Pro Phe


<210> SEQ ID NO 119
<211> LENGTH: 174
<212> TYPE: PRT
<213> ORGANISM: Klebsiella pneumoniae

<400> SEQUENCE: 119

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45
```

```
Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ala Pro Ser Ala Pro
145                 150                 155                 160

Ser Asn Glu Pro Pro Met Asp Phe Asp Asp Asp Ile Pro Phe
                165                 170


<210> SEQ ID NO 120
<211> LENGTH: 181
<212> TYPE: PRT
<213> ORGANISM: Unknown
<220> FEATURE:
<223> OTHER INFORMATION: Yersinia

<400> SEQUENCE: 120

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Gln Lys Glu Lys Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Ala Leu Gln Thr Arg Lys Trp Gln Asp Gln Ser Gly Gln Glu
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Ser Gln Gln
        115                 120                 125

Asp Gly Gly Ala Gln Gly Gly Trp Gly Gln Pro Gln Gln Pro Gln Gly
    130                 135                 140

Gly Asn Gln Phe Ser Gly Gly Gln Thr Ser Arg Pro Ala Gln Ser Ala
145                 150                 155                 160

Pro Ala Ala Gln Pro Gln Gly Gly Asn Glu Pro Pro Met Asp Phe Asp
                165                 170                 175

Asp Asp Ile Pro Phe
            180


<210> SEQ ID NO 121
<211> LENGTH: 174
<212> TYPE: PRT
<213> ORGANISM: Klebsiella pneumoniae

<400> SEQUENCE: 121
```

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Phe Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Lys Tyr Thr Thr Glu Val Val Val Asn Val Ser Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Gln Ala Pro Ala Ala Pro
145                 150                 155                 160

Ser Asn Glu Pro Pro Met Asp Phe Asp Asp Asp Ile Pro Phe
                165                 170
```

<210> SEQ ID NO 122
<211> LENGTH: 180
<212> TYPE: PRT
<213> ORGANISM: Cronobacter condimenti

<400> SEQUENCE: 122

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Leu Arg Leu Ala Thr Ser Glu Ser Trp Arg Asp Lys Gln Thr Gly Glu
        35                  40                  45

Met Lys Glu Val Thr Glu Trp His Ser Val Val Leu Tyr Gly Lys Leu
    50                  55                  60

Ala Glu Val Ala Gly Glu Tyr Leu Arg Lys Gly Ser Gln Ile Tyr Ile
65                  70                  75                  80

Glu Gly Gln Leu Arg Thr Arg Lys Trp Gln Asp Gln Ser Gly Gln Asp
                85                  90                  95

Arg Tyr Ser Thr Glu Val Val Val Asn Val Gly Gly Thr Met Gln Met
            100                 105                 110

Leu Gly Gly Arg Gln Gly Gly Gly Ala Pro Ala Gly Gly Asn Met Gly
        115                 120                 125

Gly Gly Gln Gln Gln Gly Gly Trp Gly Gln Pro Gln Gln Pro Gln Gln
    130                 135                 140

Gln Ser Gly Gly Ala Gln Phe Ser Gly Gly Ala Gln Ser Arg Pro Gln
145                 150                 155                 160

Gln Gln Ala Pro Ala Pro Ser Asn Glu Pro Pro Met Asp Phe Asp Asp
                165                 170                 175

Asp Ile Pro Phe
            180
```

<210> SEQ ID NO 123

<211> LENGTH: 174
<212> TYPE: PRT
<213> ORGANISM: Klebsiella sp. 10982

<400> SEQUENCE: 123

Met Ala Ser Arg Gly Val Asn Lys Val Ile Leu Val Gly Asn Leu Gly
1 5 10 15

Gln Asp Pro Glu Val Arg Tyr Met Pro Ser Gly Gly Ala Val Ala Asn
20 25 30

Phe Thr Leu Ala Thr Ser Glu Ser Trp Arg Asp Lys Gln Thr Gly Glu
35 40 45

Met Lys Glu Gln Thr Glu Trp His Arg Val Val Leu Phe Gly Lys Leu
50 55 60

Ala Glu Val Ala Gly Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Lys Tyr Thr Thr Glu Val Val Val Asn Val Gly Gly Thr Met Gln Met
100 105 110

Leu Gly Gly Arg Gln Gly Gly Gly Ala Pro Ala Gly Gly Gly Gln Gln
115 120 125

Gln Gly Gly Trp Gly Gln Pro Gln Gln Pro Gln Gly Gly Ser Gln Phe
130 135 140

Ser Gly Gly Ala Gln Ser Arg Pro Gln Gln Gln Ala Pro Ala Ala Pro
145 150 155 160

Ser Asn Glu Pro Pro Met Asp Phe Asp Asp Asp Ile Pro Phe
165 170

<210> SEQ ID NO 124
<211> LENGTH: 458
<212> TYPE: PRT
<213> ORGANISM: Klebsiella pneumoniae

<400> SEQUENCE: 124

Met Ala Ser Arg Gly Val Asn Lys Val Ile Leu Val Gly Asn Leu Gly
1 5 10 15

Gln Asp Pro Glu Val Arg Tyr Met Pro Ser Gly Gly Ala Val Ala Asn
20 25 30

Phe Thr Leu Ala Thr Ser Glu Ser Trp Arg Asp Lys Gln Thr Gly Glu
35 40 45

Met Lys Glu Gln Thr Glu Trp His Arg Val Val Leu Phe Gly Lys Leu
50 55 60

Ala Glu Val Ala Gly Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Lys Tyr Thr Thr Glu Val Val Val Asn Val Gly Gly Thr Met Gln Met
100 105 110

Leu Gly Gly Arg Gln Gly Gly Gly Ala Pro Ala Gly Gly Gly Gln Gln
115 120 125

Gln Gly Gly Trp Gly Gln Pro Gln Gln Pro Gln Gly Gly Asn Gln Phe
130 135 140

Ser Gly Gly Ala Gln Ser Arg Pro Gln Gln Gln Ala Pro Ala Ala Pro
145 150 155 160

Ser Asn Glu Thr Pro Met Asp Phe Asp Asp Asp Ile Pro Phe Met Ala
165 170 175

```
Ser Arg Gly Val Asn Lys Val Ile Leu Val Gly Asn Leu Gly Gln Asp
            180                 185                 190

Pro Glu Val Arg Tyr Met Pro Ser Gly Gly Ala Val Ala Asn Phe Thr
        195                 200                 205

Leu Ala Thr Ser Glu Ser Trp Arg Asp Lys Gln Thr Gly Glu Met Lys
    210                 215                 220

Glu Gln Thr Glu Trp His Arg Val Val Leu Phe Gly Lys Leu Ala Glu
225                 230                 235                 240

Val Ala Gly Glu Tyr Leu Arg Lys Gly Ser Gln Val Tyr Ile Glu Gly
                245                 250                 255

Gln Leu Arg Thr Arg Lys Trp Thr Asp Gln Ser Gly Gln Asp Lys Tyr
            260                 265                 270

Thr Thr Glu Val Val Val Asn Val Gly Gly Thr Met Gln Met Leu Gly
        275                 280                 285

Gly Arg Gln Gly Gly Gly Ala Pro Ala Gly Gly Gly Gln Gln Gln Gly
    290                 295                 300

Gly Trp Gly Gln Pro Gln Gln Pro Gln Gly Gly Asn Gln Phe Ser Gly
305                 310                 315                 320

Gly Ala Gln Ser Arg Pro Gln Gln Gln Ala Pro Ala Ala Pro Ser Asn
                325                 330                 335

Glu Thr Pro Met Asp Phe Asp Asp Asp Ile Pro Phe Ala Glu Val Ala
            340                 345                 350

Gly Glu Tyr Leu Arg Lys Gly Ser Gln Val Tyr Ile Glu Gly Gln Leu
        355                 360                 365

Arg Thr Arg Lys Trp Thr Asp Gln Ser Gly Gln Asp Lys Tyr Thr Thr
    370                 375                 380

Glu Val Val Val Asn Val Gly Gly Thr Met Gln Met Leu Gly Gly Arg
385                 390                 395                 400

Gln Gly Gly Gly Ala Pro Ala Gly Gly Gly Gln Gln Gln Gly Gly Trp
                405                 410                 415

Gly Gln Pro Gln Gln Pro Gln Gly Gly Asn Gln Phe Ser Gly Gly Ala
            420                 425                 430

Gln Ser Arg Pro Gln Gln Gln Ala Pro Ala Ala Pro Ser Asn Glu Thr
        435                 440                 445

Pro Met Asp Phe Asp Asp Asp Ile Pro Phe
    450                 455


<210> SEQ ID NO 125
<211> LENGTH: 176
<212> TYPE: PRT
<213> ORGANISM: Trabulsiella guamensis

<400> SEQUENCE: 125

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
```

```
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gln Gly Gly Trp Gly Gln Pro Gln Gln Pro Gln Gly Gly Ala
    130                 135                 140

Gln Phe Ser Gly Gly Ala Gln Ser Arg Pro Gln Gln Gln Ser Ala Pro
145                 150                 155                 160

Ala Pro Ser Asn Glu Pro Pro Met Asp Phe Asp Asp Asp Ile Pro Phe
                165                 170                 175


<210> SEQ ID NO 126
<211> LENGTH: 176
<212> TYPE: PRT
<213> ORGANISM: Enterobacter cloacae

<400> SEQUENCE: 126

Met Ala Ser Lys Gly Val Asn Lys Val Ile Leu Val Gly Asn Leu Gly
1               5                   10                  15

Gln Asp Pro Glu Val Arg Tyr Leu Pro Ser Gly Gly Ala Val Cys Ser
            20                  25                  30

Val Thr Leu Ala Thr Ser Glu Ser Trp Arg Asp Lys Ala Thr Gly Glu
        35                  40                  45

Leu Lys Glu Gln Thr Glu Trp His Arg Ile Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Ser
        115                 120                 125

Gln Gln His Gly Gly Trp Gly Gln Tyr Gln His Pro Gln Val Gly Asn
    130                 135                 140

Gln Phe Ser Gly Gly Ala Gln Ser Arg Pro Gln Gln Gln Ser Ala Pro
145                 150                 155                 160

Ala Pro Ser Asn Glu Pro Pro Met Asp Phe Asp Asp Asp Ile Pro Phe
                165                 170                 175


<210> SEQ ID NO 127
<211> LENGTH: 177
<212> TYPE: PRT
<213> ORGANISM: Trabulsiella odontotermitis

<400> SEQUENCE: 127

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
```

```
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Pro Gln Gln Gln Gly Gly Trp Gly Gln Pro Gln Gln Pro Gln Gly Gly
    130                 135                 140

Ala Gln Phe Ser Gly Gly Ala Gln Ser Arg Pro Gln Gln Gln Ser Ala
145                 150                 155                 160

Pro Ala Pro Ser Asn Glu Pro Pro Met Asp Phe Asp Asp Asp Ile Pro
                165                 170                 175

Phe


<210> SEQ ID NO 128
<211> LENGTH: 177
<212> TYPE: PRT
<213> ORGANISM: Trabulsiella odontotermitis

<400> SEQUENCE: 128

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Val Glu
                85                  90                  95

Lys Tyr Thr Thr Glu Val Val Val Asn Val Gly Gly Thr Met Gln Met
            100                 105                 110

Leu Gly Gly Arg Gln Gln Gly Ala Gly Ala Pro Ala Gly Gly Gly Gln
        115                 120                 125

Gln Gln Gly Gly Trp Gly Gln Pro Gln Gln Pro Gln Gln Gln Gly Gly
    130                 135                 140

Ala Gln Phe Ser Gly Gly Ala Gln Ser Arg Pro Gln Gln Gln Ser Ala
145                 150                 155                 160

Pro Ala Pro Ser Asn Glu Pro Pro Met Asp Phe Asp Asp Asp Ile Pro
                165                 170                 175

Phe


<210> SEQ ID NO 129
<211> LENGTH: 174
<212> TYPE: PRT
<213> ORGANISM: Kosakonia radicincitans

<400> SEQUENCE: 129

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30
```

```
Ile Thr Leu Ala Thr Ser Glu Ser Trp Arg Asp Lys Gln Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gly Gly Trp Gly Gln Pro Gln Gln Pro Gln Gly Gly Asn Gln Phe
    130                 135                 140

Ser Gly Gly Ala Gln Ser Arg Pro Gln Gln Ser Ser Ala Pro Ala Pro
145                 150                 155                 160

Ser Asn Glu Pro Pro Met Asp Phe Asp Asp Asp Ile Pro Phe
                165                 170
```

<210> SEQ ID NO 130
<211> LENGTH: 177
<212> TYPE: PRT
<213> ORGANISM: Serratia marcescens

<400> SEQUENCE: 130

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Gln Lys Glu Lys Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Ser Leu Gln Thr Arg Lys Trp Thr Asp Gln Ala Gly Val Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gln Ser Ala Gly
        115                 120                 125

Gly Gln Gly Gly Trp Gly Gln Pro Gln Gln Pro Gln Gly Gly Asn Gln
    130                 135                 140

Phe Ser Gly Gly Gln Gln Ser Arg Pro Ala Gln Asn Ser Ala Pro
145                 150                 155                 160

Ala Ala Ser Ser Asn Glu Pro Pro Met Asp Phe Asp Asp Asp Ile Pro
                165                 170                 175

Phe
```

<210> SEQ ID NO 131
<211> LENGTH: 175
<212> TYPE: PRT
<213> ORGANISM: Unknown
<220> FEATURE:
<223> OTHER INFORMATION: Kluyvera

<400> SEQUENCE: 131

```
Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Ala Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Gly Gln Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Ser Ala Pro Ala
145                 150                 155                 160

Pro Ser Asn Glu Pro Pro Met Asp Phe Asp Asp Asp Ile Pro Phe
                165                 170                 175


<210> SEQ ID NO 132
<211> LENGTH: 175
<212> TYPE: PRT
<213> ORGANISM: Enterobacter asburiae

<400> SEQUENCE: 132

Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Ala Glu
                85                  90                  95

Lys Tyr Thr Thr Glu Val Val Val Asn Val Gly Gly Thr Met Gln Met
            100                 105                 110

Leu Gly Gly Arg Gln Gly Gly Gly Thr Pro Ala Gly Gly Gly Gln Gln
        115                 120                 125

Gln Gln Gly Gly Trp Gly Gln Pro Gln Gln Pro Gln Gly Gly Asn Gln
    130                 135                 140

Phe Ser Gly Gly Ala Gln Ser Arg Pro Gln Gln Gln Ser Ala Pro Ala
145                 150                 155                 160

Pro Ser Asn Glu Pro Pro Met Asp Phe Asp Asp Asp Ile Pro Phe
                165                 170                 175


<210> SEQ ID NO 133
<211> LENGTH: 193
<212> TYPE: PRT
```

```
<213> ORGANISM: Artificial Sequence
<220> FEATURE:
<223> OTHER INFORMATION: c2 NLS-SSB fusion protein

<400> SEQUENCE: 133

Met Gln Pro Ser Leu Lys Arg Met Lys Ile Gln Pro Ser Ser Gln Pro
1               5                   10                  15

Ala Ser Arg Gly Val Asn Lys Val Ile Leu Val Gly Asn Leu Gly Gln
            20                  25                  30

Asp Pro Glu Val Arg Tyr Met Pro Asn Gly Gly Ala Val Ala Asn Ile
        35                  40                  45

Thr Leu Ala Thr Ser Glu Ser Trp Arg Asp Lys Ala Thr Gly Glu Met
    50                  55                  60

Lys Glu Gln Thr Glu Trp His Arg Val Val Leu Phe Gly Lys Leu Ala
65                  70                  75                  80

Glu Val Ala Ser Glu Tyr Leu Arg Lys Gly Ser Gln Val Tyr Ile Glu
                85                  90                  95

Gly Gln Leu Arg Thr Arg Lys Trp Thr Asp Gln Ser Gly Gln Asp Arg
            100                 105                 110

Tyr Thr Thr Glu Val Val Val Asn Val Gly Gly Thr Met Gln Met Leu
        115                 120                 125

Gly Gly Arg Gln Gly Gly Gly Ala Pro Ala Gly Gly Asn Ile Gly Gly
    130                 135                 140

Gly Gln Pro Gln Gly Gly Trp Gly Gln Pro Gln Gln Pro Gln Gly Gly
145                 150                 155                 160

Asn Gln Phe Ser Gly Gly Ala Gln Ser Arg Pro Gln Gln Ser Ala Pro
                165                 170                 175

Ala Ala Pro Ser Asn Glu Pro Pro Met Asp Phe Asp Asp Asp Ile Pro
            180                 185                 190

Phe


<210> SEQ ID NO 134
<211> LENGTH: 277
<212> TYPE: PRT
<213> ORGANISM: Artificial Sequence
<220> FEATURE:
<223> OTHER INFORMATION: c2 NLS-Bacteriophage Lambda Red beta SSAP-
      fusion protein

<400> SEQUENCE: 134

Met Gln Pro Ser Leu Lys Arg Met Lys Ile Gln Pro Ser Ser Gln Pro
1               5                   10                  15

Met Ser Thr Ala Leu Ala Thr Leu Ala Gly Lys Leu Ala Glu Arg Val
            20                  25                  30

Gly Met Asp Ser Val Asp Pro Gln Glu Leu Ile Thr Thr Leu Arg Gln
        35                  40                  45

Thr Ala Phe Lys Gly Asp Ala Ser Asp Ala Gln Phe Ile Ala Leu Leu
    50                  55                  60

Ile Val Ala Asn Gln Tyr Gly Leu Asn Pro Trp Thr Lys Glu Ile Tyr
65                  70                  75                  80

Ala Phe Pro Asp Lys Gln Asn Gly Ile Val Pro Val Val Gly Val Asp
                85                  90                  95

Gly Trp Ser Arg Ile Ile Asn Glu Asn Gln Gln Phe Asp Gly Met Asp
            100                 105                 110

Phe Glu Gln Asp Asn Glu Ser Cys Thr Cys Arg Ile Tyr Arg Lys Asp
        115                 120                 125
```

```
Arg Asn His Pro Ile Cys Val Thr Glu Trp Met Asp Glu Cys Arg Arg
    130                 135                 140

Glu Pro Phe Lys Thr Arg Glu Gly Arg Glu Ile Thr Gly Pro Trp Gln
145                 150                 155                 160

Ser His Pro Lys Arg Met Leu Arg His Lys Ala Met Ile Gln Cys Ala
                165                 170                 175

Arg Leu Ala Phe Gly Phe Ala Gly Ile Tyr Asp Lys Asp Glu Ala Glu
            180                 185                 190

Arg Ile Val Glu Asn Thr Ala Tyr Thr Ala Glu Arg Gln Pro Glu Arg
        195                 200                 205

Asp Ile Thr Pro Val Asn Asp Glu Thr Met Gln Glu Ile Asn Thr Leu
    210                 215                 220

Leu Ile Ala Leu Asp Lys Thr Trp Asp Asp Asp Leu Leu Pro Leu Cys
225                 230                 235                 240

Ser Gln Ile Phe Arg Arg Asp Ile Arg Ala Ser Ser Glu Leu Thr Gln
                245                 250                 255

Ala Glu Ala Val Lys Ala Leu Gly Phe Leu Lys Gln Lys Ala Ala Glu
            260                 265                 270

Gln Lys Val Ala Ala
        275


<210> SEQ ID NO 135
<211> LENGTH: 241
<212> TYPE: PRT
<213> ORGANISM: Artificial Sequence
<220> FEATURE:
<223> OTHER INFORMATION: c2 NLS-Bacteriophage Lambda Red Exonuclease-
      fusion protein

<400> SEQUENCE: 135

Met Gln Pro Ser Leu Lys Arg Met Lys Ile Gln Pro Ser Ser Gln Pro
1               5                   10                  15

Thr Pro Asp Ile Ile Leu Gln Arg Thr Gly Ile Asp Val Arg Ala Val
            20                  25                  30

Glu Gln Gly Asp Asp Ala Trp His Lys Leu Arg Leu Gly Val Ile Thr
        35                  40                  45

Ala Ser Glu Val His Asn Val Ile Ala Lys Pro Arg Ser Gly Lys Lys
    50                  55                  60

Trp Pro Asp Met Lys Met Ser Tyr Phe His Thr Leu Leu Ala Glu Val
65                  70                  75                  80

Cys Thr Gly Val Ala Pro Glu Val Asn Ala Lys Ala Leu Ala Trp Gly
                85                  90                  95

Lys Gln Tyr Glu Asn Asp Ala Arg Thr Leu Phe Glu Phe Thr Ser Gly
            100                 105                 110

Val Asn Val Thr Glu Ser Pro Ile Ile Tyr Arg Asp Glu Ser Met Arg
        115                 120                 125

Thr Ala Cys Ser Pro Asp Gly Leu Cys Ser Asp Gly Asn Gly Leu Glu
    130                 135                 140

Leu Lys Cys Pro Phe Thr Ser Arg Asp Phe Met Lys Phe Arg Leu Gly
145                 150                 155                 160

Gly Phe Glu Ala Ile Lys Ser Ala Tyr Met Ala Gln Val Gln Tyr Ser
                165                 170                 175

Met Trp Val Thr Arg Lys Asn Ala Trp Tyr Phe Ala Asn Tyr Asp Pro
            180                 185                 190

Arg Met Lys Arg Glu Gly Leu His Tyr Val Val Ile Glu Arg Asp Glu
        195                 200                 205
```

```
Lys Tyr Met Ala Ser Phe Asp Glu Ile Val Pro Glu Phe Ile Glu Lys
    210                 215                 220

Met Asp Glu Ala Leu Ala Glu Ile Gly Phe Val Phe Gly Glu Gln Trp
225                 230                 235                 240

Arg


<210> SEQ ID NO 136
<211> LENGTH: 692
<212> TYPE: PRT
<213> ORGANISM: Homo sapiens

<400> SEQUENCE: 136

Met Ser Ser Phe Glu Gly Gln Met Ala Glu Tyr Pro Thr Ile Ser Ile
1               5                   10                  15

Asp Arg Phe Asp Arg Glu Asn Leu Arg Ala Arg Ala Tyr Phe Leu Ser
            20                  25                  30

His Cys His Lys Asp His Met Lys Gly Leu Arg Ala Pro Thr Leu Lys
        35                  40                  45

Arg Arg Leu Glu Cys Ser Leu Lys Val Tyr Leu Tyr Cys Ser Pro Val
    50                  55                  60

Thr Lys Glu Leu Leu Leu Thr Ser Pro Lys Tyr Arg Phe Trp Lys Lys
65                  70                  75                  80

Arg Ile Ile Ser Ile Glu Ile Glu Thr Pro Thr Gln Ile Ser Leu Val
                85                  90                  95

Asp Glu Ala Ser Gly Glu Lys Glu Glu Ile Val Val Thr Leu Leu Pro
            100                 105                 110

Ala Gly His Cys Pro Gly Ser Val Met Phe Leu Phe Gln Gly Asn Asn
        115                 120                 125

Gly Thr Val Leu Tyr Thr Gly Asp Phe Arg Leu Ala Gln Gly Glu Ala
    130                 135                 140

Ala Arg Met Glu Leu Leu His Ser Gly Gly Arg Val Lys Asp Ile Gln
145                 150                 155                 160

Ser Val Tyr Leu Asp Thr Thr Phe Cys Asp Pro Arg Phe Tyr Gln Ile
                165                 170                 175

Pro Ser Arg Glu Glu Cys Leu Ser Gly Val Leu Glu Leu Val Arg Ser
            180                 185                 190

Trp Ile Thr Arg Ser Pro Tyr His Val Val Trp Leu Asn Cys Lys Ala
        195                 200                 205

Ala Tyr Gly Tyr Glu Tyr Leu Phe Thr Asn Leu Ser Glu Glu Leu Gly
    210                 215                 220

Val Gln Val His Val Asn Lys Leu Asp Met Phe Arg Asn Met Pro Glu
225                 230                 235                 240

Ile Leu His His Leu Thr Thr Asp Arg Asn Thr Gln Ile His Ala Cys
                245                 250                 255

Arg His Pro Lys Ala Glu Glu Tyr Phe Gln Trp Ser Lys Leu Pro Cys
            260                 265                 270

Gly Ile Thr Ser Arg Asn Arg Ile Pro Leu His Ile Ile Ser Ile Lys
        275                 280                 285

Pro Ser Thr Met Trp Phe Gly Glu Arg Ser Arg Lys Thr Asn Val Ile
    290                 295                 300

Val Arg Thr Gly Glu Ser Ser Tyr Arg Ala Cys Phe Ser Phe His Ser
305                 310                 315                 320

Ser Tyr Ser Glu Ile Lys Asp Phe Leu Ser Tyr Leu Cys Pro Val Asn
                325                 330                 335
```

```
Ala Tyr Pro Asn Val Ile Pro Val Gly Thr Thr Met Asp Lys Val Val
            340                 345                 350

Glu Ile Leu Lys Pro Leu Cys Arg Ser Ser Gln Ser Thr Glu Pro Lys
        355                 360                 365

Tyr Lys Pro Leu Gly Lys Leu Lys Arg Ala Arg Thr Val His Arg Asp
    370                 375                 380

Ser Glu Glu Glu Asp Asp Tyr Leu Phe Asp Asp Pro Leu Pro Ile Pro
385                 390                 395                 400

Leu Arg His Lys Val Pro Tyr Pro Glu Thr Phe His Pro Glu Val Phe
                405                 410                 415

Ser Met Thr Ala Val Ser Glu Lys Gln Pro Glu Lys Leu Arg Gln Thr
            420                 425                 430

Pro Gly Cys Cys Arg Ala Glu Cys Met Gln Ser Ser Arg Phe Thr Asn
        435                 440                 445

Phe Val Asp Cys Glu Glu Ser Asn Ser Glu Ser Glu Glu Glu Val Gly
    450                 455                 460

Ile Pro Ala Ser Leu Gln Gly Asp Leu Gly Ser Val Leu His Leu Gln
465                 470                 475                 480

Lys Ala Asp Gly Asp Val Pro Gln Trp Glu Val Phe Phe Lys Arg Asn
                485                 490                 495

Asp Glu Ile Thr Asp Glu Ser Leu Glu Asn Phe Pro Ser Ser Thr Val
            500                 505                 510

Ala Gly Gly Ser Gln Ser Pro Lys Leu Phe Ser Asp Ser Asp Gly Glu
        515                 520                 525

Ser Thr His Ile Ser Ser Gln Asn Ser Ser Gln Ser Thr His Ile Thr
    530                 535                 540

Glu Gln Gly Ser Gln Gly Trp Asp Ser Gln Ser Asp Thr Val Leu Leu
545                 550                 555                 560

Ser Ser Gln Glu Arg Asn Ser Gly Asp Ile Thr Ser Leu Asp Lys Ala
                565                 570                 575

Asp Tyr Arg Pro Thr Ile Lys Glu Asn Ile Pro Ala Ser Leu Met Glu
            580                 585                 590

Gln Asn Val Ile Cys Pro Lys Asp Thr Tyr Ser Asp Leu Lys Ser Arg
        595                 600                 605

Asp Lys Asp Val Thr Ile Val Pro Ser Thr Gly Glu Pro Thr Thr Leu
    610                 615                 620

Ser Ser Glu Thr His Ile Pro Glu Glu Lys Ser Leu Leu Asn Leu Ser
625                 630                 635                 640

Thr Asn Ala Asp Ser Gln Ser Ser Ser Asp Phe Glu Val Pro Ser Thr
                645                 650                 655

Pro Glu Ala Glu Leu Pro Lys Arg Glu His Leu Gln Tyr Leu Tyr Glu
            660                 665                 670

Lys Leu Ala Thr Gly Glu Ser Ile Ala Val Lys Lys Arg Lys Cys Ser
        675                 680                 685

Leu Leu Asp Thr
    690


<210> SEQ ID NO 137
<211> LENGTH: 708
<212> TYPE: PRT
<213> ORGANISM: Actinidia chinensis var. chinensis

<400> SEQUENCE: 137

Met Gly Ile Gln Gly Leu Leu Pro Leu Leu Lys Ser Ile Met Val Pro
```

```
1               5                   10                  15

Ile His Ile Lys Asp Leu Glu Asp Cys Cys Val Ala Ile Asp Thr Tyr
            20                  25                  30

Ser Trp Leu His Lys Gly Ala Leu Ser Cys Ser Lys Asp Leu Cys Lys
        35                  40                  45

Gly Gln Ser Thr Ser Lys His Ile Asp Tyr Cys Met Asn Arg Val Asn
    50                  55                  60

Leu Leu Gln His Tyr Gly Ile Arg Pro Ile Leu Val Phe Asp Gly Gly
65                  70                  75                  80

Pro Leu Pro Met Lys Ser Glu Gln Glu Ser Lys Arg Ala Arg Ser Arg
                85                  90                  95

Lys Glu Asn Leu Ala Cys Ala Ile Glu Asn Glu Ser Asn Gly Asn Asn
            100                 105                 110

Ala Ser Ala Tyr Lys Cys Tyr Gln Lys Ala Val Val Ile Ser Pro Ser
        115                 120                 125

Val Ala Tyr Glu Leu Ile Gln Val Leu Lys Lys Glu Asn Val Tyr Tyr
    130                 135                 140

Val Val Ala Pro Tyr Glu Ala Asp Ala Gln Met Thr Phe Leu Ala Val
145                 150                 155                 160

Ser Lys Gln Val Asp Ala Val Ile Thr Glu Asp Ser Asp Leu Ile Ala
                165                 170                 175

Phe Gly Cys Pro Arg Ile Ile Tyr Lys Met Asp Lys Leu Glu Gln Gly
            180                 185                 190

Val Glu Phe Arg Tyr Ser Met Leu Gln Gln Asn Lys Glu Leu Asn Phe
        195                 200                 205

Thr Gly Phe Thr Lys Arg Met Leu Leu Glu Met Cys Ile Leu Ser Gly
    210                 215                 220

Cys Asp Tyr Leu Gln Ser Leu Pro Gly Ile Gly Leu Lys Lys Ala His
225                 230                 235                 240

Ala Leu Val Lys Lys Phe Lys Ser Tyr Asp Lys Val Ile Lys His Leu
                245                 250                 255

Lys Tyr Ser Thr Ala Ser Val Ser Ser Ser Tyr Glu Glu Ser Phe Arg
            260                 265                 270

Lys Ala Ile Met Thr Phe Gln His Gln Arg Val Tyr Asp Pro Thr Ile
        275                 280                 285

Glu Asp Ile Val His Leu Ser Asp Leu Pro Gln Tyr Val Gly Asp Asp
    290                 295                 300

Leu Asp Phe Leu Gly Pro Ala Ile Leu Gln His Ile Ala Lys Gly Ile
305                 310                 315                 320

Ala Arg Gly Asp Leu Asp Pro Phe Thr Lys Met Pro Ile Gln Gly Val
                325                 330                 335

Asn Asn Gly Ala Gly Leu Val Asp Glu Gly Met Tyr Lys Leu Asn Asn
            340                 345                 350

Phe Lys Ser Glu Gly Phe Ala Ser Leu Glu Ala Lys Arg Arg Phe Met
        355                 360                 365

Ala Pro Arg Ser Thr Pro Lys His Arg Asn Pro Ile Thr Glu Thr Cys
    370                 375                 380

Ser Thr Val Glu His Ile Thr Glu Asp Ala Asp Ala Cys Lys Thr Asn
385                 390                 395                 400

Cys Ser Leu Glu Ser Leu Leu Asp Ser Arg Tyr Phe Asp Val Ala Ser
                405                 410                 415

Pro Ser Glu Gly Tyr Val Lys His Gly Val Ala Ala Lys Ser Pro Glu
            420                 425                 430
```

```
Ser Lys Ser Pro Ser His Gly Ser His Asp Lys Glu Glu Ile Leu Gly
        435                 440                 445

Glu Gly Asp Asn Arg Ser Pro Gln Asp Pro Leu Leu Gln Gln Phe Lys
    450                 455                 460

His Ser Ile Pro Lys Leu Cys Met Thr Leu Gln Lys Glu Arg Ala Lys
465                 470                 475                 480

Ser Val Ala Asp Ser Gly Gln Asp Lys Thr Arg Lys Glu Asn Thr Lys
                485                 490                 495

Val Ile Val Arg Ser Ser Tyr Phe Gln His Lys Leu Val Lys Glu Asn
            500                 505                 510

Asp Lys Glu Asn Ile Lys Glu Asp Val Thr Thr Asp Lys Gly Glu Asn
        515                 520                 525

Ile Asn Pro Lys Arg Glu His Lys Ser Ala Ser Asp Gly Gly Glu Ala
    530                 535                 540

Lys Thr Arg Ile Lys Asn Arg Lys Thr Ile Val Arg Ser Ser Tyr Phe
545                 550                 555                 560

Leu His Lys Ser Val Asn Glu Asn Asp Gln Asp Asn Arg His Glu Lys
                565                 570                 575

Leu Ile Ile Asn Asp Asp Phe Thr Thr His Thr His Glu Asn Gly Ile
            580                 585                 590

Pro Glu Ser Ala Ser Gly Asp Gly Tyr Phe Asn Asn Ser Ile Val Lys
        595                 600                 605

Arg Lys Val Ser Pro Val Asp Ser Val Gln Met Glu Lys Thr Asn Tyr
    610                 615                 620

Lys Cys Met Arg Met Asp Ala Ser Leu Pro Ile Glu Ser Ser Ser Ile
625                 630                 635                 640

Ser Thr Leu Asn Asn Thr Thr Met Glu Thr Lys Ala Glu Gly Gly Lys
                645                 650                 655

Phe Gly Ser Asn Ile Ser His Leu Lys Asn Tyr Ser Asp Ile Ala Glu
            660                 665                 670

Lys Ser Ile Glu Arg Phe Val Ser Val Ile Ser Ser Phe Lys Cys Ser
        675                 680                 685

Ser Ser Gly Ser Ser Ala Ser Gly Leu Arg Ala Pro Leu Arg Asn Thr
    690                 695                 700

Glu His Met Tyr
705


<210> SEQ ID NO 138
<211> LENGTH: 1062
<212> TYPE: PRT
<213> ORGANISM: Mus musculus

<400> SEQUENCE: 138

Met Glu Pro Leu Asp Glu Leu Asp Leu Leu Leu Leu Glu Glu Asp Gly
1               5                   10                  15

Gly Ala Glu Ala Val Pro Arg Val Glu Leu Leu Arg Lys Lys Ala Asp
            20                  25                  30

Ala Leu Phe Pro Glu Thr Val Leu Ser Arg Gly Val Asp Asn Arg Tyr
        35                  40                  45

Leu Val Leu Ala Val Glu Thr Ser Gln Asn Glu Arg Gly Ala Glu Glu
    50                  55                  60

Lys Arg Leu His Val Thr Ala Ser Gln Asp Arg Glu His Glu Val Leu
65                  70                  75                  80

Cys Ile Leu Arg Asn Gly Trp Ser Ser Val Pro Val Glu Pro Gly Asp
```

```
                85                  90                  95

Ile Val His Leu Glu Gly Asp Cys Thr Ser Glu Pro Trp Ile Ile Asp
            100                 105                 110

Asp Asp Phe Gly Tyr Phe Ile Leu Tyr Pro Asp Met Met Ile Ser Gly
        115                 120                 125

Thr Ser Val Ala Ser Ser Ile Arg Cys Leu Arg Arg Ala Val Leu Ser
    130                 135                 140

Glu Thr Phe Arg Gly Ser Asp Pro Ala Thr Arg Gln Met Leu Ile Gly
145                 150                 155                 160

Thr Ile Leu His Glu Val Phe Gln Lys Ala Ile Ser Glu Ser Phe Ala
                165                 170                 175

Pro Glu Arg Leu Gln Glu Leu Ala Leu Gln Thr Leu Arg Glu Val Arg
            180                 185                 190

His Leu Lys Glu Met Tyr Arg Leu Asn Leu Ser Gln Asp Glu Ile Leu
        195                 200                 205

Cys Glu Val Glu Glu Tyr Leu Pro Ser Phe Ser Lys Trp Ala Glu Asp
    210                 215                 220

Phe Met Arg Lys Gly Pro Ser Ser Glu Phe Pro Gln Met Gln Leu Ser
225                 230                 235                 240

Leu Pro Ser Asp Gly Ser Asn Arg Ser Ser Pro Cys Asn Ile Glu Val
                245                 250                 255

Val Lys Ser Leu Asp Ile Glu Glu Ser Ile Trp Ser Pro Arg Phe Gly
            260                 265                 270

Leu Lys Gly Lys Ile Asp Val Thr Val Gly Val Lys Ile His Arg Asp
        275                 280                 285

Cys Lys Met Lys Tyr Lys Val Met Pro Leu Glu Leu Lys Thr Gly Lys
    290                 295                 300

Glu Ser Asn Ser Ile Glu His Arg Ser Gln Val Val Leu Tyr Thr Leu
305                 310                 315                 320

Leu Ser Gln Glu Arg Arg Glu Asp Pro Glu Ala Gly Trp Leu Leu Tyr
                325                 330                 335

Leu Lys Thr Gly Gln Met Tyr Pro Val Pro Ala Asn His Leu Asp Lys
            340                 345                 350

Arg Glu Leu Leu Lys Leu Arg Asn Trp Leu Ala Ala Ser Leu Leu His
        355                 360                 365

Arg Val Ser Arg Ala Ala Pro Gly Glu Glu Ala Arg Leu Ser Ala Leu
    370                 375                 380

Pro Gln Ile Ile Glu Glu Glu Lys Thr Cys Lys Tyr Cys Ser Gln Ile
385                 390                 395                 400

Gly Asn Cys Ala Leu Tyr Ser Arg Ala Val Glu Glu Gln Gly Asp Asp
                405                 410                 415

Ala Ser Ile Pro Glu Ala Met Leu Ser Lys Ile Gln Glu Glu Thr Arg
            420                 425                 430

His Leu Gln Leu Ala His Leu Lys Tyr Phe Ser Leu Trp Cys Leu Met
        435                 440                 445

Leu Thr Leu Glu Ser Gln Ser Lys Asp Asn Arg Lys Thr His Gln Ser
    450                 455                 460

Ile Trp Leu Thr Pro Ala Ser Glu Leu Glu Glu Ser Gly Asn Cys Val
465                 470                 475                 480

Gly Asn Leu Val Arg Thr Glu Pro Val Ser Arg Val Cys Asp Gly Gln
                485                 490                 495

Tyr Leu His Asn Phe Gln Arg Lys Asn Gly Pro Met Pro Ala Thr Asn
            500                 505                 510
```

```
Leu Met Ala Gly Asp Arg Ile Ile Leu Ser Gly Glu Glu Arg Lys Leu
        515                 520                 525

Phe Ala Leu Ser Lys Gly Tyr Val Lys Lys Met Asn Lys Ala Ala Val
    530                 535                 540

Thr Cys Leu Leu Asp Arg Asn Leu Ser Thr Leu Pro Ala Thr Thr Val
545                 550                 555                 560

Phe Arg Leu Asp Arg Glu Glu Arg His Gly Asp Ile Ser Thr Pro Leu
                565                 570                 575

Gly Asn Leu Ser Lys Leu Met Glu Ser Thr Asp Pro Ser Lys Arg Leu
            580                 585                 590

Arg Glu Leu Ile Ile Asp Phe Arg Glu Pro Gln Phe Ile Ala Tyr Leu
        595                 600                 605

Ser Ser Val Leu Pro His Asp Ala Lys Asp Thr Val Ala Asn Ile Leu
    610                 615                 620

Lys Gly Leu Asn Lys Pro Gln Arg Gln Ala Met Lys Arg Val Leu Leu
625                 630                 635                 640

Ser Lys Asp Tyr Thr Leu Ile Val Gly Met Pro Gly Thr Gly Lys Thr
                645                 650                 655

Thr Thr Ile Cys Ala Leu Val Arg Ile Leu Ser Ala Cys Gly Phe Ser
            660                 665                 670

Val Leu Leu Thr Ser Tyr Thr His Ser Ala Val Asp Asn Ile Leu Leu
        675                 680                 685

Lys Leu Ala Lys Phe Lys Val Gly Phe Leu Arg Leu Gly Gln Ser His
    690                 695                 700

Lys Val His Pro Asp Ile Gln Lys Phe Thr Glu Glu Glu Ile Cys Arg
705                 710                 715                 720

Ser Arg Ser Ile Ala Ser Leu Ala His Leu Glu Glu Leu Tyr Asn Ser
                725                 730                 735

His Pro Ile Val Ala Thr Thr Cys Met Gly Ile Asn His Pro Ile Phe
            740                 745                 750

Ser Arg Lys Thr Phe Asp Phe Cys Ile Val Asp Glu Ala Ser Gln Ile
        755                 760                 765

Ser Gln Pro Val Cys Leu Gly Pro Leu Phe Phe Ser Arg Arg Phe Val
    770                 775                 780

Leu Val Gly Asp His Gln Gln Leu Pro Pro Leu Val Val Asn Arg Glu
785                 790                 795                 800

Ala Arg Ala Leu Gly Met Ser Glu Ser Leu Phe Lys Arg Leu Glu Arg
                805                 810                 815

Asn Glu Ser Ala Val Val Gln Leu Thr Val Gln Tyr Arg Met Asn Arg
            820                 825                 830

Lys Ile Met Ser Leu Ser Asn Lys Leu Thr Tyr Ala Gly Lys Leu Glu
        835                 840                 845

Cys Gly Ser Asp Arg Val Ala Asn Ala Val Leu Ala Leu Pro Asn Leu
    850                 855                 860

Lys Asp Ala Arg Leu Ser Leu Gln Leu Tyr Ala Asp Tyr Ser Asp Ser
865                 870                 875                 880

Pro Trp Leu Ala Gly Val Leu Glu Pro Asp Asn Pro Val Cys Phe Leu
                885                 890                 895

Asn Thr Asp Lys Val Pro Ala Pro Glu Gln Val Glu Asn Gly Gly Val
            900                 905                 910

Ser Asn Val Thr Glu Ala Arg Leu Ile Val Phe Leu Thr Ser Thr Phe
        915                 920                 925
```

```
Ile Lys Ala Gly Cys Ser Pro Ser Asp Ile Gly Val Ile Ala Pro Tyr
    930                 935                 940

Arg Gln Gln Leu Arg Ile Ile Ser Asp Leu Leu Ala Arg Ser Ser Val
945                 950                 955                 960

Gly Met Val Glu Val Asn Thr Val Asp Lys Tyr Gln Gly Arg Asp Lys
                965                 970                 975

Ser Leu Ile Leu Val Ser Phe Val Arg Ser Asn Glu Asp Gly Thr Leu
            980                 985                 990

Gly Glu Leu Leu Lys Asp Trp Arg Arg Leu Asn Val Ala Leu Thr Arg
        995                 1000                1005

Ala Lys His Lys Leu Ile Leu Leu Gly Ser Val Ser Ser Leu Lys Arg
    1010                1015                1020

Phe Pro Pro Leu Gly Thr Leu Phe Asp His Leu Asn Ala Glu Gln Leu
1025                1030                1035                1040

Ile Leu Asp Leu Pro Ser Arg Glu His Glu Ser Leu Ser His Ile Leu
                1045                1050                1055

Gly Asp Cys Gln Arg Asp
            1060


<210> SEQ ID NO 139
<211> LENGTH: 702
<212> TYPE: PRT
<213> ORGANISM: Saccharomyces cerevisiae

<400> SEQUENCE: 139

Met Gly Ile Gln Gly Leu Leu Pro Gln Leu Lys Pro Ile Gln Asn Ala
1               5                   10                  15

Val Ser Leu Arg Arg Tyr Glu Gly Glu Val Leu Ala Ile Asp Gly Tyr
            20                  25                  30

Ala Trp Leu His Arg Ala Ala Cys Ser Cys Ala Tyr Glu Leu Ala Met
        35                  40                  45

Gly Lys Pro Thr Asp Lys Tyr Leu Gln Phe Phe Ile Lys Arg Phe Ser
    50                  55                  60

Leu Leu Lys Thr Phe Lys Val Glu Pro Tyr Leu Val Phe Asp Gly Asp
65                  70                  75                  80

Ala Ile Pro Val Lys Lys Ser Thr Glu Ser Lys Arg Arg Asp Lys Arg
                85                  90                  95

Lys Glu Asn Lys Ala Ile Ala Glu Arg Leu Trp Ala Cys Gly Glu Lys
            100                 105                 110

Lys Asn Ala Met Asp Tyr Phe Gln Lys Cys Val Asp Ile Thr Pro Glu
        115                 120                 125

Met Ala Lys Cys Ile Ile Cys Tyr Cys Lys Leu Asn Gly Ile Arg Tyr
    130                 135                 140

Ile Val Ala Pro Phe Glu Ala Asp Ser Gln Met Val Tyr Leu Glu Gln
145                 150                 155                 160

Lys Asn Ile Val Gln Gly Ile Ile Ser Glu Asp Ser Asp Leu Leu Val
                165                 170                 175

Phe Gly Cys Arg Arg Leu Ile Thr Lys Leu Asn Asp Tyr Gly Glu Cys
            180                 185                 190

Leu Glu Ile Cys Arg Asp Asn Phe Ile Lys Leu Pro Lys Lys Phe Pro
        195                 200                 205

Leu Gly Ser Leu Thr Asn Glu Glu Ile Ile Thr Met Val Cys Leu Ser
    210                 215                 220

Gly Cys Asp Tyr Thr Asn Gly Ile Pro Lys Val Gly Leu Ile Thr Ala
225                 230                 235                 240
```

```
Met Lys Leu Val Arg Arg Phe Asn Thr Ile Glu Arg Ile Ile Leu Ser
                245                 250                 255

Ile Gln Arg Glu Gly Lys Leu Met Ile Pro Asp Thr Tyr Ile Asn Glu
            260                 265                 270

Tyr Glu Ala Ala Val Leu Ala Phe Gln Phe Gln Arg Val Phe Cys Pro
        275                 280                 285

Ile Arg Lys Lys Ile Val Ser Leu Asn Glu Ile Pro Leu Tyr Leu Lys
    290                 295                 300

Asp Thr Glu Ser Lys Arg Lys Arg Leu Tyr Ala Cys Ile Gly Phe Val
305                 310                 315                 320

Ile His Arg Glu Thr Gln Lys Lys Gln Ile Val His Phe Asp Asp Asp
                325                 330                 335

Ile Asp His His Leu His Leu Lys Ile Ala Gln Gly Asp Leu Asn Pro
            340                 345                 350

Tyr Asp Phe His Gln Pro Leu Ala Asn Arg Glu His Lys Leu Gln Leu
        355                 360                 365

Ala Ser Lys Ser Asn Ile Glu Phe Gly Lys Thr Asn Ser Thr Asn Ser
    370                 375                 380

Glu Ala Lys Val Lys Pro Ile Glu Ser Phe Phe Gln Lys Met Thr Lys
385                 390                 395                 400

Leu Asp His Tyr Pro Lys Val Ala Asn Asn Ile His Ser Leu Arg Gln
                405                 410                 415

Ala Glu Asp Lys Leu Thr Met Ala Ile Lys Arg Arg Lys Leu Ser Asn
            420                 425                 430

Ala Asn Val Val Gln Glu Thr Leu Lys Asp Thr Arg Ser Lys Phe Phe
        435                 440                 445

Asn Lys Pro Ser Met Thr Val Val Glu Asn Phe Lys Glu Lys Gly Asp
    450                 455                 460

Ser Thr Gln Asp Phe Lys Glu Asp Thr Asn Ser Gln Ser Leu Glu Glu
465                 470                 475                 480

Pro Val Ser Glu Ser Gln Leu Ser Thr Gln Ile Pro Ser Ser Phe Ile
                485                 490                 495

Thr Thr Asn Leu Glu Asp Asp Asp Asn Leu Ser Glu Glu Val Ser Glu
            500                 505                 510

Val Val Ser Asp Thr Glu Glu Asp Arg Lys Asn Ser Glu Gly Lys Ile
        515                 520                 525

Ile Gly Asn Glu Ile Tyr Asn Thr Asp Asp Asp Gly Asp Gly Asp Thr
    530                 535                 540

Ser Glu Asp Tyr Ser Glu Thr Ala Glu Ser Arg Val Pro Thr Ser Ser
545                 550                 555                 560

Thr Thr Ser Phe Pro Gly Ser Ser Gln Arg Ser Ile Ser Gly Cys Thr
                565                 570                 575

Lys Val Leu Gln Lys Phe Arg Tyr Ser Ser Ser Phe Ser Gly Val Asn
            580                 585                 590

Ala Asn Arg Gln Pro Leu Phe Pro Arg His Val Asn Gln Lys Ser Arg
        595                 600                 605

Gly Met Val Tyr Val Asn Gln Asn Arg Asp Asp Asp Cys Asp Asp Asn
    610                 615                 620

Asp Gly Lys Asn Gln Ile Met Gln Arg Pro Leu Leu Arg Lys Ser Leu
625                 630                 635                 640

Ile Gly Ala Arg Ser Gln Arg Ile Val Ile Asp Met Lys Ser Val Asp
                645                 650                 655
```

```
Glu Arg Lys Ser Phe Asn Ser Ser Pro Ile Leu His Glu Glu Ser Lys
            660                 665                 670

Lys Arg Asp Ile Glu Thr Thr Lys Ser Ser Gln Ala Arg Pro Ala Val
        675                 680                 685

Arg Ser Ile Ser Leu Leu Ser Gln Phe Val Tyr Lys Gly Lys
    690                 695                 700


<210> SEQ ID NO 140
<211> LENGTH: 486
<212> TYPE: PRT
<213> ORGANISM: Unknown
<220> FEATURE:
<223> OTHER INFORMATION: herpesvirus

<400> SEQUENCE: 140

Met Glu Ala Thr Pro Thr Pro Ala Asp Leu Phe Ser Glu Asp Tyr Leu
1               5                   10                  15

Val Asp Thr Leu Asp Gly Leu Thr Val Asp Asp Gln Gln Ala Val Leu
            20                  25                  30

Ala Ser Leu Ser Phe Ser Lys Phe Leu Lys His Ala Lys Val Arg Asp
        35                  40                  45

Trp Cys Ala Gln Ala Lys Ile Gln Pro Ser Met Pro Ala Leu Arg Met
    50                  55                  60

Ala Tyr Asn Tyr Phe Leu Phe Ser Lys Val Gly Glu Phe Ile Gly Ser
65                  70                  75                  80

Glu Asp Val Cys Asn Phe Phe Val Asp Arg Val Phe Gly Gly Val Arg
                85                  90                  95

Leu Leu Asp Val Ala Ser Val Tyr Ala Ala Cys Ser Gln Met Asn Ala
            100                 105                 110

His Gln Arg His His Ile Cys Cys Leu Val Glu Arg Ala Thr Ser Ser
        115                 120                 125

Gln Ser Leu Asn Pro Val Trp Asp Ala Leu Arg Asp Gly Ile Ile Ser
    130                 135                 140

Ser Ser Lys Phe His Trp Ala Val Lys Gln Gln Asn Thr Ser Lys Lys
145                 150                 155                 160

Ile Phe Ser Pro Trp Pro Ile Thr Asn Asn His Phe Val Ala Gly Pro
                165                 170                 175

Leu Ala Phe Gly Leu Arg Cys Glu Glu Val Val Lys Thr Leu Leu Ala
            180                 185                 190

Thr Leu Leu His Pro Asp Glu Ala Asn Cys Leu Asp Tyr Gly Phe Met
        195                 200                 205

Gln Ser Pro Gln Asn Gly Ile Phe Gly Val Ser Leu Asp Phe Ala Ala
    210                 215                 220

Asn Val Lys Thr Asp Thr Glu Gly Arg Leu Gln Phe Asp Pro Asn Cys
225                 230                 235                 240

Lys Val Tyr Glu Ile Lys Cys Arg Phe Lys Tyr Thr Phe Ala Lys Met
                245                 250                 255

Glu Cys Asp Pro Ile Tyr Ala Ala Tyr Gln Arg Leu Tyr Glu Ala Pro
            260                 265                 270

Gly Lys Leu Ala Leu Lys Asp Phe Phe Tyr Ser Ile Ser Lys Pro Ala
        275                 280                 285

Val Glu Tyr Val Gly Leu Gly Lys Leu Pro Ser Glu Ser Asp Tyr Leu
    290                 295                 300

Val Ala Tyr Asp Gln Glu Trp Glu Ala Cys Pro Arg Lys Lys Arg Lys
305                 310                 315                 320
```

```
Leu Thr Pro Leu His Asn Leu Ile Arg Glu Cys Ile Leu His Asn Ser
                325                 330                 335

Thr Thr Glu Ser Asp Val Tyr Val Leu Thr Asp Pro Gln Asp Thr Arg
            340                 345                 350

Gly Gln Ile Ser Ile Lys Ala Arg Phe Lys Ala Asn Leu Phe Val Asn
        355                 360                 365

Val Arg His Ser Tyr Phe Tyr Gln Val Leu Leu Gln Ser Ser Ile Val
    370                 375                 380

Glu Glu Tyr Ile Gly Leu Asp Ser Gly Ile Pro Arg Leu Gly Ser Pro
385                 390                 395                 400

Lys Tyr Tyr Ile Ala Thr Gly Phe Phe Arg Lys Arg Gly Tyr Gln Asp
                405                 410                 415

Pro Val Asn Cys Thr Ile Gly Gly Asp Ala Leu Asp Pro His Val Glu
            420                 425                 430

Ile Pro Thr Leu Leu Ile Val Thr Pro Val Tyr Phe Pro Arg Gly Ala
        435                 440                 445

Lys His Arg Leu Leu His Gln Ala Ala Asn Phe Trp Ser Arg Ser Ala
    450                 455                 460

Lys Asp Thr Phe Pro Tyr Ile Lys Trp Asp Phe Ser Tyr Leu Ser Ala
465                 470                 475                 480

Asn Val Pro His Ser Pro
                485
```

<210> SEQ ID NO 141
<211> LENGTH: 521
<212> TYPE: PRT
<213> ORGANISM: Unknown
<220> FEATURE:
<223> OTHER INFORMATION: UL12 exonuclease

<400> SEQUENCE: 141

```
Met Glu Leu Glu Pro Val Gly Lys Lys Tyr Arg Pro Glu Arg Glu Asp
1               5                   10                  15

Ser Ser Lys Gly Arg Lys Ile Leu Thr Val Ser Val Asn Ser Gln Leu
            20                  25                  30

Gln Gly Ala Ser Pro Thr Leu Gly Thr Arg Ala His Pro Pro His Ser
        35                  40                  45

Glu Leu Thr Asp Tyr Thr Phe Ser Arg Tyr Ile Leu Tyr His Leu Ala
    50                  55                  60

Pro Ser Glu Leu Lys Glu Ala Ile His Pro Leu Tyr His Arg Leu Asn
65                  70                  75                  80

Tyr Ile Ala Asp Val Ile Lys Arg Gly Thr Ser Glu Gly Arg Trp Leu
                85                  90                  95

Gly Tyr Pro Tyr Ser Cys Ile Leu Asp Thr Glu Asp Glu Leu Arg Asn
            100                 105                 110

Glu Ser Arg Arg Asn Thr Ser Ser Pro Ser Asp His Ala Leu Arg Trp
        115                 120                 125

Cys Leu Leu Val Glu Ser Phe Thr Ile Glu Gln Ala Asn Cys Asp Leu
    130                 135                 140

Trp His Ile Phe Arg Gln Ser Leu Leu Thr Ala Ser Ser Val Lys Trp
145                 150                 155                 160

Thr Asp Asp Gly Lys Leu Asp Thr Val Gly Ile Met Ser Asp Asn Ser
                165                 170                 175

Thr Ala Tyr Val Glu Thr Cys Ser Val Ala Phe Gly Lys His Asn Glu
            180                 185                 190
```

```
Pro Leu Ala Lys Ser Leu Val Thr Met Phe Cys Leu Asn His Ser Arg
        195                 200                 205

His Val His Asn Thr Ser Pro Arg Arg Glu Asn Val Phe Val Phe Glu
    210                 215                 220

Asp Val Ser Asp Arg Thr Ile Gln Ser Glu Ser Asp Tyr Ser Cys Gly
225                 230                 235                 240

Leu Met Ile Asp Thr Arg Thr Gly Met Val Gly Ala Ser Leu Asp Met
                245                 250                 255

Leu Val Cys Glu Arg Asp Pro Phe Gly Leu Leu Gln Pro Asp Ser Glu
            260                 265                 270

Asn Gln Ala Ile Glu Thr Tyr Glu Ile Lys Cys Arg Ala Lys Tyr Ala
        275                 280                 285

Phe Cys Pro Asp Lys Arg Ser Glu Leu Ser Gln Cys Tyr Glu Arg Leu
    290                 295                 300

Leu Asn Val Arg Thr Met Gly Ser Leu Arg Leu Phe Ile Ser Ala Ile
305                 310                 315                 320

Gln Arg Pro Cys Val Asp Tyr Phe Gln Pro Gly Asn Val Pro Arg Ser
                325                 330                 335

Lys Glu Ala Leu Ile Thr Ser Asn Glu Glu Trp Lys Val Gly Asn Ser
            340                 345                 350

Ala Tyr His Ala Ala Gln Ser Arg Ile Arg Cys Asn Ala Phe Asp Lys
        355                 360                 365

Cys His Leu Glu Leu Asn Ser Asn Val Gln Ser Arg Val Trp Leu Phe
    370                 375                 380

Gly Glu Pro Asp Leu Glu Thr Asp Thr Ile Tyr Pro Leu Pro Trp Asp
385                 390                 395                 400

Thr Gly Lys Leu Ser Leu Asp Val Pro Ile Phe Ser Asn Pro Arg His
                405                 410                 415

Pro Asn Phe Lys Gln Ile Tyr Leu Gln Thr Tyr Val Ala Ala Gly Tyr
            420                 425                 430

Phe Gly Glu Arg Arg Thr Thr Pro Phe Leu Val Thr Phe Ile Gly Arg
        435                 440                 445

Trp Arg Lys Arg Arg Glu Phe Gly Lys Lys Phe Ser Leu Ile Ala Asp
    450                 455                 460

Ser Gly Leu Gly Lys Pro Ile Ser Thr Val His Ala Asp Gln Ala Ile
465                 470                 475                 480

Pro Val Leu Leu Ile Val Thr Pro Val Ile Val Asp Glu Ala Phe Tyr
                485                 490                 495

Gly Glu Ile Glu Ser Ala Gly Cys Arg Ala Phe Gly Glu Leu Val Lys
            500                 505                 510

Gln Leu Trp Ala Lys Gln Pro His Thr
        515                 520


<210> SEQ ID NO 142
<211> LENGTH: 664
<212> TYPE: PRT
<213> ORGANISM: Escherichia coli

<400> SEQUENCE: 142

Met Ser Lys Val Phe Ile Cys Ala Ala Ile Pro Asp Glu Leu Ala Thr
1               5                   10                  15

Arg Glu Glu Gly Ala Val Ala Val Ala Thr Ala Ile Glu Ala Gly Asp
            20                  25                  30

Glu Arg Arg Ala Arg Ala Lys Phe His Trp Gln Phe Leu Glu His Tyr
        35                  40                  45
```

```
Pro Ala Ala Gln Asp Cys Ala Tyr Lys Phe Ile Val Cys Glu Asp Lys
    50                  55                  60

Pro Gly Ile Pro Arg Pro Ala Leu Asp Ser Trp Asp Ala Glu Tyr Met
65                  70                  75                  80

Gln Glu Asn Arg Trp Asp Glu Glu Ser Ala Ser Phe Val Pro Val Glu
                85                  90                  95

Thr Glu Ser Asp Pro Met Asn Val Thr Phe Asp Lys Leu Ala Pro Glu
            100                 105                 110

Val Gln Asn Ala Val Met Val Lys Phe Asp Thr Cys Glu Asn Ile Thr
        115                 120                 125

Val Asp Met Val Ile Ser Ala Gln Glu Leu Leu Gln Glu Asp Met Ala
    130                 135                 140

Thr Phe Asp Gly His Ile Val Glu Ala Leu Met Lys Met Pro Glu Val
145                 150                 155                 160

Asn Ala Met Tyr Pro Glu Leu Lys Leu His Ala Ile Gly Trp Val Lys
                165                 170                 175

His Lys Cys Ile Pro Gly Ala Lys Trp Pro Glu Ile Gln Ala Glu Met
            180                 185                 190

Arg Ile Trp Lys Lys Arg Arg Glu Gly Glu Arg Lys Glu Thr Gly Lys
        195                 200                 205

Tyr Thr Ser Val Val Asp Leu Ala Arg Ala Arg Ala Asn Gln Gln Tyr
    210                 215                 220

Thr Glu Asn Ser Thr Gly Lys Ile Ser Pro Val Ile Ala Ala Ile His
225                 230                 235                 240

Arg Glu Tyr Lys Gln Thr Trp Lys Thr Leu Asp Asp Glu Leu Ala Tyr
                245                 250                 255

Ala Leu Trp Pro Gly Asp Val Asp Ala Gly Asn Ile Asp Gly Ser Ile
            260                 265                 270

His Arg Trp Ala Lys Lys Glu Val Ile Asp Asn Asp Arg Glu Asp Trp
        275                 280                 285

Lys Arg Ile Ser Ala Ser Met Arg Lys Gln Pro Asp Ala Leu Arg Tyr
    290                 295                 300

Asp Arg Gln Thr Ile Phe Gly Leu Val Arg Glu Arg Pro Ile Asp Ile
305                 310                 315                 320

His Lys Asp Pro Ile Ala Leu Asn Lys Tyr Ile Cys Glu Tyr Leu Thr
                325                 330                 335

Thr Lys Gly Val Phe Glu Asn Glu Glu Thr Asp Leu Gly Thr Val Asp
            340                 345                 350

Val Leu Gln Ser Ser Glu Thr Gln Thr Asp Ala Val Glu Thr Glu Val
        355                 360                 365

Ser Asp Ile Pro Lys Asn Glu Thr Ala Pro Glu Ala Glu Pro Ser Val
    370                 375                 380

Glu Arg Glu Gly Pro Phe Tyr Phe Leu Phe Ala Asp Lys Asp Gly Glu
385                 390                 395                 400

Lys Tyr Gly Arg Ala Asn Lys Leu Ser Gly Leu Asp Lys Ala Leu Ala
                405                 410                 415

Ala Gly Ala Thr Glu Ile Thr Lys Glu Glu Tyr Phe Ala Arg Lys Asn
            420                 425                 430

Gly Thr Tyr Thr Gly Leu Pro Gln Asn Val Asp Thr Ala Glu Asp Ser
        435                 440                 445

Glu Gln Pro Glu Pro Ile Lys Val Thr Ala Asp Glu Val Asn Lys Ile
    450                 455                 460
```

```
Met Gln Ala Ala Asn Ile Ser Gln Pro Asp Ala Asp Lys Leu Leu Ala
465                 470                 475                 480

Ala Ser Arg Gly Glu Phe Val Glu Glu Ile Ser Asp Pro Asn Asp Pro
                485                 490                 495

Lys Trp Val Lys Gly Ile Gln Thr Arg Asp Ser Val Asn Gln Asn Gln
            500                 505                 510

His Glu Ser Glu Arg Asn Tyr Gln Lys Ala Glu Gln Asn Ser Thr Asn
        515                 520                 525

Ala Leu Gln Asn Glu Pro Glu Thr Lys Gln Pro Glu Pro Val Ala Gln
    530                 535                 540

Gln Glu Val Glu Lys Val Cys Thr Ala Cys Gly Gln Thr Gly Gly Gly
545                 550                 555                 560

Asn Cys Pro Asp Cys Gly Ala Val Met Gly Asp Ala Thr Tyr Gln Glu
                565                 570                 575

Thr Phe Asp Glu Glu Tyr Gln Val Glu Val Gln Glu Asp Asp Pro Glu
            580                 585                 590

Glu Met Glu Gly Ala Glu His Pro His Lys Glu Asn Thr Gly Gly Asn
        595                 600                 605

Gln His His Asn Ser Asp Asn Glu Thr Gly Glu Thr Ala Asp His Ser
    610                 615                 620

Ile Lys Val Asn Gly His His Glu Ile Thr Ser Thr Ser Arg Ala Gly
625                 630                 635                 640

Ile His Leu Met Ile Asp Leu Glu Thr Met Gly Lys Asn Pro Asp Ala
                645                 650                 655

Pro Ile Ile Cys Asn Arg Leu Ile
            660
```

<210> SEQ ID NO 143
<211> LENGTH: 300
<212> TYPE: PRT
<213> ORGANISM: Unknown
<220> FEATURE:
<223> OTHER INFORMATION: Enterobacteria phage T7

<400> SEQUENCE: 143

```
Met Ala Leu Leu Asp Leu Lys Gln Phe Tyr Glu Leu Arg Glu Gly Cys
1               5                   10                  15

Asp Asp Lys Gly Ile Leu Val Met Asp Gly Asp Trp Leu Val Phe Gln
            20                  25                  30

Ala Met Ser Ala Ala Glu Phe Asp Ala Ser Trp Glu Glu Glu Ile Trp
        35                  40                  45

His Arg Cys Cys Asp His Ala Lys Ala Arg Gln Ile Leu Glu Asp Ser
    50                  55                  60

Ile Lys Ser Tyr Glu Thr Arg Lys Lys Ala Trp Ala Gly Ala Pro Ile
65                  70                  75                  80

Val Leu Ala Phe Thr Asp Ser Val Asn Trp Arg Lys Glu Leu Val Asp
                85                  90                  95

Pro Asn Tyr Lys Ala Asn Arg Lys Ala Val Lys Lys Pro Val Gly Tyr
            100                 105                 110

Phe Glu Phe Leu Asp Ala Leu Phe Glu Arg Glu Glu Phe Tyr Cys Ile
        115                 120                 125

Arg Glu Pro Met Leu Glu Gly Asp Asp Val Met Gly Val Ile Ala Ser
    130                 135                 140

Asn Pro Ser Ala Phe Gly Ala Arg Lys Ala Val Ile Ile Ser Cys Asp
145                 150                 155                 160
```

```
Lys Asp Phe Lys Thr Ile Pro Asn Cys Asp Phe Leu Trp Cys Thr Thr
                165                 170                 175

Gly Asn Ile Leu Thr Gln Thr Glu Glu Ser Ala Asp Trp Trp His Leu
            180                 185                 190

Phe Gln Thr Ile Lys Gly Asp Ile Thr Asp Gly Tyr Ser Gly Ile Ala
        195                 200                 205

Gly Trp Gly Asp Thr Ala Glu Asp Phe Leu Asn Asn Pro Phe Ile Thr
    210                 215                 220

Glu Pro Lys Thr Ser Val Leu Lys Ser Gly Lys Asn Lys Gly Gln Glu
225                 230                 235                 240

Val Thr Lys Trp Val Lys Arg Asp Pro Glu Pro His Glu Thr Leu Trp
                245                 250                 255

Asp Cys Ile Lys Ser Ile Gly Ala Lys Ala Gly Met Thr Glu Glu Asp
            260                 265                 270

Ile Ile Lys Gln Gly Gln Met Ala Arg Ile Leu Arg Phe Asn Glu Tyr
        275                 280                 285

Asn Phe Ile Asp Lys Glu Ile Tyr Leu Trp Arg Pro
    290                 295                 300


<210> SEQ ID NO 144
<211> LENGTH: 267
<212> TYPE: PRT
<213> ORGANISM: Escherichia coli

<400> SEQUENCE: 144

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240
```

```
Cys Glu Thr Gly Ile Asp Tyr Glu Ile Arg Ser Met Glu Lys Pro Ser
                245                 250                 255

Asp His Ala Pro Val Trp Ala Thr Phe Arg Arg
            260                 265


<210> SEQ ID NO 145
<211> LENGTH: 236
<212> TYPE: PRT
<213> ORGANISM: Mus musculus

<400> SEQUENCE: 145

Met Ser Glu Pro Pro Arg Ala Glu Thr Phe Val Phe Leu Asp Leu Glu
1               5                   10                  15

Ala Thr Gly Leu Pro Asn Met Asp Pro Glu Ile Ala Glu Ile Ser Leu
            20                  25                  30

Phe Ala Val His Arg Ser Ser Leu Glu Asn Pro Glu Arg Asp Asp Ser
        35                  40                  45

Gly Ser Leu Val Leu Pro Arg Val Leu Asp Lys Leu Thr Leu Cys Met
    50                  55                  60

Cys Pro Glu Arg Pro Phe Thr Ala Lys Ala Ser Glu Ile Thr Gly Leu
65                  70                  75                  80

Ser Ser Glu Ser Leu Met His Cys Gly Lys Ala Gly Phe Asn Gly Ala
                85                  90                  95

Val Val Arg Thr Leu Gln Gly Phe Leu Ser Arg Gln Glu Gly Pro Ile
            100                 105                 110

Cys Leu Val Ala His Asn Gly Phe Asp Tyr Asp Phe Pro Leu Leu Cys
        115                 120                 125

Thr Glu Leu Gln Arg Leu Gly Ala His Leu Pro Gln Asp Thr Val Cys
    130                 135                 140

Leu Asp Thr Leu Pro Ala Leu Arg Gly Leu Asp Arg Ala His Ser His
145                 150                 155                 160

Gly Thr Arg Ala Gln Gly Arg Lys Ser Tyr Ser Leu Ala Ser Leu Phe
                165                 170                 175

His Arg Tyr Phe Gln Ala Glu Pro Ser Ala Ala His Ser Ala Glu Gly
            180                 185                 190

Asp Val His Thr Leu Leu Leu Ile Phe Leu His Arg Ala Pro Glu Leu
        195                 200                 205

Leu Ala Trp Ala Asp Glu Gln Ala Arg Ser Trp Ala His Ile Glu Pro
    210                 215                 220

Met Tyr Val Pro Pro Asp Gly Pro Ser Leu Glu Ala
225                 230                 235


<210> SEQ ID NO 146
<211> LENGTH: 43
<212> TYPE: DNA
<213> ORGANISM: Unknown
<220> FEATURE:
<223> OTHER INFORMATION: Hammerhead ribozyme

<400> SEQUENCE: 146

aaattactga tgagtccgtg aggacgaaac gagtaagctc gtc                      43


<210> SEQ ID NO 147
<211> LENGTH: 68
<212> TYPE: DNA
<213> ORGANISM: Unknown
<220> FEATURE:
<223> OTHER INFORMATION: Hepatitis delta virus (HDV) ribozyme
```

<400> SEQUENCE: 147
ggccggcatg gtcccagcct cctcgctggc gccggctggg caacatgctt cggcatggcg 60
aatgggac 68

<210> SEQ ID NO 148
<211> LENGTH: 14
<212> TYPE: PRT
<213> ORGANISM: Artificial Sequence
<220> FEATURE:
<223> OTHER INFORMATION: Amino acid linker

<400> SEQUENCE: 148

Met Ala Pro Lys Lys Lys Arg Lys Val Gly Gly Ser Gly Ser
1 5 10

<210> SEQ ID NO 149
<211> LENGTH: 2243
<212> TYPE: DNA
<213> ORGANISM: Solanum lycopersicum

<400> SEQUENCE: 149
atcgtatcca gtgcaccata ttttttggcg attaccactc atattattgt gtttagtaga 60
tattttaggt gcataattga tctcttcttt aaaactaggg gcacttatta ttatacatcc 120
acttgacact tgctttagtt ggctattttt tttatttttt attttttgtc aactacccca 180
atttaaattt tatttgatta agatattttt atggacctac tttataatta aaaatatttt 240
ctatttgaaa aggaaggaca aaaatcatac aattttggtc caactactcc tctctttttt 300
tttttggctt tataaaaaag gaaagtgatt agtaataaat aattaaataa tgaaaaaagg 360
aggaaataaa attttcgaat taaaatgtaa aagagaaaaa ggagagggag taatcattgt 420
ttaactttat ctaaagtacc ccaattcgat tttacatgta tatcaaatta tacaaatatt 480
ttattaaaat atagatattg aataatttta ttattcttga acatgtaaat aaaaattatc 540
tattatttca atttttatat aaactattat ttgaaatctc aattatgatt ttttaatatc 600
actttctatc catgataatt tcagcttaaa aagttttgtc aataattaca ttaattttgt 660
tgatgaggat gacaagattt cggtcatcaa ttacatatac acaaattgaa atagtaagca 720
acttgatttt ttttctcata atgataatga caaagacacg aaaagacaat tcaatattca 780
cattgattta tttttatatg ataataatta caataataat attcttataa agaaagagat 840
caattttgac tgatccaaaa atttatttat ttttactata ccaacgtcac taattatatc 900
taataatgta aaacaattca atcttactta aatattaatt tgaaataaac tatttttata 960
acgaaattac taaatttatc caataacaaa aaggtcttaa gaagacataa attctttttt 1020
tgtaatgctc aaataaattt gagtaaaaaa gaatgaaatt gagtgatttt tttttaatca 1080
taagaaaata aataattaat ttcaatataa taaaacagta atataatttc ataaatggaa 1140
ttcaatactt acctcttaga tataaaaaat aaatataaaa ataaagtgtt tctaataaac 1200
ccgcaattta aataaaatat ttaatatttt caatcaaatt taaataatta tattaaaata 1260
tcgtagaaaa agagcaatat ataatacaag aaagaagatt taagtacaat tatcaactat 1320
tattatactc taattttgtt atatttaatt tcttacggtt aaggtcatgt tcacgataaa 1380
ctcaaaatac gctgtatgag gacatatttt aaattttaac caataataaa actaagttat 1440
ttttagtata tttttttgtt taacgtgact taatttttct tttctagagg agcgtgtaag 1500
tgtcaacctc attctcctaa ttttcccaac cacataaaaa aaaaataaag gtagcttttg 1560

-continued

```
cgtgttgatt tggtacacta cacgtcatta ttacacgtgt tttcgtatga ttggttaatc   1620

catgaggcgg tttcctctag agtcggccat accatctata aaataaagct ttctgcagct   1680

catttttca tcttctatct gatttctatt ataatttctc tgaattgcct tcaaatttct    1740

ctttcaaggt tagaattttt ctctattttt tggtttttgt ttgtttagat tctgagttta   1800

gttaatcagg tgctgttaaa gccctaaatt ttgagttttt ttcggttgtt ttgatggaaa   1860

atacctaaca attgagtttt ttcatgttgt tttgtcggag aatgcctaca attggagttc   1920

ctttcgttgt tttgatgaga aagcccctaa tttgagtgtt tttccgtcga tttgatttta   1980

aaggtttata ttcgagtttt tttcgtcggt ttaatgagaa ggcctaaaat aggagttttt   2040

ctggttgatt tgactaaaaa agccatggaa ttttgtgttt ttgatgtcgc tttggttctc   2100

aaggcctaag atctgagttt ctccggttgt tttgatgaaa aagccctaaa attggagttt   2160

ttatcttgtg ttttaggttg ttttaatcct tataatttga gtttttcgt tgttctgatt    2220

gttgttttta tgaatttcct gca                                           2243
```